United States Patent
Kim et al.

(10) Patent No.: US 11,814,687 B2
(45) Date of Patent: Nov. 14, 2023

(54) METHODS FOR CHARACTERIZING BLADDER CANCER

(71) Applicants: The Broad Institute, Inc., Cambridge, MA (US); The General Hospital Corporation, Boston, MA (US); Baylor College of Medicine, Houston, TX (US); The Brigham and Women's Hospital, Inc., Boston, MA (US); Northwestern University, Evanston, IL (US); The Johns Hopkins University, Baltimore, MD (US); United States Government as represented by the U.S. Department of Veterans Affairs, Washington, DC (US)

(72) Inventors: Jaegil Kim, Cambridge, MA (US); Gad Getz, Boston, MA (US); Seth Paul Lerner, Houston, TX (US); David Kwiatkowski, Boston, MA (US); Joshua Meeks, Evanston, IL (US); Joaquim Bellmunt, Cambridge, MA (US); David McConkey, Baltimore, MD (US)

(73) Assignees: The Broad Institute, Inc., Cambridge, MA (US); The General Hospital Corporation, Boston, MA (US); Baylor College of Medicine, Houston, TX (US); The Brigham and Women's Hospital, Inc., Boston, MA (US); Northwestern University, Evanston, IL (US); The Johns Hopkins University, Baltimore, MD (US); United States Government as represented by the U.S. Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/988,317

(22) Filed: Aug. 7, 2020

(65) Prior Publication Data
US 2020/0370133 A1    Nov. 26, 2020

Related U.S. Application Data

(63) Continuation of application No. PCT/US2019/017300, filed on Feb. 8, 2019.

(60) Provisional application No. 62/794,447, filed on Jan. 18, 2019, provisional application No. 62/628,756, filed on Feb. 9, 2018.

(51) Int. Cl.
*C12Q 1/6886* (2018.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2009/0226905 A1* | 9/2009 | Joubert | G01N 33/57419 435/7.1 |
| 2015/0292030 A1 | 10/2015 | McConkey et al. | |
| 2016/0258026 A1* | 9/2016 | Davicioni | G01N 33/57484 |

FOREIGN PATENT DOCUMENTS

WO    2015073949 A1    5/2015

OTHER PUBLICATIONS

Robertson et al Cell. Oct. 2017, 171: 540-556, e1-e15 (Year: 2017).*
Batista de Costa et al Clinical Cancer Research. 2019. 25(13):3908-3920 (Year: 2019).*
Kawai et al American Urological Association Annual Meeting. May 2016. Abstract MP45-04, 2 pages (Year: 2016).*
Heggard et al. International Journal of Cancer. May 4, 2011. 102. 130: 1378-1386 (Year: 2011).*
Hanke et al. Clinical Chemistry. 2007. 53: 2070-2077 (Year: 2007).*
Min et al. BMC Genomics. 2010. 11:96 (Year: 2010).*
Al-Ahmadie et al., "Frequent somatic CDH1 loss-of-function mutations in plasmacytoid variant bladder cancer," Nature Genetics, Apr. 2016, vol. 48, No. 4, pp. 356-358.
Balbas-Martinez et al., "Recurrent inactivation of STAG2 in bladder cancer is not associated with aneuploidy," Nature Genetics, Dec. 2013, vol. 45, No. 12, pp. 1464-1469.
Biton et al., "Independent Component Analysis Uncovers the Landscape of the Bladder Tumor Transcriptome and Reveals Insights into Luminal and Basal Subtypes," Cell Reports, Nov. 20, 2014, vol. 9, pp. 1235-1245.
Breyer et al., "ESR1, ERBB2, and Ki67 mRNA expression predicts stage and grade of non-muscle-invasive bladder carcinoma (NMIBC)," Virchows Archiv, 2016, vol. 469, pp. 547-552.
Cappellen et al., "Frequent activating mutations of FGFR3 in human bladder and cervix carcinomas," Nature Genetics, Sep. 1999, vol. 23, pp. 18-20.
Castro et al., "Regulators of genetic risk of breast cancer identified by integrative network analysis," Nature Genetics, Jan. 2016, vol. 48, No. 1, pp. 12-21.
Choi et al., "Identification of Distinct Basal and Luminal Subtypes of Muscle-Invasive Bladder Cancer with Different Sensitivities to Frontline Chemotherapy," Cancer Cell, Feb. 10, 2014, vol. 25, pp. 152-165.

(Continued)

*Primary Examiner* — Carla J Myers
(74) *Attorney, Agent, or Firm* — Greenberg Traurig, LLP; Melissa Hunter-Ensor; Nathan Hsu

(57) ABSTRACT

The present invention features methods for characterizing mutational profiles in patients with bladder cancer.

7 Claims, 101 Drawing Sheets

(56) References Cited

OTHER PUBLICATIONS

Choi et al., "Intrinsic basal and luminal subtypes of muscle-invasive bladder cancer," Nature Reviews Urology, Jul. 2014, vol. 11, pp. 400-410.

Cibulskis et al., "Sensitive detection of somatic point mutations in impure and heterogeneous cancer samples," Nature Biotechnology, Mar. 2013, vol. 31, No. 3, pp. 213-219.

Cuzick et al., "Prognostic value of an RNA expression signature derived from cell cycle proliferation genes in patients with prostate cancer: a retrospective study," The Lancet Oncology, Mar. 2011, vol. 12, pp. 245-255.

Dadhania et al., "Meta-Analysis of the Luminal and Basal Subtypes of Bladder Cancer and the Identification of Signature Immunohistochemical Markers for Clinical Use," EBioMedicine, 2016, vol. 12, pp. 105-117.

Damrauer et al., "Intrinsic subtypes of high-grade bladder cancer reflect the hallmarks of breast cancer biology," Proceedings of the National Academy of Sciences of the United States of America, Feb. 25, 2014, vol. 111, No. 8, pp. 3110-3115.

Degraff et al., "When urothelial differentiation pathways go wrong: Implications for bladder cancer development and progression," Urologic Oncology: Seminars and Original Investigations, 2013, vol. 31, pp. 802-811.

Dennison et al., "High Intratumoral Stromal Content Defines Reactive Breast Cancer as a Low-risk Breast Cancer Subtype," Clinical Cancer Research, Oct. 15, 2016, vol. 22, No. 20, pp. 5068-5078.

Dyrskjot et al., "Gene Expression in the Urinary Bladder: a Common Carcinoma in Situ Gene Expression Signature Exists Disregarding Histopathological Classification," Cancer Research, Jun. 1, 2004, vol. 64, pp. 4040-4048.

Eriksson et al., "Molecular subtypes of urothelial carcinoma are defined by specific gene regulatory systems," BMC Medical Genomics, 2015, vol. 8, Article No. 25, pp. 1-15.

Getz et al., "Comment on 'the consensus coding sequences of human breast and colorectal cancers,'" Science, Sep. 14, 2007, vol. 317, Article No. 5844, p. 1500b.

Godoy et al., "Effects of Androgen and Estrogen Receptor Signaling Pathways on Bladder Cancer Initiation and Progression," Bladder Cancer, 2016, vol. 2, pp. 127-137.

Gui et al., "Frequent mutations of chromatin remodeling genes in transitional cell carcinoma of the bladder," Nature Genetics, Sep. 2011, vol. 43, No. 9, pp. 875-878.

Jones et al., "Pharmacogenomics: Biomarker-Directed Therapy for Bladder Cancer," The Urologic Clinics of North America, Feb. 2016, vol. 43, No. 1, pp. 77-86.

Kardos et al., "Claudin-low bladder tumors are immune infiltrated and actively immune suppressed," JCI Insight, 2016, vol. 1, No. 3, e85902, pp. 1-17.

Karkera et al., "Oncogenic Characterization and Pharmacologic Sensitivity of Activating Fibroblast Growth Factor Receptor (FGFR) Genetic Alterations to the Selective FGFR Inhibitor Erdafitinib," Molecular Cancer Therapeutics, Aug. 2017, vol. 16, No. 8, pp. 1717-1726.

Kim et al., "Somatic ERCC2 mutations are associated with a distinct genomic signature in urothelial tumors," Nature Genetics, Jun. 2016, vol. 48, No. 6, pp. 600-606.

Knowles et al., "Molecular biology of bladder cancer: new insights into pathogenesis and clinical diversity," Nature Reviews Cancer, Jan. 2015, vol. 15, No. 1, pp. 25-41.

Kostic et al., "PathSeq: software to identify or discover microbes by deep sequencing of human tissue," Nature Biotechnology, May 2011, vol. 29, No. 5, pp. 393-396.

Lawrence et al., "Discovery and saturation analysis of cancer genes across 21 tumour types," Nature, Jan. 23, 2014, vol. 505, pp. 495-501.

Ler et al., "Loss of tumor suppressor KDM6A amplifies PRC2-regulated transcriptional repression in bladder cancer and can be targeted through inhibition of EZH2," Science Translational Medicine, Feb. 22, 2017, vol. 9, eaai8312, pp. 1-13.

Lim et al., "Fibroblast Growth Factor Receptor 1 Overexpression Is Associated with Poor Survival in Patients with Resected Muscle Invasive Urothelial Carcinoma," Yonsei Medical Journal, Jul. 2016, vol. 57, No. 4, pp. 831-839.

Mermel et al., "GISTIC2.0 facilitates sensitive and confident localization of the targets of focal somatic copy-number alteration in human cancers," Genome Biology, 2011, vol. 12, Article No. R41, pp. 1-14.

Neeley et al., "Variable slope normalization of reverse phase protein arrays," Bioinformatics, 2009, vol. 25, No. 11, pp. 1384-1389.

Nogova et al., "Evaluation of BGJ398, a Fibroblast Growth Factor Receptor 1-3 Kinase Inhibitor, in Patients With Advanced Solid Tumors Harboring Genetic Alterations in Fibroblast Growth Factor Receptors: Results of a Global Phase I, Dose-Escalation and Dose-Expansion Study," Journal of Clinical Oncology, Jan. 10, 2017, vol. 35, No. 2, pp. 157-165.

Rebouissou et al., "CDKN2A homozygous deletion is associated with muscle invasion in FGFR3-mutated urothelial bladder carcinoma," The Journal of Pathology, 2012, vol. 227, No. 3, pp. 315-324.

Roberts et al., "An APOBEC cytidine deaminase mutagenesis pattern is widespread in human cancers," Nature Genetics, Aug. 2013, vol. 45, No. 8, pp. 970-976.

Rosenberg et al., "Atezolizumab in patients with locally advanced and metastatic urothelial carcinoma who have progressed following treatment with platinum-based chemotherapy: a single-arm, multicentre, phase 2 trial," The Lancet, May 7, 2016, vol. 387, No. 10031, pp. 1909-1920.

Seiler et al., "Impact of Molecular Subtypes in Muscle-invasive Bladder Cancer on Predicting Response and Survival after Neoadjuvant Chemotherapy," European Urology, 2017, vol. 72, pp. 544-554.

Sjodahl et al., "A Molecular Taxonomy for Urothelial Carcinoma," Clinical Cancer Research, Jun. 15, 2012, vol. 18, No. 12, pp. 3377-3386.

Sjodahl et al., "Molecular classification of urothelial carcinoma: global mRNA classification versus tumour-cell phenotype classification," The Journal of Pathology, 2017, vol. 242, pp. 113-125.

Van Allen et al., "Somatic ERCC2 Mutations Correlate with Cisplatin Sensitivity in Muscle-Invasive Urothelial Carcinoma," Cancer Discovery, Oct. 2014, vol. 4, No. 10, pp. 1140-1153.

Van Rhijn et al., "The Fibroblast Growth Factor Receptor 3 (FGFR3) Mutation Is a Strong Indicator of Superficial Bladder Cancer with Low Recurrence Rate," Cancer Research, 2001, vol. 61, pp. 1265-1268.

Warrick et al., "FOXA1, GATA3 and PPARγ Cooperate to Drive Luminal Subtype in Bladder Cancer: a Molecular Analysis of Established Human Cell Lines," Scientific Reports, 2016, vol. 6, Article No. 38531, pp. 1-15.

Williamson et al., "p16 (CDKN2) is a major deletion target at 9p21 in bladder cancer," Human Molecular Genetics, 1995, vol. 4, No. 9, pp. 1569-1577.

Wu et al., "BRD4 Regulates EZH2 Transcription through Upregulation of C-MYC and Represents a Novel Therapeutic Target in Bladder Cancer," Molecular Cancer Therapeutics, May 2016, vol. 15, No. 5, pp. 1029-1042.

Zack et al., "Pan-cancer patterns of somatic copy No. alteration," Nature Genetics, Oct. 2013, vol. 45, No. 10, pp. 1134-1140.

Robertson et al., "Comprehensive Molecular Characterization of Muscle-Invasive Bladder Cancer," Cell, Oct. 19, 2017, vol. 171, No. 3, pp. 540-556.

The Cancer Genome Atlas Research Network, "Comprehensive Molecular Characterization of Urothelial Bladder Carcinoma," Nature, Mar. 20, 2014, vol. 507, No. 7492, pp. 315-322.

International Search Report and Written Opinion for corresponding International Patent Application No. PCT/US19/17300, dated Jul. 10, 2019 (18 pages).

* cited by examiner

G (Continued)

G (Continued)

Panel 1

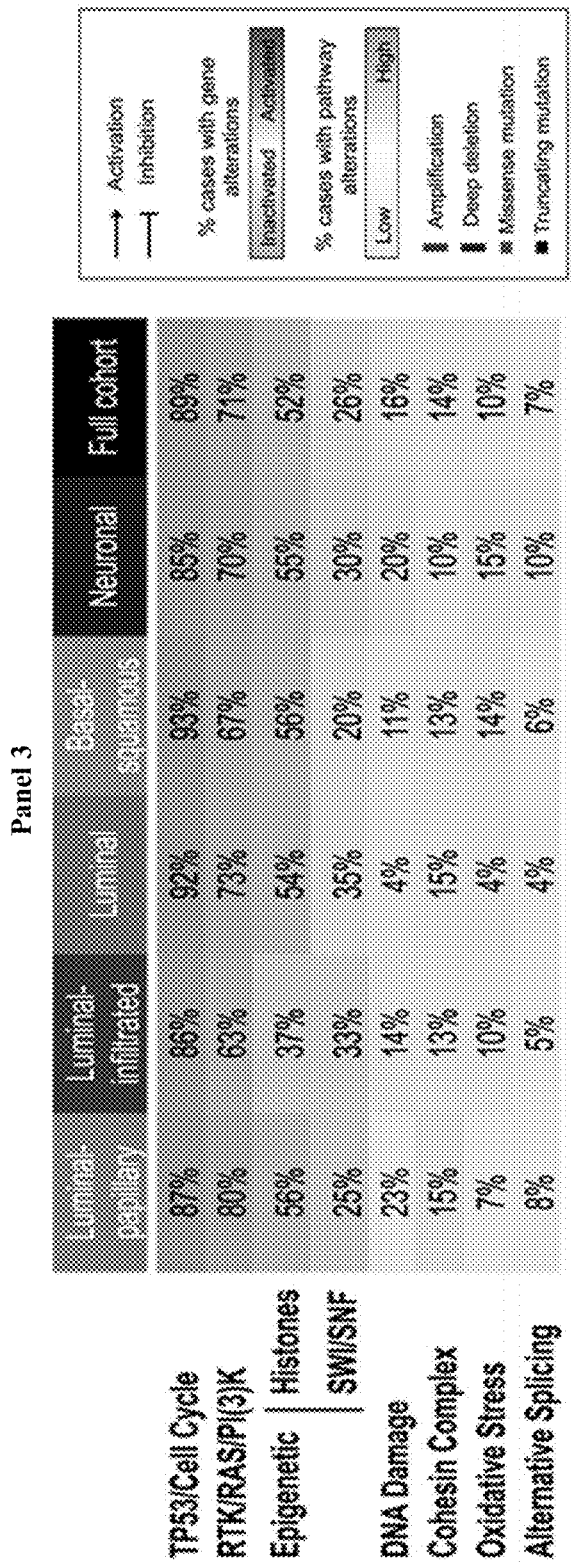
FIG. 8 (Continued) Panel 3

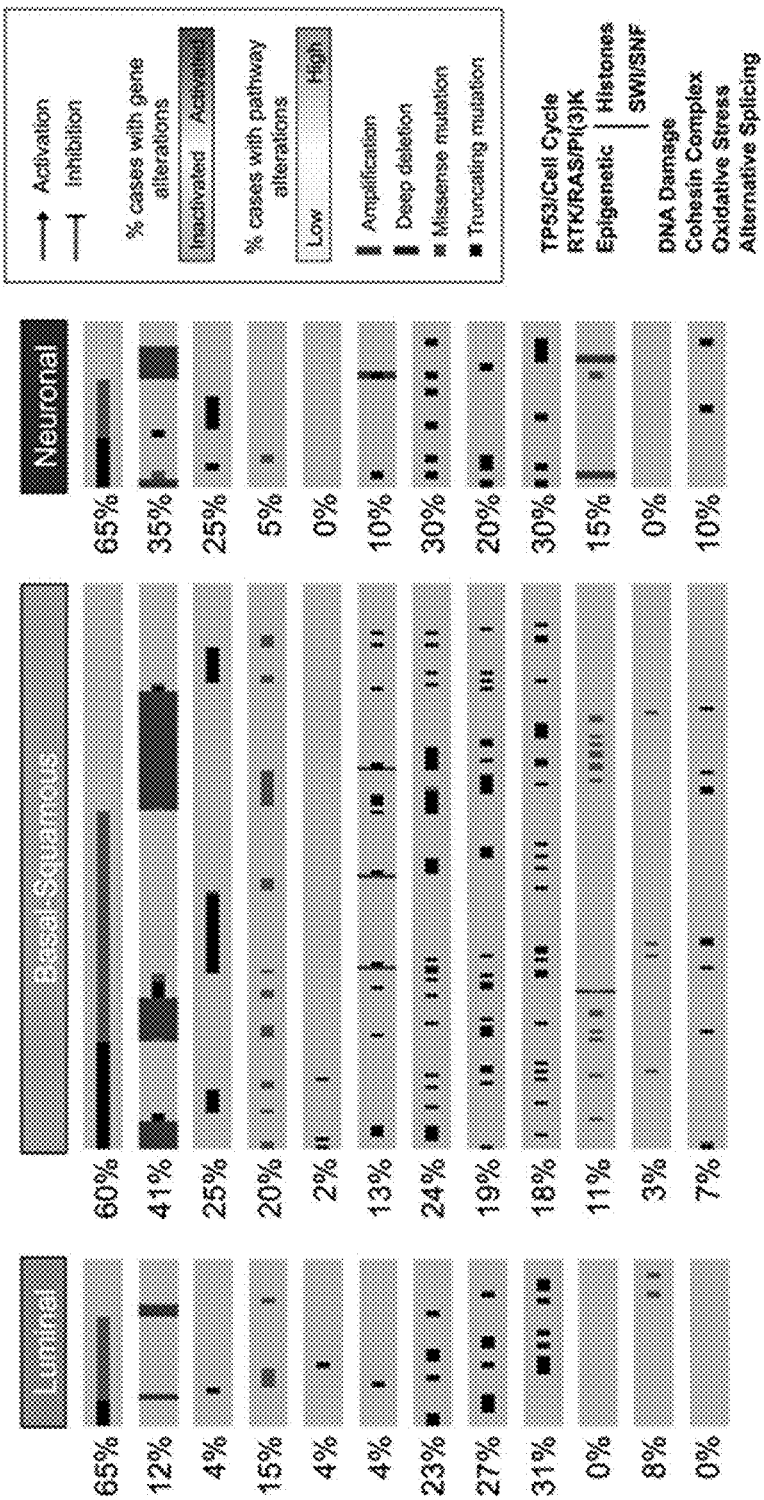
FIG. 8 (Continued) Panel 5

D (Continued)

D (Continued)

A (Continued)

FIG. 13 (Continued)
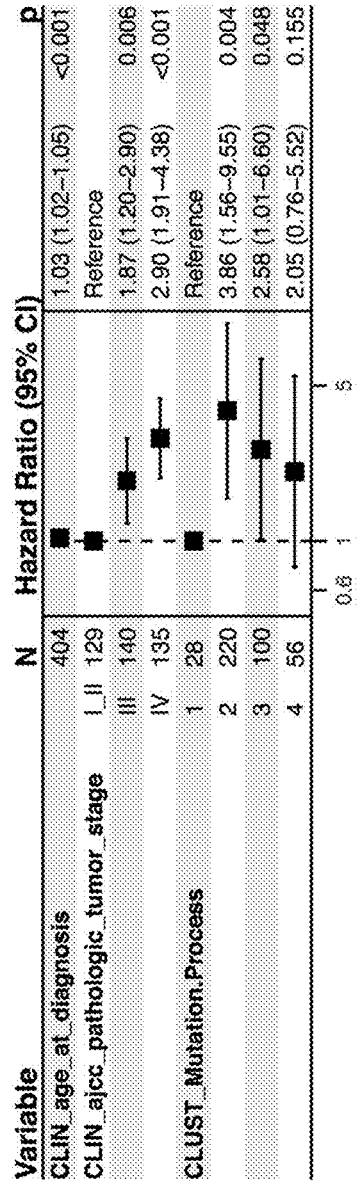
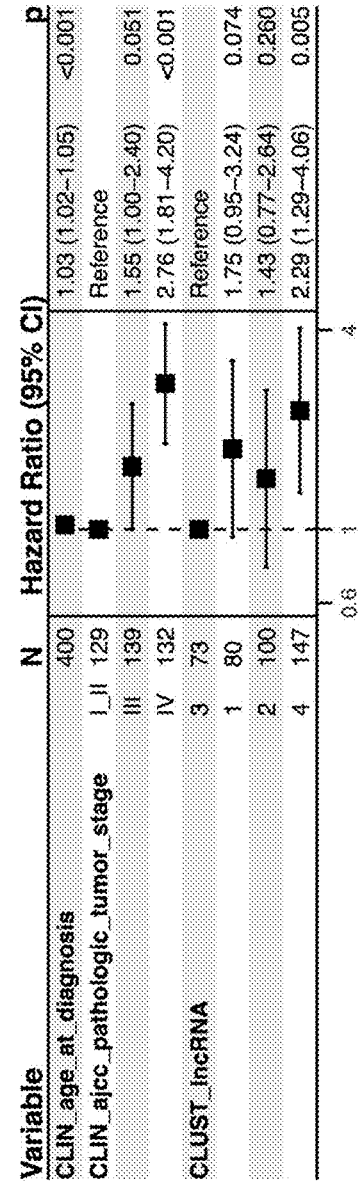

FIG. 18

Comparison to Other Classifiers

For TCGA 254 MIBC samples

UNC classification

| | Luminal-Papillary | Luminal | Luminal-Infiltrated | Basal-Squamous | Neuronal |
|---|---|---|---|---|---|
| Luminal | 77 | 17 | 22 | 2 | 5 |
| Basal | 2 | 0 | 20 | 80 | 9 |

MDA classification

| | Luminal-Papillary | Luminal | Luminal-Infiltrated | Basal-Squamous | Neuronal |
|---|---|---|---|---|---|
| Luminal | 71 | 15 | 2 | 1 | 5 |
| Basal | 0 | 0 | 5 | 78 | 8 |
| p53-like | 8 | 2 | 35 | 3 | 1 |

Lund classification

| | Luminal-Papillary | Luminal | Luminal-Infiltrated | Basal-Squamous | Neuronal |
|---|---|---|---|---|---|
| Genomically Unstable | 39 | 2 | 0 | 0 | 0 |
| Inf-epithelial | 10 | 13 | 34 | 10 | 2 |
| Inf-Mesenchymal | 0 | 0 | 8 | 15 | 1 |
| SC-like/Urobasal B | 0 | 0 | 0 | 63 | 0 |
| Urobasal | 30 | 0 | 0 | 0 | 0 |
| Variant | 0 | 2 | 0 | 4 | 11 |

Application to GSE13507 (103 NMIBC + 62 MIBC)

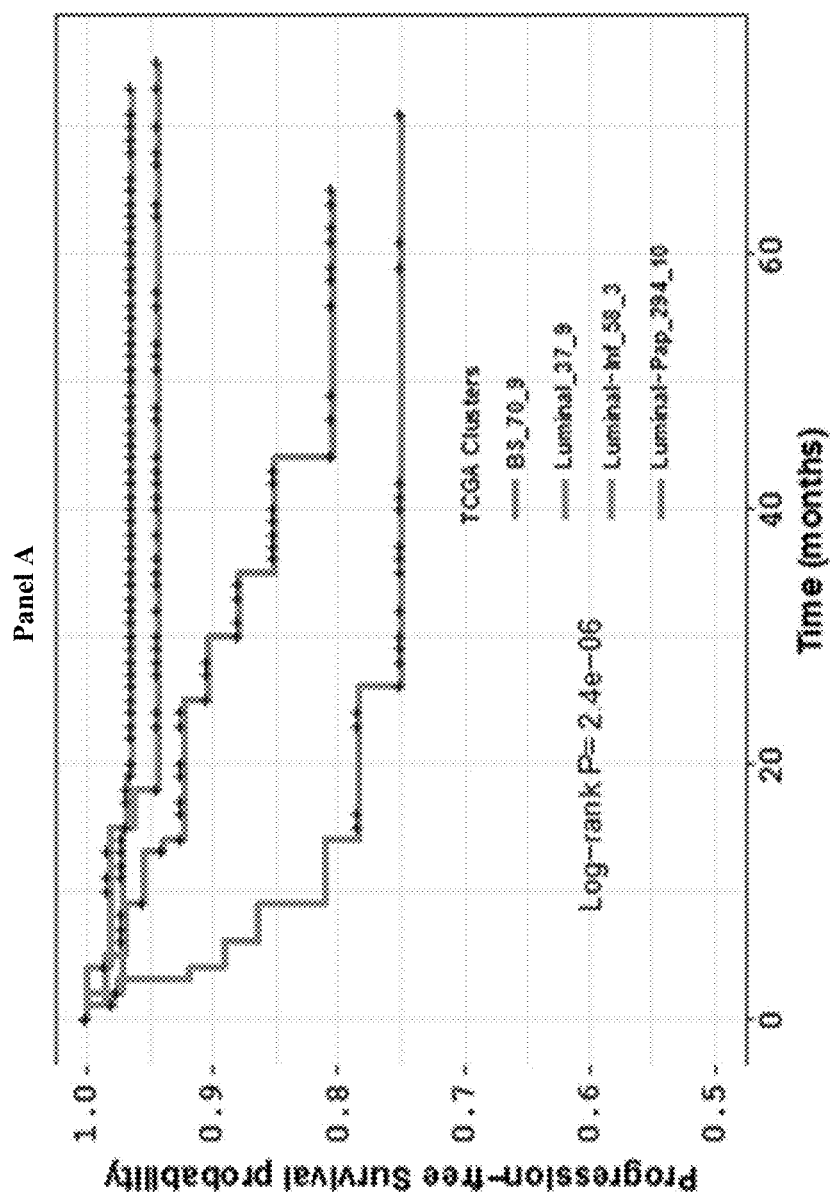
FIG. 21 Panel A

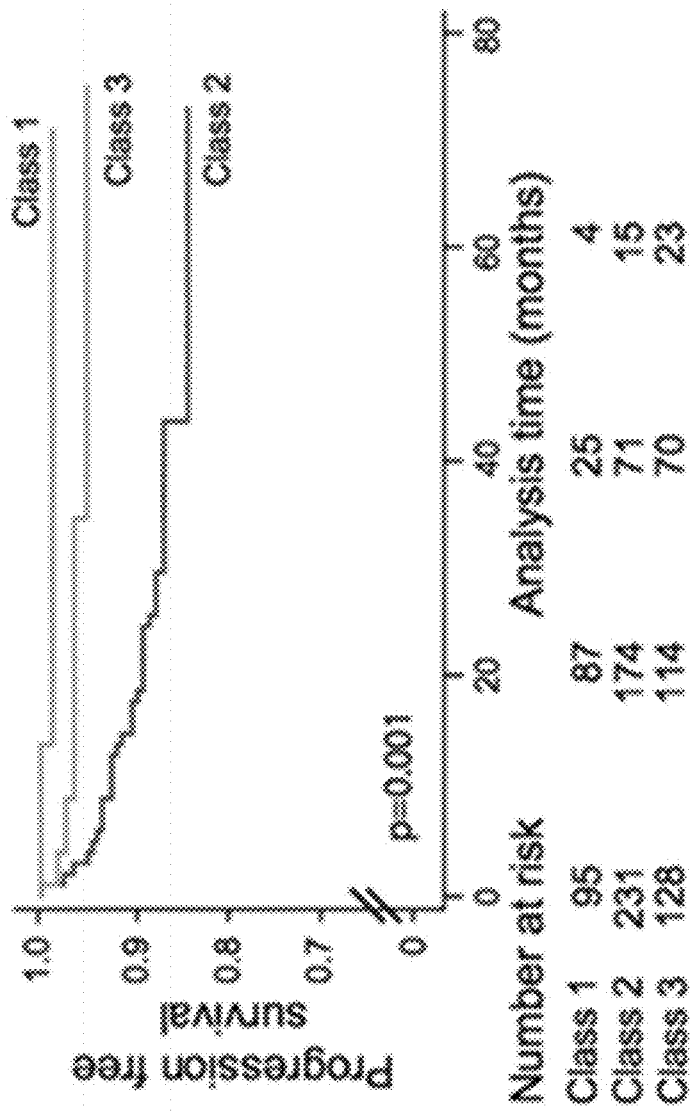
FIG. 21 (Continued) Panel B

Panel C

TCGA Classifier — More Specific to Neuronal Subtypes

Panel A

Panel B

FIG. 23 (Continued)

Panel C

| | TCGA.SSEC1 | TCGA.SSEC2 | TCGA.SSEC3 | TCGA.SSEC4 | TCGA.SSEC5 |
|---|---|---|---|---|---|
| TCGA.original1 | 15 | 8 | 0 | 0 | 3 |
| TCGA.original2 | 12 | 51 | 6 | 1 | 8 |
| TCGA.original3 | 0 | 12 | 125 | 2 | 3 |
| TCGA.original4 | 1 | 0 | 2 | 17 | 0 |
| TCGA.original5 | 5 | 1 | 7 | 5 | 124 |

FIG. 24

Panel A

| | urobasal.A | Infiltrated | Genomically.unstab |
|---|---|---|---|
| TCGA.Lum | 3 | 2 | 32 |
| TCGA.Lum-Inf | 2 | 45 | 11 |
| TCGA.BS | 6 | 27 | 37 |
| TCGA.Neuronal | 0 | 0 | 1 |
| TCGA.Lum-Pap | 158 | 55 | 81 |

FIG. 24 (Continued)

Panel B

GSE32894 - Lund Data

| | MS1a | MS1b | MS2a.1 | MS2a.2 | MS2b.1 | MS2b2.1 | MS2b2.2 |
|---|---|---|---|---|---|---|---|
| Lum | 0 | 2 | 12 | 23 | 3 | 0 | 0 |
| Lum-Inf | 0 | 1 | 0 | 4 | 21 | 0 | 0 |
| BS | 3 | 0 | 0 | 5 | 13 | 14 | 29 |
| Neuronal | 0 | 0 | 1 | 3 | 0 | 0 | 0 |
| Lum-Pap | 50 | 75 | 17 | 20 | 6 | 6 | 0 |

MS1a/b – Urobasal A = exclusively Lum-Pap
MS2a.1/2 – GU = Lum + Lum+Pap
MS2b.1 – Lum-Inf + some BS
MS2b2.1/2 = exclusively BS Panel C Panel A Panel B Panel C

METHODS FOR CHARACTERIZING BLADDER CANCER

CROSS-REFERENCE TO RELATED APPLICATION

This application is the U.S. national phase under 35 U.S.C. 111(a) and a continuation of PCT Patent Application No.: PCT/US2019/017300, filed on Feb. 8, 2019, which claims the benefit of and priority to the following U.S. Provisional Application Nos. 62/628,756, filed Feb. 9, 2018, and 62/794,447, filed on Jan. 18, 2019; respectively. The entire contents of which are incorporated herein by reference.

STATEMENT OF RIGHTS TO INVENTIONS MADE UNDER FEDERALLY SPONSORED RESEARCH

This invention was made with government support under Grant Nos. HG003067, CA091846, CA143845, and CA120964 awarded by the National Institutes of Health, and Grant No. BX003692 awarded by the United States Department of Veterans Affairs. The government has certain rights in the invention.

BACKGROUND OF THE INVENTION

Urothelial bladder cancer is a heterogeneous epithelial malignancy that presents most commonly as an exophytic tumor confined to the mucosa or lamina propria. However, 25% of patients have muscle-invasive bladder cancer (MIBC) or metastatic disease at the time of initial diagnosis and have a worse prognosis. New, improved methods for identifying such patients and aggressively treating such patients are urgently needed.

SUMMARY OF THE INVENTION

As described below, the present invention features methods for characterizing mutational profiles in patients with bladder cancer. The method involves the use of mRNA-based expression subtypes that may stratify a patient's response to a therapeutic treatment.

In one aspect, the invention features a method of characterizing bladder cancer in a subject, the method involving detecting in a biological sample of the subject an alteration in the expression of a target that is any one or more of luminal markers uroplakin genes UPK2, UPK1A, urothelial differentiation markers FOXA1, GATA3, and PPARG, and genes KRT20, and SNX31;

any one or more of luminal-papillary markers FGFR, FGFR3-TACC3 fusions, lncRNAs DANCR, GAS5, MALAT1, NEAT1, NORAD (LINC00657), UCA1, ZNF667-AS1 (MORT), LINC00152, GATA3, FOXA1, PPARγ, TP63, sonic-hedgehog signaling (SHH);

any one or more of luminal-infiltrated markers CD274 (PD-L1) and PDCD1 (PD-1);

any one or more of basal-squamous markers including basal and stem-like markers CD44, KRT5, KRT6A, KRT14, and COL17A1; squamous differentiation markers TGM1, DSC3, TP63, GSDMC, and PI3, TP53, CIS signature genes CRTAC1, CTSE, PADI3, MSN, and NR3C1, and immune markers CD274, PDCD1LG2, 1DO1, CXCL11, L1CAM, SAA1 and CTLA4;

any one or more of neuronal markers including neuronal differentiation and development genes MSI1, PLEKHG4B, GNG4, PEG10, RND2, APLP1, SOX2, TUBB2B, TP53, RB1 and E2F3 and neuroendocrine markers CHGA, CHGB, SCG2, ENO2, SYP, NCAM1; and any one or more of the targets from among those listed in Tables 2-4.

In another aspect, the invention features a method of characterizing luminal markers in a bladder cancer in a subject, the method involving detecting in a biological sample of the subject an alteration in the expression of a luminal marker that is any one or more of uroplakin genes UPK2, UPK1A, urothelial differentiation markers FOXA1, GATA3, and PPARG, and genes KRT20, and SNX31.

In another aspect, the invention features a method of characterizing luminal-papillary markers in a bladder cancer in a subject, the method involving detecting in a biological sample of the subject an alteration in the expression of a luminal-papillary marker that is any one or more of FGFR, FGFR3-TACC3 fusions, lncRNAs DANCR, GAS5, MALAT1, NEAT1, NORAD (LINC00657), UCA1, ZNF667-AS1 (MORT), LINC00152, GATA3, FOXA1, PPARγ, TP63, and sonic-hedgehog signaling (SHH).

In another aspect, the invention features a method of characterizing luminal-infiltrated markers in a bladder cancer in a subject, the method involving detecting in a biological sample of the subject an alteration in the expression of a luminal-infiltrated marker that is any one or more of CD274 (PD-L1) and PDCD1 (PD-1).

In another aspect, the invention features a method of characterizing basal-squamous markers in a bladder cancer in a subject, the method involving detecting in a biological sample of the subject an alteration in the expression of a basal-squamous markers that is any one or more of basal and stem-like markers CD44, KRT5, KRT6A, KRT14, and COL17A1; squamous differentiation markers TGM1, DSC3, TP63, GSDMC, and PI3, TP53, CIS signature genes CRTAC1, CTSE, PADI3, MSN, and NR3C1, and immune markers CD274, PDCD1LG2, 1DO1, CXCL11, L1CAM, SAA1 and CTLA4.

In another aspect, the invention features a method of characterizing a neuronal marker in a bladder cancer in a subject, the method involving detecting in a biological sample of the subject an alteration in the expression of a neuronal marker that is any one or more of neuronal differentiation and development genes MSI1, PLEKHG4B, GNG4, PEG10, RND2, APLP1, SOX2, TUBB2B, TP53, RB1 and E2F3 and neuroendocrine markers CHGA, CHGB, SCG2, ENO2, SYP, NCAM1.

In another aspect, the invention features a method of characterizing a bladder cancer in a subject, the method involving analyzing in a biological sample of the subject a marker from those listed in Tables 2-4.

In various embodiments of any of the above aspects or any other aspect of the invention delineated herein, the method further involves detecting any one or more of the following proteins: GATA3, EGFR, CDH1, and HER2. In other embodiments of any of the above aspects, the detecting miRNAs that is any one or more of miR-200s, miR-99a, and miR-100. In still other embodiments of any of the above aspects, the method further involves detecting TP53 and RB1 mutations. In still embodiments of any of the above aspects, the biological sample was a urothelial tumor. In still embodiments of any of the above aspects, the method further involves detecting an RB1, CDKN1A4, CDKN2A, ATM, ERCC, FGFR3, PIK3CA, and RAS, ERBB2, KDM6A, KMT2A, KMT2C, KMT2D, CREBBP, EP300, KANSL1, ARID1A, ASXL1, and ASXL2 mutation or a homozygous deletion.

In another aspect, the invention provides a polynucleotide probe that hybridizes to a target delineated in a previous aspect or elsewhere in the application.

In another aspect, the invention provides a primer pair that hybridizes to and amplifies a target delineated in a previous aspect or elsewhere in the application.

In another aspect, the invention provides a nucleic acid array for expression-based assessment of bladder cancer, said array containing at least ten probes immobilized on a solid support, each of said probes being between about 15 and about 500 nucleotides in length, each of said probes being derived from a sequence corresponding to, or complementary to, a transcript of a target or marker of any of the above aspects.

In another aspect, the invention provides a method for expression-based assessment of bladder cancer, said method involving: (a) determining the expression level of one or more transcripts of one or more genes in a test sample obtained from said subject to provide an expression pattern profile, said one or more genes selected from a target or marker of any of the above aspects, and (c) comparing said expression pattern profile with a reference expression pattern profile.

In another aspect, the invention provides a method of analyzing a bladder cancer in an individual in need thereof, involving: (a) obtaining an expression profile from a sample obtained from the individual, wherein the expression profile involves assaying a target or marker of any one of claims 1-12; and (b) comparing the expression profile from the sample to an expression profile of a control or standard.

In another aspect, the invention provides a method of prescribing a treatment regimen for a bladder cancer to an individual in need thereof, involving:

(a) obtaining an expression profile from a sample obtained from the individual, wherein the expression profile contains a target or marker of any previous aspect;

(b) comparing the expression profile from the sample to an expression profile of a control or standard; and (c) prescribing a treatment regimen based on (i) the deviation of the expression profile of the sample from a control or standard derived from a healthy individual or population of healthy individuals, or (ii) the similarity of the expression profiles of the sample and a control or standard derived from an individual or population of individuals who have or have had the cancer.

In another aspect, the invention provides a method of treating a selected subject for bladder cancer, the method involving administering to the patient a checkpoint inhibitor, wherein the subject is selected by detecting increased expression of uroplakin genes and an umbrella cell phenotype in a biological sample from the subject.

In another aspect, the invention provides a method of treating a selected subject, the method involving administering to the subject a tyrosine kinase inhibitor of FGFR3, wherein the subject is selected by identifying a luminal-papillary subtype, wherein the luminal-papillary subtype is characterized by an FGFR3 mutations, a fusion with TACC3, and/or amplification; by papillary histology; by active sonic hedgehog signaling; and by low CIS scores. In one embodiment, the inhibitor is AZ12908010, AZD4547, or PD173074.

In another aspect, the invention provides a method of treating a selected subject, the method involving administering to the subject an immune checkpoint therapy, wherein the subject is selected by characterizing a biological sample of the subject as having a luminal-infiltrated subtype characterized by increased expression of EMT markers, myofibroblast markers, and of the miR-200s. In one embodiment, the therapy is atezolizumab.

In another aspect, the invention provides a method of treating a selected subject, the method involving administering to the subject a cisplatin-based NAC or immune checkpoint therapy, wherein the subject is selected by characterizing a biological sample of the subject as having a basal-squamous subtype including squamous differentiation, basal keratin expression, and increased expression of CD274 (PD-L1) and CTLA4 immune markers.

In another aspect, the invention provides a method of treating a selected subject, the method involving administering to the subject Etoposide-cisplatin therapy, wherein a biological sample from the subject is characterized by expression of neuroendocrine/neuronal markers. In one embodiment, the biological sample is also characterized by a proliferative state. In one embodiment, the neuronal markers are MSI1, PLEKHG4B, GNG4, PEG10, RND2, APLP1, SOX2, TUBB2B, TP53, RB1 and E2F3 and the neuroendocrine markers are CHGA, CHGB, SCG2, ENO2, SYP, NCAM1

In another aspect, the invention provides a kit for analyzing a bladder cancer, containing: (a) a probe set that hybridizes to a plurality of targets or marker of any previous aspect or any other aspect of the invention delineated herein; and (b) a computer model or algorithm for analyzing an expression level and/or expression profile of the target sequences in a sample. In one embodiment, the kit further contains a computer model or algorithm for correlating the expression level or expression profile with disease state or outcome. In another embodiment, the kit further includes a computer model or algorithm for designating a treatment modality for the subject.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "ameliorate" is meant decrease, suppress, attenuate, diminish, arrest, or stabilize the development or progression of a disease.

By "agent" is meant any small molecule chemical compound, antibody, nucleic acid molecule, or polypeptide, or fragments thereof.

By "alteration" is meant a change (increase or decrease) in the sequence, expression level, or activity of a gene or polypeptide as detected by standard art known methods such as those described herein. As used herein, an alteration includes a 10% change in expression or activity levels, preferably a 25% change, more preferably a 40% change, and most preferably a 50% or greater change in expression levels.

In this disclosure, "comprises," "comprising," "containing," and "having" and the like can have the meaning ascribed to them in U.S. Patent law, and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include bladder cancer. In some embodiments, the bladder cancer is urothelial bladder cancer, non-muscle invasive (NMIBC), or muscle-invasive bladder cancer (MIBC).

By "effective amount" is meant the amount of a compound or composition described herein required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "mutation" is meant a change in a polypeptide or polynucleotide sequence relative to a reference sequence. In some embodiments, the reference sequence is a wild-type sequence. Exemplary mutations include point mutations, missense mutations, amino acid substitutions, and frameshift mutations. A "loss-of-function mutation" is a mutation that decreases or abolishes an activity or function of a polypeptide. A "gain-of-function mutation" is a mutation that enhances or increases an activity or function of a polypeptide.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "regulon" is meant a gene whose product induces and/or represses a target gene or target gene set.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition, or symptoms associated therewith be completely eliminated.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example, within two standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1D show images of urothelial carcinoma, not otherwise specified and FIGS. 1E-1H show images urothelial carcinoma with variant histology. FIG. 1A is an image showing an example of high tumor content with minimal stromal component. The scale bar is 700 μm. FIG. 1B is an image showing an example of moderate tumor content with stromal and immune cell components. The scale bar is 500 μm. FIG. 1C is an image showing an example of highly infiltrating tumor with relatively low tumor content, high stromal component and brisk immune cell infiltrate. The scale bar is 200 μm. FIG. 1D is an image of urothelial carcinoma, not otherwise specified (NOS) with evidence of tumor necrosis (*). The scale bar is 300 μm. FIG. 1E is an image of urothelial carcinoma with squamous differentiation with evidence of keratin formation (k). The scale bar is 200 μm. FIG. 1F is an image of another example of urothelial carcinoma with squamous differentiation with evidence intercellular bridges (arrows). The scale bar is 100 μm. FIG. 1G is an image of urothelial carcinoma, micropapillary variant. Characteristically, multiple small clusters of tumor cells are present in clear "lacunar" spaces. The scale bar is 300 μm. FIG. 1H is an image of small cell/neuroendocrine carcinoma of the bladder. Primitive appearing tumor cells with scant cytoplasm and nuclear molding are shown. The scale bar is 200 μm.

FIG. 2A is an image showing the alteration landscape for 412 primary tumors. Top to bottom: Synonymous and non-synonymous somatic mutation rates, with one ultra-mutated sample with a polymerase POL ε (POLE) signature. Mutational signature (MSig) cluster, apolipoprotein B mRNA editing enzyme, catalytic polypeptide-like (APOBEC) mutation load, and neoantigen load by quartile. Normalized activity of 4 mutational signatures. Combined tumor stage (T1,2 vs. T3,4) and node status, papillary histology, and gender. Somatic mutations for significantly mutated genes (SMGs) with frequency ≥7%. Copy number alterations for selected genes, and FGFR3 and PPARG gene fusions. FIG. 2B are graphs showing Kaplan-Meier plots for overall survival (Left to Right): Overall mutation burden (SNVs); Mutation signature clusters (MSig1-4); APOBEC-mediated mutation load; Neoantigen load; see also FIG. 3.

FIG. 3A shows graphs (above) showing mutational signatures. The spectrum of total SNVs and four mutational signatures in 96 base substitution contexts (mutated pyrimidines and adjacent 5' and 3' bases) are shown. Note that because the dynamic range for the signatures was large, Y-axis upper limits were different for each signature. Below: signature activities. The number of mutations assigned to each mutational process (Counts) and the normalized contributions across samples. Analysis involved 409 of 412 tumors (FIG. 26). One sample was excluded that had a clear POLE signature, and samples that had only 1 and 3 SNVs were also excluded. FIG. 3B and FIG. 3C are graphs showing the comparison of APOBEC mutation loads inferred using Bayesian non-negative matrix factorization (NMF), with those obtained using a knowledge-based, experimentally defined Pattern of Mutagenesis by APOBEC Cytidine Deaminases (P-MACD). FIG. 3B is a graph showing the correlation of mutation load assigned to APOBEC mutagenesis by Bayesian NMF (y-axis) and APOBEC mutation load determined by P-MACD (x-axis). Pattern of Mutagenesis by APOBEC Cytidine Deaminases (P-MACD)-defined mutation load is shown with pseudo count of 0.1 to visualize zero values. FIG. 3C is a graph showing that the number of mutations with stringent APOBEC signature (tCw to tTw, or tCw to tGw; x-axis) correlated strongly with the number of mutations not conforming to stringent APOBEC signature. DK-A6AW is the outlier ultra-mutated POLE mutant sample. FIG. 3D is a graph showing APOBEC expression vs. levels of APOBEC-signature mutagenesis. Levels of APOBEC-signature mutagenesis were determined for each tumor sample using motif-based analysis (methods: Pattern of Mutagenesis by APOBEC Cytidine Deaminases, P-MACD), and were grouped into No, Low, and High categories. The level of expression of 8 different APOBEC family members are shown as $\log_2(RSEM)$. messenger RNA (mRNA) levels of APOBEC3A and APOBEC3B were statistically associated with increased levels of APOBEC-signature mutagenesis. P values are from a Kruskal-Wallis test and were Bonferroni-corrected for multiple testing. APOBEC1 and APOBEC4 are not included because their expression levels were not detectable in most samples. FIG. 3E is an image showing unsupervised hierarchical clustering of 409 samples (MSig clusters) based on the number of mutations assigned to four mutational processes. FIG. 3F consists of three panels and shows graphs of SNVs, ERCC2 signature mutations, and smoking status, for n=409 tumor samples (see FIG. 3A). MSig4 cluster samples were enriched in both ERCC2 signature mutations and ERCCR mutations. ERCC2 signature mutations were highest in smokers with ERCC2 mutations. Wild-type ERCC2, ERCC2 signature mutations were at higher levels in smokers than in non-smokers. In FIG Panel 1 of FIG. 3F shows association of overall mutation burden (SNVs) vs. smoking status. Panel 2 of FIG. 3F shows association of ERCC2 signature mutations vs. combined status of smoking and ERCC2 mutations. P values are from a Wilcoxon rank-sum test. Panel 3 of FIG. 3F shows association of ERCC2 signature mutations vs. smoking status. FIG. 3G and FIG. 3H are images showing mutation/focal copy number MutCN clusters based on significantly mutated gene (SMG) mutations and focal somatic copy number alterations (SCNAs). FIG. 3G is an image showing unsupervised Bayesian NMF clustering of mutations in SMGs and focal copy number events (see Methods section below), which identified four DNA-based clusters with differential enrichments of characteristic genetic alterations. Genetic alterations in 53 SMG mutations and 25 focal SCNAs (labels on the left) across 408 samples are indicated by light grey on a dark background. FIG. 3H is an image showing normalized strength of association of 78 genetic alterations to the four MutCN clusters. FIG. 3I is an image showing protein domain architectures for peroxisome proliferator-activated receptor gamma (PPARG) fusions. In each of the five schematic fusion diagrams, the left part indicates the 5' gene, and the right part indicates the location of the fusion breakpoint relative to two PPARG protein domains. Top to bottom: makorin ring finger protein 2 (MKRN2)-PPARG retains both DNA-binding (ZnF C4) and ligand-binding (HOLI) domains; tRNA splicing endonuclease subunit 2 (TSEN2)-PPARG retains full ZnF_C4 and HOLI domains; TSEN2-PPARG retains partial ZnF_C4 and a full HOLI domain; TSEN2-PPARG retains only a full HOLI domain; TSEN2-PPARG retains only a partial HOLI domain.

FIG. 4A and FIG. 4B are images showing unsupervised clustering using cytosine-phosphate-guanine (CpG) sites that are cancer-specifically hypermethylated (FIG. 4A) or hypomethylated (FIG. 4B). Shown in FIG. 4A and FIG. 4B are heatmap representations of DNA methylation profiles of CpG sites with most-variable DNA methylation values (rows) in the 421 tumor samples (columns). Clusters derived by consensus clustering, and selected molecular and clinical features are depicted above each heatmap; heatmaps for DNA methylation profiles of 21 normal-adjacent tissues are to the left, and of two leukocyte samples are to the right. For subtypes from other platforms, only those that were statistically associated with the DNA methylation subtypes are shown. CpG sites that are located within gene promoter (PR) or gene body (GB) regions are indicated by the horizontal black bars on the right-hand side of the clustered heatmaps. FIG. 4C is a graph showing the distribution of ABSOLUTE purity across the DNA hypomethylation subtypes. FIG. 4D is an image showing the concordance between hypermethylation subtypes (rows) and hypomethylation subtypes (columns), shown as a heatmap of odds ratios. A large odds ratio indicates that the sample membership in two clusters is strongly concordant. White vs. black represents low vs. high odds ratios. FIG. 4E is a graph showing Kaplan-Meier analysis comparing patient survival for the five DNA hypomethylation-based clusters. FIG. 4F are graphs showing twelve genes for which DNA hypomethylation in subtype 4 may contribute to RSEM abundance being higher in that subtype. Relationship of beta to RSEM abundance. Dot shades indicate hypomethylation subtypes, with smaller vs. larger dots reflecting lower/higher ABSOLUTE purity (range 0.09 to 1.0). Squares indicate 14 adjacent tissue normal samples. FIG. 4G are graphs showing epigenetically-silenced genes in bladder cancer. Scatter plots showing negative relationships between DNA methylation (x-axis) and gene expression (y-axis) for genes frequently epigenetically silenced in bladder cancer. Each dot represents a tumor sample. Shown are eight genes with biological or clinical interest, as described below. FIG. 4H are graphs showing that genes are inactivated by multiple mechanisms in bladder cancer. Shown are three significantly mutated genes that are both deleted and epigenetically silenced. For each gene, the scatter plot on the left shows the relationship between DNA methylation (x axis) and gene expression (y axis). The plot on the right displays mutually exclusive occurrence of mutation, deletion, and epigenetic silencing, with the frequency of each alteration shown on the right. Individual tumors are represented by dots that are color-coded by the type of alteration as indicated on the plots.

Figure 4:
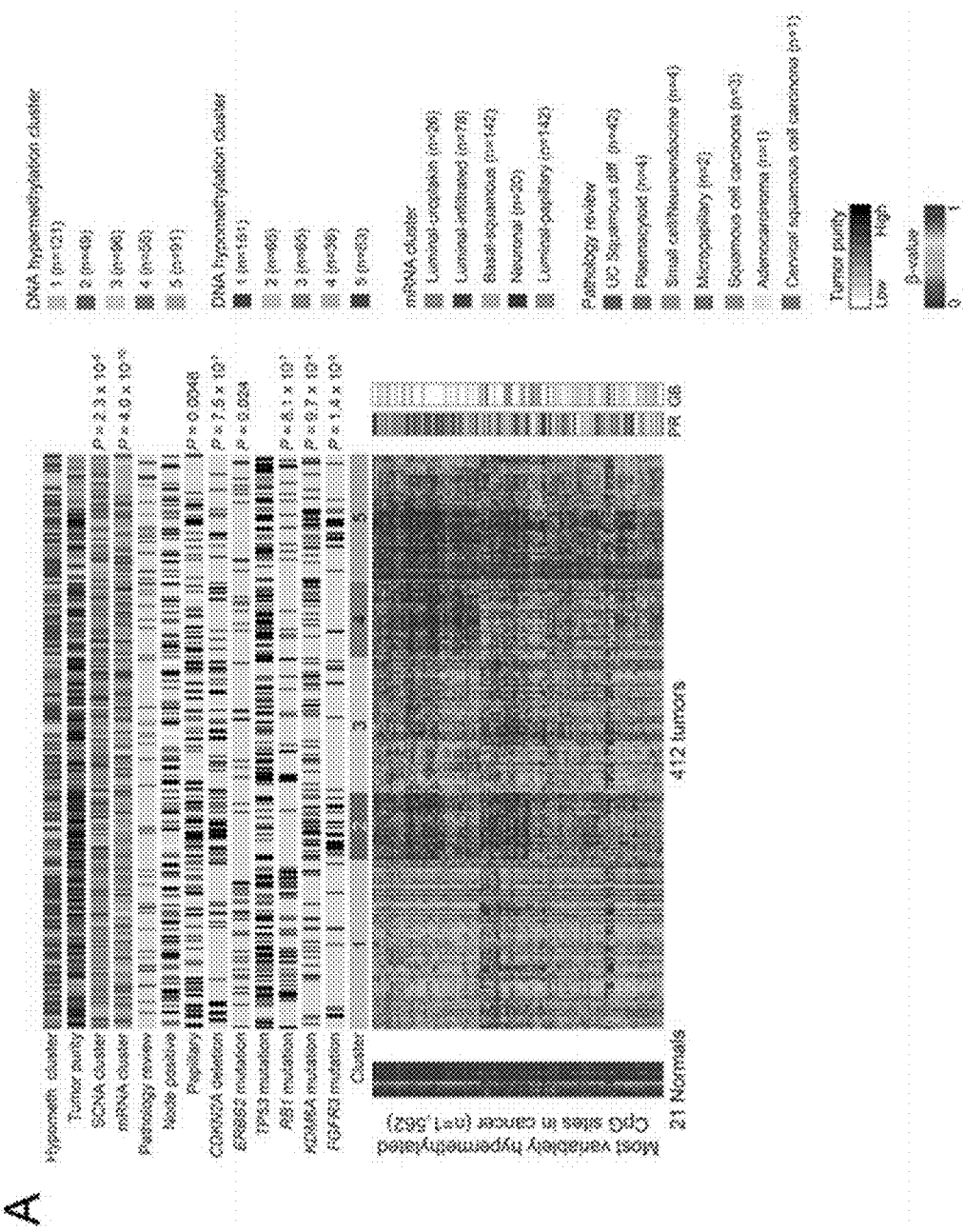
FIGS. 4A-4H are graphs and images showing DNA methylation subtypes, and genes inactivated by DNA methylation or by multiple mechanisms. Related to FIG. 5.
Figure 4:
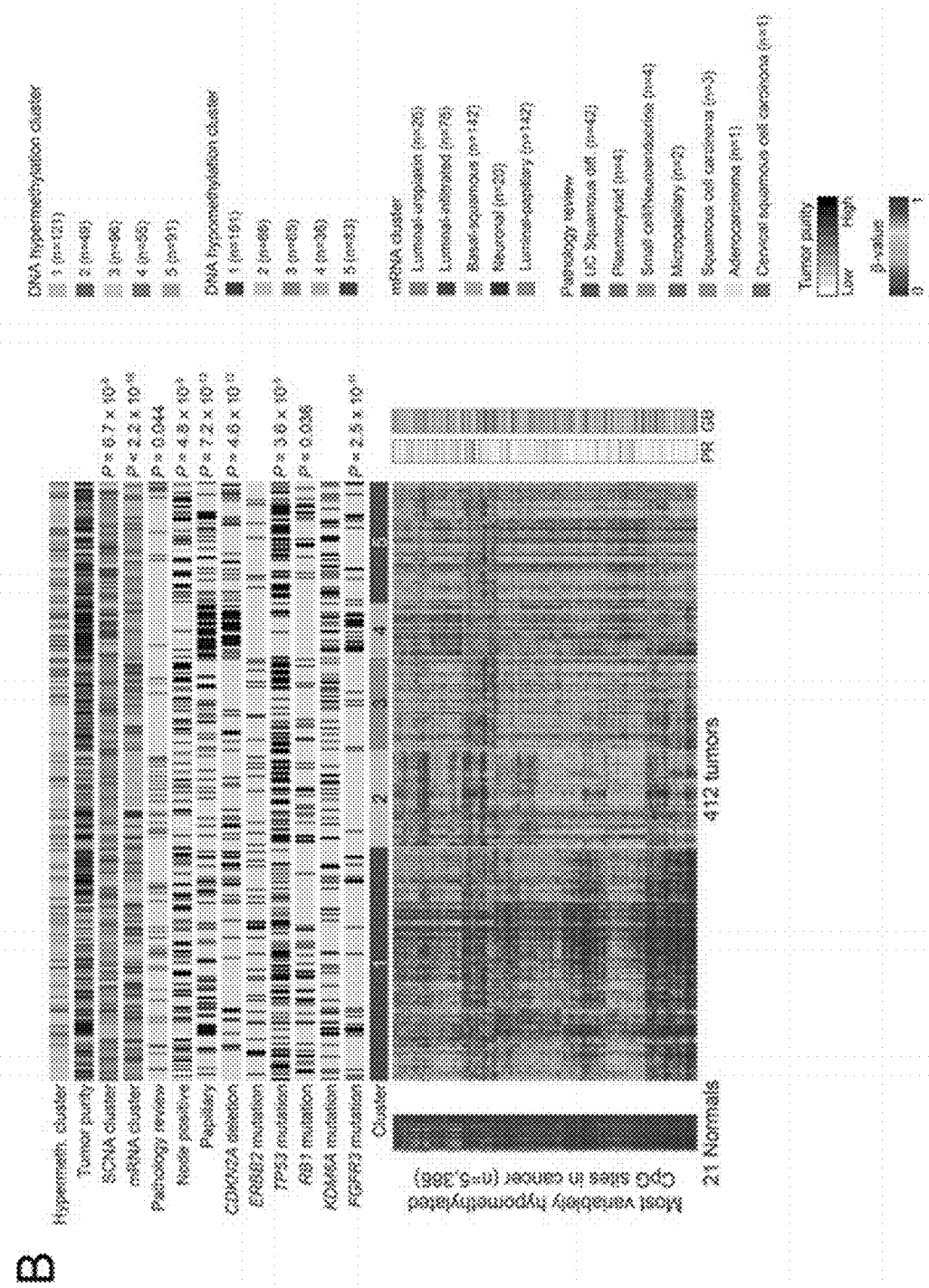
Figure 4:
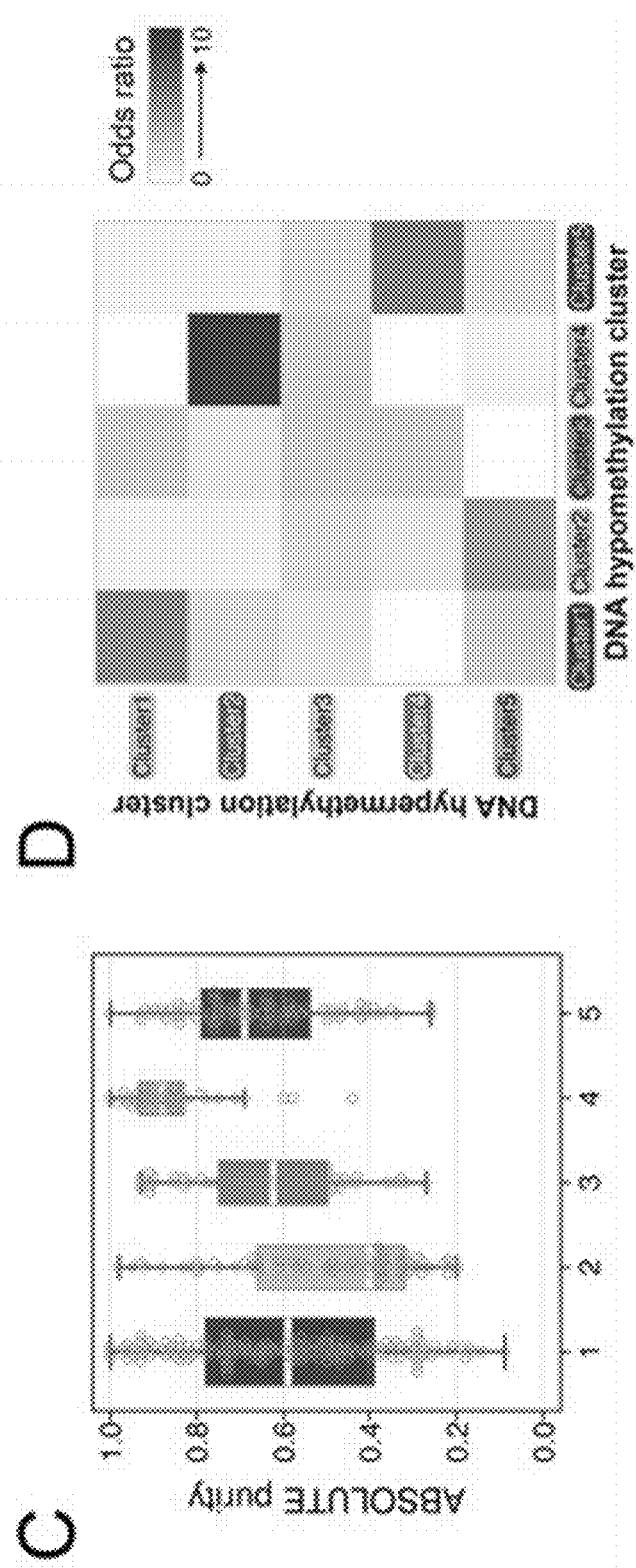
Figure 4:
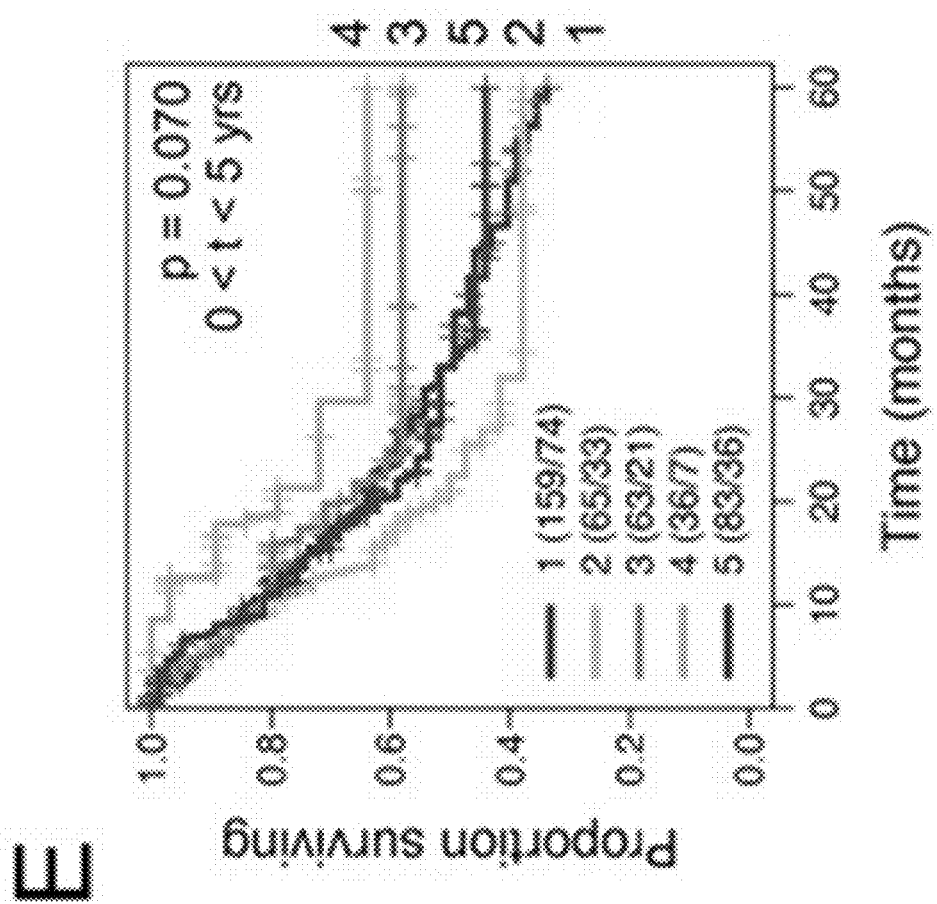
Figure 4:
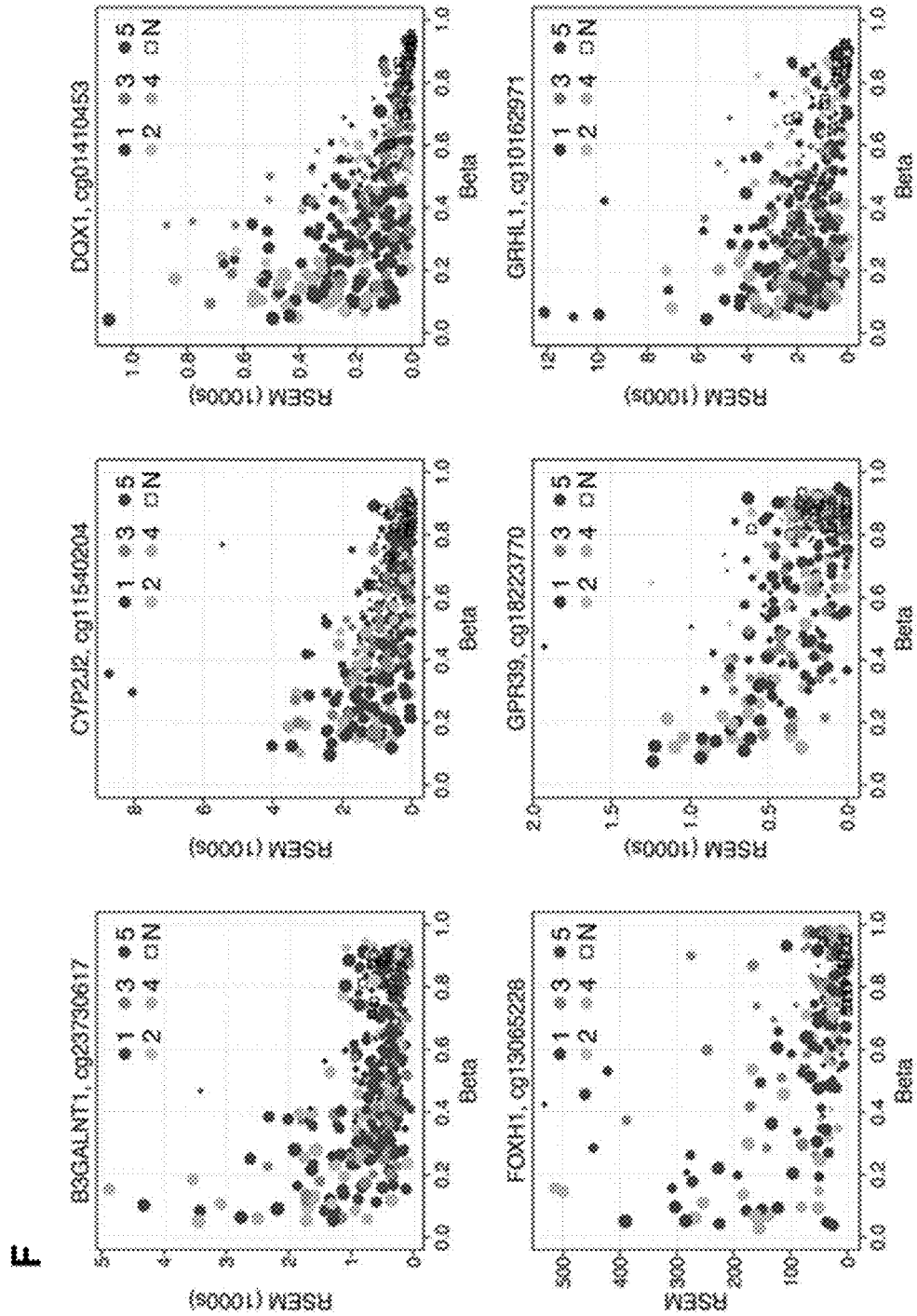
Figure 4:
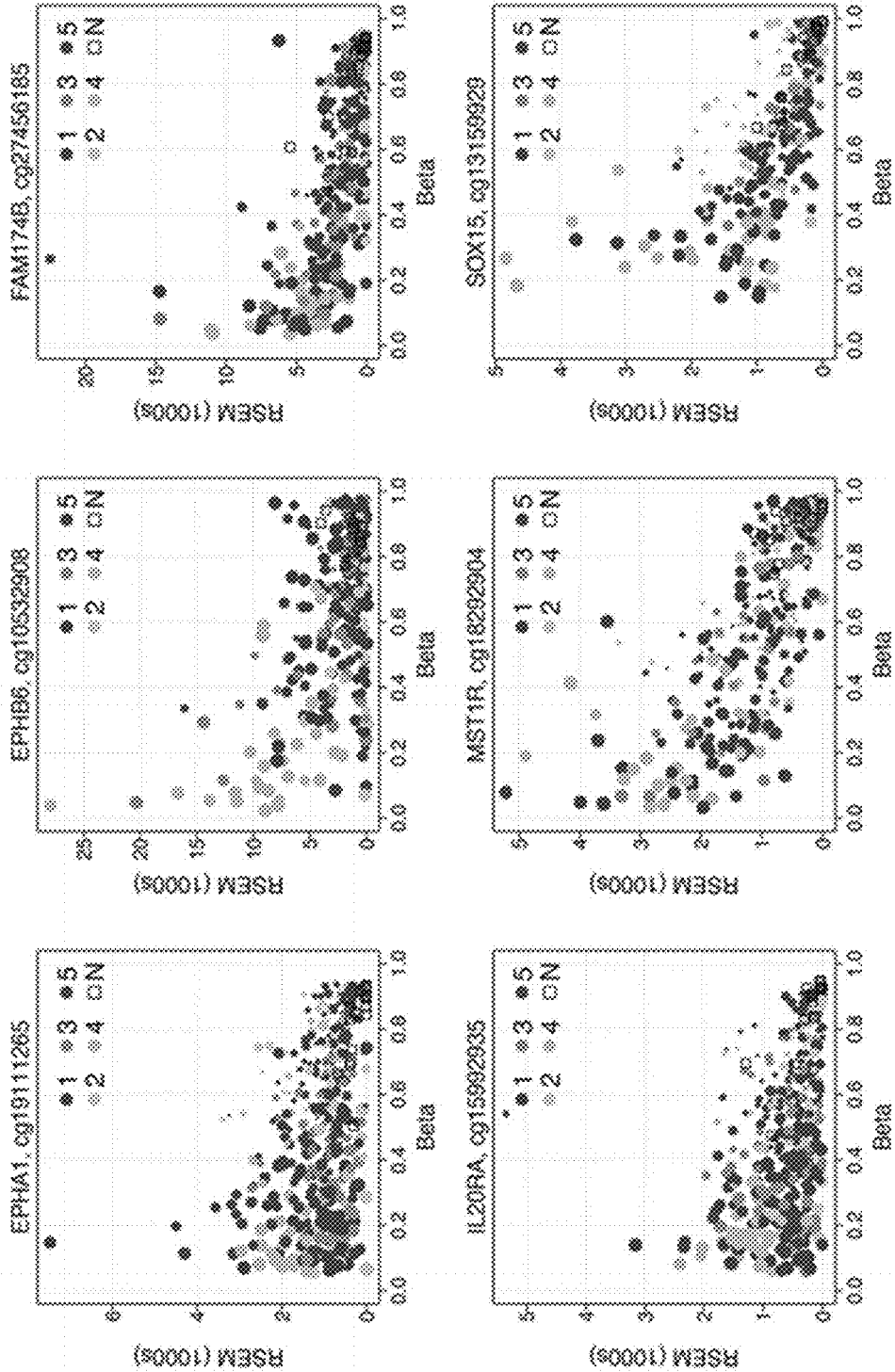
Figure 4:
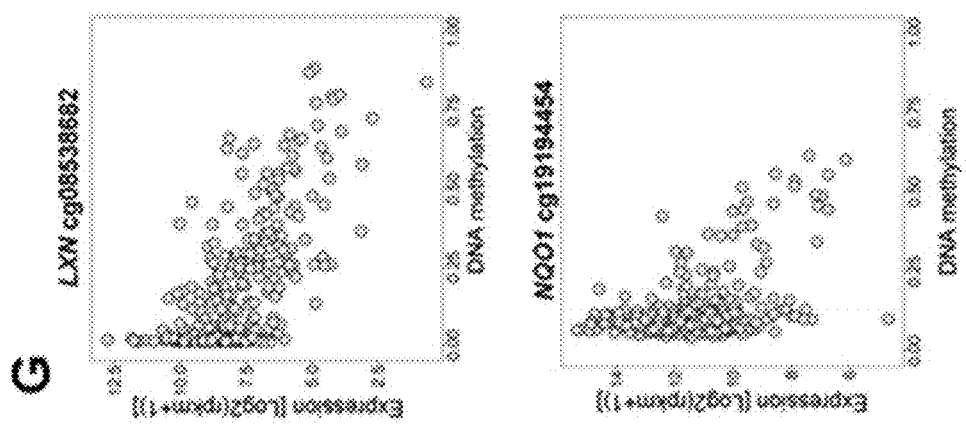
Figure 4:
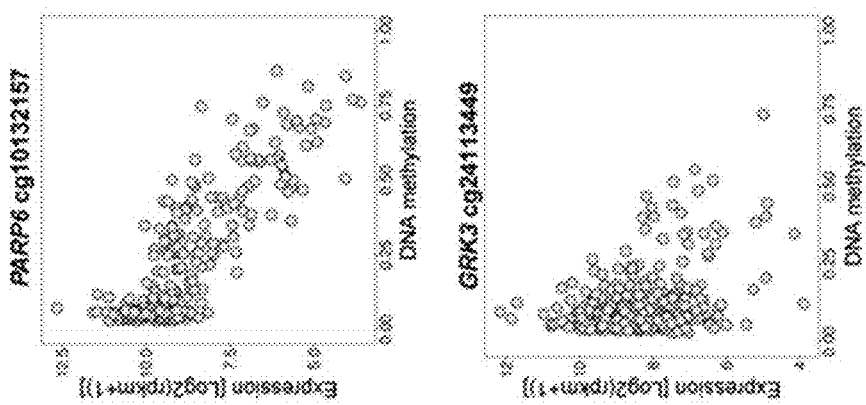
Figure 4:
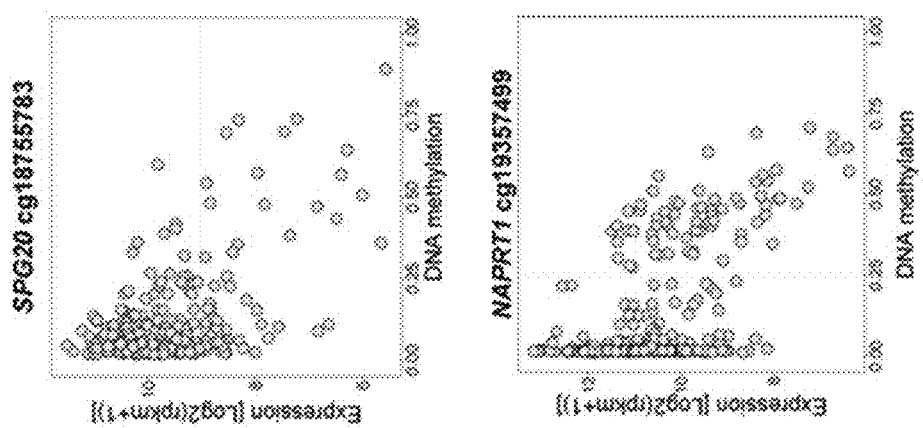
Figure 4:
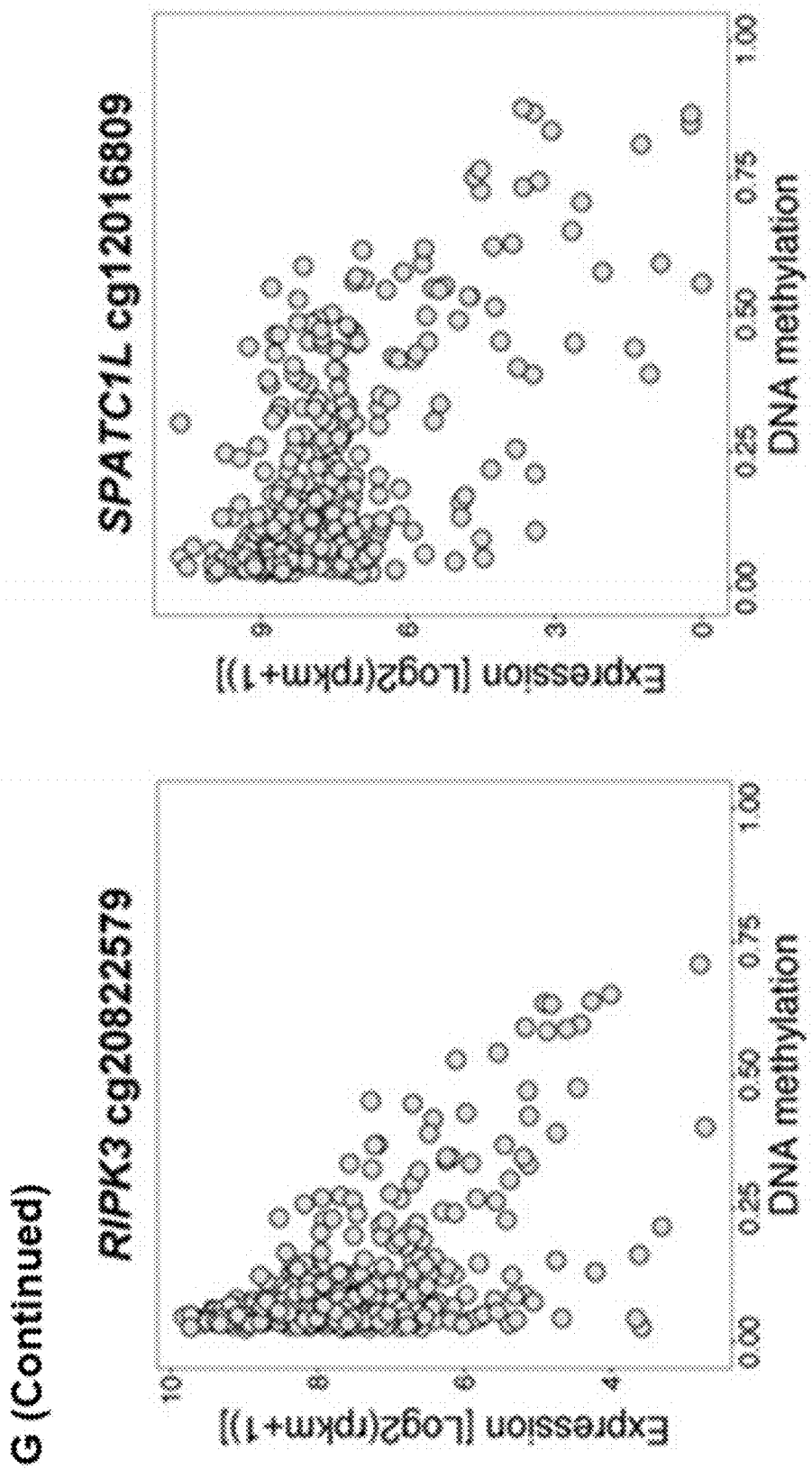
Figure 4:
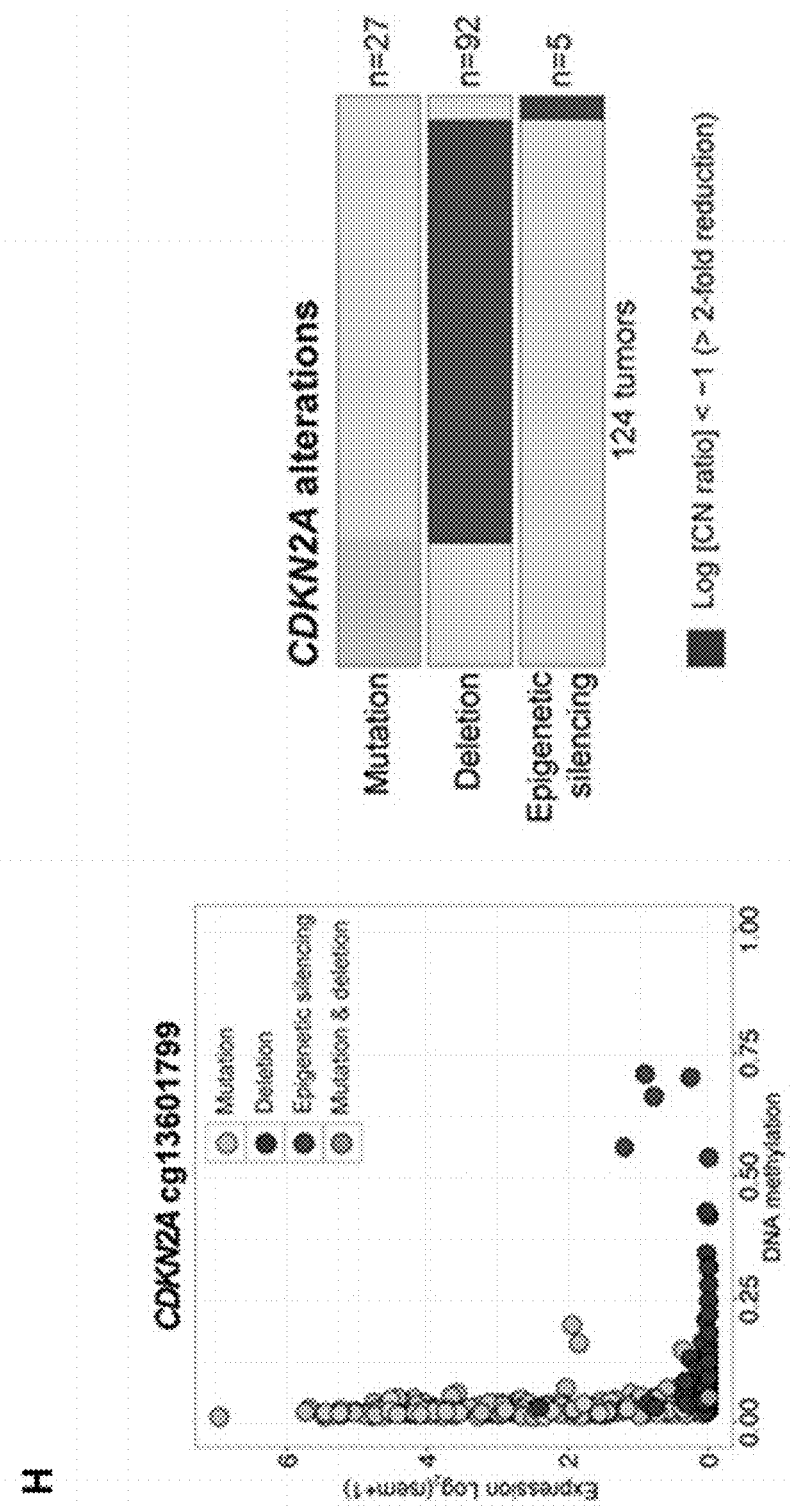
Figure 4:
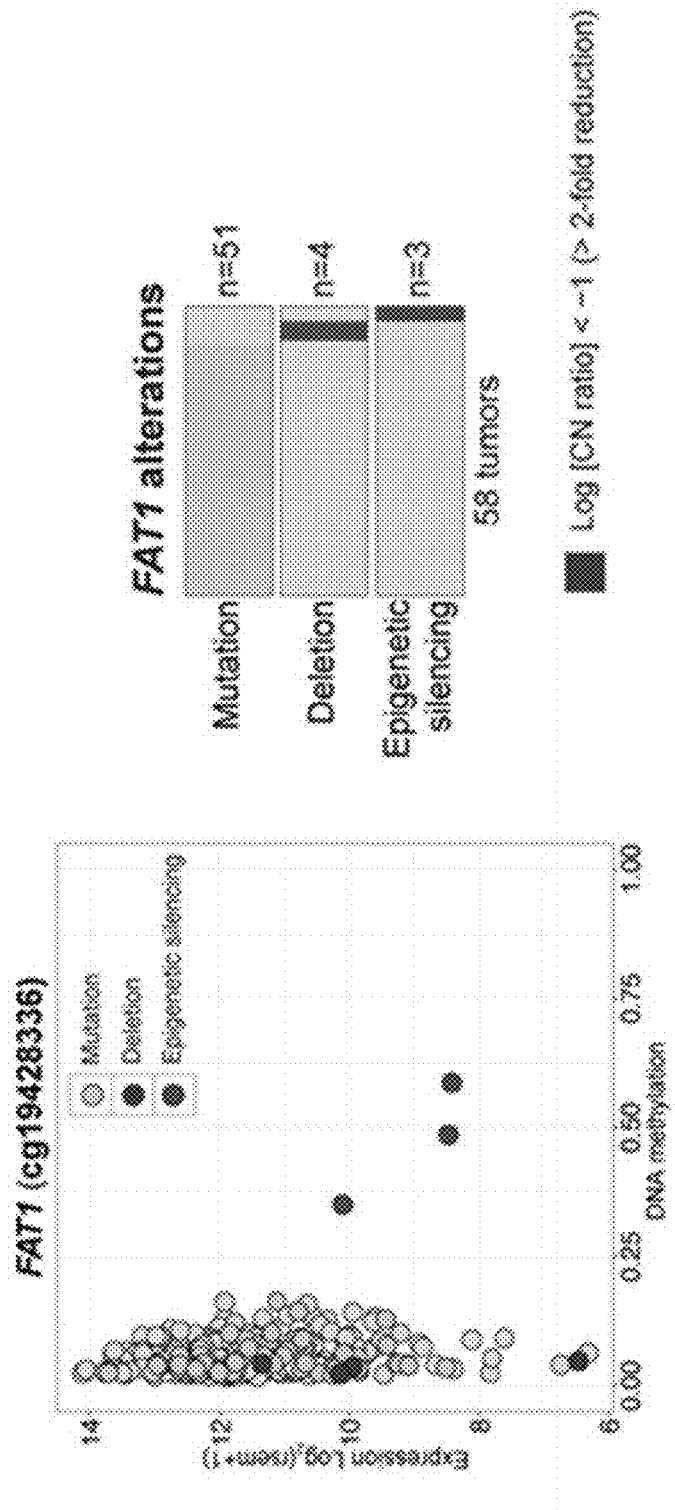
Figure 4:
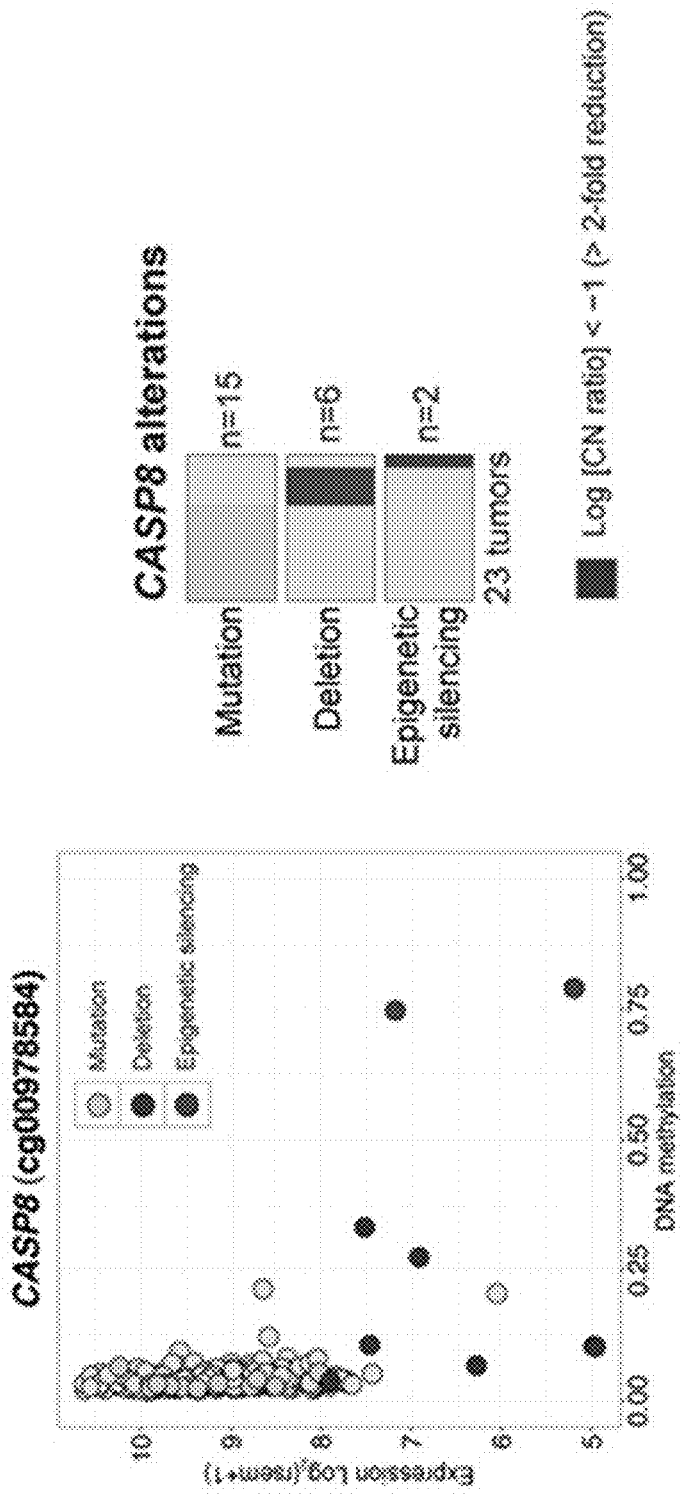
Figure 6:
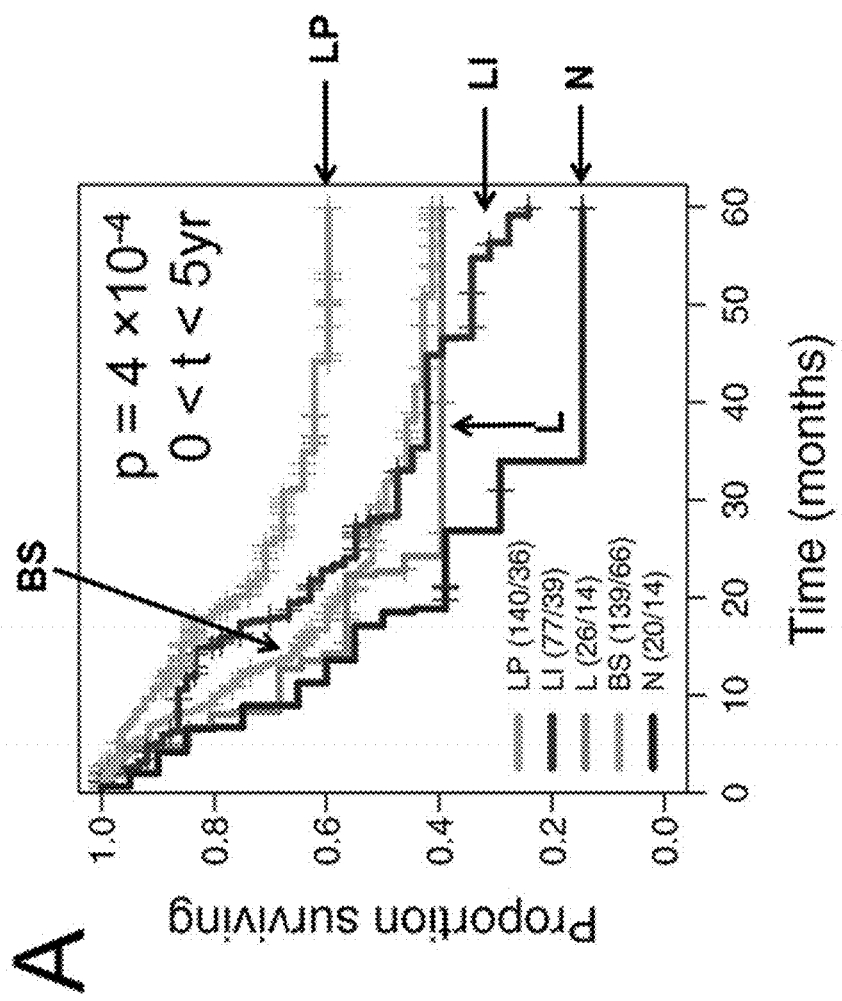
Figure 6:
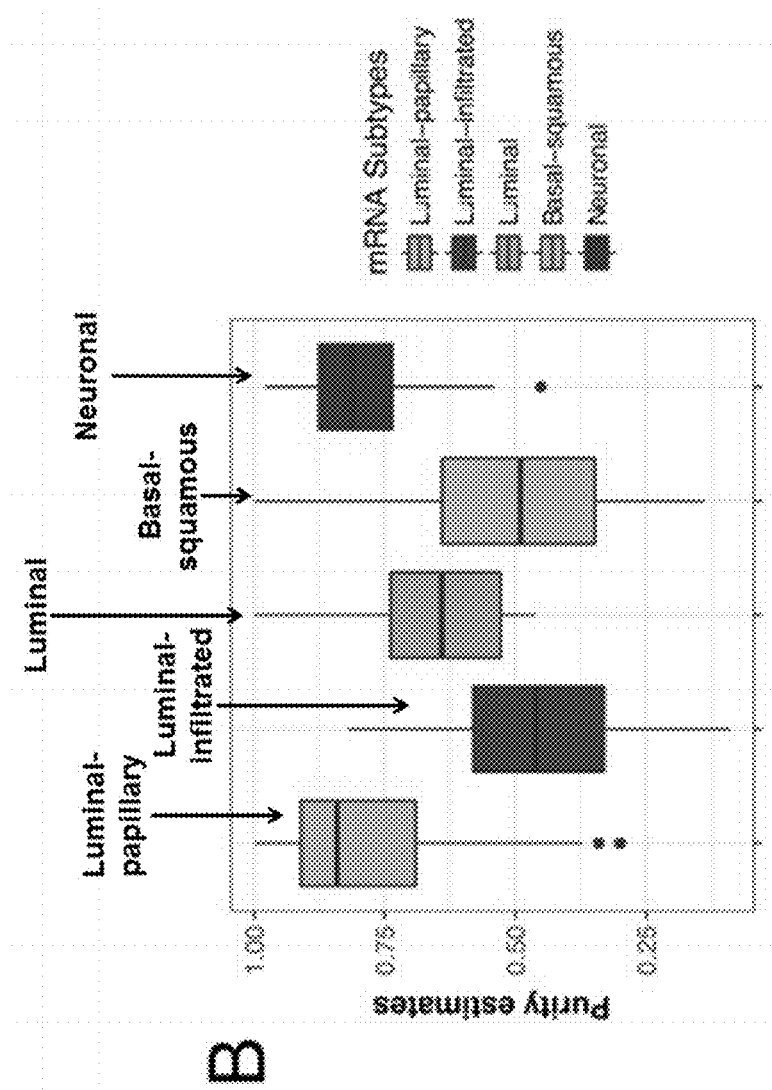
Figure 6:
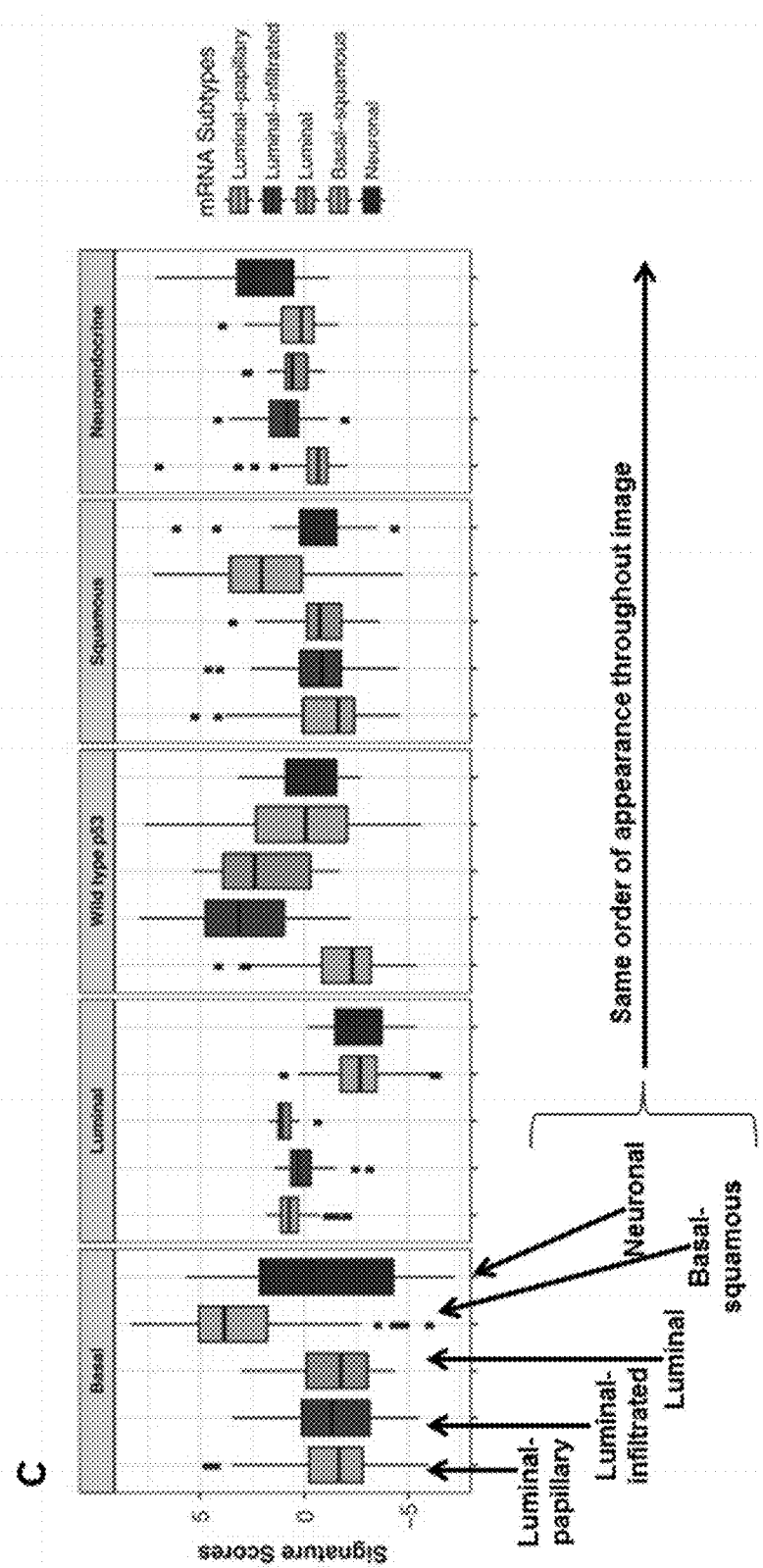
Figure 6:
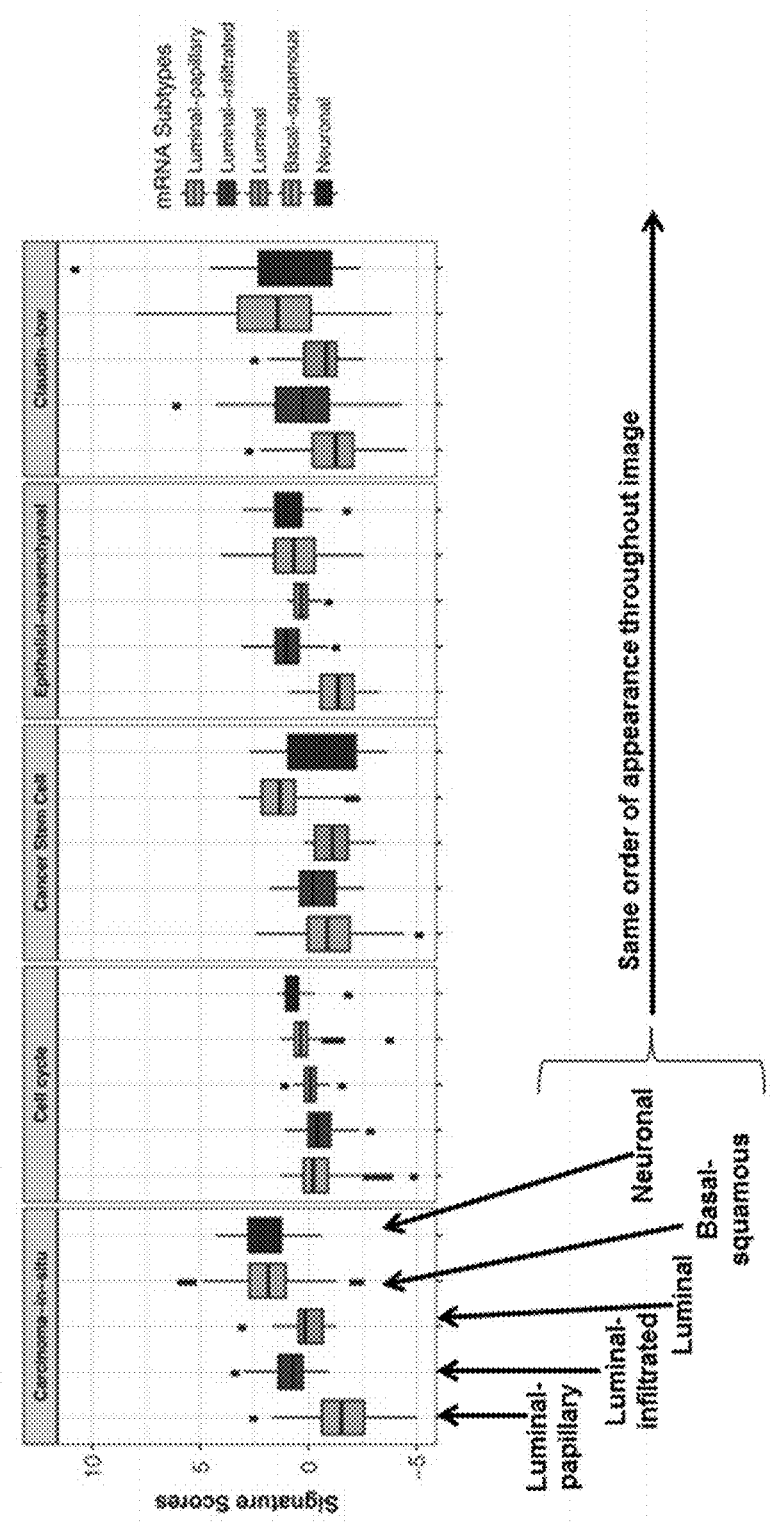
Figure 6:
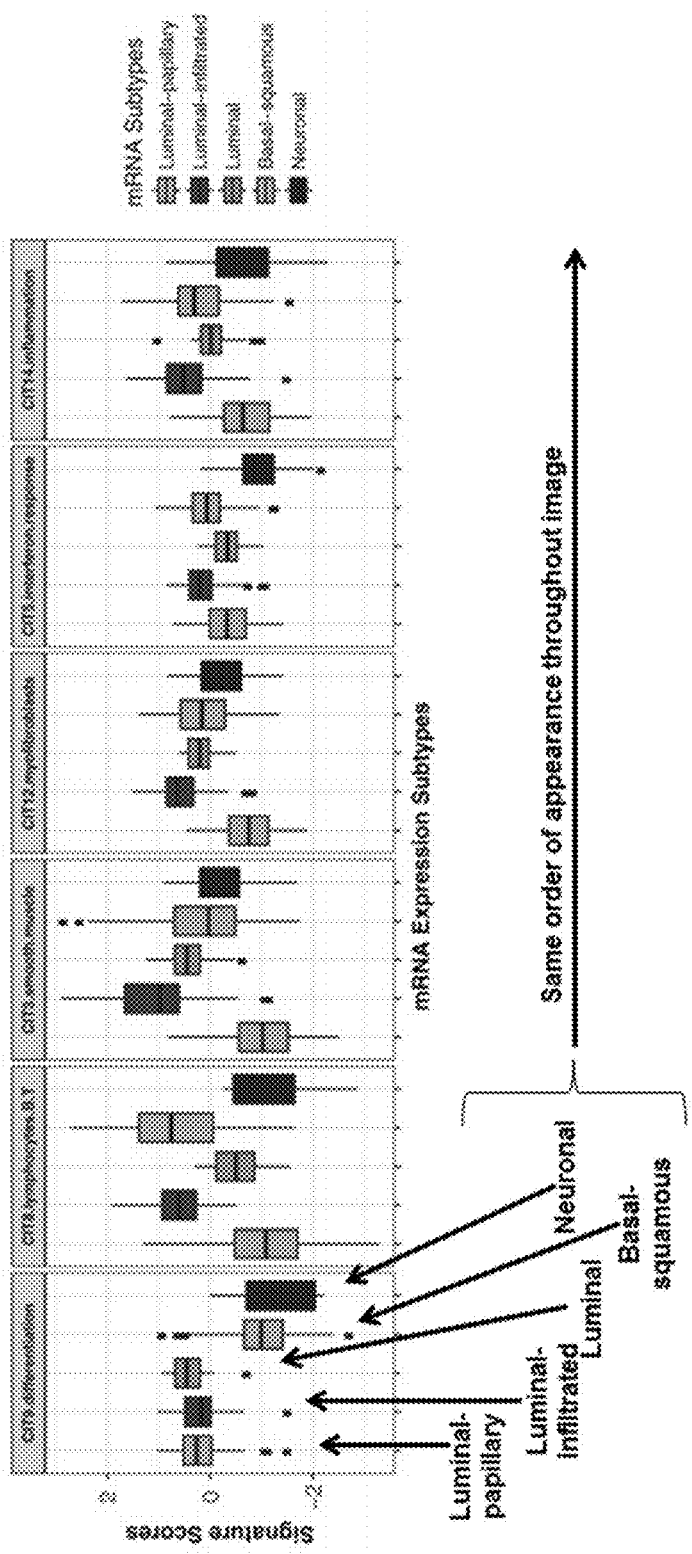
Figure 6:
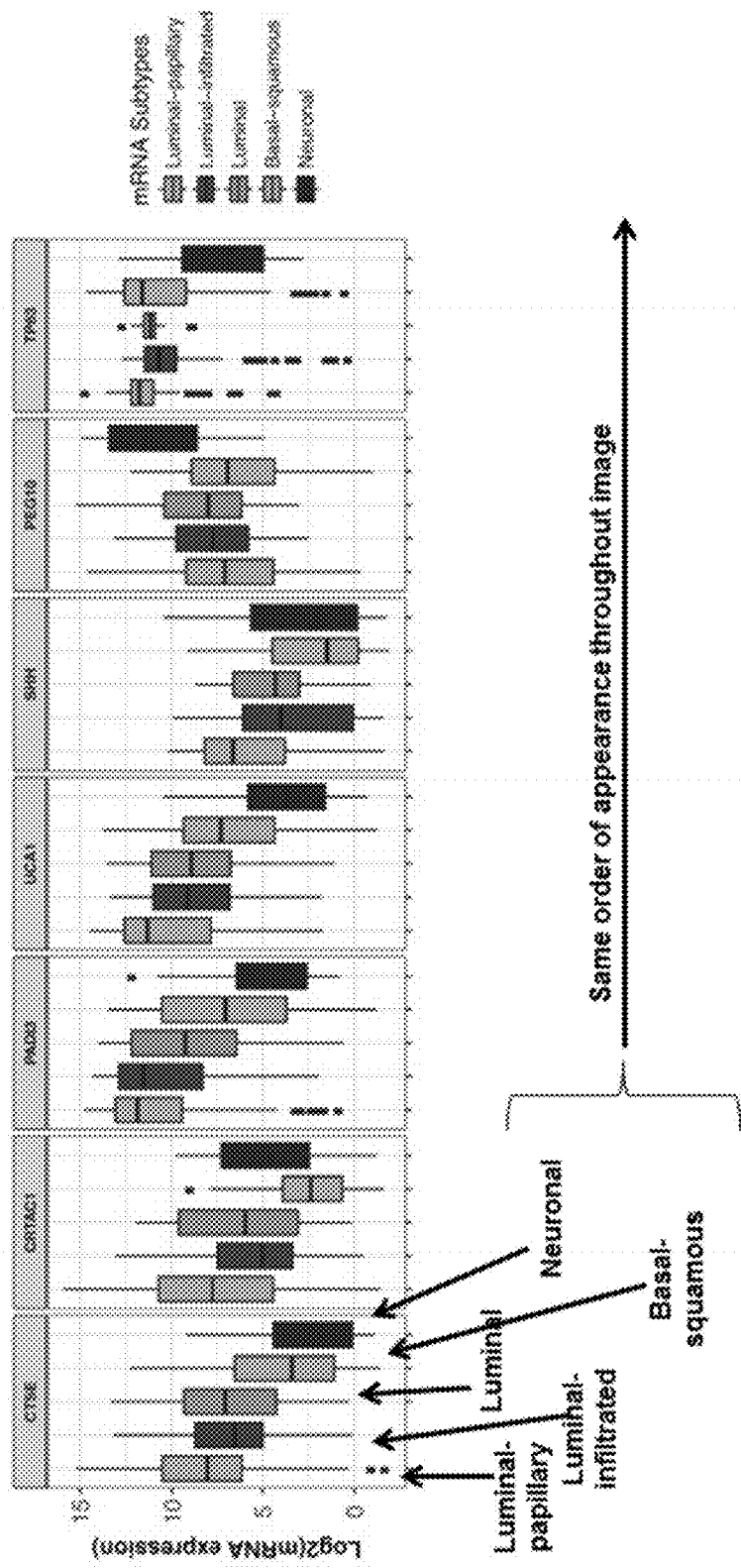
Figure 6:
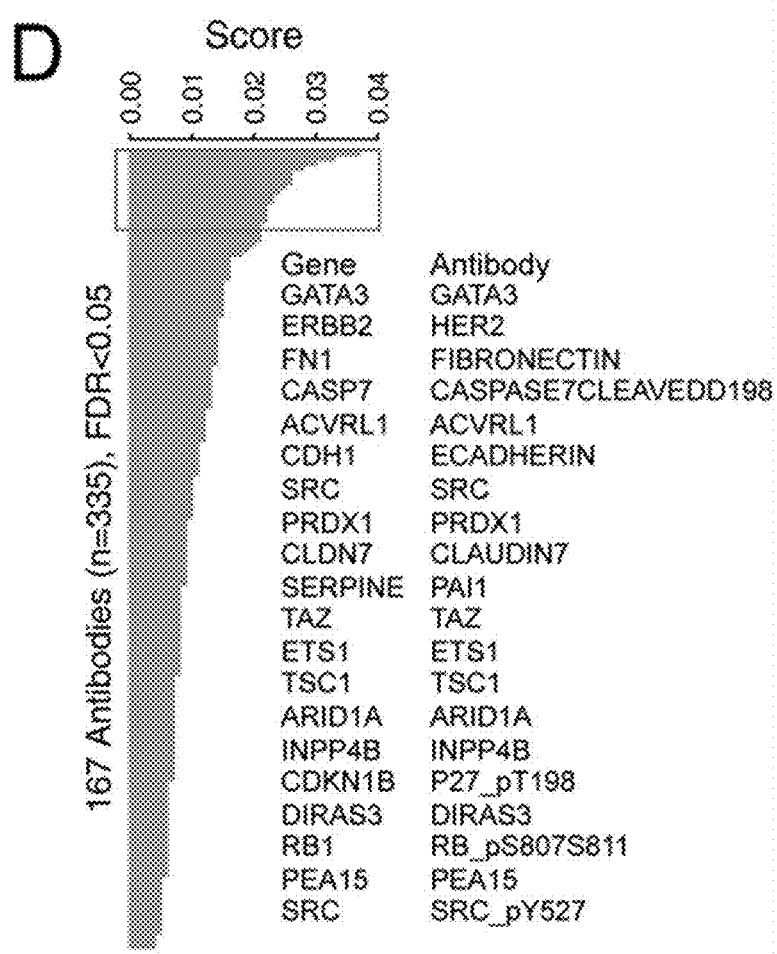
Figure 6:
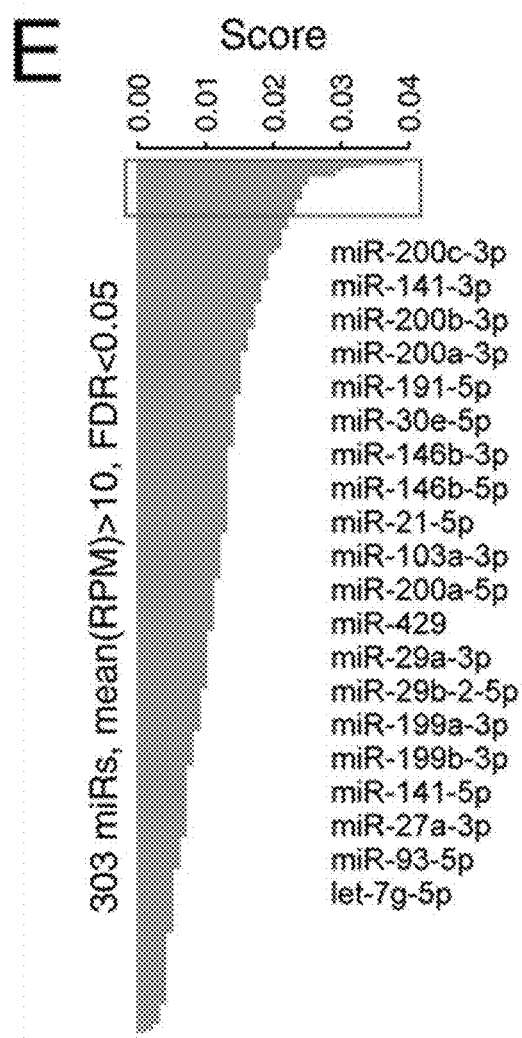
Figure 11:
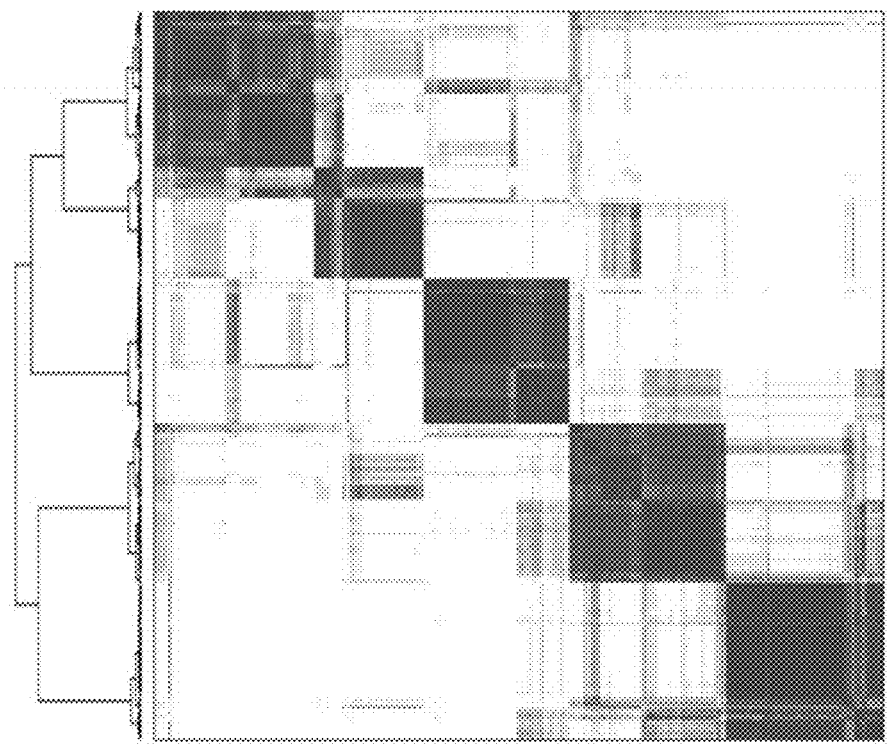
Figure 11:
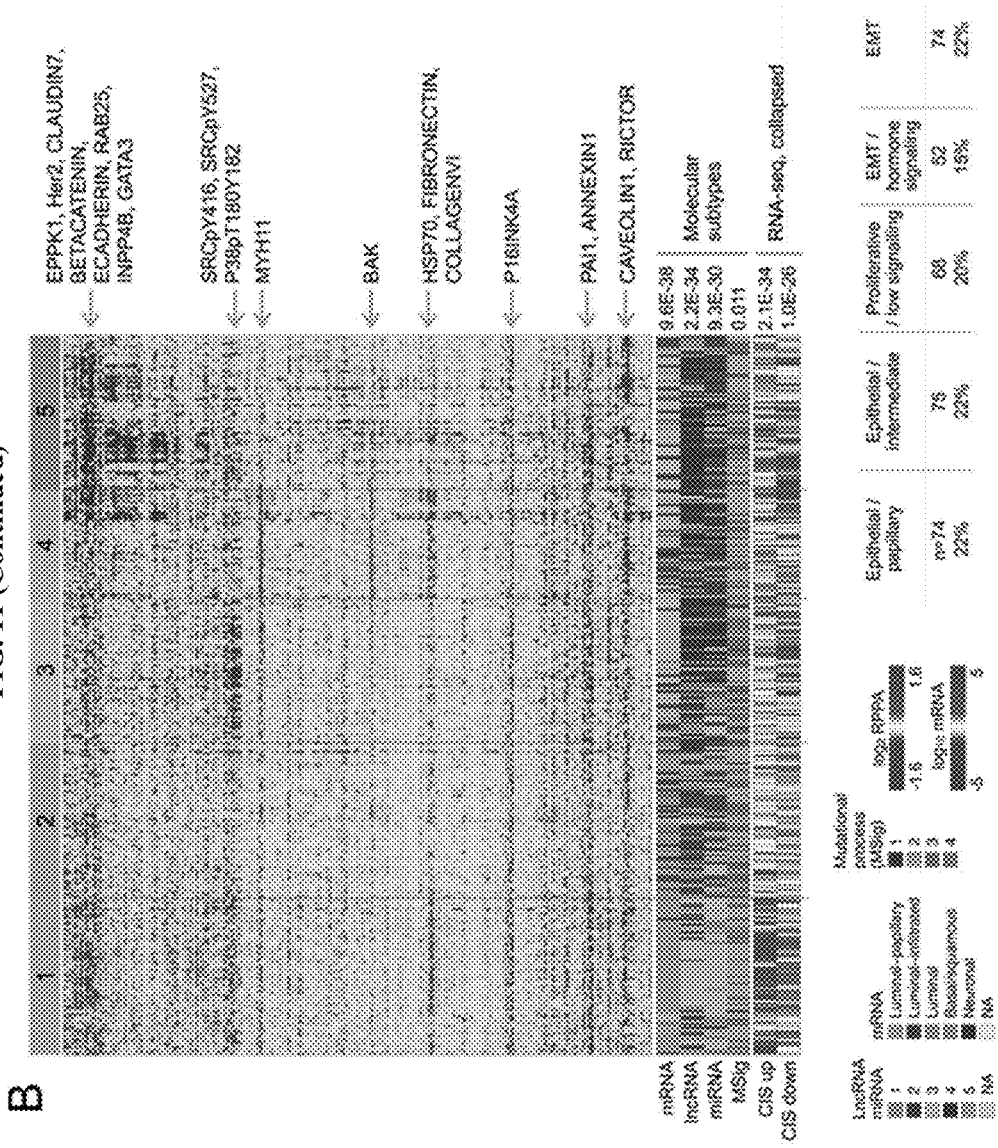
Figure 11:
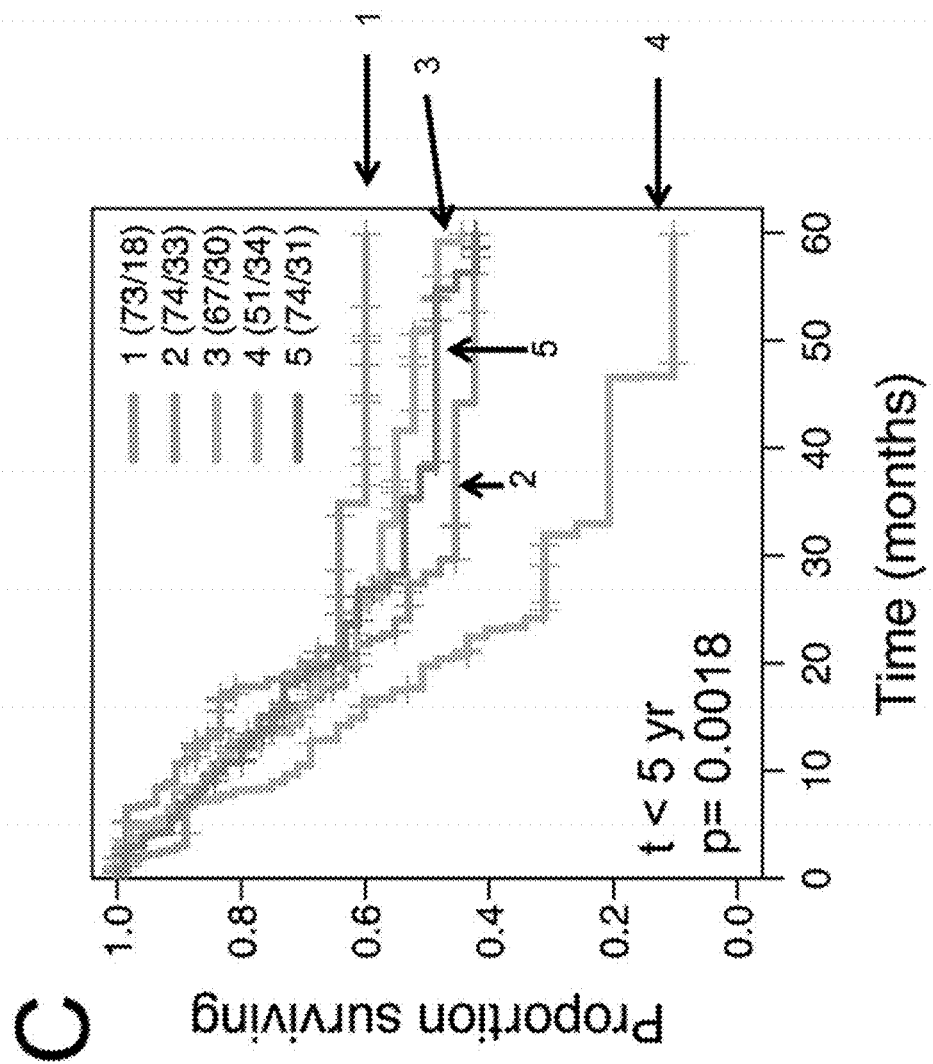
Figure 11:
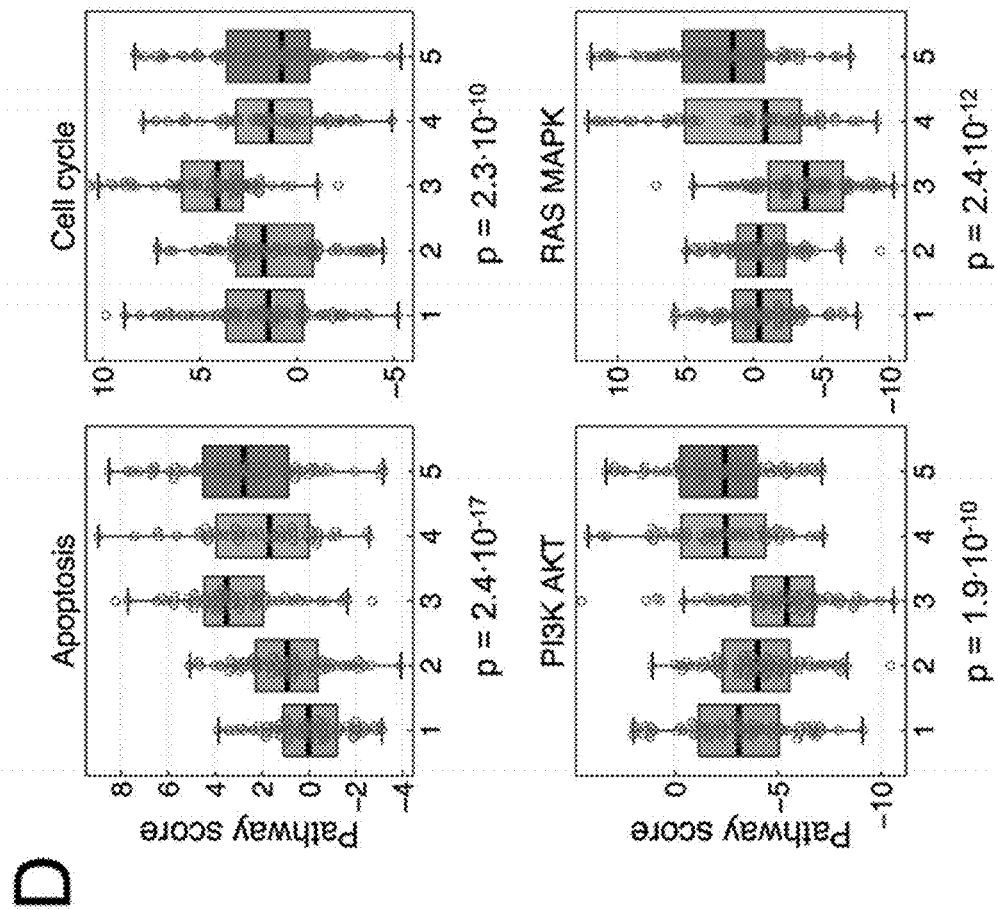
Figure 11:
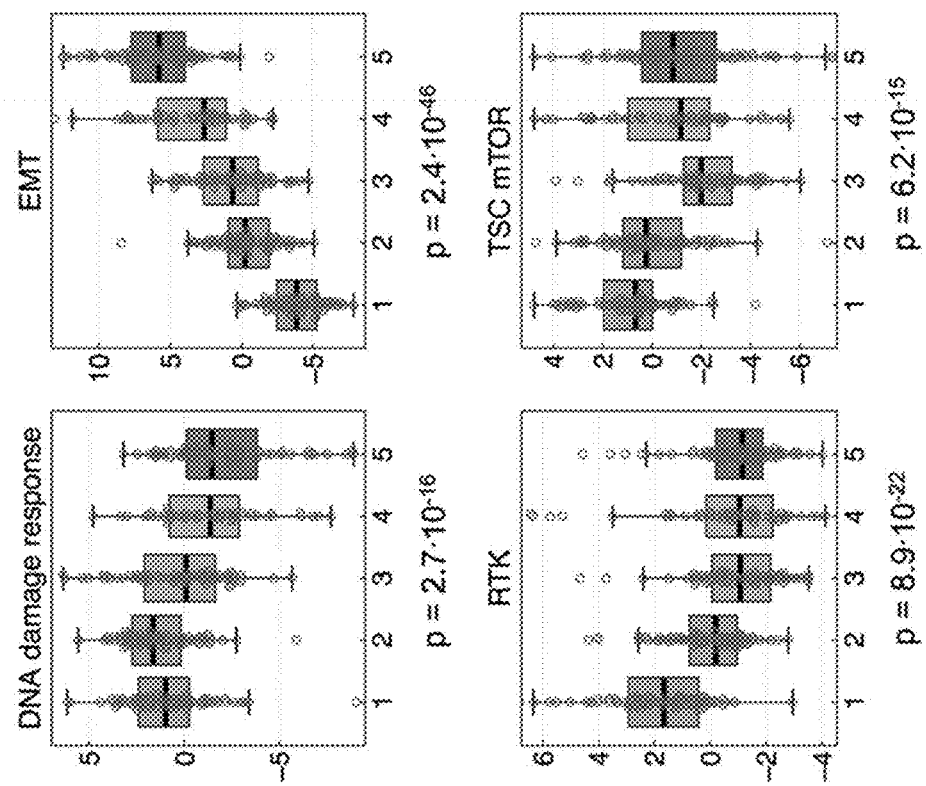
Figure 11:
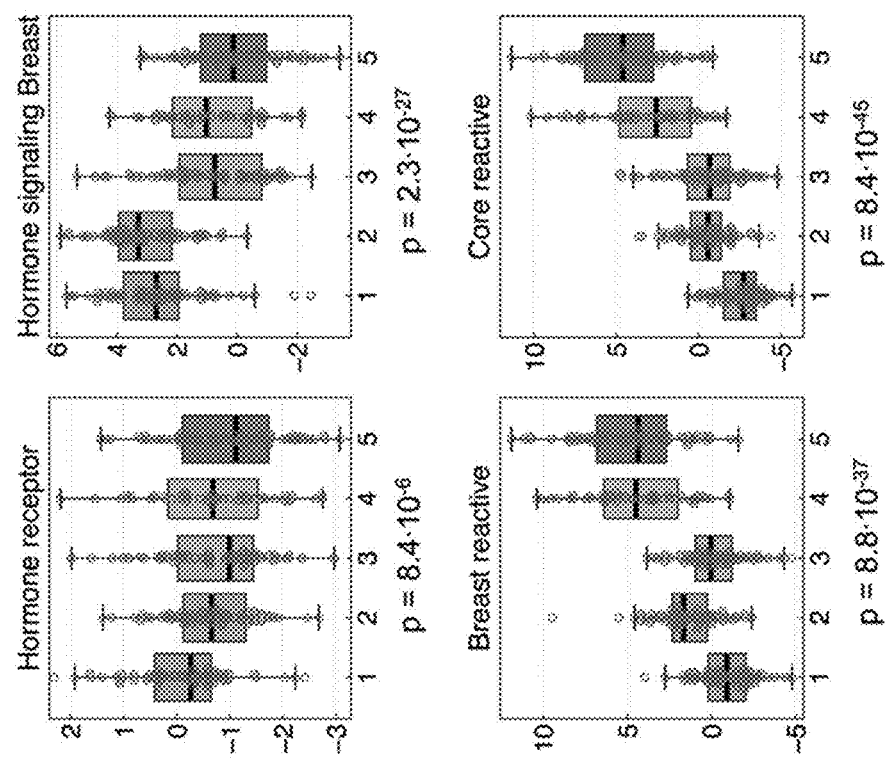

See also FIG. 4, FIG. 6, and FIG. 11.

FIGS. 6A-6E are graphs showing mRNA expression analysis. Related to FIG. 5. FIG. 6A is a graph showing a Kaplan-Meier plot for overall survival across the five mRNA expression subtypes, censored at 5 years, with a log-rank p value. LP: luminal-papillary, LI: luminal-infiltrated, L: luminal, BS: basal-squamous, N: neuronal. FIG. 6B is a graph showing distributions of ABSOLUTE purity estimates for the mRNA subtypes. FIG. 6C is a graph showing gene expression signature scores for genes sets. For members and literature sources for gene sets, see Methods, below; mRNA Expression Profiling: Gene expression signature scores. Top: Basal, luminal, wild type p53, squamous-differentiation, and neuroendocrine. Second from the top: Carcinoma-in-situ, cell-cycle, cancer-stem cell markers, genes associated with EMT (epithelial-mesenchymal transition), and claudin-low markers. Third from top: CIT (Cartes d'Identité des Tumeurs) gene sets, including tumor cell component 9; stromal components 3, 8 and 12; and components 5 and 14, neither of which could be attributed to tumor or stromal cells. Bottom: Expression levels of selected genes. FIG. 6D and FIG. 6E are graphs showing RPPA antibodies (FIG. 6D) and miRNA mature strands (FIG. 6E) that were differentially abundant across the mRNA subtypes. Barplots show SAM multiclass scores, with higher scores indicating antibodies or miRNAs that were more variable across the subtypes. Text lists give the genes/antibodies and miRNAs with the largest 20 multiclass scores.

Figure 7:
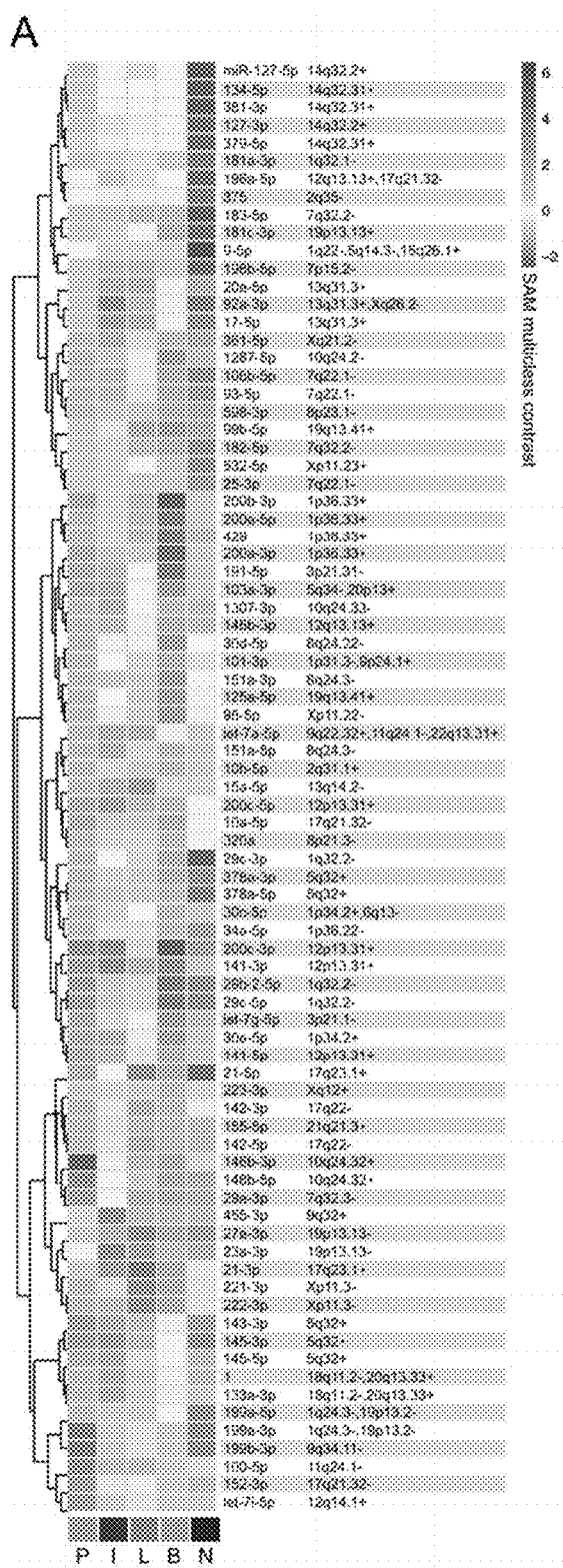
Figure 7:
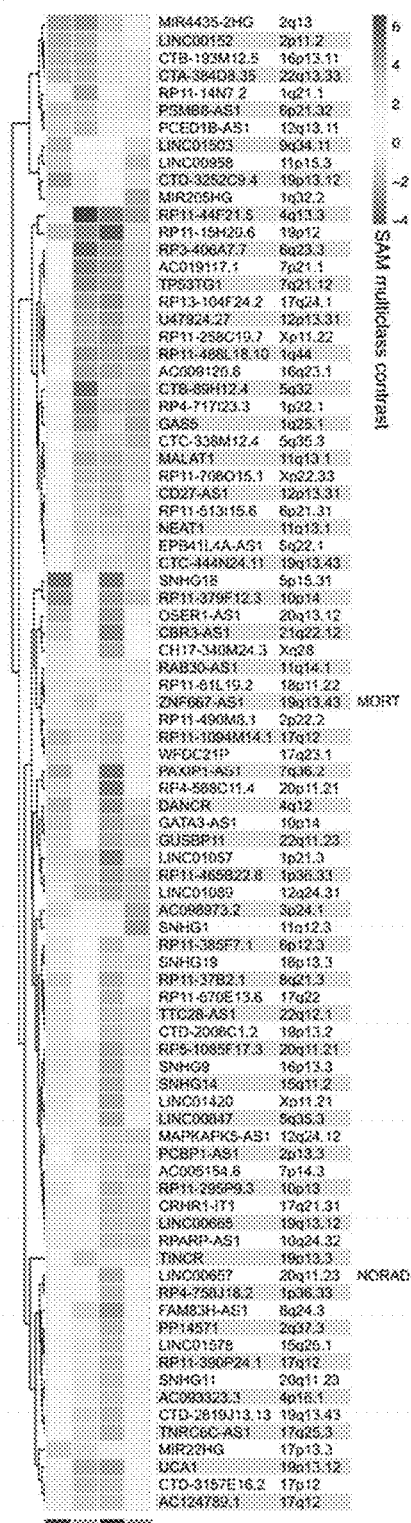
Figure 7:
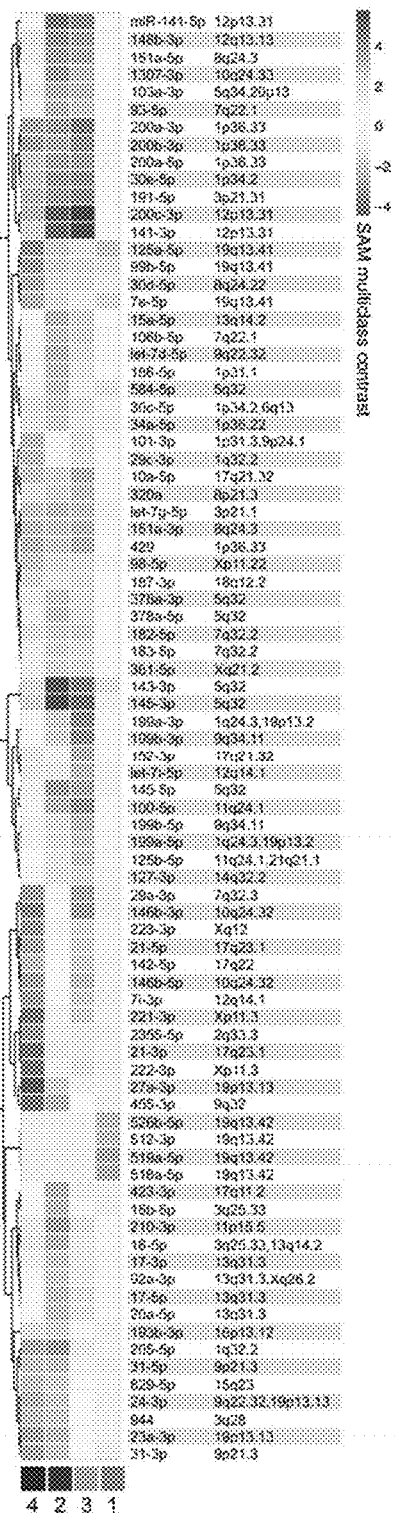
Figure 7:
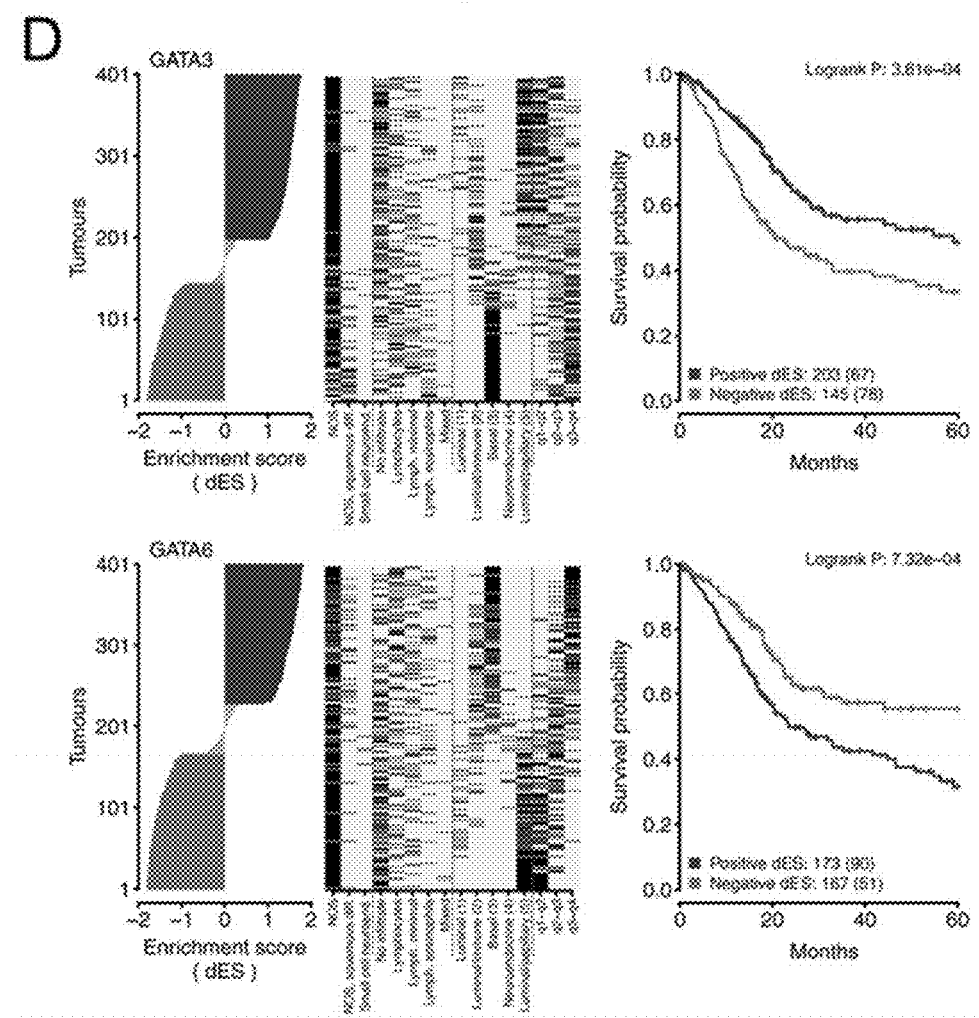
Figure 7:
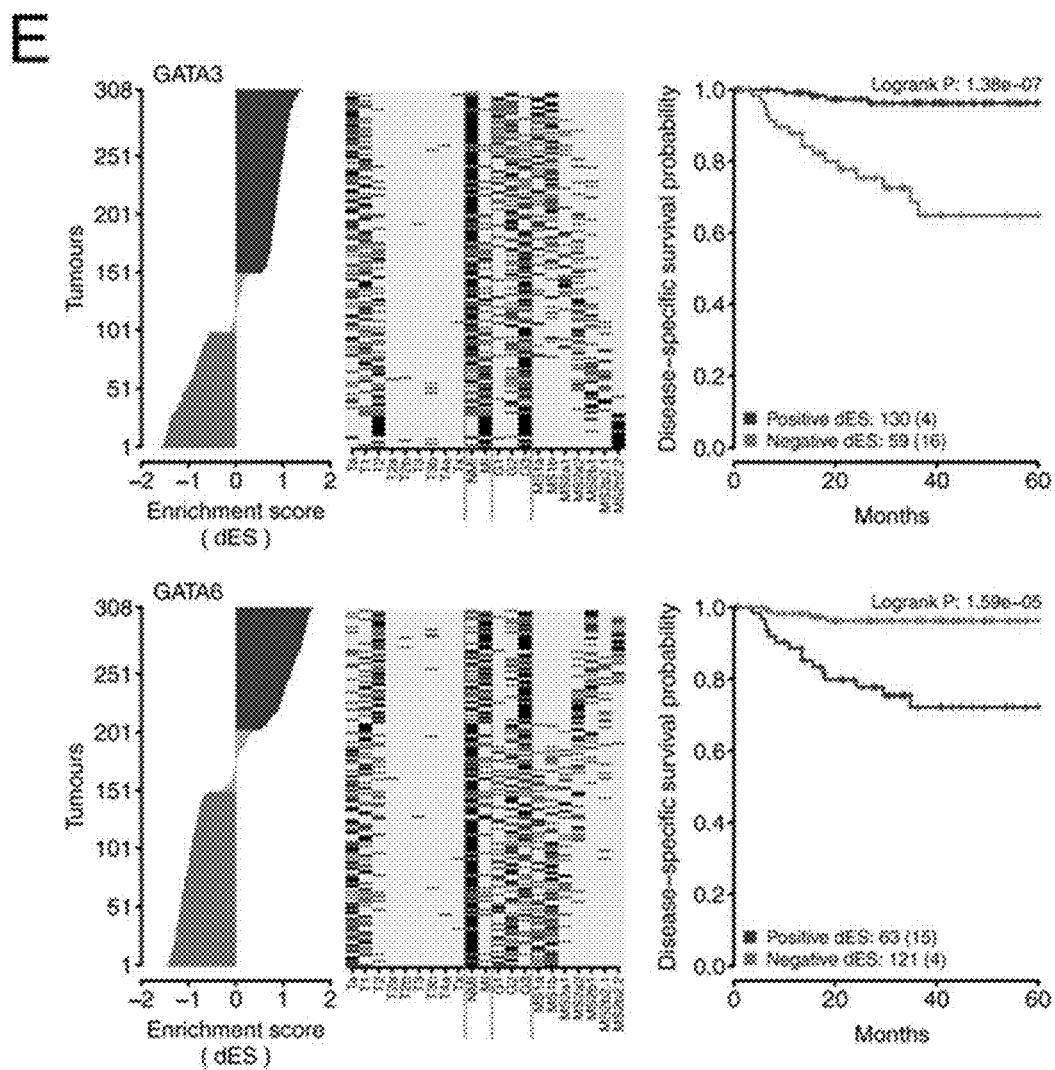
Figure 7:
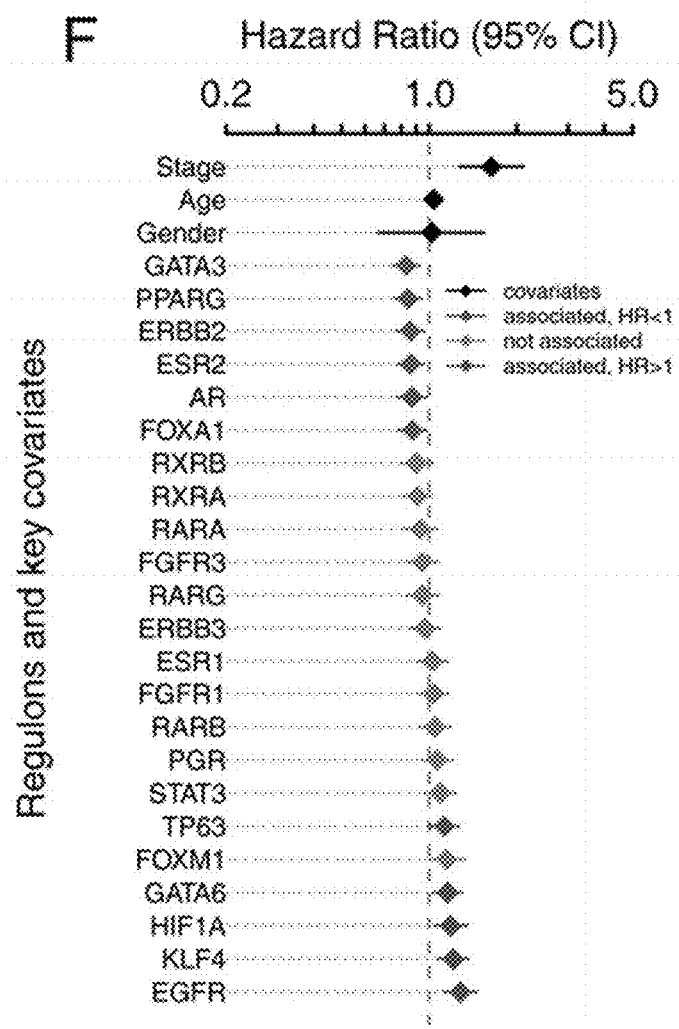
Figure 7:
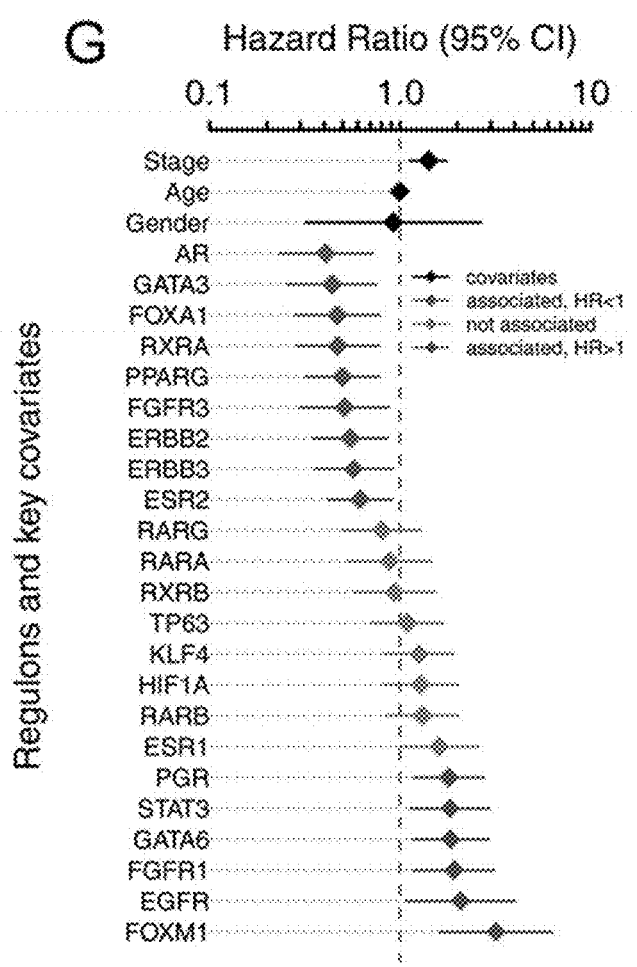
Figure 7:
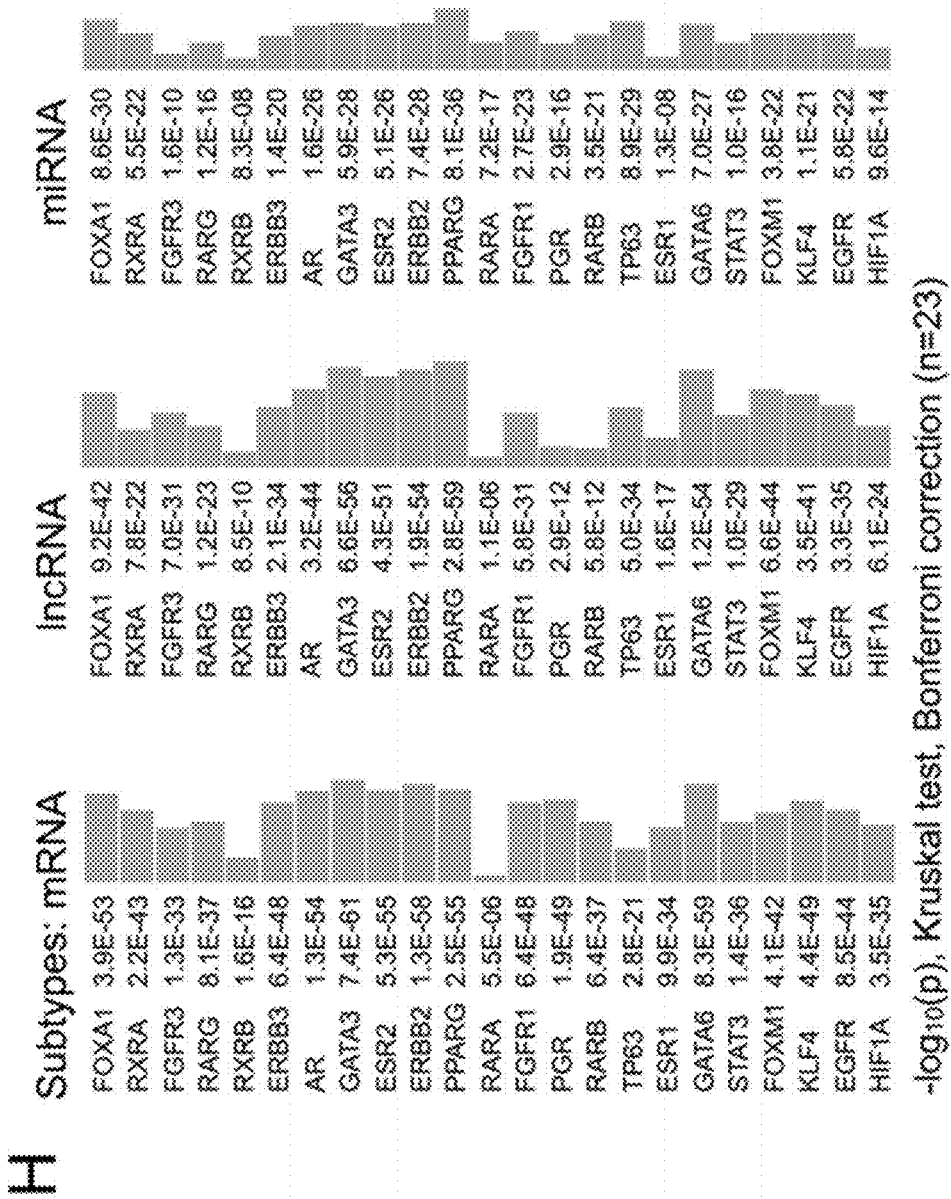

FIGS. 7A-7H are graphs showing noncoding RNAs and regulons. Related to FIG. 9A and FIG. 9B. FIG. 7A is a graph showing miRNAs that were differentially abundant across the messenger RNA subtypes, shown as contrasts from a SAM multiclass analysis, for a subset of miRNAs that were highly ranked as differentially abundant in a SAM multiclass analysis. Subtypes are: P, luminal-papillary. I, luminal-infiltrated. L, luminal. B, basal-squamous. N, neuronal. FIG. 7B is a graph showing long non-coding RNAs (lncRNAs) that were differentially abundant across the lncRNA subtypes, shown as a heatmap of contrasts from a SAM multiclass analysis for a subset of lncRNAs that were highly ranked as differentially abundant. FIG. 7C is a graph showing miRNAs that were differentially abundant across the miRNA clusters, shown as contrasts from a SAM multiclass analysis, for a subset of miRNAs that were highly ranked as differentially abundant. FIGS. 7D-7G are graphs showing regulon analysis for 23 urothelial/bladder carcinoma (BLCA)-associated regulators (see Methods (below): Regulon analysis: Candidate regulators). FIG. 7D are graphs showing the TCGA muscle-invasive bladder cancer (MIBC) cohort (Left to Right): for the transcription factors GATA3 and GATA6, sorted profiles of differential enrichment score (dES), with a subset of covariates for the score-sorted cohort, and a Kaplan-Meier plot for sample groups that have activated vs. repressed regulon activity or status. FIG. 7E are graphs showing similar profiles as shown in FIG. 7D, but for the non-muscle invasive bladder cancer (NMIBC)/MIBC Sjodahl cohort (n=308) (Sjodahl et al. 2012), using predicted regulon targets identified in the TCGA cohort. FIG. 7F and FIG. 7G are graphs showing Cox multivariate survival analysis of regulons, with stage, age and gender, assessed in (FIG. 7F) the TCGA cohort and (FIG. 7G) the Sjodahl 2012 cohort, using predicted regulon targets identified in the TCGA cohort. Hazard ratios with 95% confidence intervals. FIG. 7H is a graph showing the statistical significance of variation in regulon activity enrichment scores (dES) across mRNA, lncRNA and miRNA subtypes. Barplots show $-\log_{10}$ of Bonferroni-corrected (n=23) Kruskal-Wallis p values.

Figure 8:
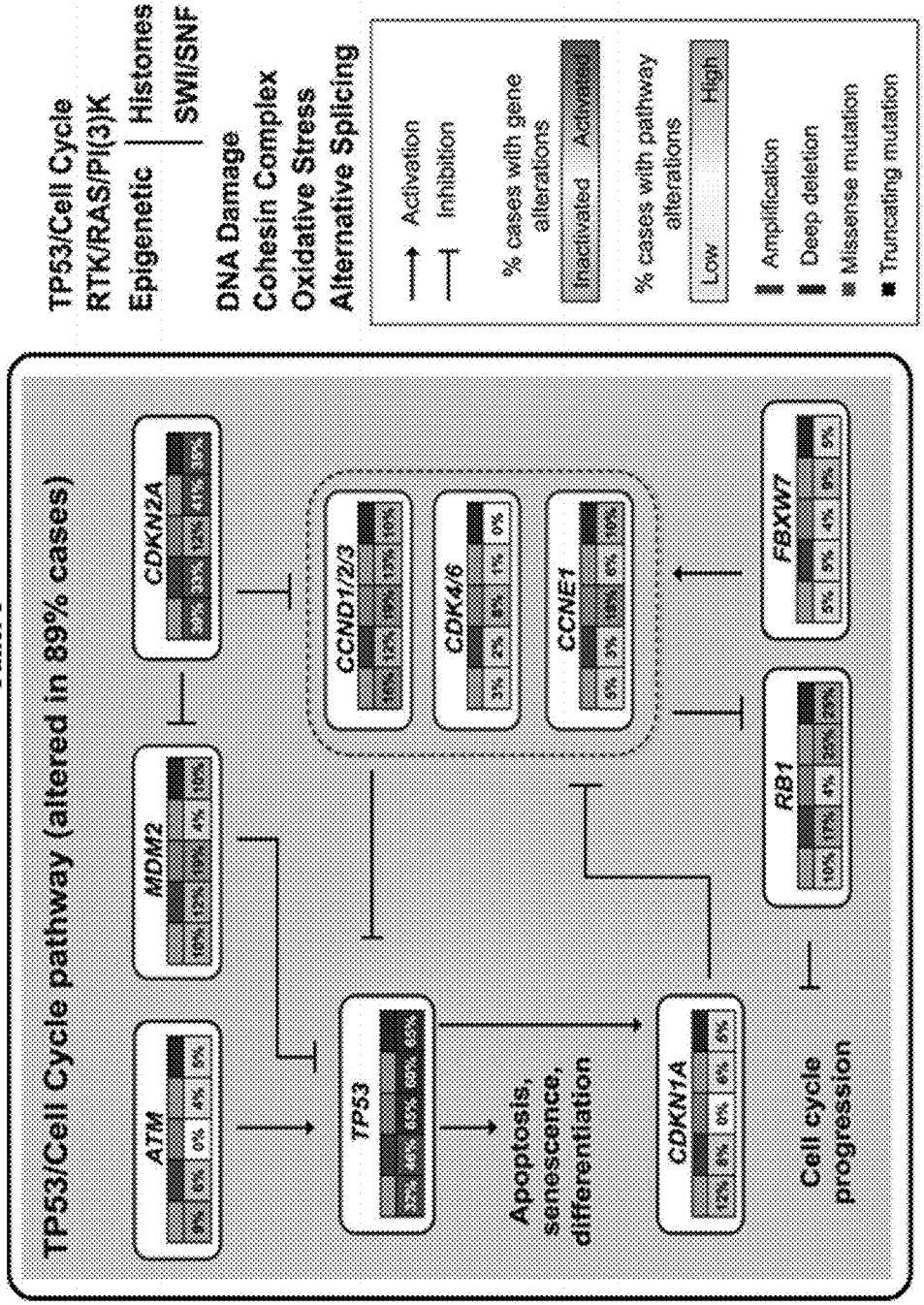
Figure 8:
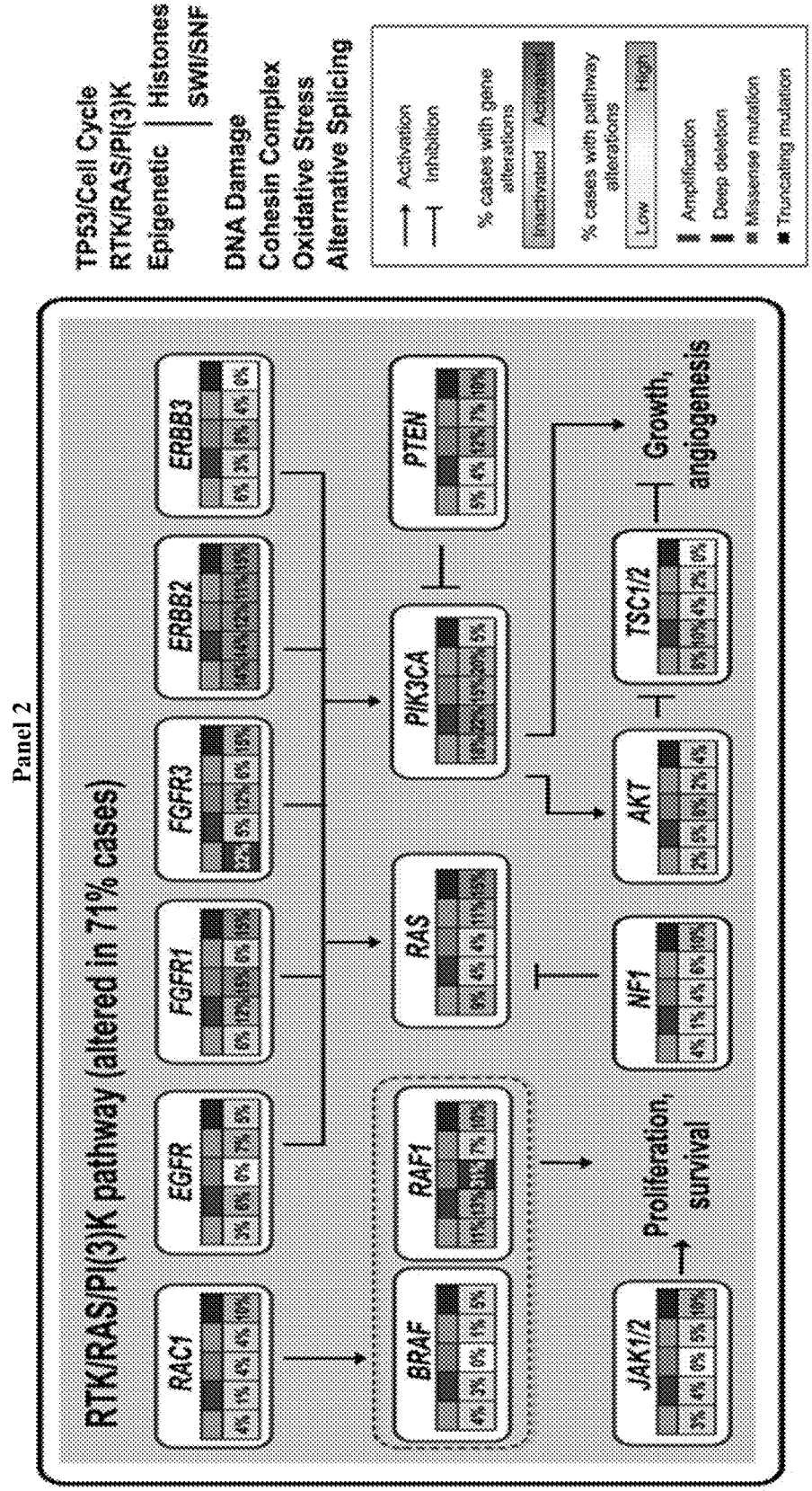
Figure 8:
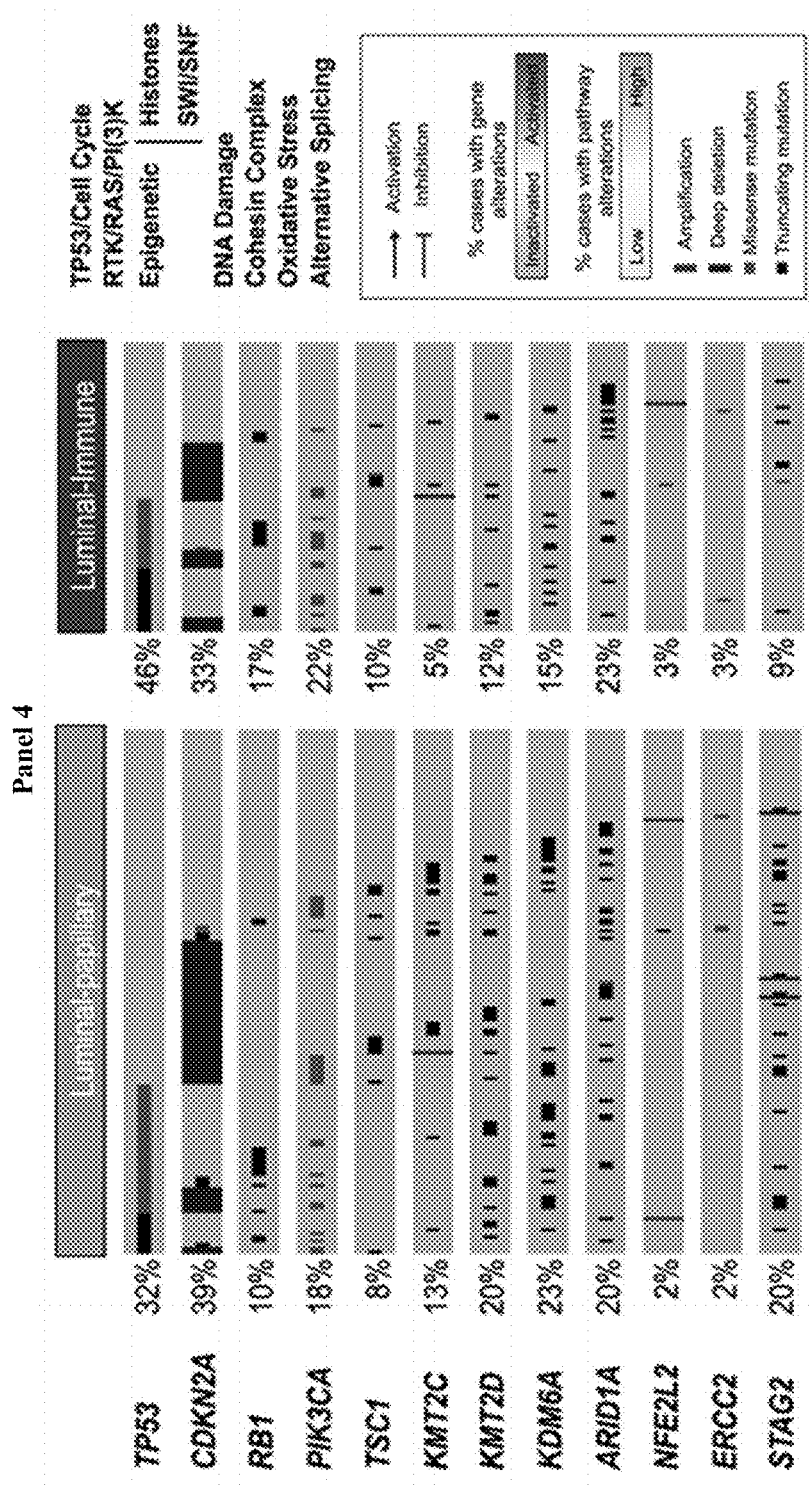

FIG. 8 consists of 5 panels depicting graphs and images showing somatic alterations in signaling pathways across mRNA subtypes. Somatic alterations include mutations and copy-number changes (i.e. deep deletions and high-level amplifications, from Genomic Identification of Significant Targets in Cancer (GISTIC) results). Missense mutations are counted only if they have known oncogenic function based on OncoKB (http://www.oncokb.org) annotations, or have previously been reported in the Catalog of Somatic Mutations in Cancer (COSMIC), or occur at known mutational hotspots. The table (Panel 3) shows the fraction of samples with alterations in selected signaling pathways. In the pathway diagrams (Panel 1, and Panel 2), edges show pairwise molecular interactions; boxes outlined in red denote alterations leading to pathway activation, while boxes outlined in blue denote predicted pathway inactivation. The oncoprint illustrates type and frequency of alteration, as well as patterns of co-occurrence, for selected genes from the pathways highlighted in the table.

FIGS. 9A and 9B are graphs and images showing lncRNA expression subtypes. FIG. 9A depicts a heatmap and covariates for four unsupervised lncRNA consensus clusters. Top to bottom: normalized abundance heatmap for 171 lncRNAs; profile of silhouette width calculated from the consensus membership heatmap, $W_{cm}$; covariates for clinical parameters, molecular subtypes, purity, mutations in TP53 and FGFR3, FGFR3 and PPARG gene fusions; row-scaled mRNA levels for 3 genes; collapsed CIS gene sets (Dyrskjot et al., 2004) (Methods (below); CIS up=genes up-regulated in CIS; CIS down=genes down-regulated in CIS); row-scaled regulon activity profiles (showing activated, undefined, or repressed status) for 23 regulators; RNA-seq-based epithelial-mesenchymal transition (EMT) scores (Mak et al., 2016). The following p values are Bonferroni-corrected: for mutated genes (for 58 SMGs), gene fusions (for 23 fusions), regulon activity (for 23 regulators), and mRNA-seq (for 12 genes). FIG. 9B shows a Kaplan-Meier plot for overall 5-year survival according to lncRNA subtype. See also FIGS. 7A-7H.

FIGS. 10A and 10B are graphs and images showing microRNA (miRNA) expression subtypes. FIG. 10A depicts a heatmap and covariates for a 4-cluster unsupervised consensus clustering solution. Top to bottom: Normalized heatmap showing a subset of 142 miRNAs that had a mean RPM≥50 and an absolute value of tumor-vs-normal fold change ≥1.5. Profile of silhouette width calculated from the consensus membership heatmap, $W_{cm}$, with lower values indicating samples that are atypical cluster members. Covariate tracks for clinical parameters, genomic platform subtypes, purity, mutations in TP53 and FGFR3, and FGFR3 and PPARG gene fusions. Row-scaled regulon activity profiles for 23 regulators that have been associated with bladder cancer. Row-scaled mRNA levels for 12 genes, then for collapsed CIS gene sets (Dyrskjot et al., 2004) (Methods; CIS up=genes up-regulated in CIS; CIS down=genes down-regulated in CIS); and RNA-seq-based EMT scores (Mak et al., 2016). The following p values are Bonferroni-corrected: for mutated genes (for 58 SMGs), gene fusions (for 23 fusions), regulon activity (for 23 regulators), and mRNA-seq (12 genes). FIG. 10B shows a Kaplan-Meier plot for overall survival data that has been censored at 5 years. See also FIGS. 7A-7H.

FIGS. 11A-11D show graphs and images of RPPA proteomics analysis for 343 BLCA samples and 208 antibodies. Related to FIG. 5. FIG. 11A is an image showing a consensus matrix for five unsupervised clusters. FIG. 11B shows a normalized abundance heatmap. Arrows mark selected proteins that are differentially expressed in certain clusters. Covariate tracks show unsupervised subtypes for mRNA, lncRNA, miRNA and MSig mutational signatures. Collapsed RNA-seq tracks are shown for two carcinoma-in-situ (CIS) gene sets. FIG. 11C are graphs showing Kaplan-Meier curves for overall survival for the five clusters, censored at 5 years. FIG. 11D are graphs showing the distributions of pathway scores, with p values from Kruskal-Wallis tests.

Figure 12:
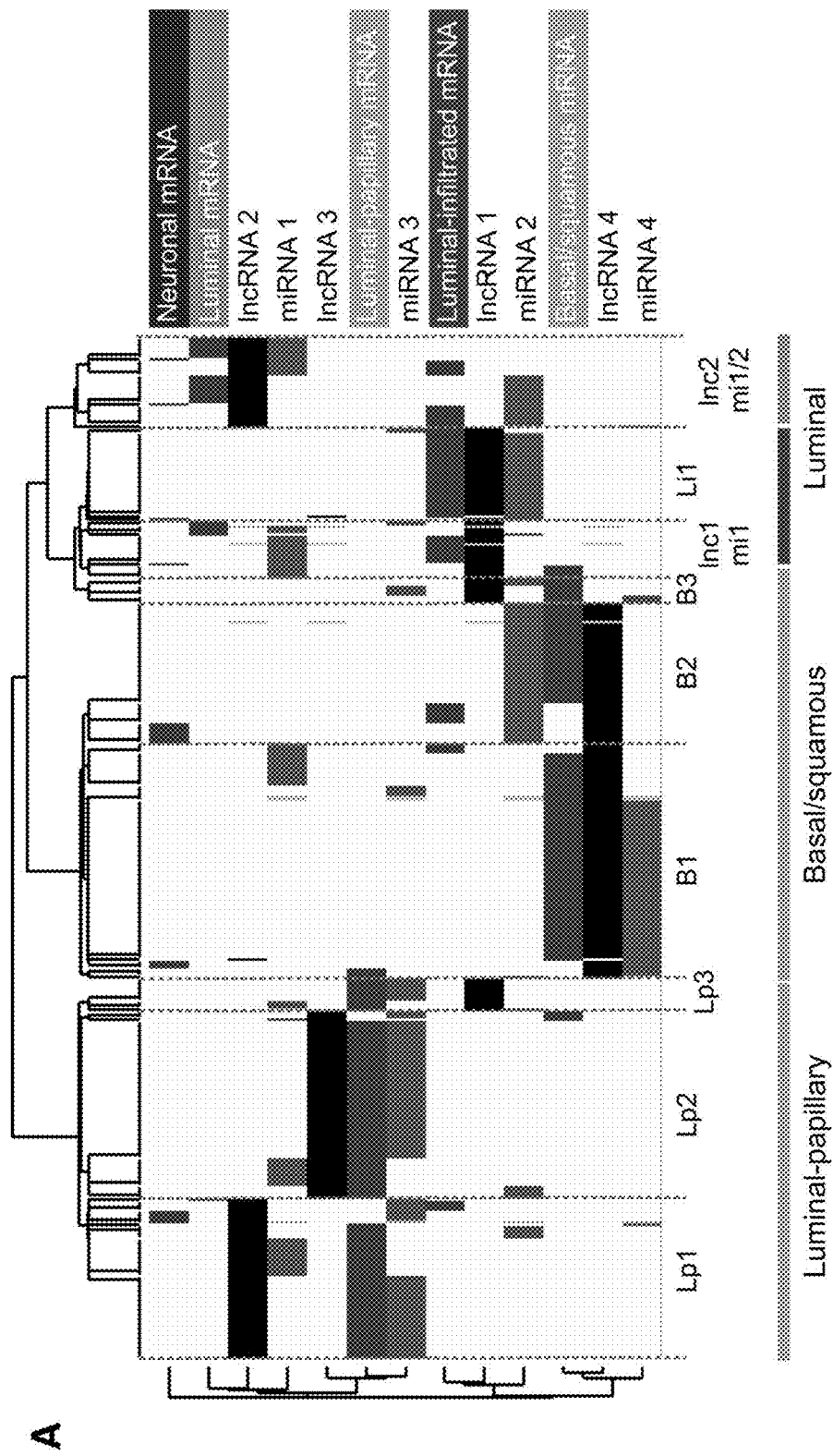
Figure 12:
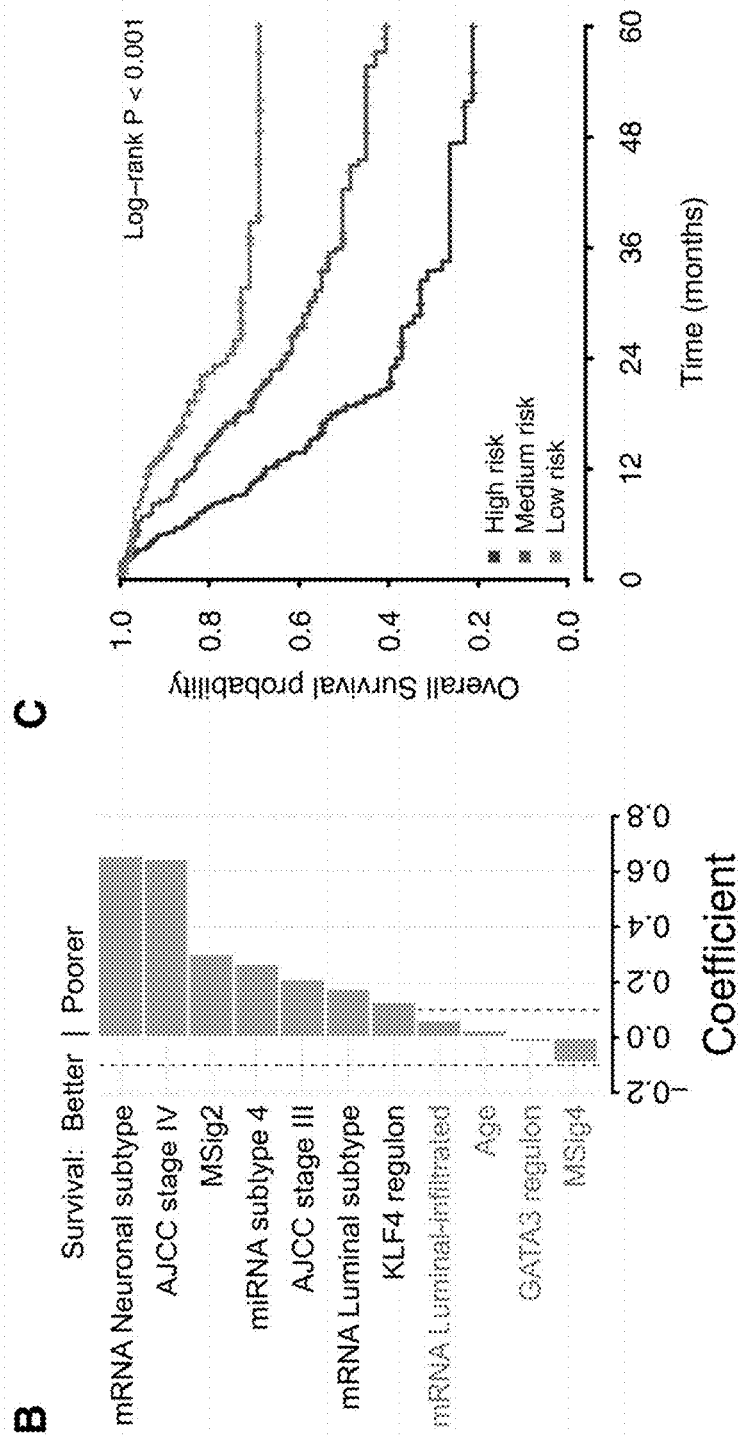

FIGS. 12A-12C are graphs and images showing integrated analysis. FIG. 12A is an image showing cluster of cluster assignments analysis (COCA). Unsupervised clustering of subtype calls. Subtype calls for mRNA, lncRNA, and miRNA are shaded by separate data type. Annotations at the right of and below the heatmap use differ shades of grey and black for mRNA subtypes. FIG. 12B and FIG. 12C are graphs showing multivariate Cox analysis for overall survival. FIG. 12B is a graph showing coefficients ($\beta$) from the LASSO-penalized multivariate Cox regression on 15 covariates that were significant (corrected p<0.05) in univariate survival calculations. Dashed lines indicate $|\beta|=0.1$; variables shown in grey text have coefficients with $|\beta|<0.1$. FIG. 12C shows a Kaplan-Meier plot predicted from the cohort, for three tertile risk groups, at 48 months. See also FIGS. 11A-11D.

Figure 13:
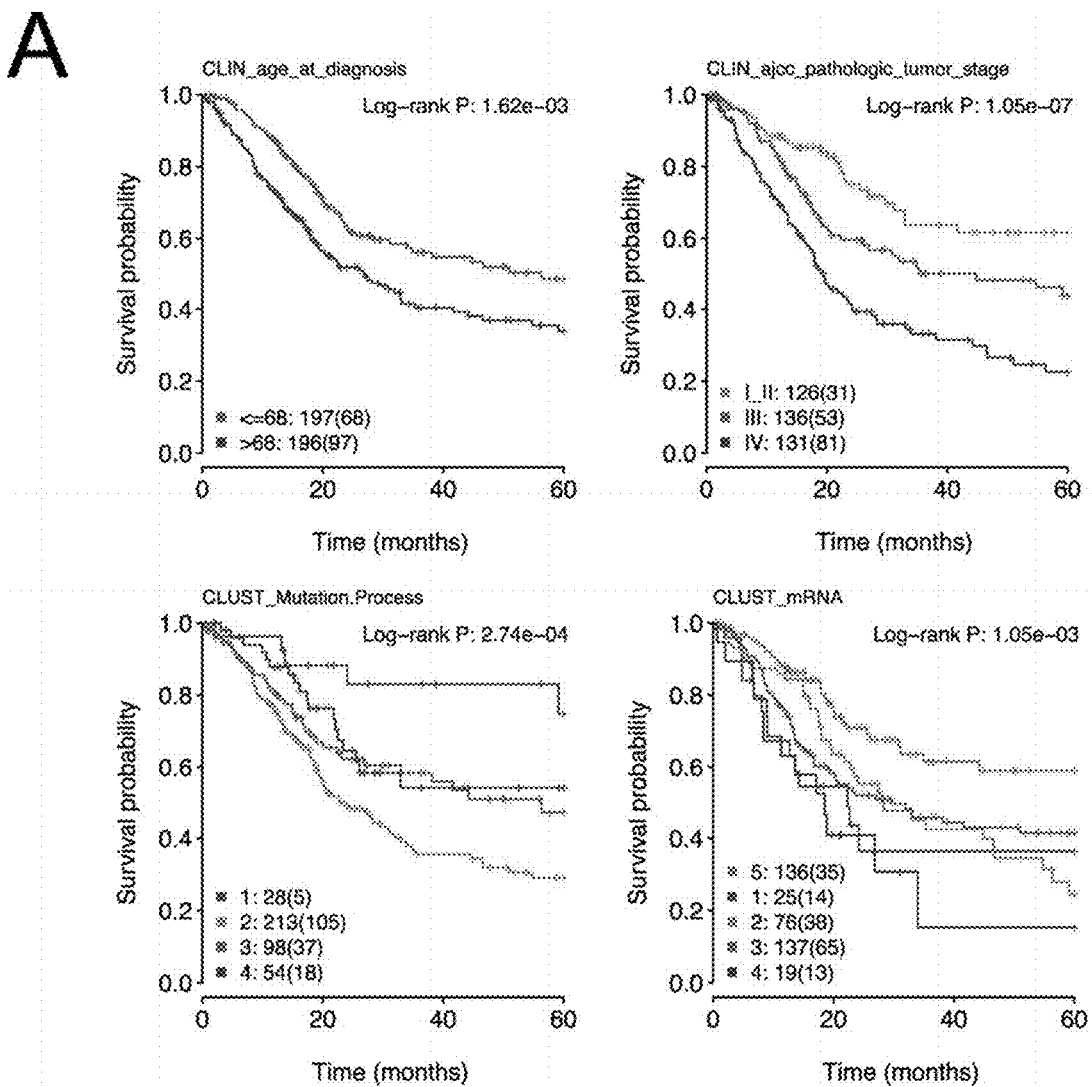
Figure 13:
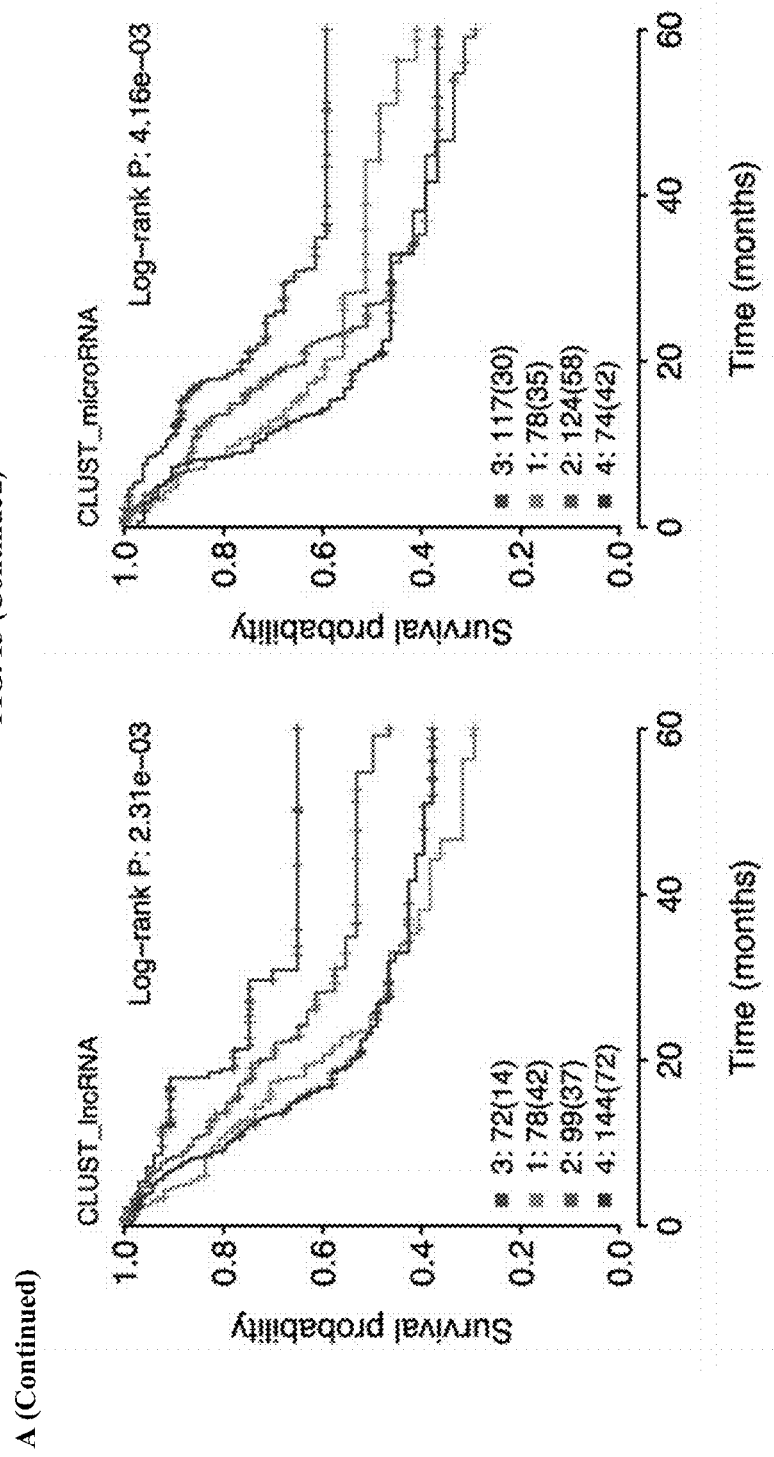
Figure 13:
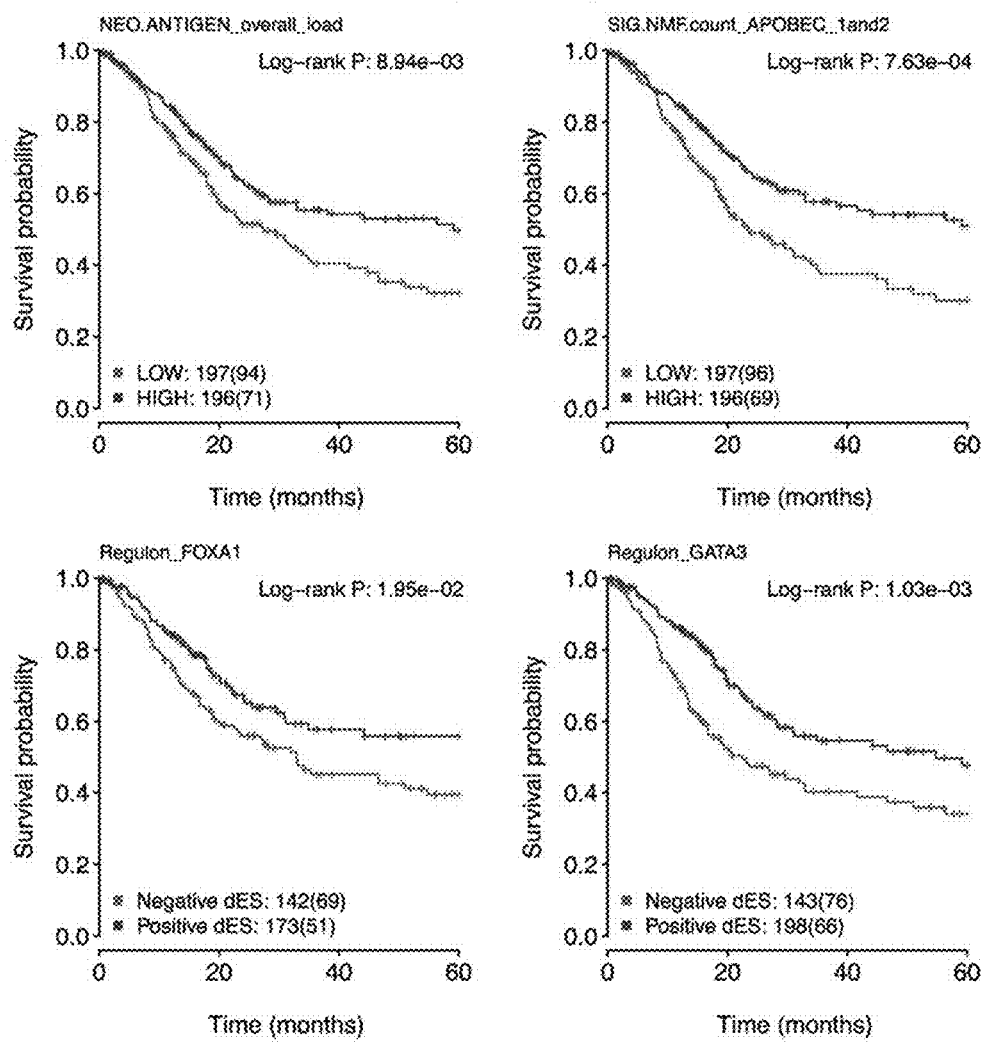
Figure 13:
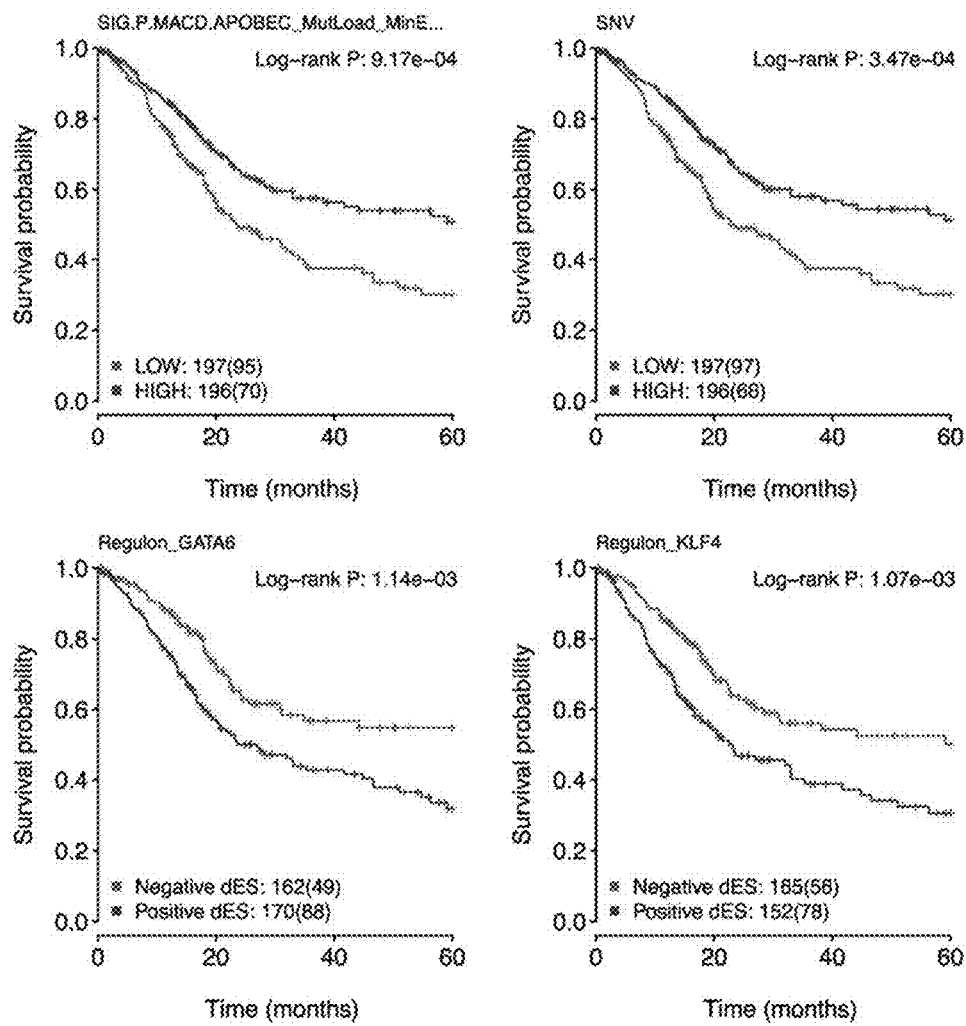
Figure 13:
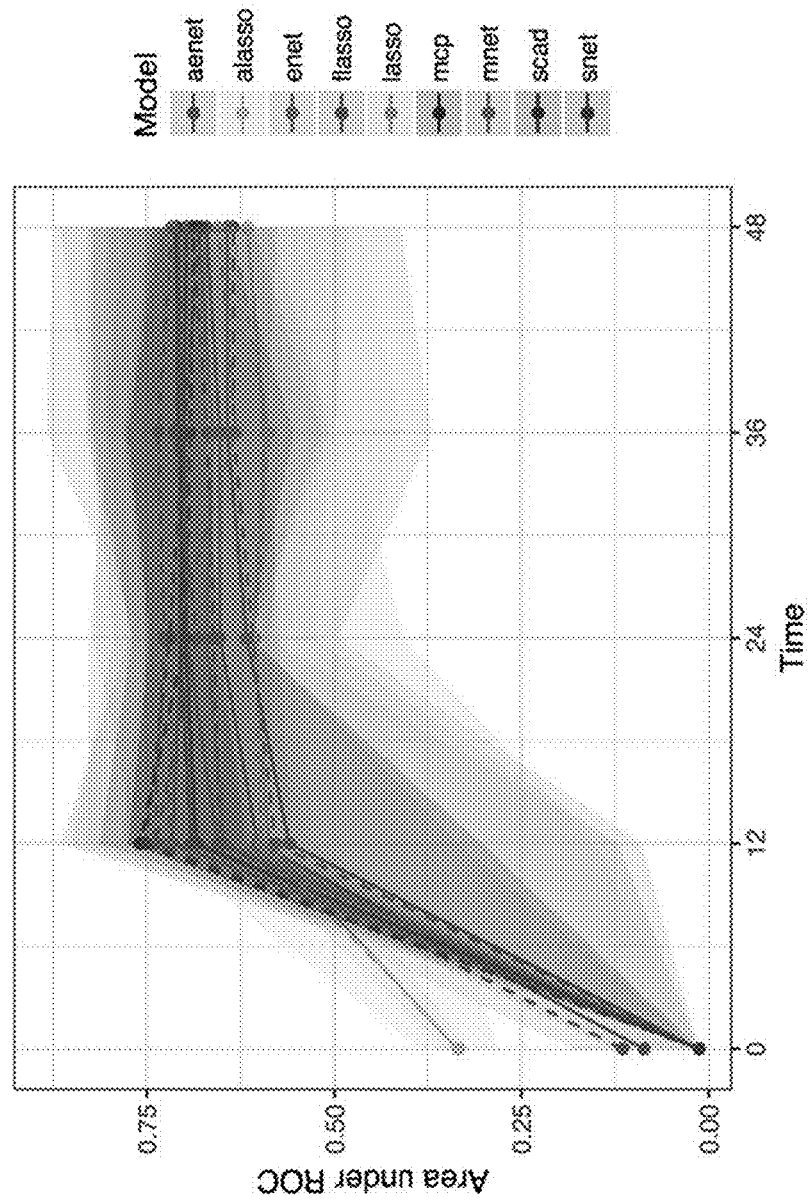
Figure 13:
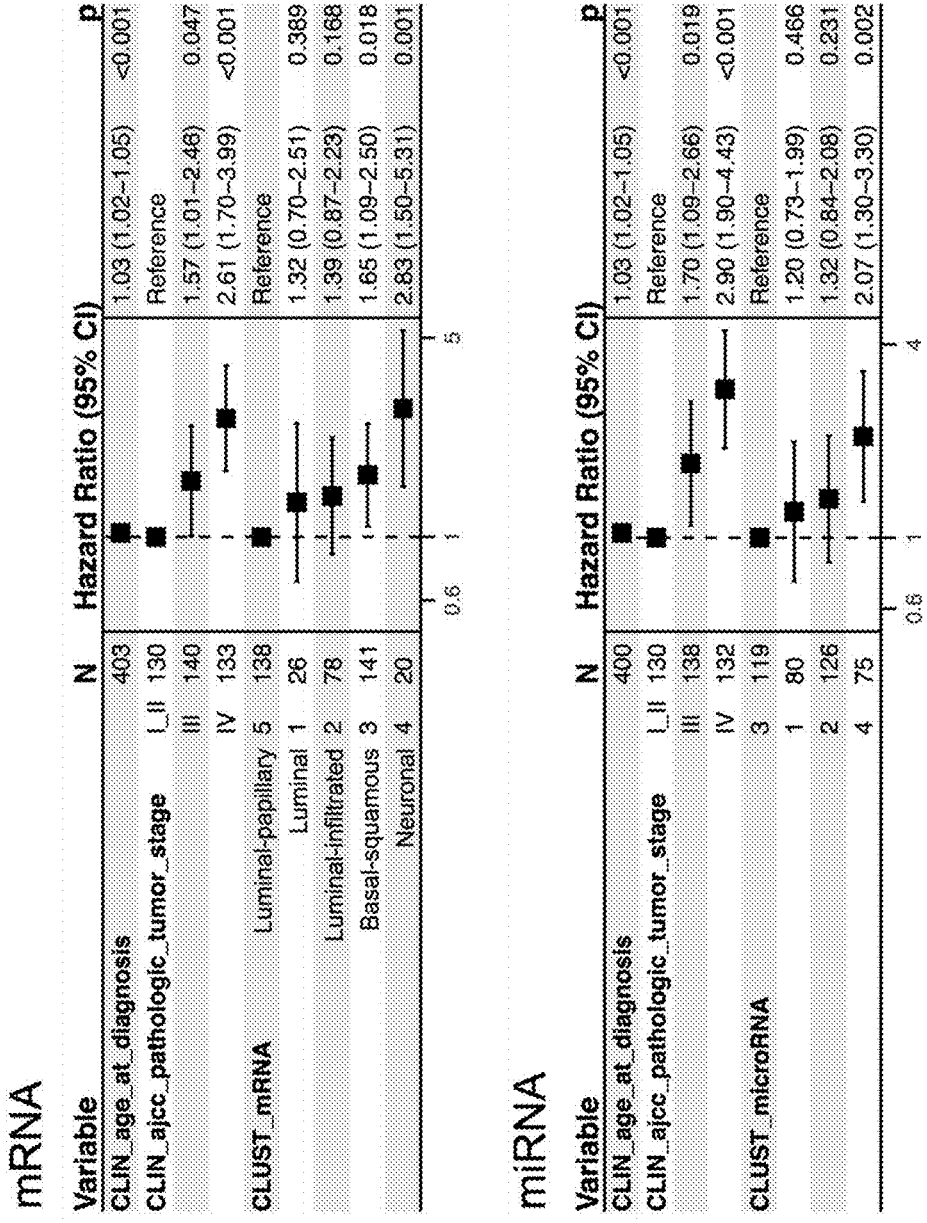

FIGS. 13A-13C are graphs and images showing univariate and multivariate survival analysis. Related to FIGS. 12A-12C. FIG. 13A shows Kaplan-Meier plots for the 14 covariates that were statistically significant in univariate calculations (BH-corrected log-rank P<0.05) and were retained for multivariate analysis. The number of curves in each plot corresponds to the number of categories used in univariate calculations. mRNA subtypes 1 to 5 correspond to 1, luminal; 2, luminal-infiltrated; 3, basal-squamous; 4, neuronal; and 5, luminal-papillary. For lncRNA, miRNA, mRNA and Mutational Process, reference variables were the subtype with the best survival. FIG. 13B is a graph showing time-dependent area-under-the-curve (AUC) curves for nine candidate penalized regression methods, for the full model. For lncRNA, miRNA, mRNA and Mutational Process, the reference variable set was the subtype with the best survival. FIG. 13C is an image showing forest plots for multivariate Cox regressions for age, American Joint Committee on Cancer (AJCC) stage, and mRNA, lncRNA, miRNA and MSig subtypes, with the reference variable for each covariate set to the best-survival subtype. Main effects are shown as hazard ratios with 95% confidence intervals.

Figure 14:
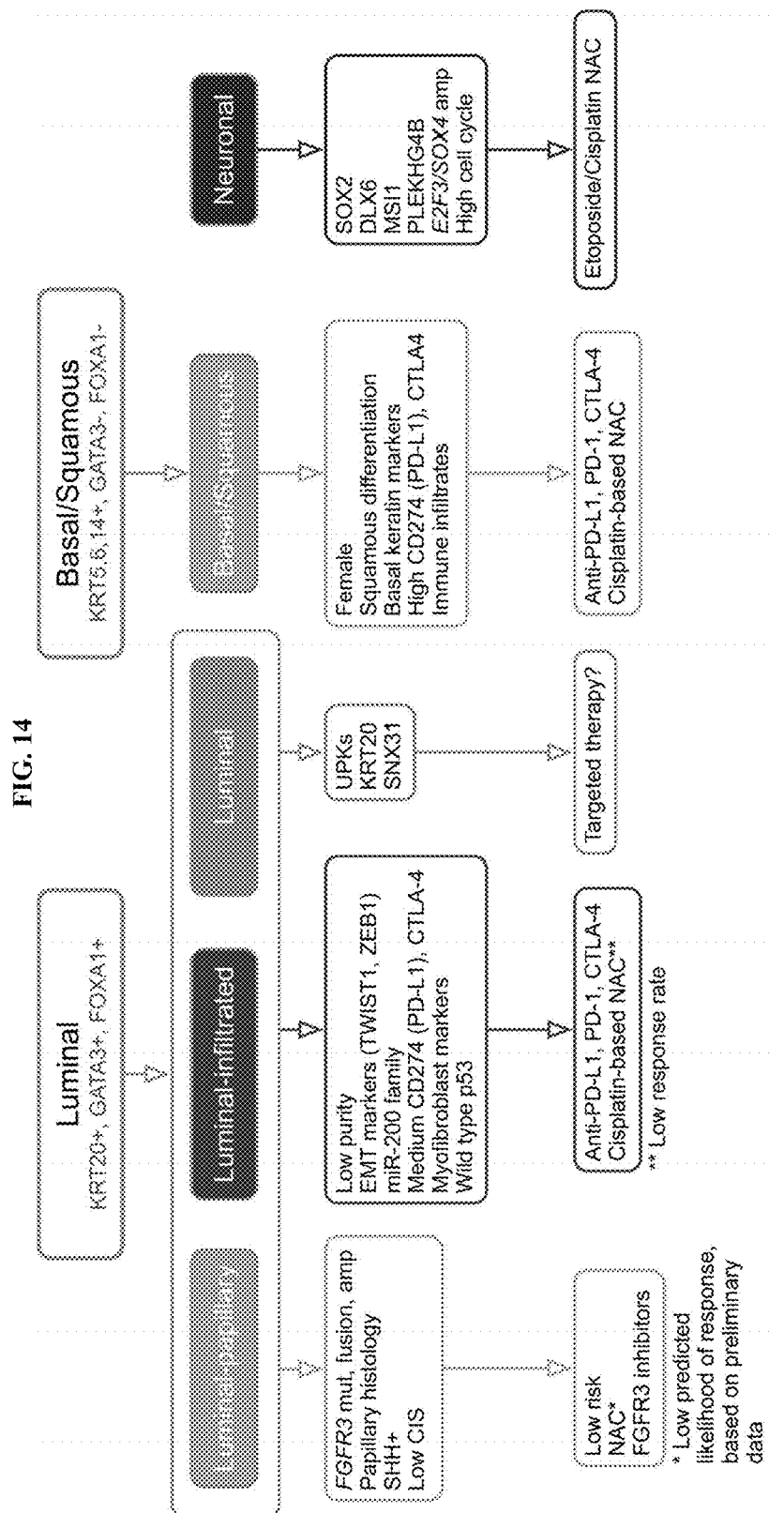

FIG. 14 is an image showing a proposed schema of expression-based, subtype-stratified therapeutic approach as a framework for prospective hypothesis testing in clinical trials. * For luminal-papillary cases, the low predicted likelihood of response is based on preliminary data from (Seiler et al., 2017). See Examples.

Figure 15:
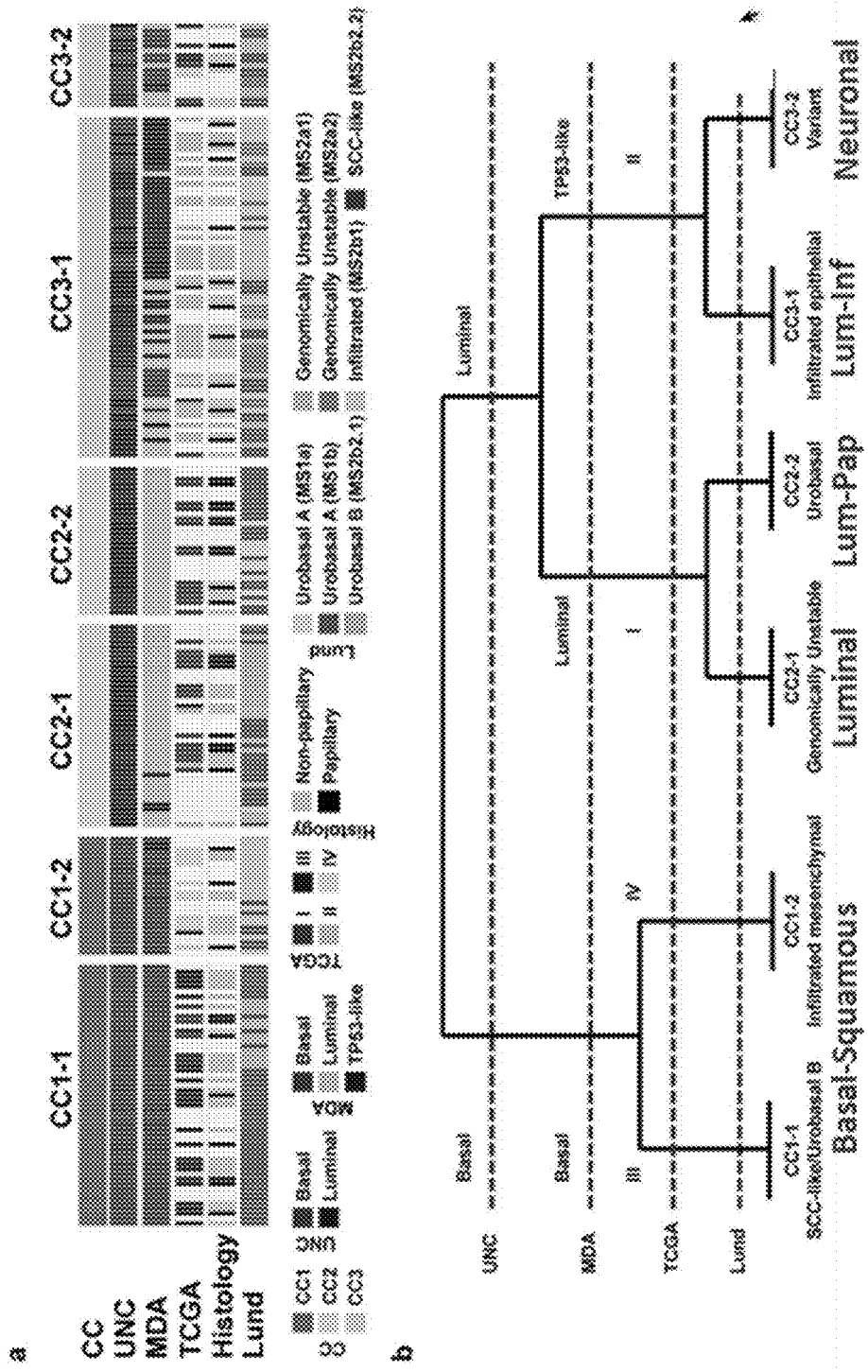

FIG. 15 is an image showing bladder expression subtype classifiers. The Lund classifier represents the five molecular subclasses of urothelial cell carcinoma disclosed in Sjodahl et al., 2012: Urobasal A, Genomically Unstable, Infiltrated, Urobasal B, and SCC-like. The UNC classifier represents the 47-gene classifier from the UNC group—luminal and basal (Damrauer et al., 2014). The MDA centroid-based classifier is based on the MD Anderson (MDA) group classification of three tumor classes: luminal, basal, and p53-like (Choi et al., 2014b). The TCGA I/II/III/IV classifier is based on a prior study (Cancer Genome Atlas Research Network (2014a) Nature 507, 315-322). The TCGA classifier, located at the bottom of FIG. 15, is based on the present disclosure of five expression subtypes: Luminal, Luminal-infiltrated, Basal-squamous, Neuronal, Luminal-Papillary. "CC" refers to consensus clusters.

Figure 16:
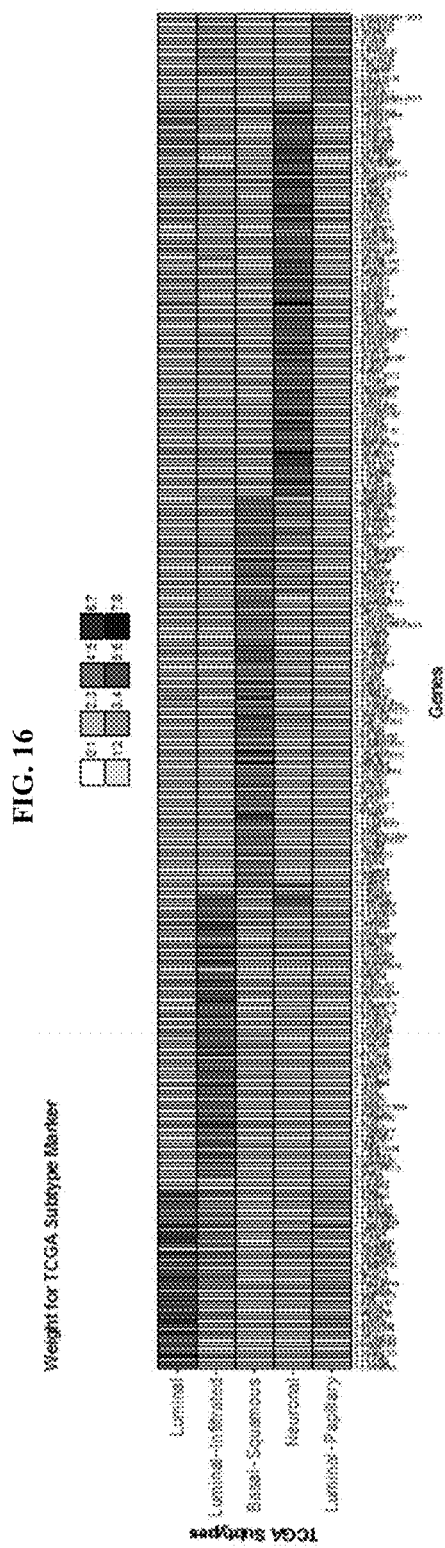

FIG. 16 is an image showing marker selection for TCGA subtype classifier.

Figure 17:
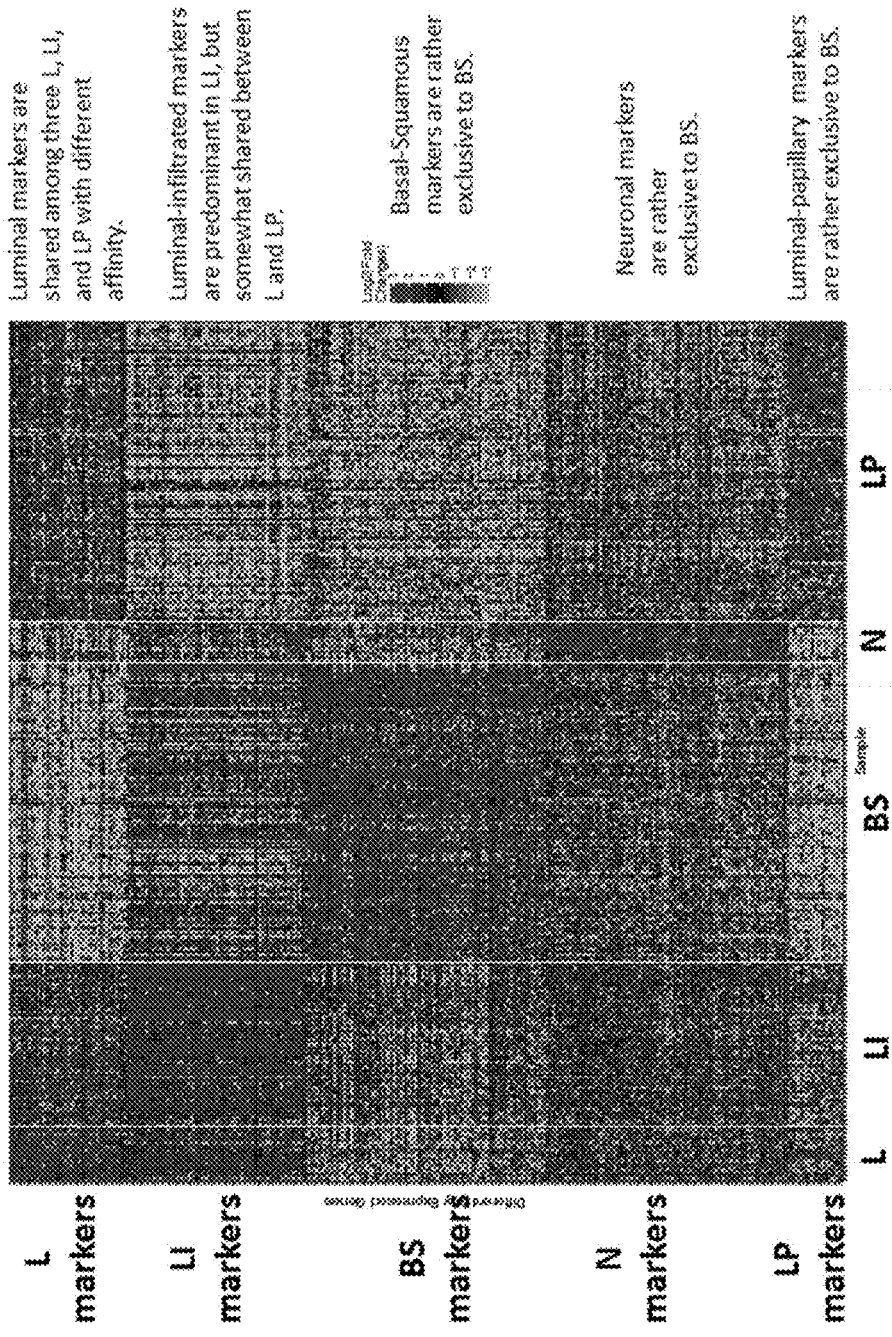

FIG. 17 is an image of a heatmap showing expression of TCGA samples in selected markers.

FIG. 18 is an image showing comparison to other markers.

Figure 19:
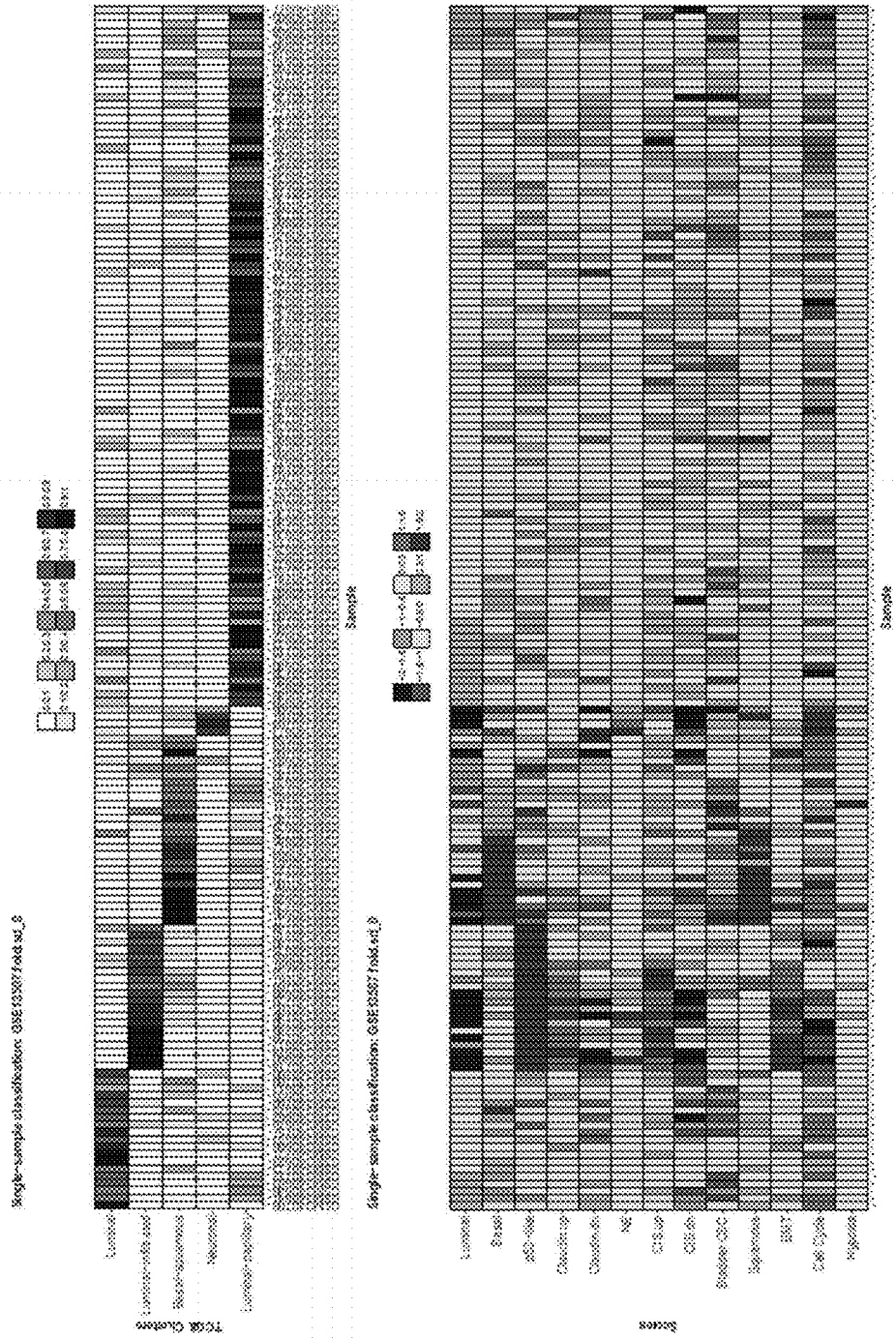

FIG. 19 is an image showing application to Gene Expression Omnibus (GEO) Data Set, GSE13507 (103 non-muscle invasive bladder cancer (NMIBC)+62 MIBC).

Figure 20:
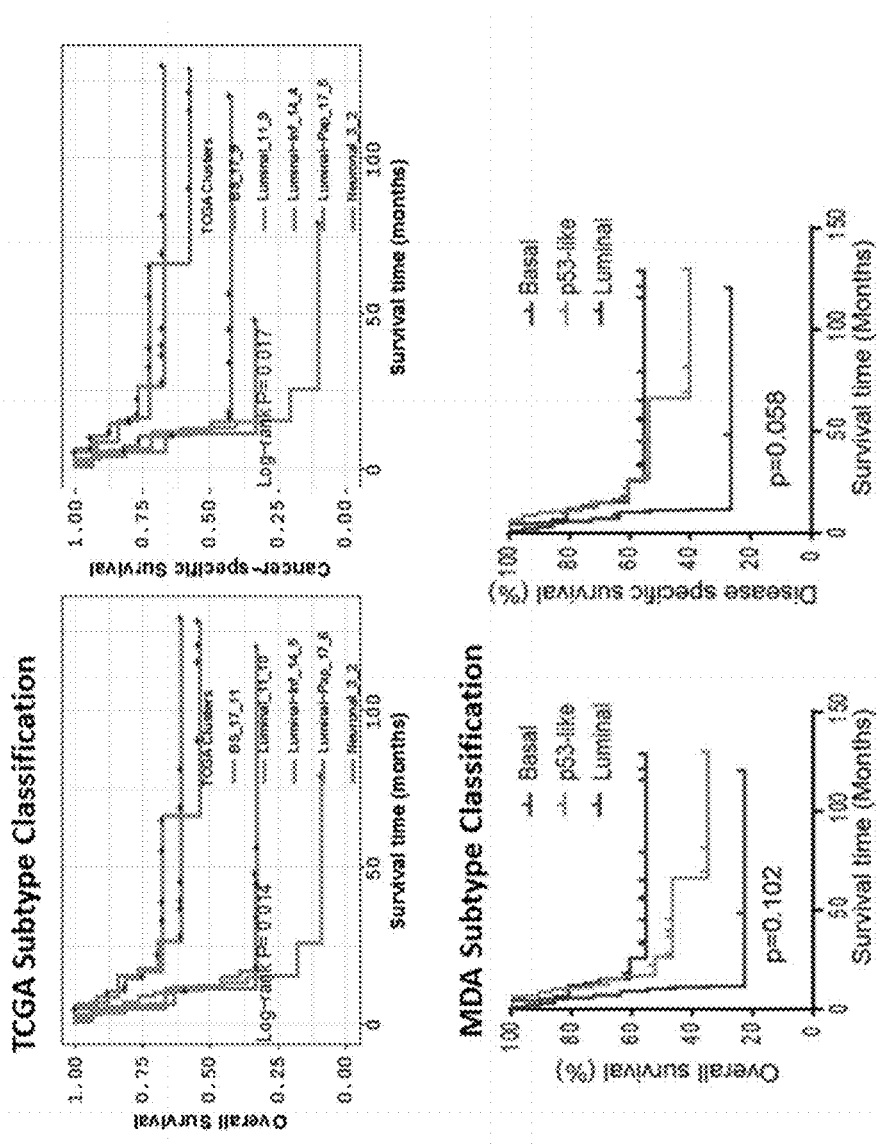

FIG. 20 are graphs showing the prognostic significance of TCGA expression subtype classification.

Figure 21:
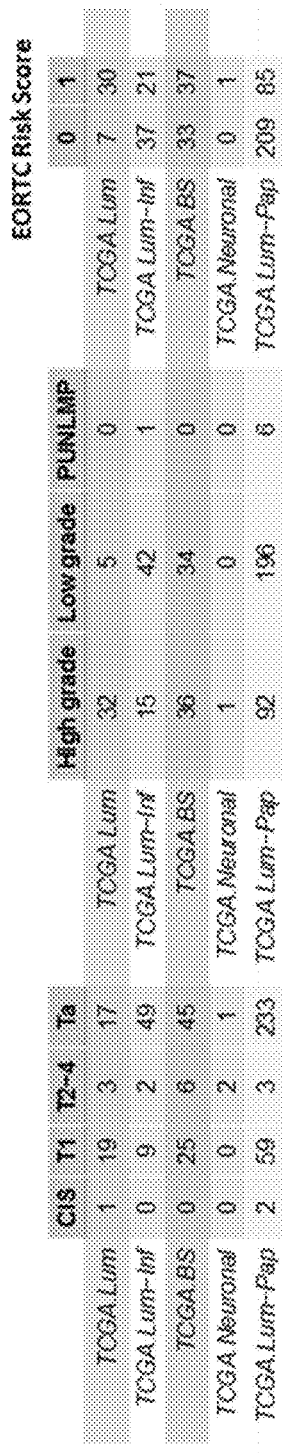

FIG. 21 shows three panels consisting of two graphs (FIG. 21 Panel A, FIG. 21 Panel B), and a table (FIG. 21 Panel C), showing progression free survival (457 NMIBC W/O Neuronal Samples). The TCGA Luminal samples in NMIC is associated with the poorest survival and significantly enriched in T1 vs. Ta, high grade vs. low grade, high-EORTC-risk vs low risk. Basa-squamous is intermediate. Luminal-pap and Luminal-inf are associated with a better survival.

Figure 22:
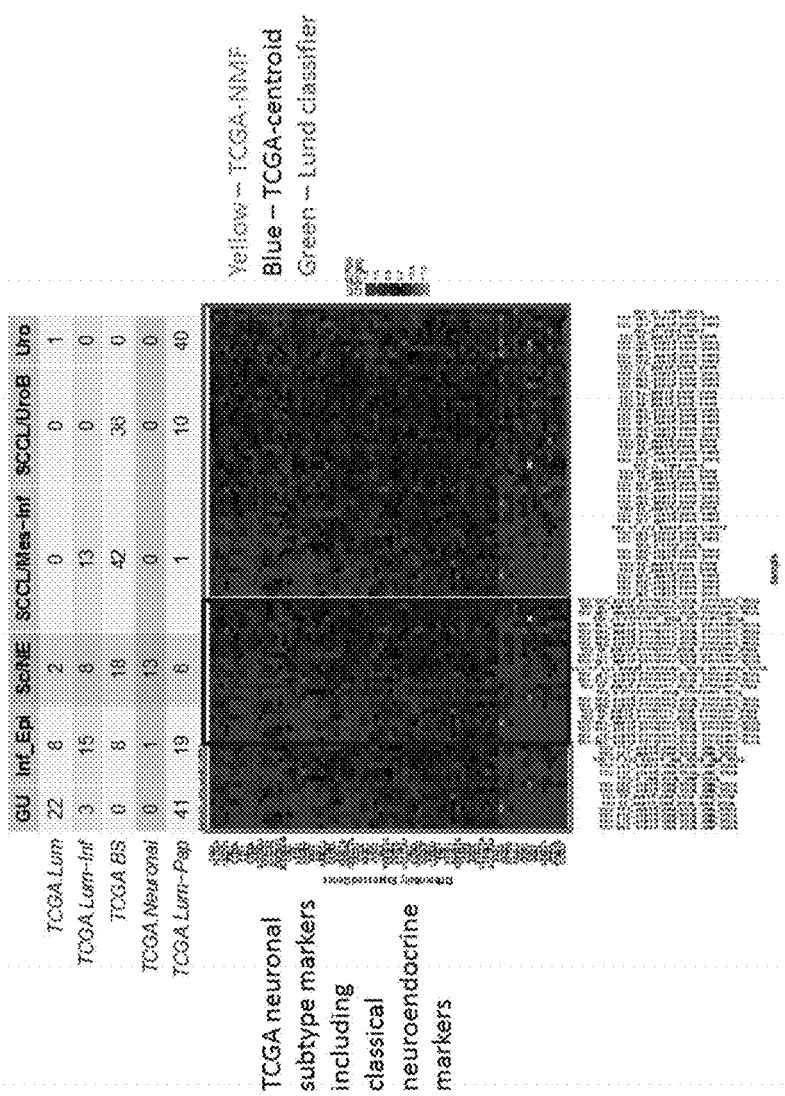

FIG. 22 is a table and heatmap showing the TCGA classifier more specific to neuronal subtypes.

Figure 23:
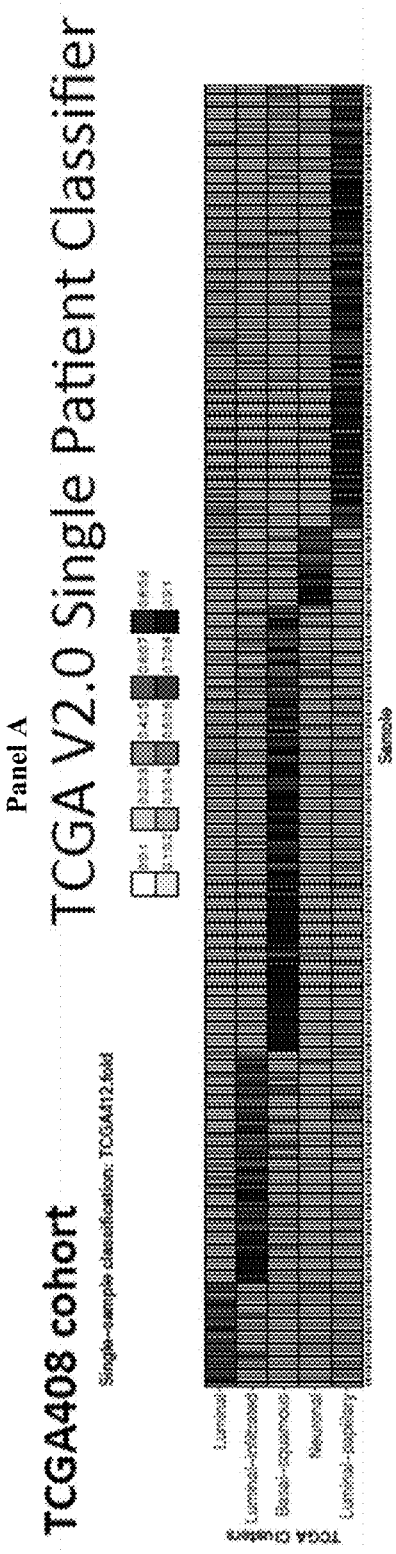
Figure 23:
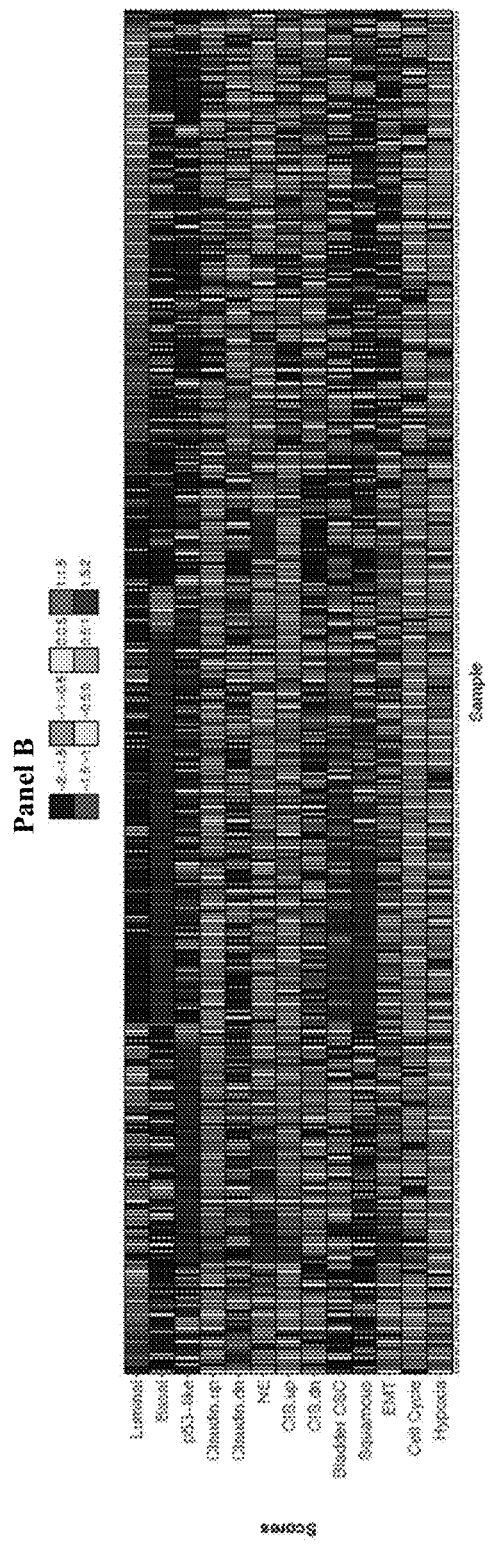

FIG. 23 shows three panels consisting of two graphs (FIG. 23 Panel A, FIG. 23 Panel B) and a table (FIG. 23 Panel C) of the TCGA V2.0 Single Patient Classifier.

Figure 24:
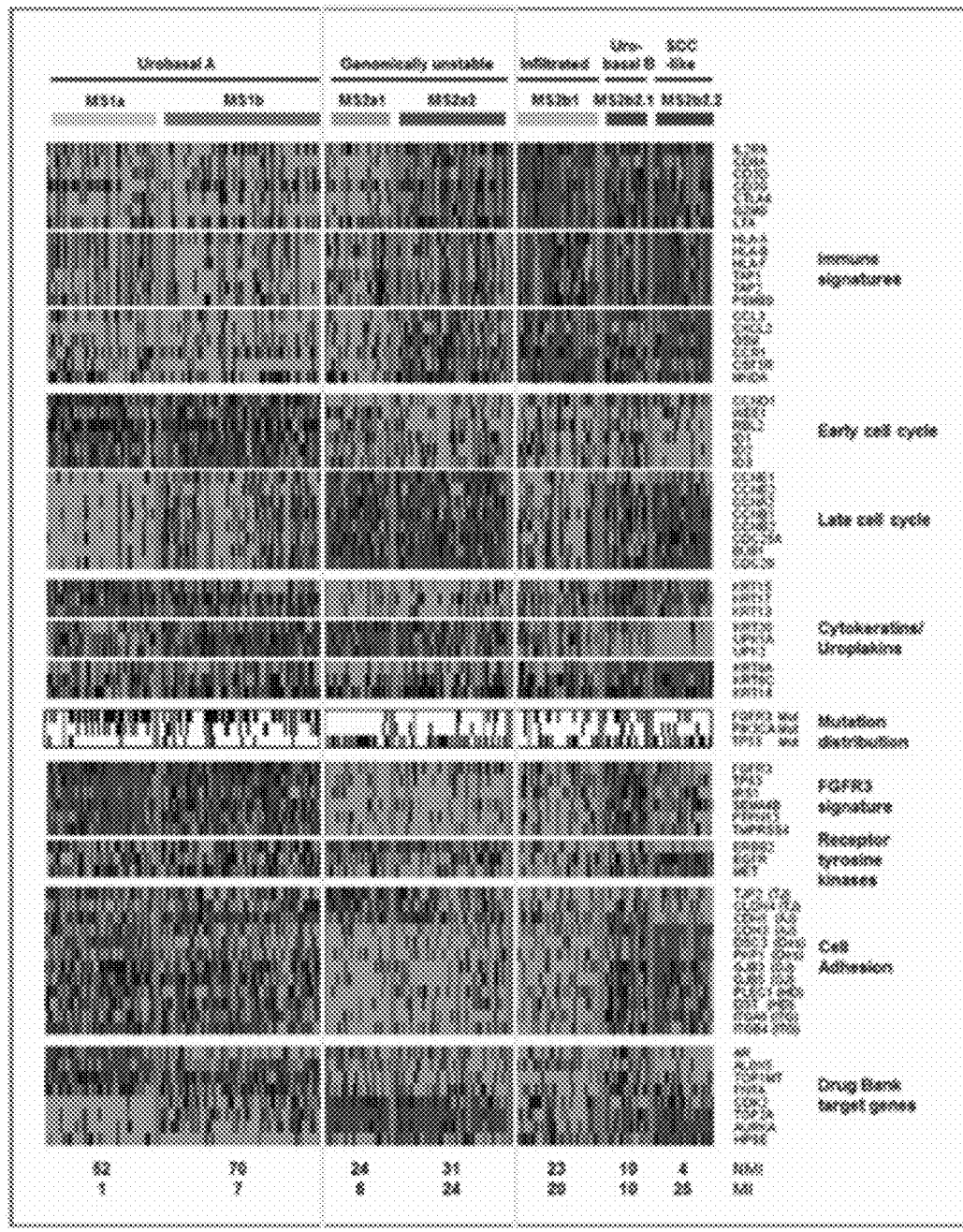

FIG. 24 shows three panels consisting of two tables (FIG. 24 Panel A, FIG. 24 Panel B) and a graph (FIG. 24 Panel C) depicting TCGA Luminal is corresponding to Lund-GU.

Figure 25:
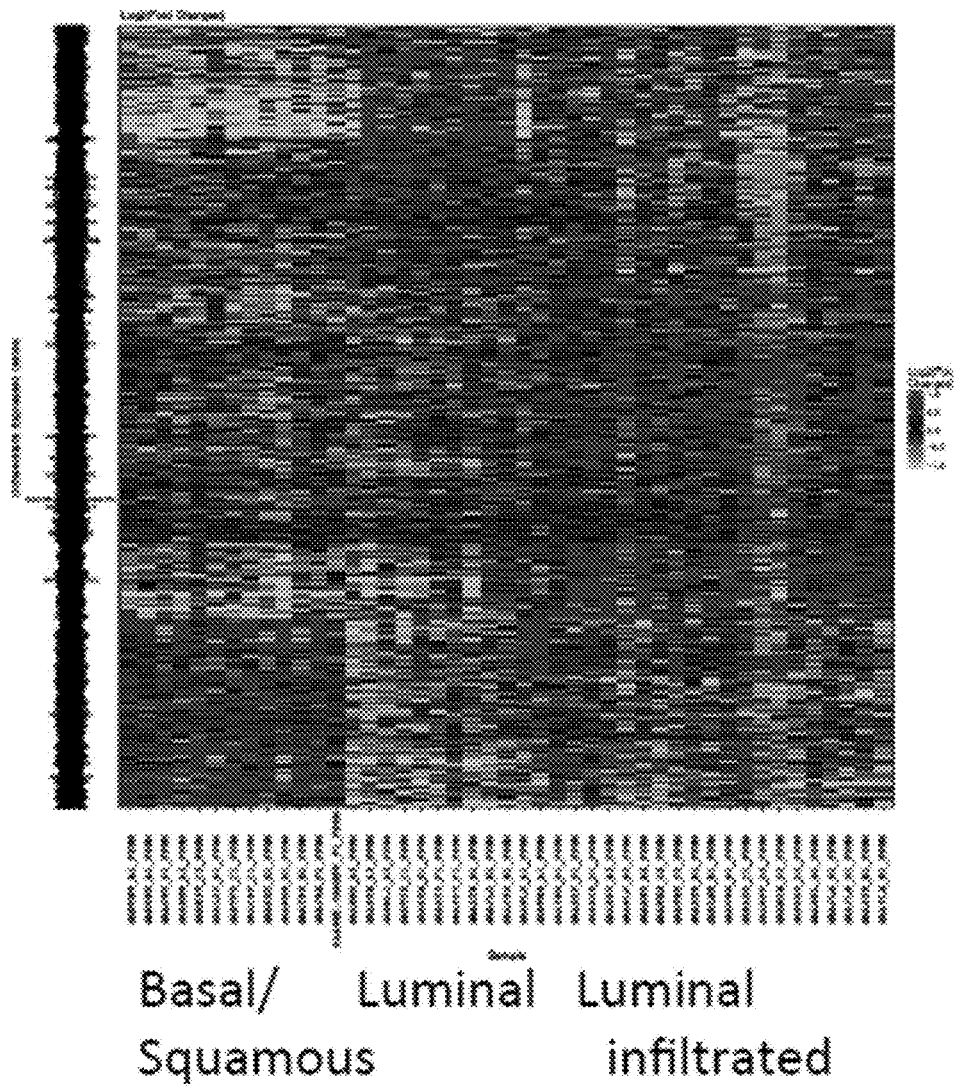
Figure 25:
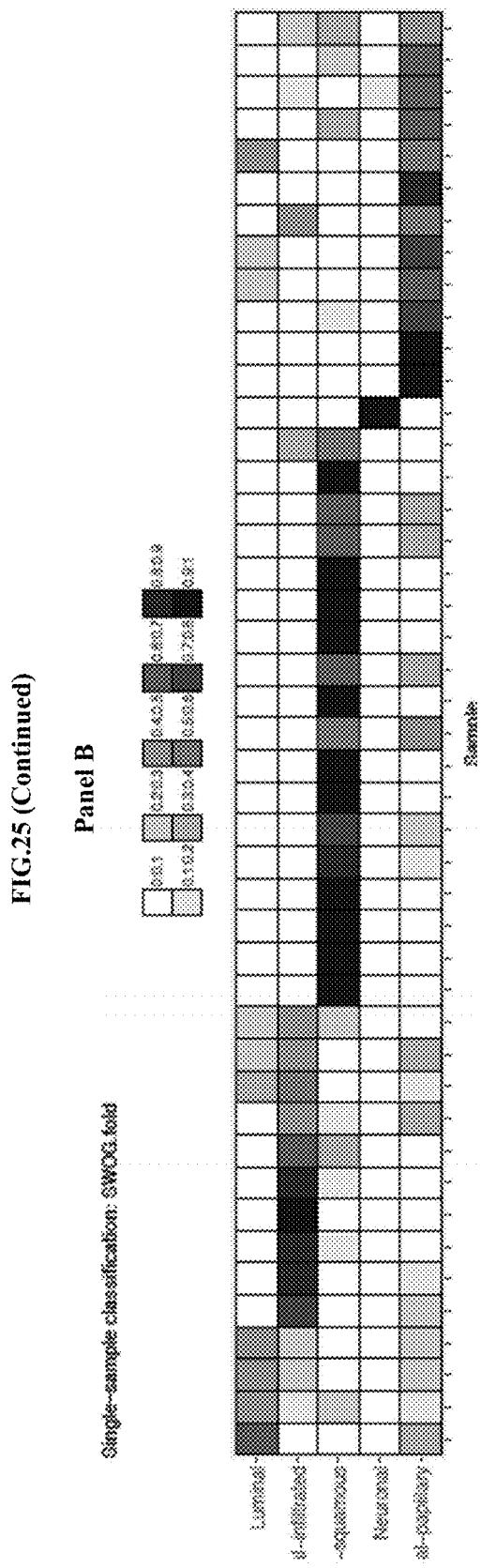
Figure 25:
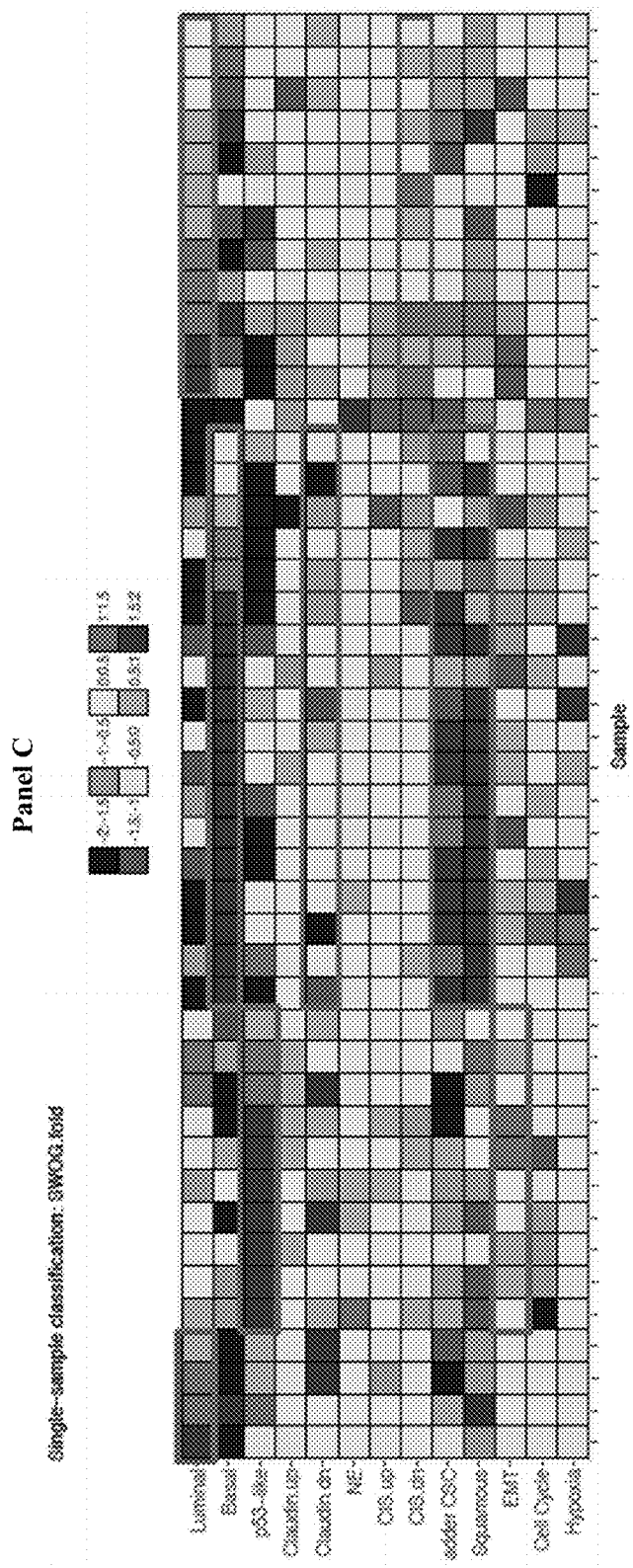

FIG. 25 shows three panels consisting of three graphs (Panel A, Panel B, and Panel C) depicting unsupervised NMF clustering (n=45) (Panel A) and the SWOG S-1011 Single Patient Classifier.

Figure 26:
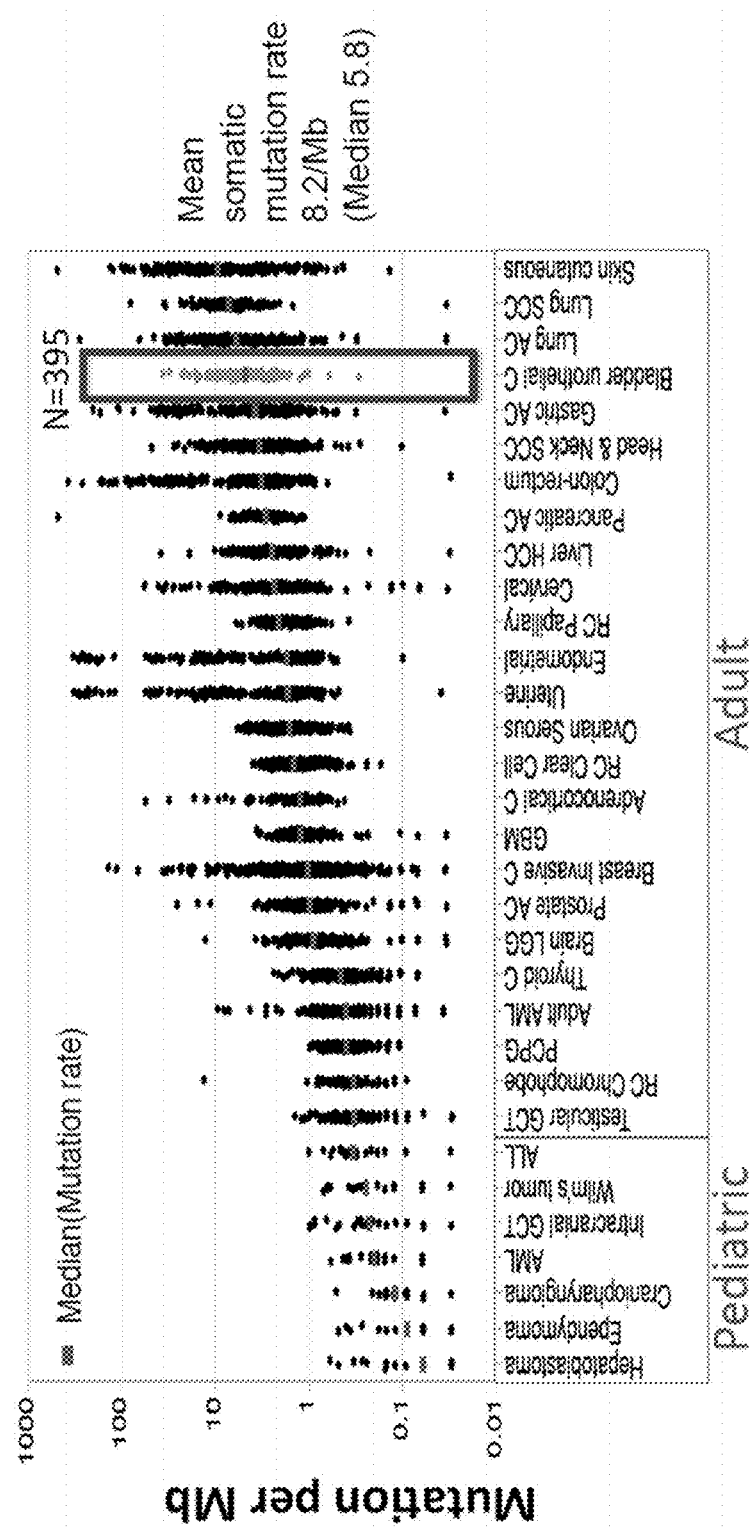

FIG. 26 is a graph showing bladder cancer somatic mutation rate.

Figure 27:
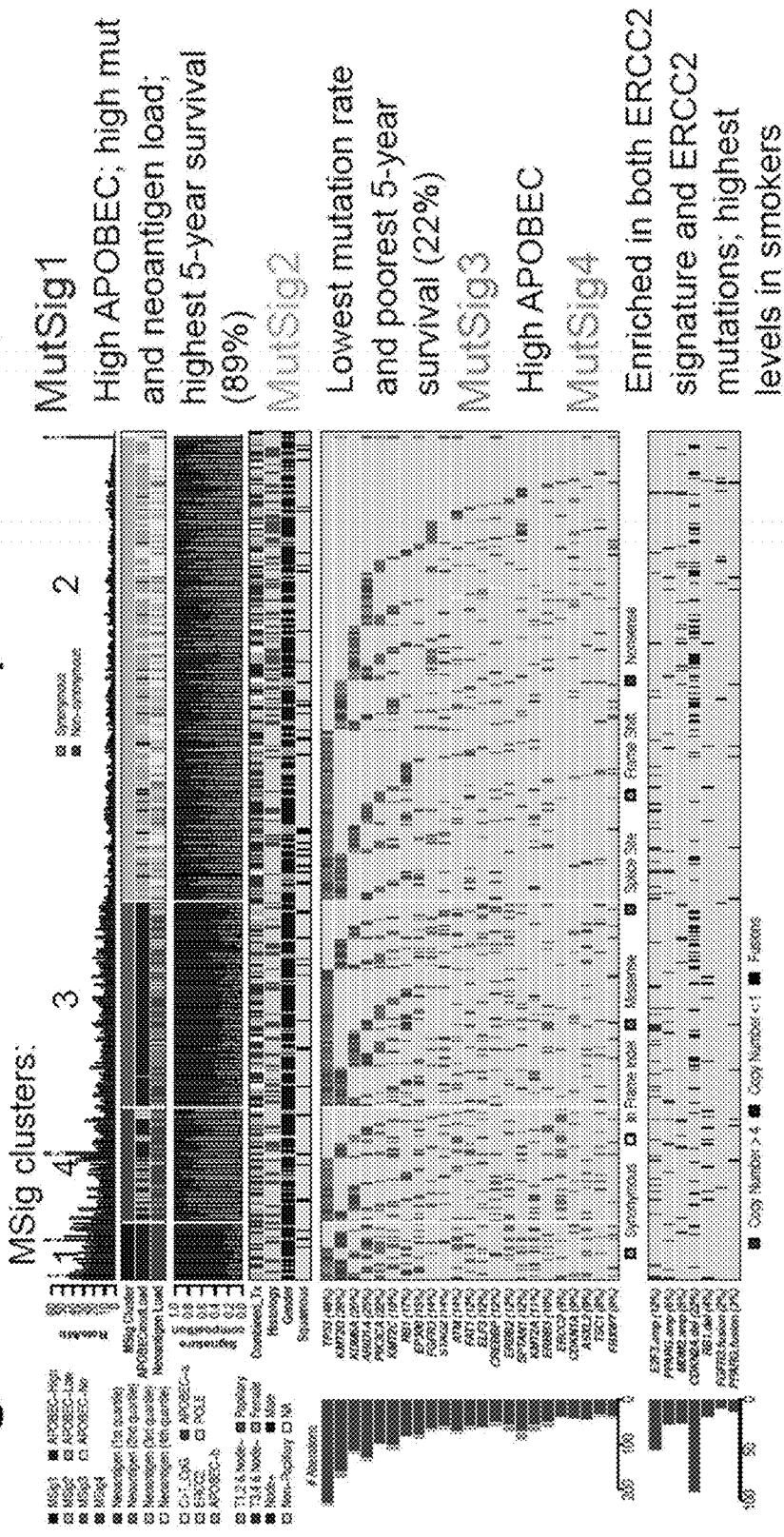

FIG. 27 is a graph showing integrated mutation and amplifications/deletions.

Figure 28:
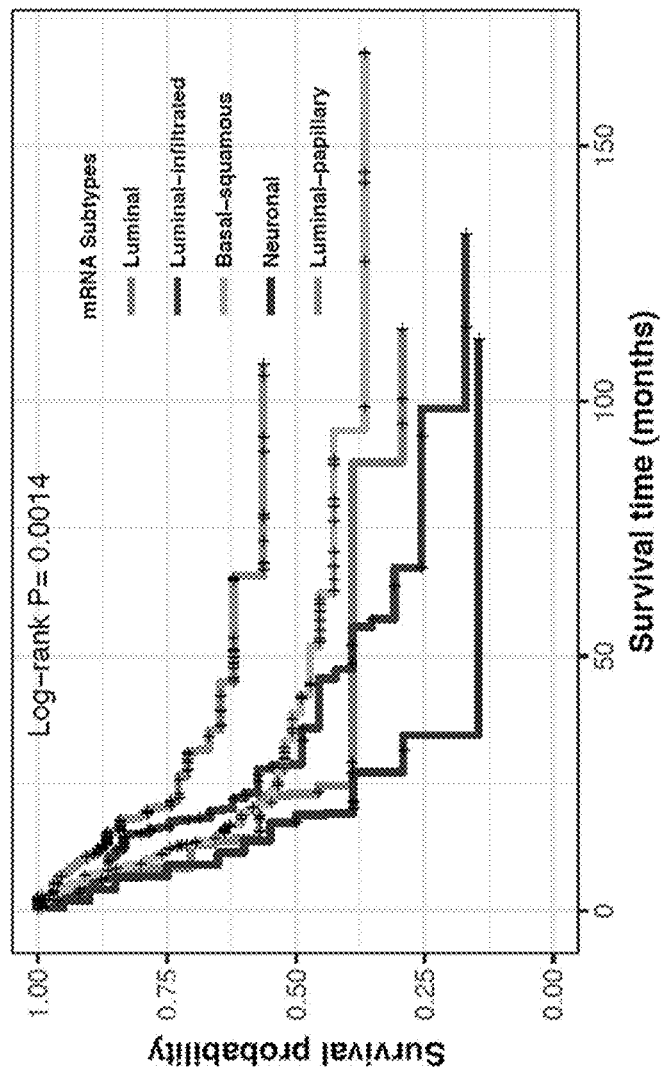

FIG. 28 is a graph showing molecular subtypes and outcome.

Figure 29:
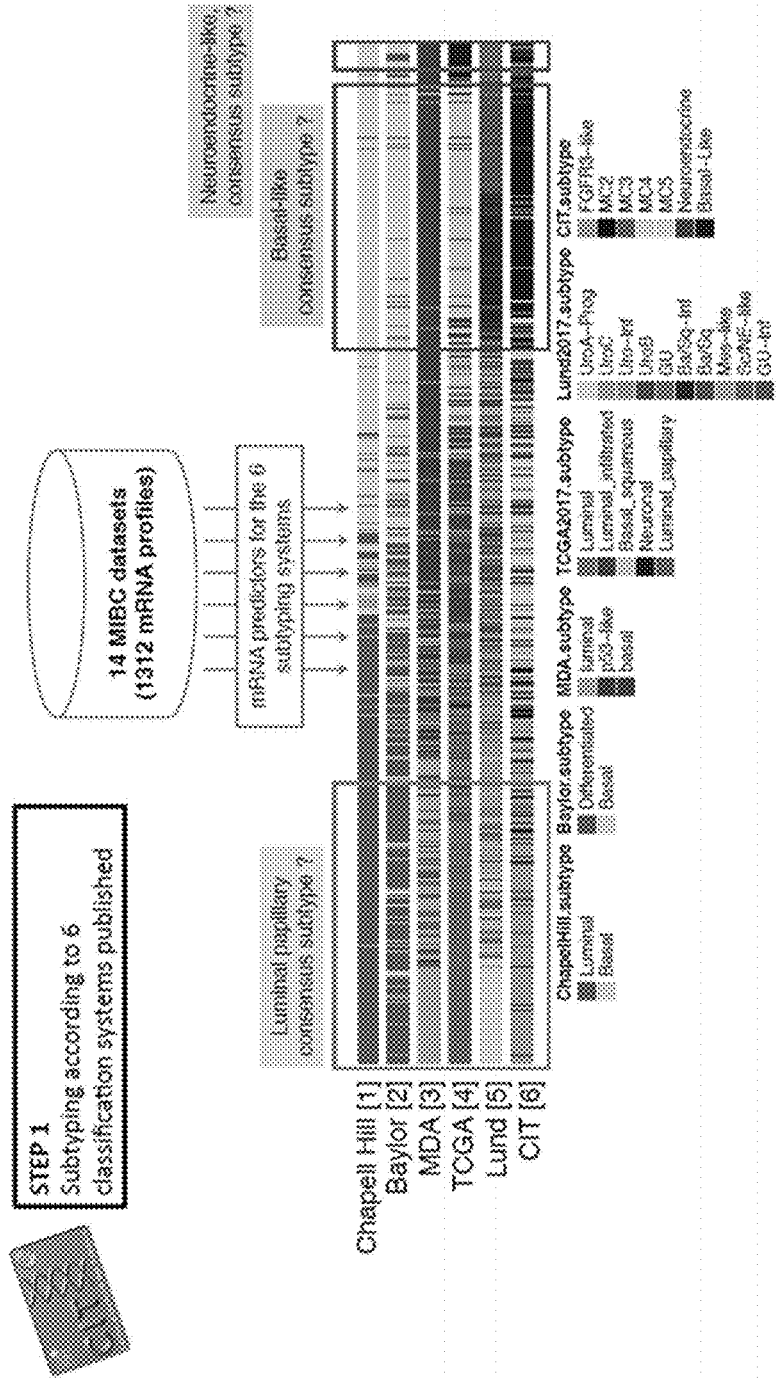

FIG. 29 is an image showing subtyping according to 6 classification systems as well as the classification system disclosed herein.

Figure 3:
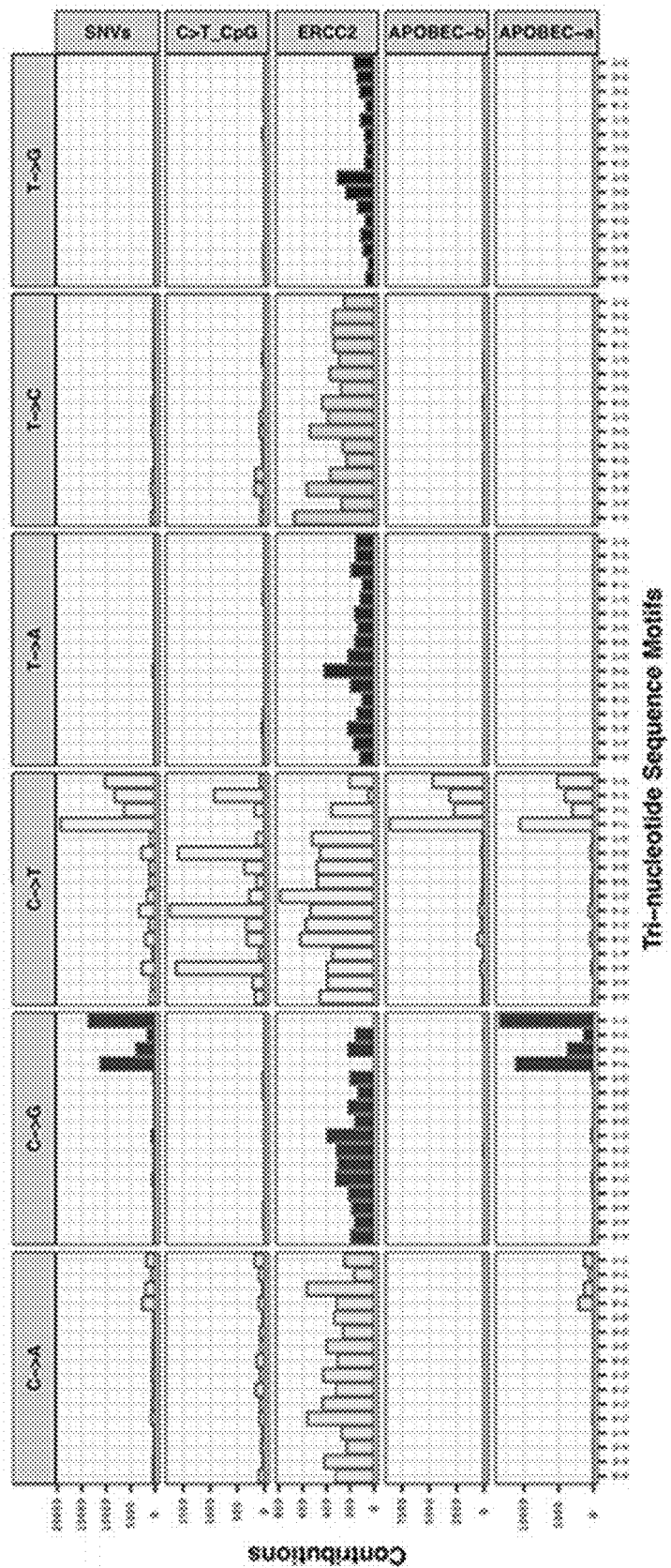
FIGS. 3A-3I are graphs and images showing somatic DNA mutational signatures and rearrangements. Related to FIGS. 2A and 2B.
Figure 3:
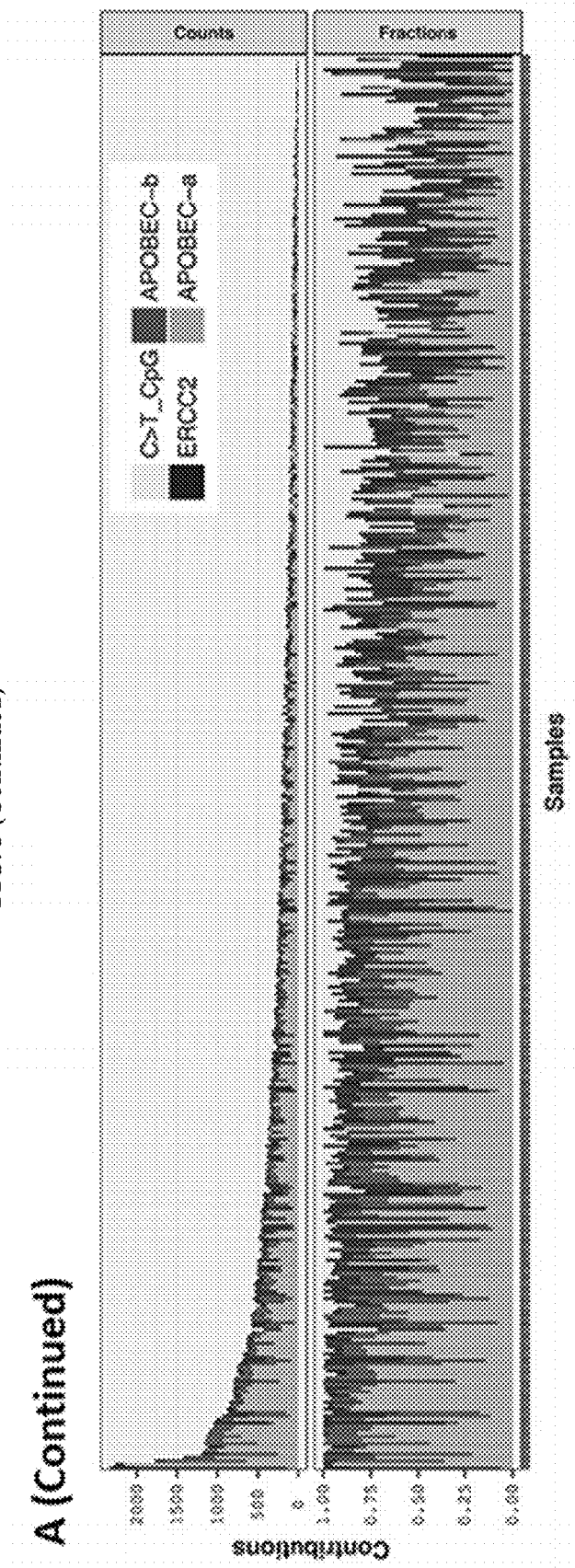
Figure 3:
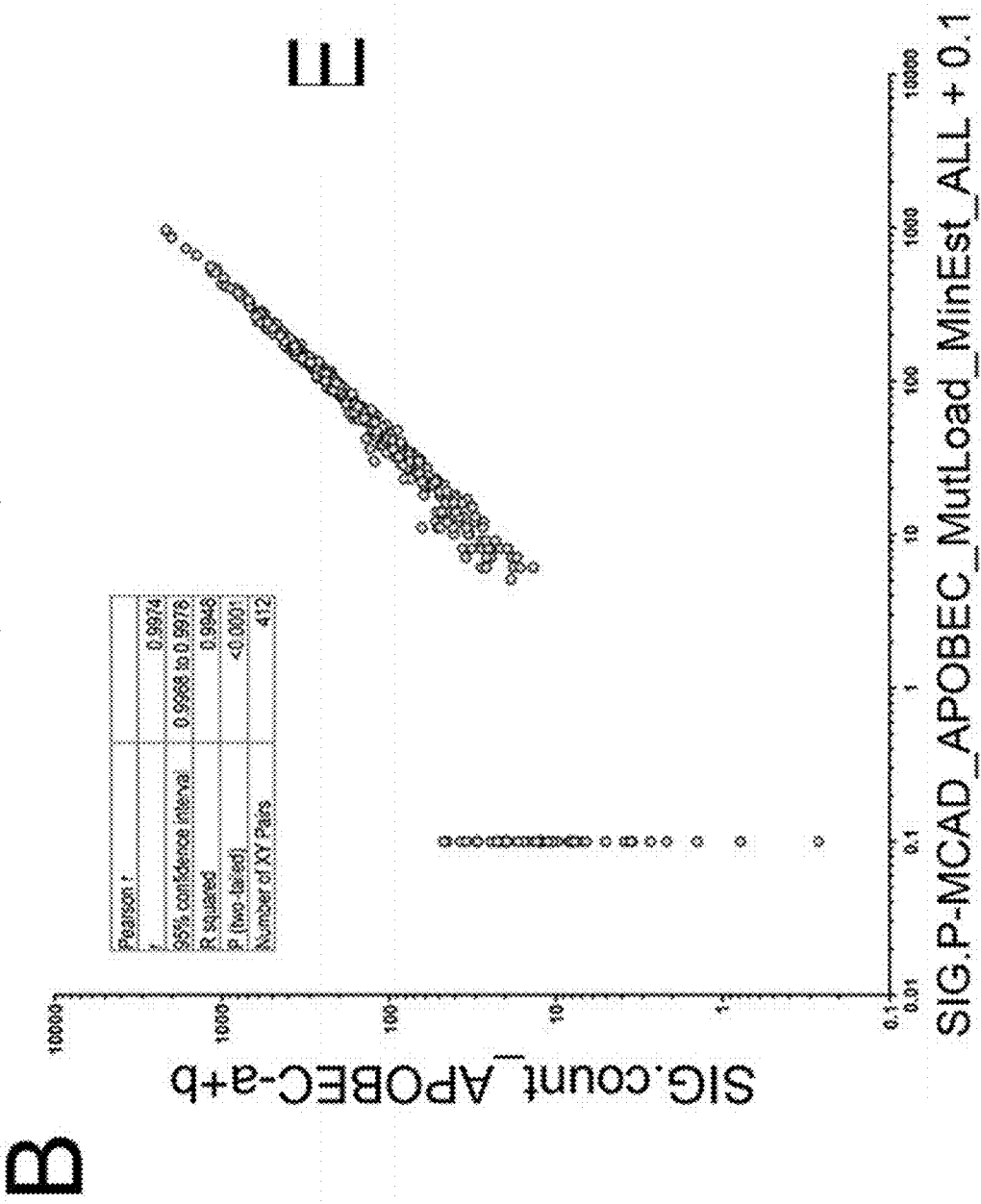
Figure 3:
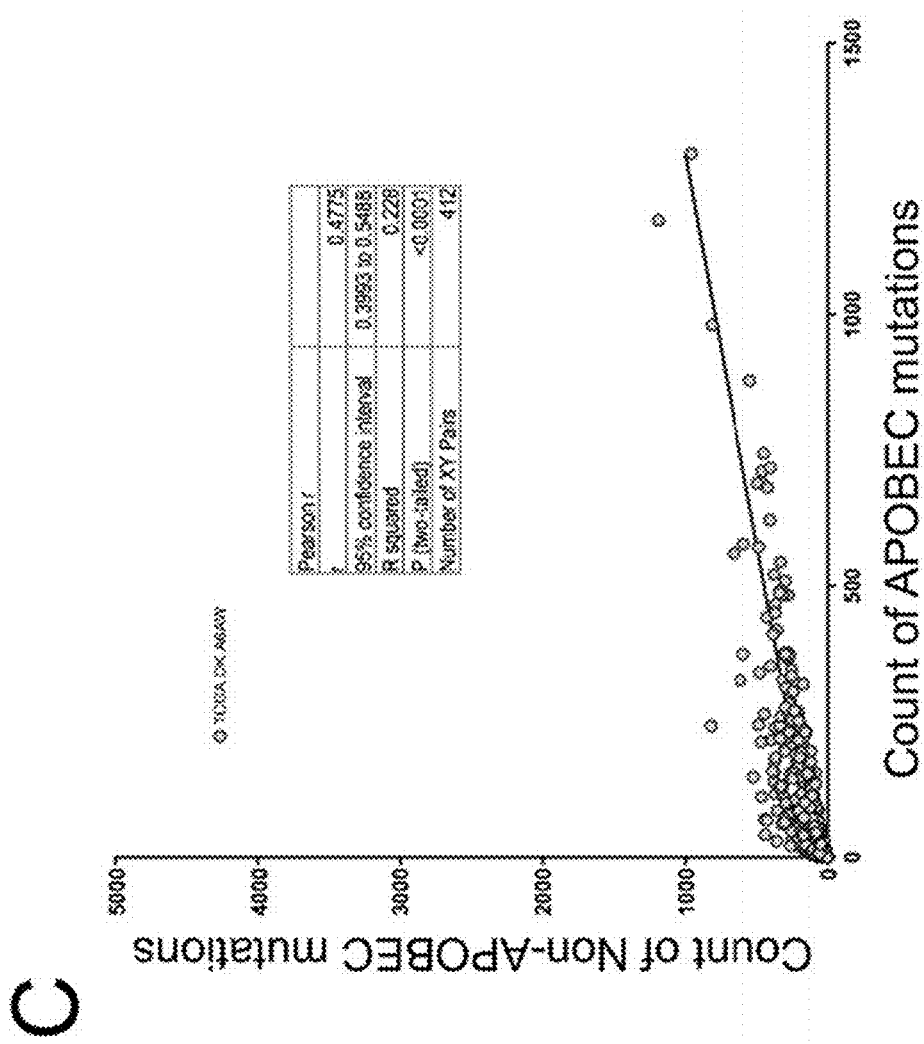
Figure 3:
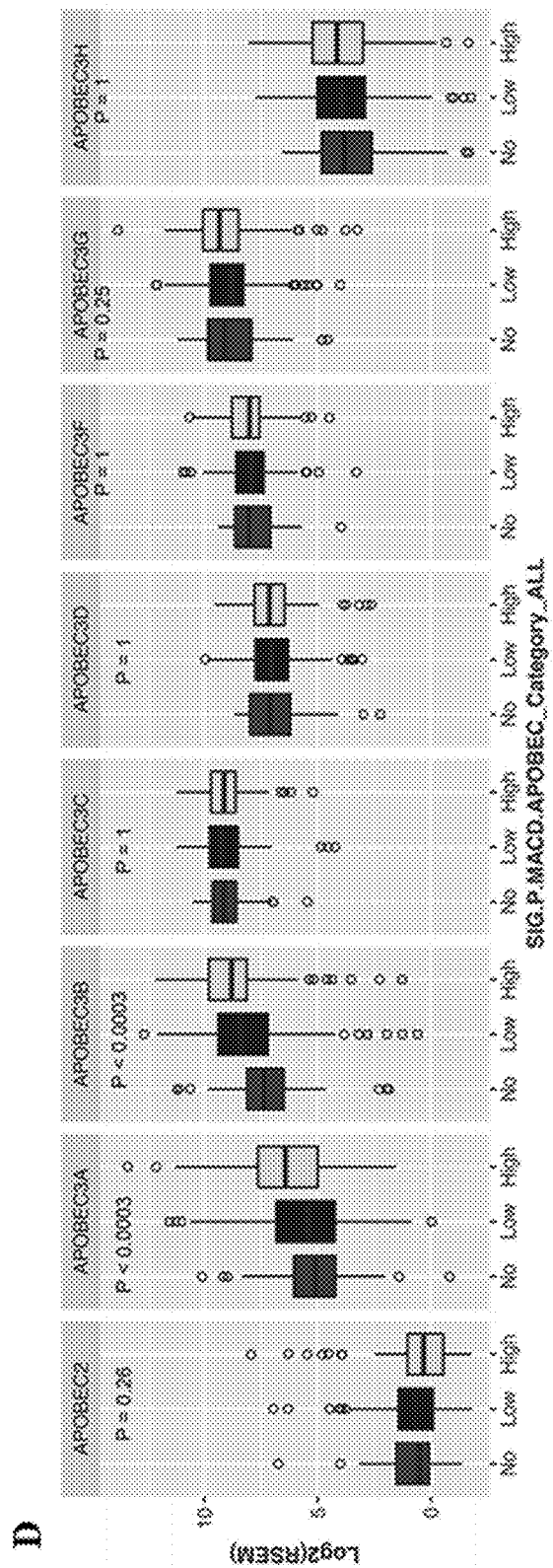
Figure 3:
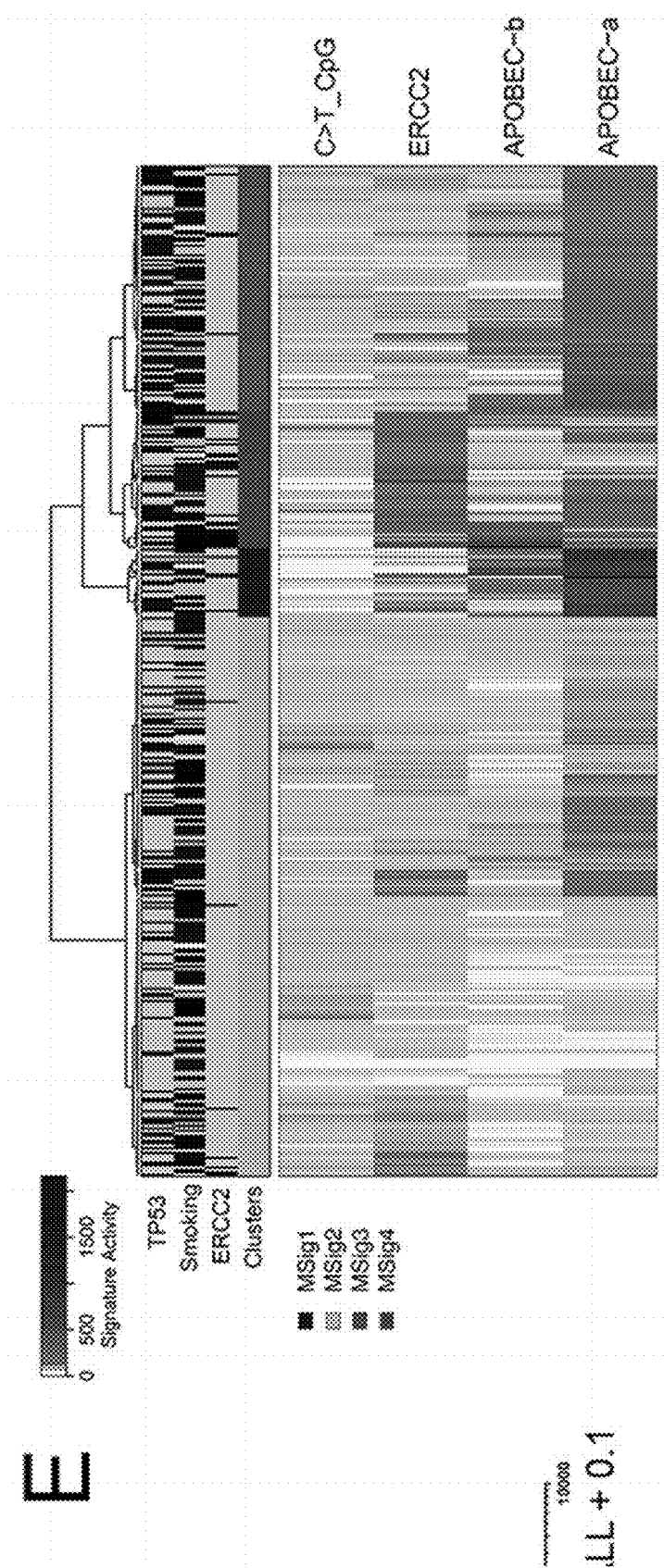
Figure 3:
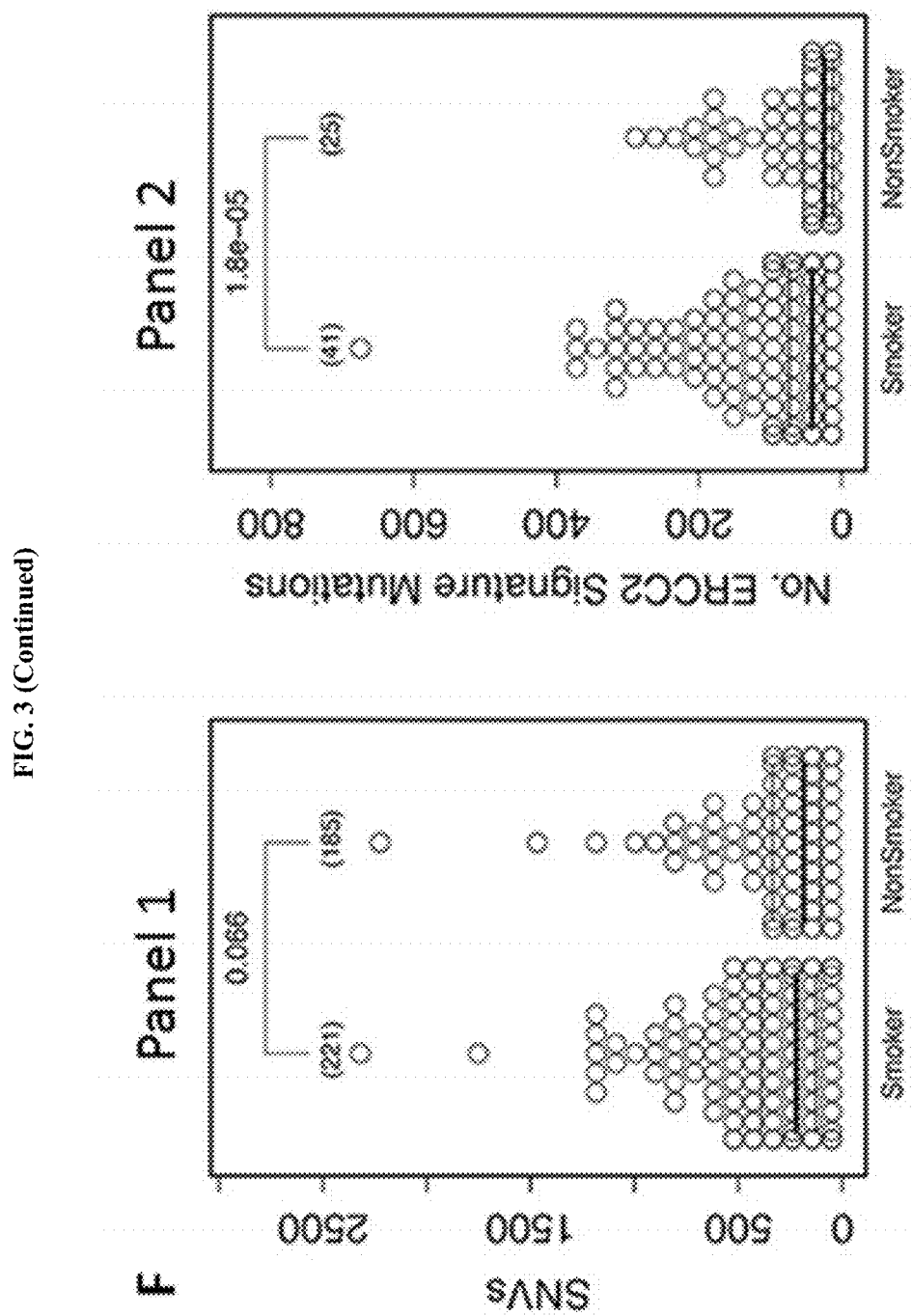
Figure 3:
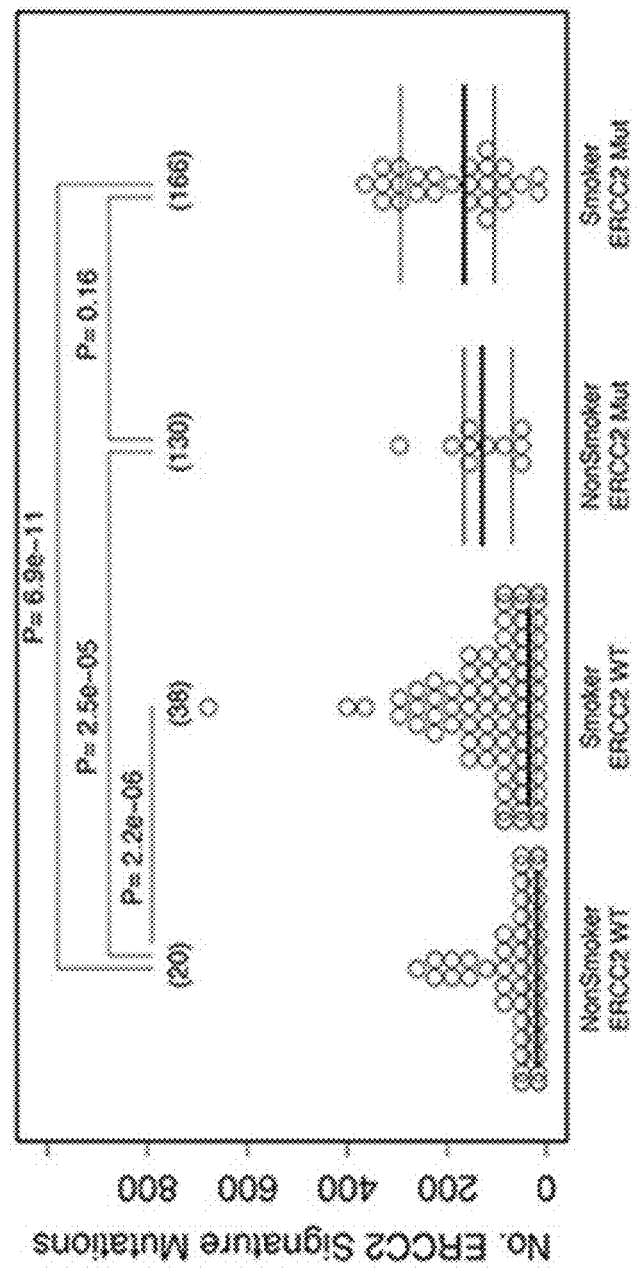
Figure 3:
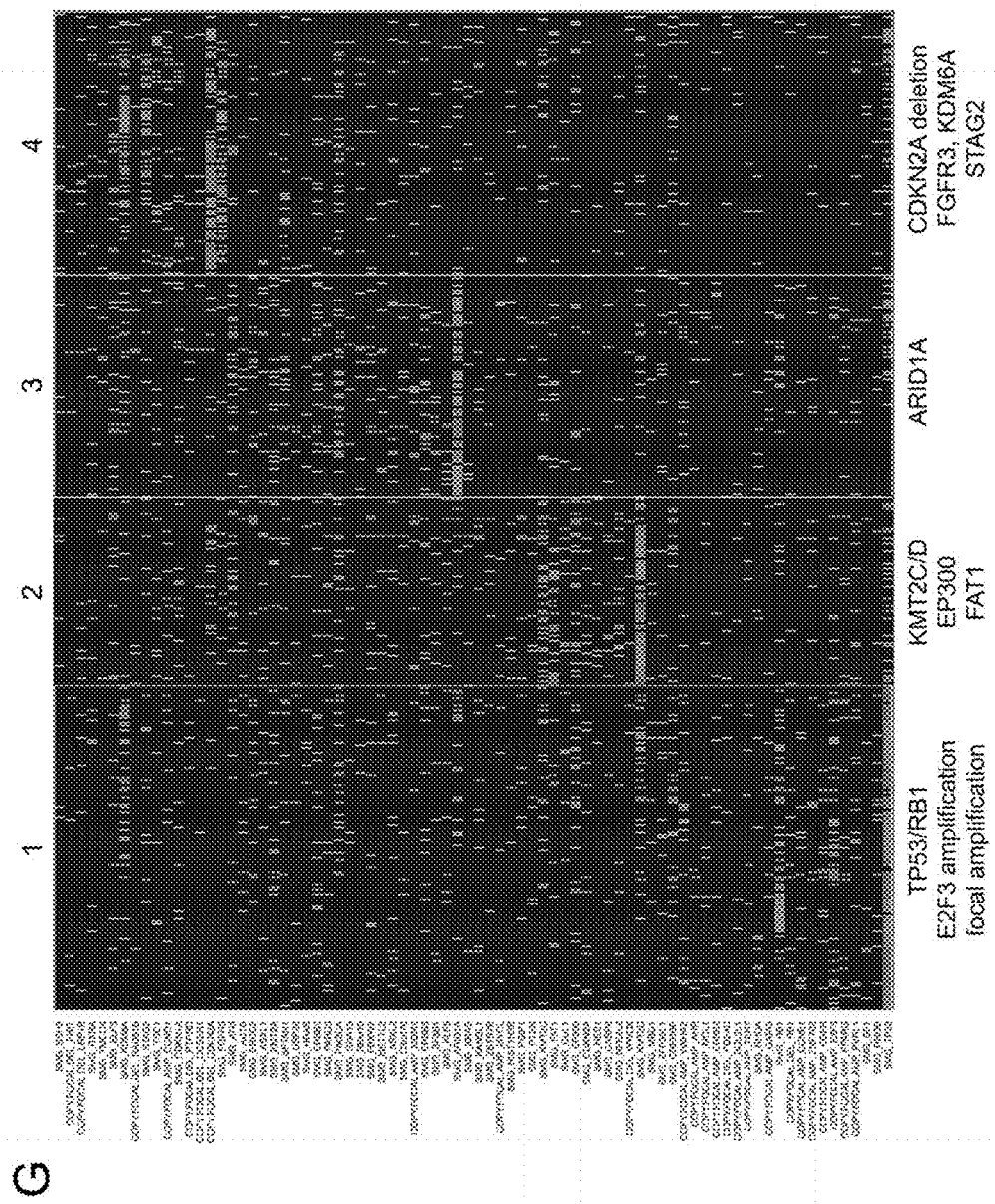
Figure 3:
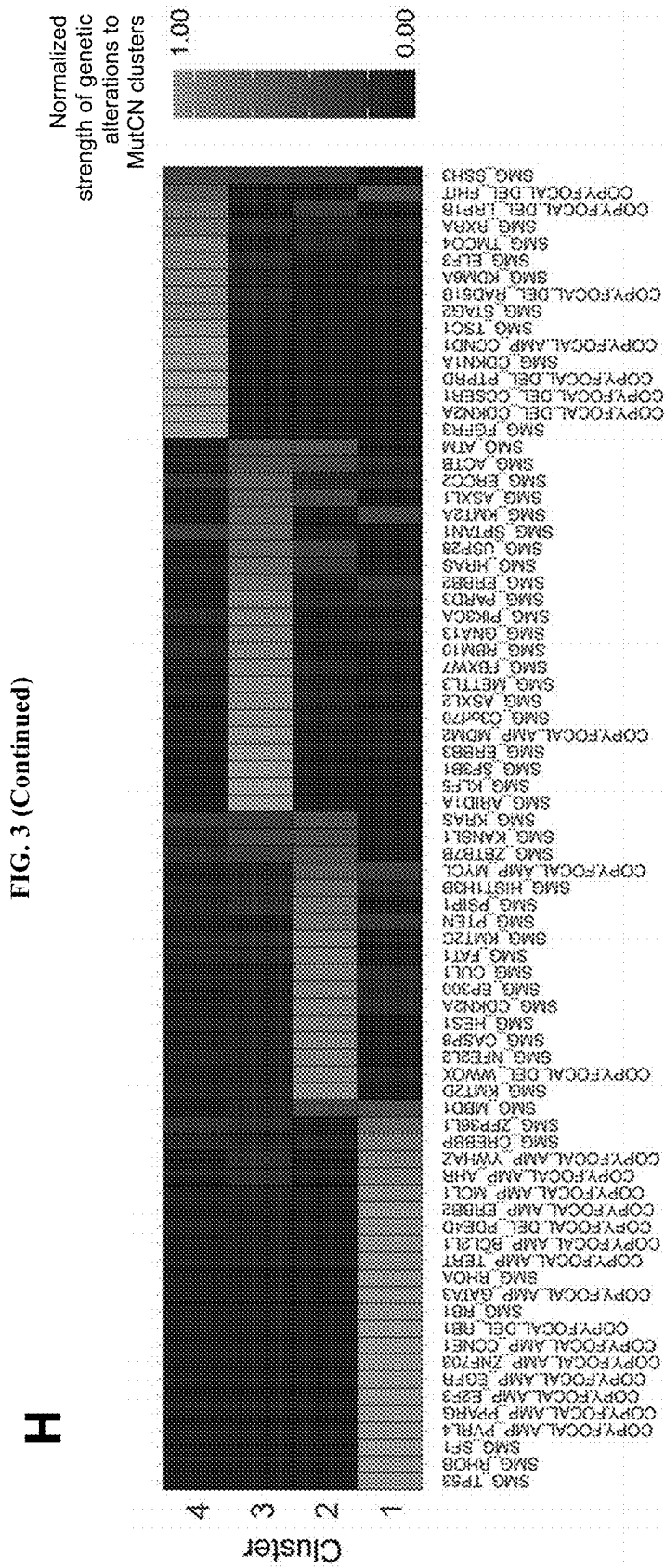
Figure 3:
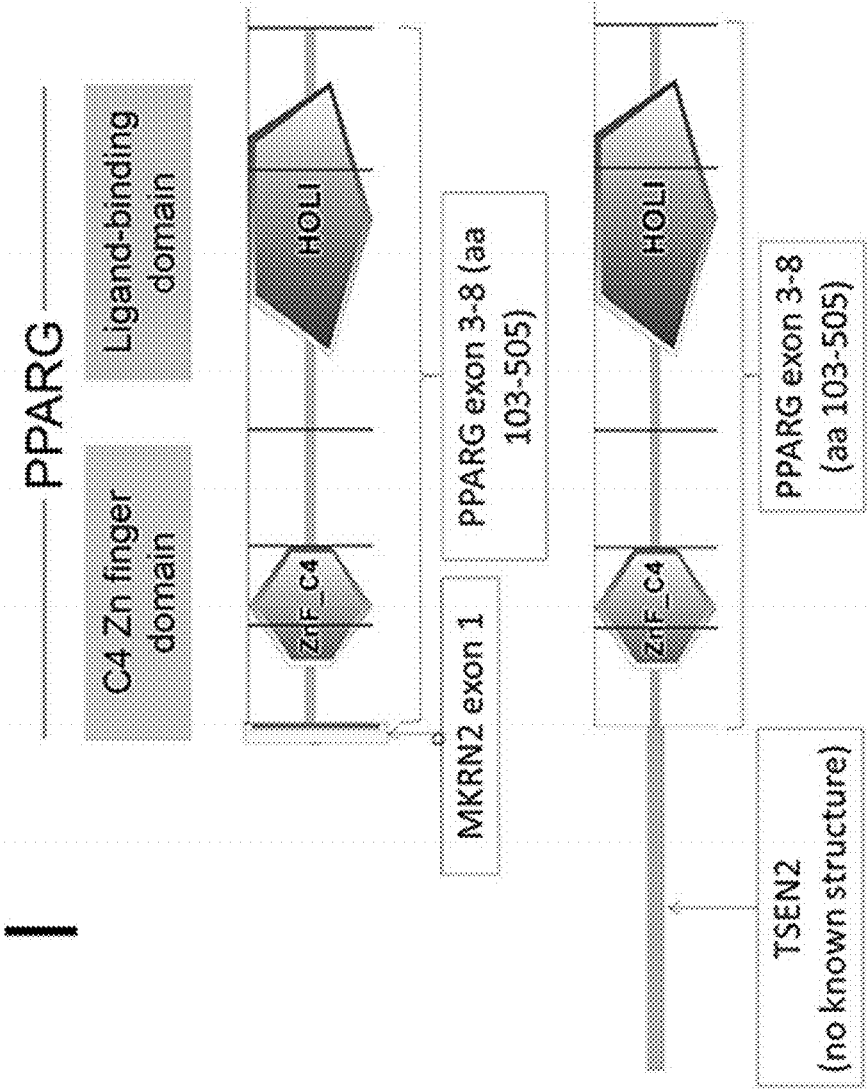
Figure 3:
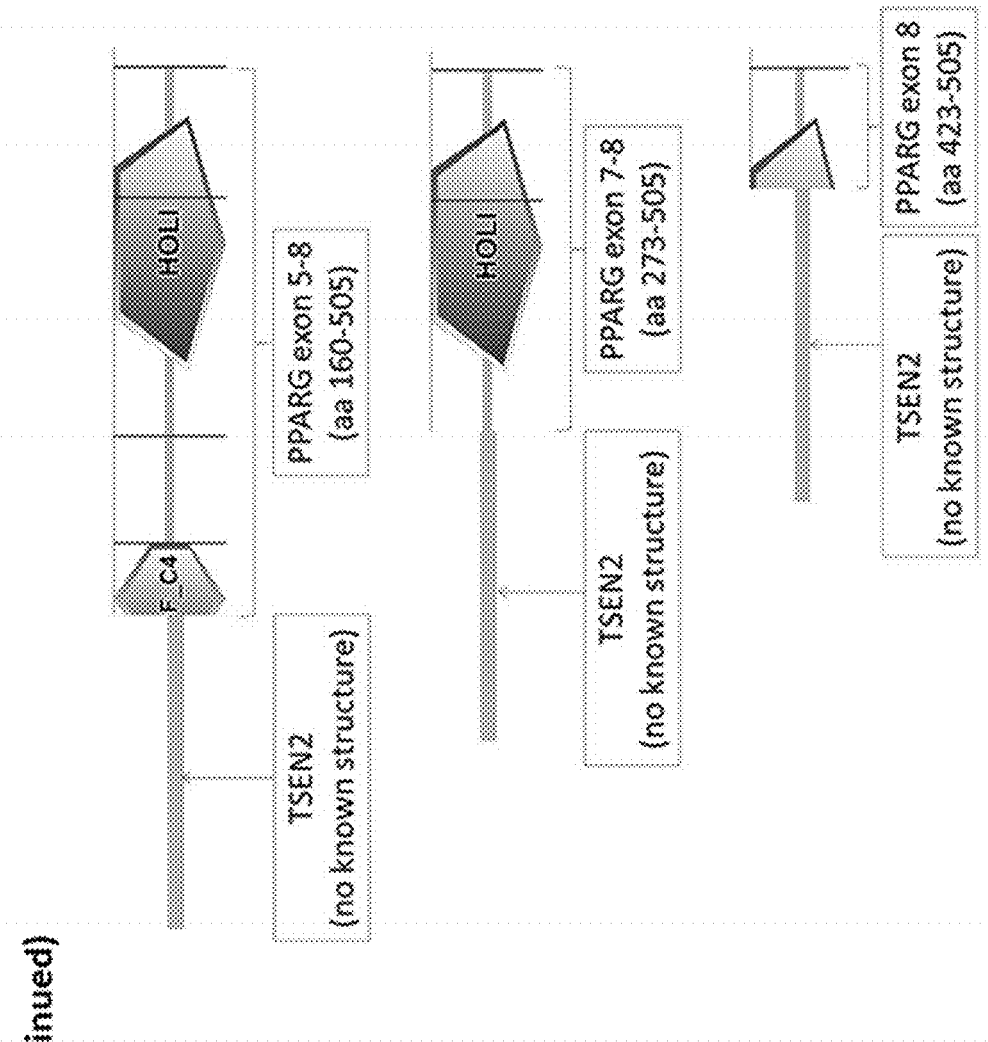
Figure 30:
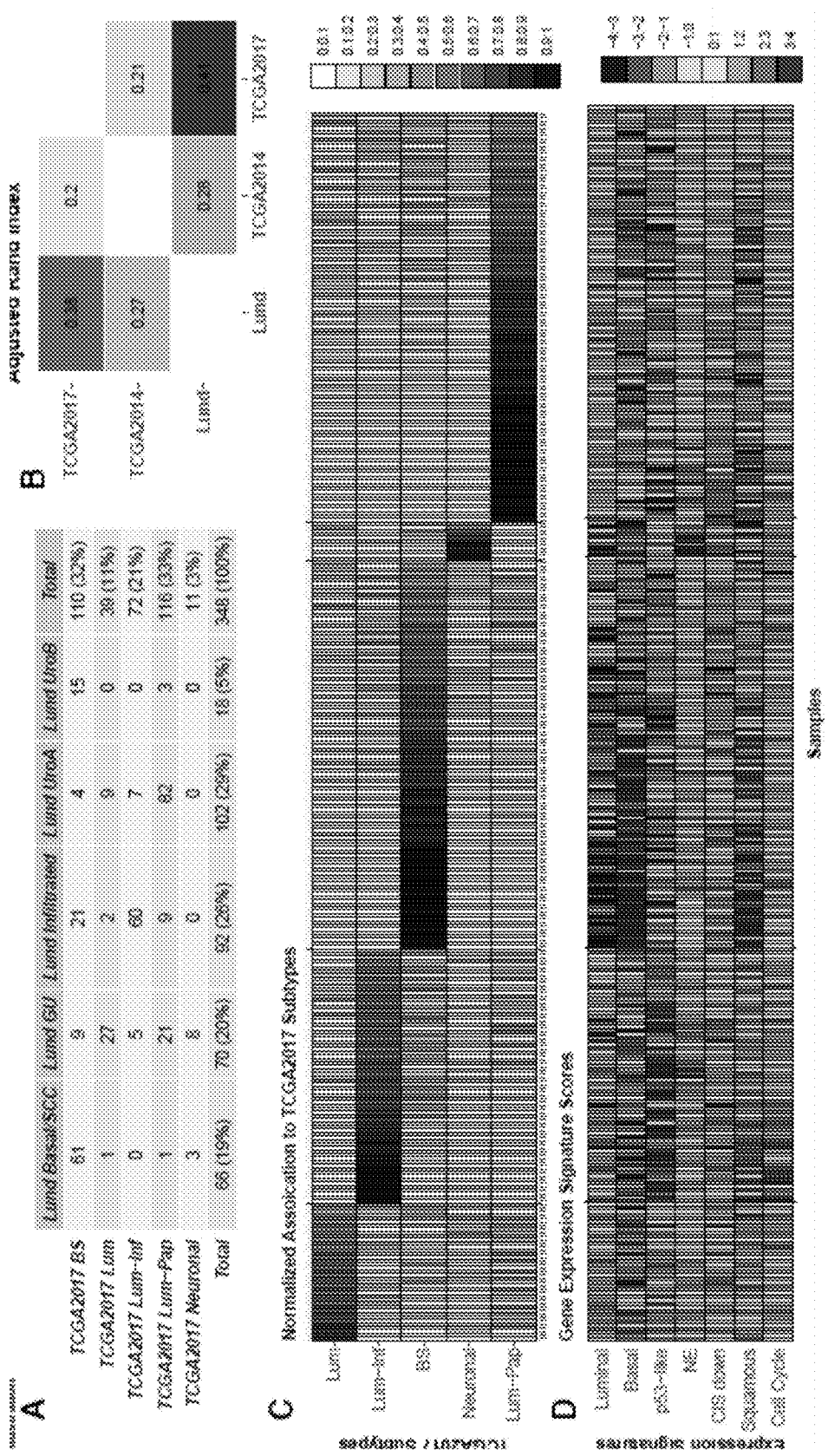
Figure 30E:
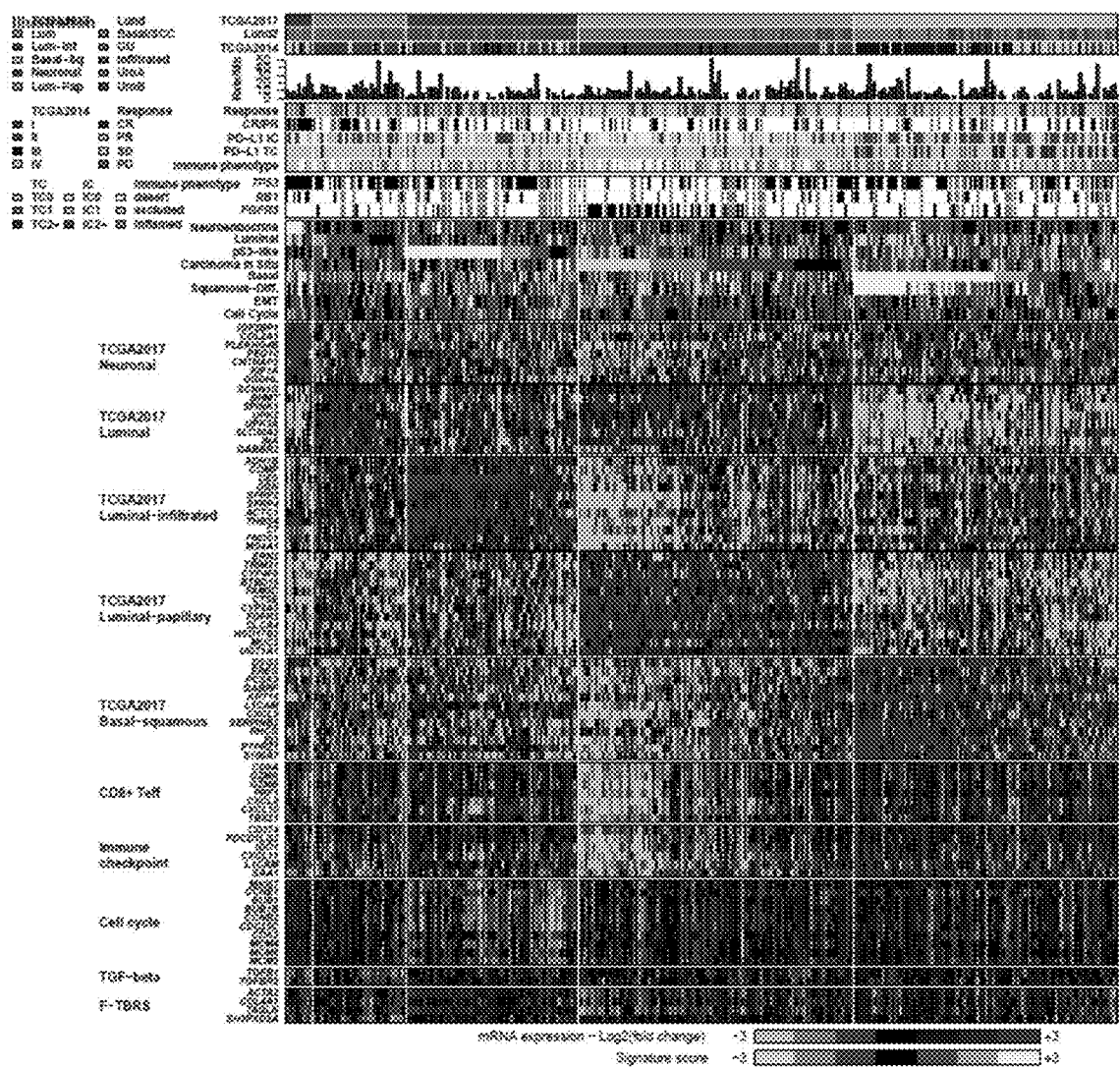

FIG. 30 shows TCGA single patient classifier applied to the IMvigor 210 mRNA expression data for 348 tumor samples. FIG. 30A shows the numbers of patients assigned to each expression subtype and the comparison to the reported Lund subtypes. FIG. 30B shows the adjusted rand index (ARI) among TCGA2017, TCGA2014, and Lund classifications for 348 patients (upper-left) and 298 patients with response data (lower-right). FIG. 30C (middle panel) shows the cluster assignment probability for each patient and bottom panel (FIG. 30D) shows comparison to common gene expression signatures and their association with each of the subtypes (Red is high expression and blue is low expression). CIS—carcinoma-in-situ and NE—neuroendocrine in (FIG. 30D). FIG. 30E—Top, TCGA2017 subtypes classification: neuronal, luminal, luminal-infiltrated, luminal-papillary, and basal-squamous from left to right. Covariates: reported 5 Lund UC and 4 TCGA2014 classification; overall tumor mutation burden (TMB); reported response to atezolizumab therapy, PD-L1 expression in immune and tumor cells, and immune phenotype classification; key genetic alterations; normalized gene expression signature score (yellow is high and blue is low); log 2 (fold change against the median expression across samples) for selected subtype markers, and markers for CD8+ Teff, immune-checkpoint, cell-cycle, TGF-beta, European Urology 12/1/18 F-TBRS. Samples within neuronal, luminal, luminal-infiltrated, luminal-papillary, basalsquamous subtype are ordered by neuronal, luminal, p53-like, carcinoma-in-situ, basal signature scores, respectively. Marker genes for CD8+ Teff, immune-checkpoint, cell-cycle, TGFbeta, and F-TBRS were profiled from FIG. 3 in Mariathasan et al1. Top: gene expression signature scores (top) across TCGA2017 and Lund subtypes. Bottom: log 2(fold change) and log 2(raw expression) (bottom) across TCGA2017 subtypes for neuroendocrine markers (CHGA, CHGB, SYP, ENO2) and neuronal subtype marker (SOX2, TUBB2B, PEG10)

FIG. 31A-D shows four panels. FIG. 31A is a table showing the stratification of patients in TCGA2017 and Lund subtypes into four response categories, complete response (CR), partial response (PR), stable disease (SD), progressive disease (PD), and CR+PR. FIG. 31B shows the objective response rate of IMvigor 210 patients to atezolizumab according to TGCA 2017, TCGA 2014 and Lund subtypes. Overall survival probabilities in the IMvigor 210 full cohort (n=348) in the TCGA2017 subtypes (FIG. 31C) and the Lund subtypes (FIG. 31D).

Figure 32:
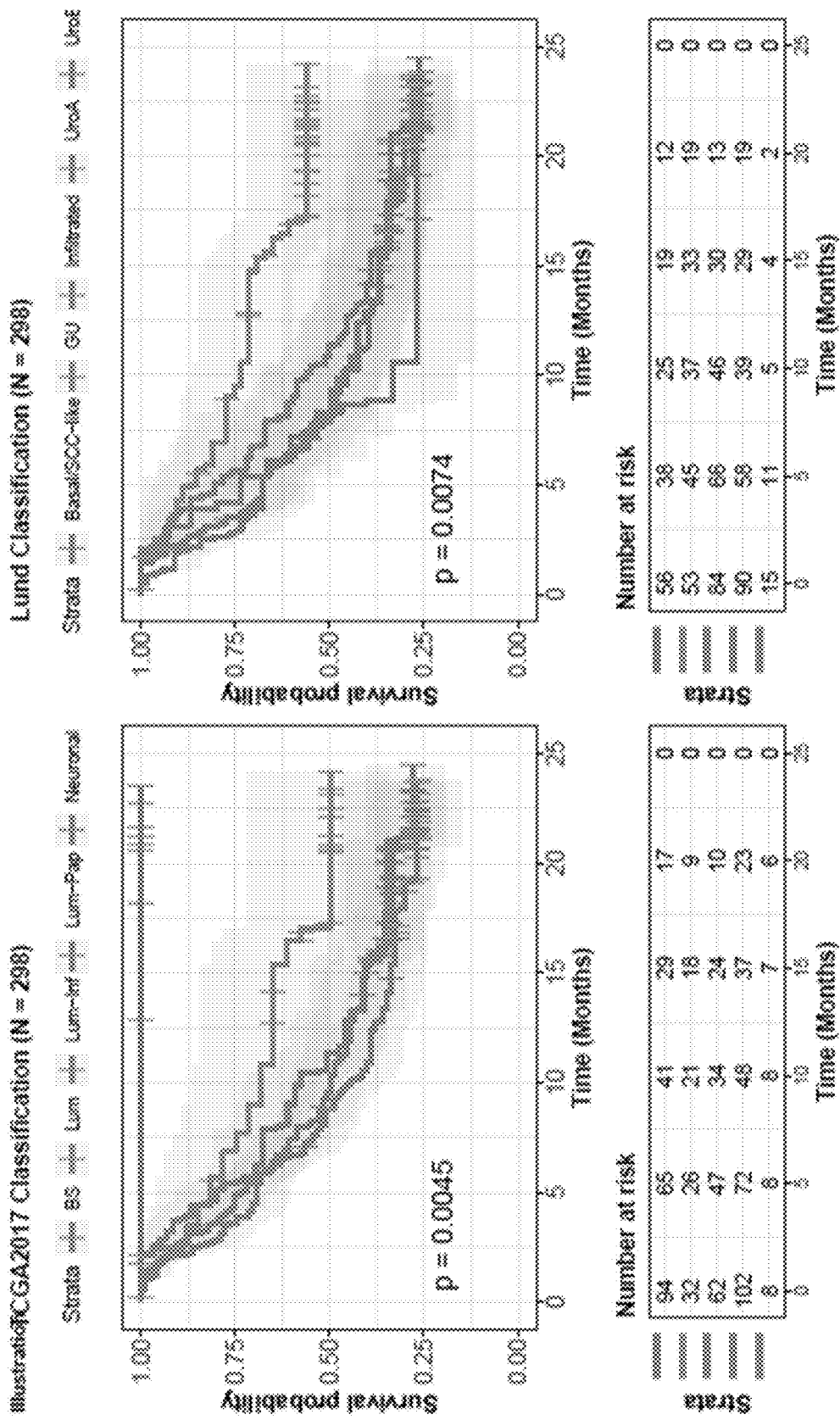

FIG. 32 (top panels) show the overall survival probabilities in the IMvigor 210 cohort with response data (n=298) in the TCGA2017 subtypes (left) and the Lund subtypes (right).

Figure 33:
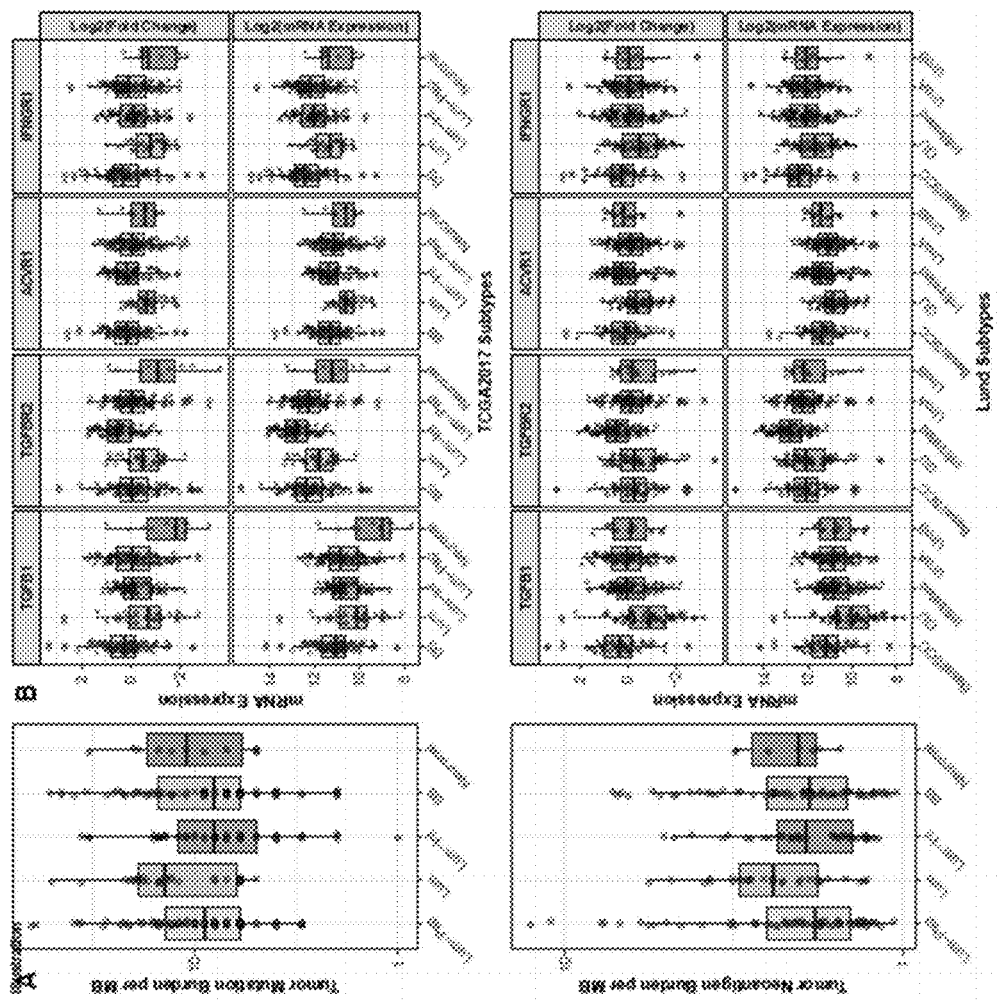

FIG. 33A is a box plot showing the reported tumor mutation burden and neoantigen burden (bottom) stratified by the TCGA2017 subtypes. FIG. 33B includes box plots showing Log 2(fold change) and log 2(raw expression) of TGF-beta pathway genes in the TCGA2017 (top) and Lund (bottom) subtypes.

DETAILED DESCRIPTION OF THE INVENTION

The present invention features methods for characterizing mutational profiles in patients with bladder cancer (e.g., urothelial bladder cancer, muscle-invasive bladder cancer). The method involves the identification and use of mRNA-based expression subtypes (e.g., luminal, luminal-infiltrated, basal-squamous, neuronal, and luminal-papillary) that may stratify a patient's response to a therapeutic treatment.

As described in detail below, the present invention is based, at least in part, on the discovery of five bladder cancer mRNA-based expression subtypes that may stratify a patient's response to different treatments. The present invention provides a comprehensive analysis of 412 muscle-invasive bladder cancers characterized by multiple TCGA analytical platforms. Fifty-eight genes were significantly mutated, and the overall mutational load was associated with APOBEC-signature mutagenesis. Clustering by mutation signature identified a high-mutation subset with 75% 5-year survival. mRNA expression clustering refined prior clustering analyses and identified a poor-survival 'neuronal' subtype in which the majority of tumors lacked small cell or neuroendocrine histology. Clustering by mRNA, lncRNA, and miRNA expression converged to identify subsets with differential epithelial-mesenchymal transition status, carcinoma-in-situ scores, histologic features, and survival. The analyses of the present invention identified 5 expression subtypes that may stratify response to different treatments.

The present invention includes a comprehensive analysis of the full TCGA cohort of 412 MIBC cases. The expanded cohort allowed for the identification of: 32 additional significantly mutated genes; that APOBEC-signature mutagenesis is associated with both a high mutation rate and improved clinical outcome; an expression subtype that termed herein as 'neuronal'; and multiple recurrent translocations that lead to fusion genes. Clustering expression profiles for mRNA, long noncoding RNA, and miRNA further confirmed distinct subsets of MIBC with differential survival.

In other embodiments, the invention provides methods for selecting a patient for treatment with atezolizumab, wherein the selected patient has a bladder cancer characterized as expressing polynucleotide or polypeptide markers SOX2, TUBB2B, and PEG10.

Markers of the Invention

The present invention has identified markers of prognostic significance for patients with bladder cancer. The markers may stratify a patient's response to a therapeutic treatment. Non-limiting examples of markers of the present invention include: (1) luminal markers, (2) luminal-papillary markers, (3) luminal-infiltrating markers, (4) basal-squamous markers, and (5) neuronal markers.

Luminal markers include uroplakin genes (UPK2, UPK1A), urothelial differentiation markers (FOXA1, GATA3, PPARG), and genes that are highly expressed in terminally differentiated urothelial umbrella cells (KRT20, and SNX31).

Luminal-papillary markers include FGFR, FGFR3-TACC3 fusions, lncRNA subtypes 2 and 3 (DANCR, GAS5, MALAT1, NEAT1, NORAD (LINC00657), UCA1, ZNF667-AS1 (MORT), LINC00152, GATA3, FOXA1, PPARγ and TP63), and sonic-hedgehog signaling (SHH).

Luminal-infiltrated markers include CD274 (PD-L1) and PDCD1 (PD-1).

Basal-squamous markers include basal and stem-like markers (CD44, KRT5, KRT6A, KRT14, COL17A1), squamous differentiation markers (TGM1, DSC3, TP63, GSDMC, PI3), TP53, CIS signature genes (CRTAC1, CTSE, PADI3, MSN, NR3C1), and immune markers (CD274, PDCD1LG2, IDO1, CXCL11, L1CAM SAA1 CTLA4).

Neuronal markers include neuronal differentiation and development genes (MSI1, PLEKHG4B, GNG4, PEG10, RND2, APLP1, SOX2, TUBB2B), as well as typical neuroendocrine (NE) markers (CHGA, CHGB, SCG2, ENO2, SYP, NCAM1). Neuronal markers may also include TP53, RB1 and E2F3.

Non-limiting examples of additional markers include markers that are subject to epigenetic silencing, which may offer additional potential therapeutic targets. These markers include CDKN2A, FAT1, and CASP8. Silenced genes included latexin (LXN), Poly(ADP-ribose) polymerase PARP6 (26%), nicotinate phosphoribosyltransferase (NAPRT), and spermatogenesis and centriole associated 1-like (SPATC1L).

Biologic Samples

Samples for use with in the methods of the invention include nucleic acid molecules suitable for providing RNAs expression information. In principle, the biological sample from which the expressed RNA is obtained and analyzed for target sequence expression can be any material suspected of comprising cancer tissue or cells. The diagnostic sample can be a biological sample used directly in a method of the invention. Alternatively, the diagnostic sample can be a sample prepared from a biological sample. In one embodiment, the biological sample is a urothelial tumor.

In one embodiment, the sample or portion of the sample comprising or suspected of comprising cancer tissue or cells can be any source of biological material, including cells, tissue or fluid, including bodily fluids. Non-limiting examples of the source of the sample include an aspirate, a needle biopsy, a cytology pellet, a bulk tissue preparation or a section thereof obtained for example by surgery or autopsy, lymph fluid, blood, plasma, serum, tumors, and organs. In some embodiments, the sample is from urine. Alternatively, the sample is from blood, plasma or serum. In some embodiments, the sample is from saliva.

The samples may be archival samples, having a known and documented medical outcome, or may be samples from current patients whose ultimate medical outcome is not yet known.

In some embodiments, the sample may be dissected prior to molecular analysis. The sample may be prepared via macrodissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Hely solution, osmic acid solution and Carnoy solution.

Crosslinking fixatives can comprise any agent suitable for forming two or more covalent bonds, for example an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion; see methods.

One or more alcohols may be used to fix tissue, alone or in combination with other fixatives. Exemplary alcohols used for fixation include methanol, ethanol and isopropanol. Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek® V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFMFM, Cryo-Gef™, and OCT Compound (Electron Microscopy Sciences, Hatfield, Pa.). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

RNA Extraction

RNA can be extracted and purified from biological samples using any suitable technique. A number of techniques are known in the art, and several are commercially available (e.g., FormaPure nucleic acid extraction kit, Agencourt Biosciences, Beverly Mass., High Pure FFPE RNA Micro Kit, Roche Applied Science, Indianapolis, Ind.). RNA can be extracted from frozen tissue sections using TRIzol (Invitrogen, Carlsbad, Calif.) and purified using RNeasy Protect kit (Qiagen, Valencia, Calif.). RNA can be further purified using DNAse I treatment (Ambion, Austin, Tex.) to eliminate any contaminating DNA. RNA concentrations can be made using a Nanodrop ND-1000 spectrophotometer (Nanodrop Technologies, Rockland, Del.). RNA can be further purified to eliminate contaminants that interfere with cDNA synthesis by cold sodium acetate precipitation. RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

Preparation of Probes and Primers

Expression of a marker of the invention is analyzed using a probe or primer that targets that marker. The polynucleotide probes or primers of the present invention can be prepared by conventional techniques well-known to those skilled in the art. For example, the polynucleotide probes can be prepared using solid-phase synthesis using commercially available equipment. As is well-known in the art, modified oligonucleotides can also be readily prepared by similar methods. The polynucleotide probes can also be synthesized directly on a solid support according to methods standard in the art. This method of synthesizing polynucleotides is particularly useful when the polynucleotide probes are part of a nucleic acid array.

Polynucleotide probes or primers can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261. Still further techniques include bead based techniques such as those described in PCT Appl. No. PCT/US93/04145 and pin based methods such as those described in U.S. Pat. No. 5,288,514. Additional flow channel or spotting methods applicable to attachment of sensor polynucleotides to a substrate are described in U.S. patent application Ser. No. 07/980,523, filed Nov. 20, 1992, and U.S. Pat. No. 5,384,261.

Alternatively, the polynucleotide probes of the present invention can be prepared by enzymatic digestion of the naturally occurring target gene, or mRNA or cDNA derived therefrom, by methods known in the art.

Coding and Non-Coding Targets

The methods disclosed include assaying the expression level of a plurality of markers. The markers may comprise coding targets and/or non-coding targets of a protein-coding gene or a non protein-coding gene. A protein-coding gene structure may comprise an exon and an intron. The exon may further comprise a coding sequence (CDS) and an untranslated region (UTR). The protein-coding gene may be transcribed to produce a pre-mRNA and the pre-mRNA may be processed to produce a mature mRNA. The mature mRNA may be translated to produce a protein.

A non protein-coding gene structure may comprise an exon and intron. Usually, the exon region of a non protein-coding gene primarily contains a UTR. The non protein-coding gene may be transcribed to produce a pre-mRNA and the pre-mRNA may be processed to produce a non-coding RNA (ncRNA).

A coding target may comprise a coding sequence of an exon. A non-coding target may comprise a UTR sequence of an exon, intron sequence, intergenic sequence, promoter sequence, non-coding transcript, CDS antisense, intronic antisense, UTR antisense, or non-coding transcript antisense. A non-coding transcript may comprise a non-coding RNA (ncRNA).

In some embodiments, the plurality of targets may be differentially expressed.

In some embodiments, the plurality of targets comprises one or more targets selected from those listed herein. In particular embodiments, the targets comprise luminal markers (e.g., uroplakin genes (UPK2, UPK1A), urothelial differentiation markers (FOXA1, GATA3, PPARG), and genes that are highly expressed in terminally differentiated urothelial umbrella cells (KRT20, and SNX31)).

In some embodiments, the plurality of targets comprise luminal-papillary markers including FGFR, FGFR3-TACC3 fusions, lncRNA subtypes 2 and 3 (DANCR, GAS5, MALAT1, NEAT1, NORAD (LINC00657), UCA1, ZNF667-AS1 (MORT), LINC00152, GATA3, FOXA1, PPARγ and TP63), and sonic-hedgehog signaling (SHH).

In some embodiments, the plurality of targets comprise luminal-infiltrated markers including CD274 (PD-L1) and PDCD1 (PD-1).

In some embodiments, the plurality of targets comprise basal-squamous markers including basal and stem-like markers (e.g., CD44, KRT5, KRT6A, KRT14, COL17A1), squamous differentiation markers (TGM1, DSC3, TP63, GSDMC, PI3), TP53, CIS signature genes (CRTAC1, CTSE, PADI3, MSN, NR3C1), and immune markers (CD274, PDCD1LG2, 1DO1, CXCL11, L1CAM, SAA1 CTLA4).

In some embodiments, the plurality of targets comprise neuronal markers including neuronal differentiation and development genes (MSI1, PLEKHG4B, GNG4, PEG10, RND2, APLP1, SOX2, TUBB2B), as well as typical neuroendocrine (NE) markers (e.g., CHGA, CHGB, SCG2, ENO2, SYP, NCAM1). Neuronal markers may also include TP53, RB1 and E2F3.

In some embodiments, the plurality of targets comprises at least about 2, at least about 3, at least about 4, at least about 5, at least about 6, at least about 7, at least about 8, at least about 9, or at least about 10 targets selected from those presented herein. In other instances, the plurality of targets comprises at least about 12, at least about 15, at least about 17, at least about 20, at least about 22, at least about 25, at least about 27, at least about 30, at least about 32, at least about 35, at least about 37, or at least about 40 targets selected from luminal markers, luminal papillary markers, luminal-infiltrated markers, basal-squamous markers, and neuronal markers In some instances, the plurality of targets comprises a coding target, non-coding target, or any combination thereof. In some instances, the coding target comprises an exonic sequence. In other instances, the non-coding target comprises a non-exonic sequence. Alternatively, a non-coding target comprises a UTR sequence, an intronic sequence, or a non-coding RNA transcript. In some instances, a non-coding target comprises sequences which partially overlap with a UTR sequence or an intronic sequence. A non-coding target also includes non-exonic transcripts. Exonic sequences may comprise regions on a protein-coding gene, such as an exon, UTR, or a portion thereof. Non-exonic sequences may comprise regions on a protein-coding, non protein-coding gene, or a portion thereof. For example, non-exonic sequences may comprise intronic regions, promoter regions, intergenic regions, a non-coding transcript, an exon anti-sense region, an intronic anti-sense region, UTR anti-sense region, non-coding transcript anti-sense region, or a portion thereof. In other instances, the plurality of targets comprises a non-coding RNA transcript.

Amplification and Hybridization

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification and other reactions. mRNA can first be treated with reverse transcriptase and a primer to create cDNA prior to detection, quantitation and/or amplification; this can be done in vitro with purified mRNA or in situ, e.g., in cells or tissues affixed to a slide.

By "amplification" is meant any process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse translation and then optionally from further amplification reactions. The amplification product may include all or a portion of a target sequence, and may optionally be labeled. A variety of amplification methods are suitable for use, including polymerase-based methods and ligation-based methods. Exemplary amplification techniques include the polymerase chain reaction method (PCR), the lipase chain reaction (LCR), ribozyme-based methods, self sustained sequence replication (3SR), nucleic acid sequence-based amplification (NASBA), the use of Q Beta replicase, reverse transcription, nick translation, and the like.

Asymmetric amplification reactions may be used to preferentially amplify one strand representing the target sequence that is used for detection as the target polynucleotide. In some cases, the presence and/or amount of the amplification product itself may be used to determine the expression level of a given target sequence. In other instances, the amplification product may be used to hybridize to an array or other substrate comprising sensor polynucleotides which are used to detect and/or quantitate target sequence expression.

The first cycle of amplification in polymerase-based methods typically fauns a primer extension product complementary to the template strand. If the template is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that can produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase or enzyme activity. The enzyme can be thermolabile or thermostable. Mixtures of enzymes can also be used.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

Where the amplification product is to be used for hybridization to an array or microarray, a number of suitable commercially available amplification products are available. These include amplification kits available from NuGEN, Inc. (San Carlos, Calif.), including the WT-Ovation™ System, WT-Ovation™ System v2, WT-Ovation™ Pico System, WT-Ovation'm FFPE Exon Module, WT-Ovation™ FFPE Exon Module RiboAmp and RiboAmp.sup.Plus RNA Amplification Kits (MDS Analytical Technologies (formerly Arcturus) (Mountain View, Calif.), Genisphere, Inc. (Hatfield, Pa.), including the RampUp Plus™ and SenseAmp™ RNA Amplification kits, alone or in combination. Amplified nucleic acids may be subjected to one or more purification reactions after amplification and labeling, for example using magnetic beads (e.g., RNAClean magnetic beads, Agencourt Biosciences).

Multiple RNA biomarkers can be analyzed using real-time quantitative multiplex RT-PCR platforms and other multiplexing technologies such as GenomeLab GeXP Genetic Analysis System (Beckman Coulter, Foster City, Calif.), SmartCycler® 9600 or GeneXpert® Systems (Cepheid, Sunnyvale, Calif.), ABI 7900 HT Fast Real Time PCR system (Applied Biosystems, Foster City, Calif.), LightCycler® 480 System (Roche Molecular Systems, Pleasanton, Calif.), xMAP 100 System (Luminex, Austin, Tex.) Solexa Genome Analysis System (Illumina, Hayward, Calif.), OpenArray Real Time qPCR (BioTrove, Woburn, Mass.) and BeadXpress System (Illumina, Hayward, Calif.).

Probes/Primers

The present invention provides for a probe set for selecting a subject, diagnosing, monitoring and/or predicting a status or outcome of a bladder cancer in a subject comprising a plurality of probes, wherein (i) the probes in the set are capable of detecting an expression level of at least one target; and (ii) the expression level determines the status of the subject.

The probe set may comprise one or more polynucleotide probes. Individual polynucleotide probes comprise a nucleotide sequence derived from the nucleotide sequence of the target sequences or complementary sequences thereof. The nucleotide sequence of the polynucleotide probe is designed such that it corresponds to, or is complementary to the target sequences. The polynucleotide probe can specifically hybridize under either stringent or lowered stringency hybridization conditions to a region of the target sequences, to the complement thereof, or to a nucleic acid sequence (such as a cDNA) derived therefrom.

The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the invention, the polynucleotide probe is complementary to a region of a target mRNA derived from a target sequence in the probe set. Computer programs can also be employed to select probe sequences that may not cross hybridize or may not hybridize non-specifically.

In some instances, microarray hybridization of RNA, extracted from bladder cancer tissue samples and amplified, may yield a dataset that is then summarized and normalized using a technique known in the art.

One skilled in the art understands that the nucleotide sequence of the polynucleotide probe need not be 100% complementary to its target sequence in order to specifically hybridize thereto. The polynucleotide probes of the present invention, therefore, comprise a nucleotide sequence that is at least about 85% complementary to a region of the coding target or non-coding target selected from those listed herein.

Methods of determining sequence identity are known in the art and can be determined, for example, by using the BLASTN program of the University of Wisconsin Computer Group (GCG) software or provided on the NCBI website. The nucleotide sequence of the polynucleotide probes of the present invention may exhibit variability by differing (e.g. by nucleotide substitution, including transition or transversion) at one, two, three, four or more nucleotides from the sequence of the coding target or non-coding target.

Other criteria known in the art may be employed in the design of the polynucleotide probes of the present invention. For example, the probes can be designed to have <50% G content and/or between about 25% and about 70% G+C content. Strategies to optimize probe hybridization to the target nucleic acid sequence can also be included in the process of probe selection.

Hybridization under particular pH, salt, and temperature conditions can be optimized by taking into account melting temperatures and by using empirical rules that correlate with desired hybridization behaviors. Computer models may be used for predicting the intensity and concentration-dependence of probe hybridization.

The polynucleotide probes of the present invention may range in length from about 15 nucleotides to the full length of the coding target or non-coding target. In one embodiment of the invention, the polynucleotide probes are at least about 15 nucleotides in length. In another embodiment, the polynucleotide probes are at least about 20 nucleotides in length. In a further embodiment, the polynucleotide probes are at least about 25 nucleotides in length. In another embodiment, the polynucleotide probes are between about 15 nucleotides and about 500 nucleotides in length. In other embodiments, the polynucleotide probes are between about 15 nucleotides and about 450 nucleotides, about 15 nucleotides and about 400 nucleotides, about 15 nucleotides and about 350 nucleotides, about 15 nucleotides and about 300 nucleotides, about 15 nucleotides and about 250 nucleotides, about 15 nucleotides and about 200 nucleotides in length. In some embodiments, the probes are at least 15 nucleotides in length. In some embodiments, the probes are at least 15 nucleotides in length. In some embodiments, the probes are at least 20 nucleotides, at least 25 nucleotides, at least 50 nucleotides, at least 75 nucleotides, at least 100 nucleotides, at least 125 nucleotides, at least 150 nucleotides, at least 200 nucleotides, at least 225 nucleotides, at least 250 nucleotides, at least 275 nucleotides, at least 300 nucleotides, at least 325 nucleotides, at least 350 nucleotides, at least 375 nucleotides in length.

The polynucleotide probes of a probe set can comprise RNA, DNA, RNA or DNA mimetics, or combinations thereof, and can be single-stranded or double-stranded. Thus the polynucleotide probes can be composed of naturally-occurring nucleobases, sugars and covalent internucleoside (backbone) linkages as well as polynucleotide probes having non-naturally-occurring portions which function similarly. Such modified or substituted polynucleotide probes may provide desirable properties such as, for example, enhanced affinity for a target gene and increased stability. The probe set may comprise a coding target and/or a non-coding target. Preferably, the probe set comprises a combination of a coding target and non-coding target.

The system of the present invention further provides for primers and primer pairs capable of amplifying target sequences defined by the probe set, or fragments or subsequences or complements thereof. The nucleotide sequences of the probe set may be provided in computer-readable media for in silico applications and as a basis for the design of appropriate primers for amplification of one or more target sequences of the probe set.

Primers based on the nucleotide sequences of target sequences can be designed for use in amplification of the target sequences. For use in amplification reactions such as PCR, a pair of primers can be used. The exact composition of the primer sequences is not critical to the invention, but for most applications the primers may hybridize to specific sequences of the probe set under stringent conditions, particularly under conditions of high stringency, as known in the art. The pairs of primers are usually chosen so as to generate an amplification product of at least about 50 nucleotides, more usually at least about 100 nucleotides. Algorithms for the selection of primer sequences are generally known, and are available in commercial software packages. These primers may be used in standard quantitative or qualitative PCR-based assays to assess transcript expression levels of RNAs defined by the probe set. Alternatively, these primers may be used in combination with probes, such as molecular beacons in amplifications using real-time PCR.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to faun a linear polymeric compound, with the normal linkage or backbone of RNA and DNA being a 3' to 5' phosphodiester linkage. Specific examples of polynucleotide probes or primers useful in this invention include oligonucleotides containing modified backbones or non-natural internucleoside linkages. As defined in this specification, oligonucleotides having modified backbones include both those that retain a phosphorus atom in the backbone and those that lack a phosphorus atom in the backbone. For the purposes of the present invention, and as sometimes referenced in the art, modified oligonucleotides that do not have a phosphorus atom in their internucleoside backbone can also be considered to be oligonucleotides.

Exemplary polynucleotide probes or primers having modified oligonucleotide backbones include, for example, those with one or more modified internucleotide linkages that are phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3' amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid fauns are also included.

Other modifications may also be made at other positions on the polynucleotide probes or primers, particularly the 3' position of the sugar on the 3' terminal nucleotide or in 2'-5' linked oligonucleotides and the 5' position of 5' terminal nucleotide. Polynucleotide probes or primers may also have sugar mimetics such as cyclobutyl moieties in place of the pentofuranosyl sugar.

Polynucleotide probes or primers may also include modifications or substitutions to the nucleobase. As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; The Concise Encyclopedia Of Polymer Science And Engineering, (1990) pp 858-859, Kroschwitz, J. L, ed. John Wiley & Sons; Englisch et al., Angewandte Chemie, Int. Ed., 30:613 (1991); and Sanghvi, Y. S., (1993) Antisense Research and Applications, pp 289-302, Crooke, S. T. and Lebleu, B., ed., CRC Press. Certain of these nucleobases are particularly useful for increasing the binding affinity of the polynucleotide probes of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability.

One skilled in the art recognizes that it is not necessary for all positions in a given polynucleotide probe or primer to be uniformly modified. The present invention, therefore, contemplates the incorporation of more than one of the aforementioned modifications into a single polynucleotide probe or even at a single nucleoside within the probe or primer.

One skilled in the art also appreciates that the nucleotide sequence of the entire length of the polynucleotide probe or primer does not need to be derived from the target sequence. Thus, for example, the polynucleotide probe may comprise nucleotide sequences at the 5' and/or 3' termini that are not derived from the target sequences. Nucleotide sequences which are not derived from the nucleotide sequence of the target sequence may provide additional functionality to the polynucleotide probe. For example, they may provide a restriction enzyme recognition sequence or a "tag" that facilitates detection, isolation, purification or immobilization onto a solid support. Alternatively, the additional nucleotides may provide a self-complementary sequence that allows the primer/probe to adopt a hairpin configuration. Such configurations are necessary for certain probes, for example, molecular beacon and Scorpion probes, which can be used in solution hybridization techniques.

The polynucleotide probes or primers can incorporate moieties useful in detection, isolation, purification, or immobilization, if desired. Such moieties are well-known in the art (see, for example, Ausubel et al., (1997 & updates) Current Protocols in Molecular Biology, Wiley & Sons, New York) and are chosen such that the ability of the probe to hybridize with its target sequence is not affected.

Examples of suitable moieties are detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like.

A label can optionally be attached to or incorporated into a probe or primer polynucleotide to allow detection and/or quantitation of a target polynucleotide representing the target sequence of interest. The target polynucleotide may be the expressed target sequence RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different targets may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the invention described herein include any substance which can be detected when bound to or incorporated into the biomolecule of interest. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a polynucleotide may comprise a biotin-binding species, and an optically detectable label may be conjugated to biotin and then bound to the labeled polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Polynucleotides from the described target sequences may be employed as probes for detecting target sequences expression, for ligation amplification schemes, or may be used as primers for amplification schemes of all or a portion of a target sequences. When amplified, either strand produced by amplification may be provided in purified and/or isolated form.

Complements may take any polymeric form capable of base pairing to the species recited in (a)-(e), including nucleic acid such as RNA or DNA, or may be a neutral polymer such as a peptide nucleic acid. Polynucleotides of the invention can be selected from the subsets of the recited nucleic acids described herein, as well as their complements.

The polynucleotides may be provided in a variety of formats, including as solids, in solution, or in an array. The polynucleotides may optionally comprise one or more labels, which may be chemically and/or enzymatically incorporated into the polynucleotide.

In one embodiment, solutions comprising polynucleotide and a solvent are also provided. In some embodiments, the solvent may be water or may be predominantly aqueous. In some embodiments, the solution may comprise at least two, three, four, five, six, seven, eight, nine, ten, twelve, fifteen, seventeen, twenty or more different polynucleotides, including primers and primer pairs, of the invention. Additional substances may be included in the solution, alone or in combination, including one or more labels, additional solvents, buffers, biomolecules, polynucleotides, and one or more enzymes useful for performing methods described herein, including polymerases and ligases. The solution may further comprise a primer or primer pair capable of amplifying a polynucleotide of the invention present in the solution.

In some embodiments, one or more polynucleotides provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenediflumide, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and include semiconductor nanocrystals.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

Preparation of Probes and Primers

The polynucleotide probes or primers of the present invention can be prepared by conventional techniques well-known to those skilled in the art. For example, the polynucleotide probes can be prepared using solid-phase synthesis using commercially available equipment. As is well-known in the art, modified oligonucleotides can also be readily prepared by similar methods. The polynucleotide probes can also be synthesized directly on a solid support according to methods standard in the art. This method of synthesizing polynucleotides is particularly useful when the polynucleotide probes are part of a nucleic acid array.

Polynucleotide probes or primers can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261. Still further techniques include bead based techniques such as those described in PCT Appl. No. PCT/US93/04145 and pin based methods such as those described in U.S. Pat. No. 5,288,514. Additional flow channel or spotting methods applicable to attachment of sensor polynucleotides to a substrate are described in U.S. patent application Ser. No. 07/980,523, filed Nov. 20, 1992, and U.S. Pat. No. 5,384,261.

Alternatively, the polynucleotide probes of the present invention can be prepared by enzymatic digestion of the naturally occurring target gene, or mRNA or cDNA derived therefrom, by methods known in the art.

Characterization of Markers/Targets

Any method of detecting and/or quantitating the expression of the marker can in principle be used in the invention. The markers can be directly detected and/or quantitated, or may be copied and/or amplified to allow detection of amplified copies of the expressed target sequences or its complement.

Methods for detecting and/or quantifying a marker can include Northern blotting, sequencing, array or microarray hybridization, by enzymatic cleavage of specific structures (e.g., an Invader® assay, Third Wave Technologies, e.g. as described in U.S. Pat. Nos. 5,846,717, 6,090,543; 6,001,567; 5,985,557; and 5,994,069) and amplification methods, e.g. RT-PCR, including in a TaqMan® assay (PE Biosystems, Foster City, Calif., e.g. as described in U.S. Pat. Nos. 5,962,233 and 5,538,848), and may be quantitative or semi-quantitative, and may vary depending on the origin, amount and condition of the available biological sample. Combinations of these methods may also be used. For example, nucleic acids may be amplified, labeled and subjected to microarray analysis.

In some instances, markers may be detected by sequencing. Sequencing methods may comprise whole genome sequencing or exome sequencing. Sequencing methods such as Maxim-Gilbert, chain-termination, or high-throughput systems may also be used. Additional, suitable sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, and SOLiD sequencing.

Additional methods for detecting and/or quantifying a target include single-molecule sequencing (e.g., Helicos, PacBio), sequencing by synthesis (e.g., Illumina, Ion Torrent), sequencing by ligation (e.g., ABI SOLID), sequencing by hybridization (e.g., Complete Genomics), in situ hybridization, bead-array technologies (e.g., Luminex xMAP, Illumina BeadChips), branched DNA technology (e.g., Panomics, Genisphere). Sequencing methods may use fluorescent (e.g., Illumina) or electronic (e.g., Ion Torrent, Oxford Nanopore) methods of detecting nucleotides.

Still other methods and compositions for gene expression is characterizing using Nanostring technology, RNAseq, or an Affymetrix-expression array.

Reverse Transcription for QRT-PCR Analysis

Reverse transcription can be performed by any method known in the art. For example, reverse transcription may be performed using the Omniscript kit (Qiagen, Valencia, Calif.), Superscript III kit (Invitrogen, Carlsbad, Calif.), for RT-PCR. Target-specific priming can be performed in order to increase the sensitivity of detection of target sequences and generate target-specific cDNA.

TaqMan Gene Expression Analysis

TaqMan RT-PCR can be performed using Applied Biosystems Prism (ABI) 7900 HT instruments in a 5 1.11 volume with target sequence-specific cDNA equivalent to 1 ng total RNA.

Primers and probes concentrations for TaqMan analysis are added to amplify fluorescent amplicons using PCR cycling conditions such as 95 degrees C. for 10 minutes for one cycle, 95 degrees C. for 20 seconds, and 60 degrees C. for 45 seconds for 40 cycles. A reference sample can be assayed to ensure reagent and process stability. Negative controls (e.g., no template) should be assayed to monitor any exogenous nucleic acid contamination.

Classification Arrays

The invention provides for arrays featuring a probe set or probes derived that bind a target of the invention. In the context of the present invention, an "array" is a spatially or logically organized collection of polynucleotide probes. An array comprising probes specific for a coding target, non-coding target, or a combination thereof may be used. Alternatively, an array comprising probes specific for two or more of transcripts of a target selected from any of Tables 2, 4, 11 and 55 or a product derived thereof can be used. Desirably, an array may be specific for 5, 10, 15, 20, 25, 30, 50, 75, 100, 150, 200 or more of transcripts of a target selected from any of Tables 2, 4, 11 and 55. In some instances, the target is selected from Table 2. In other instances, the target is selected from Table 4. In some embodiments, the target is selected from Table 11. Expression of these sequences may be detected alone or in combination with other transcripts. In some embodiments, an array is used which comprises a wide range of sensor probes for bladder-specific expression products, along with appropriate control sequences. In some instances, the array may comprise the Human Exon 1.0 ST Array (HuEx 1.0 ST, Affymetrix, Inc., Santa Clara, Calif.).

Typically the polynucleotide probes are attached to a solid substrate and are ordered so that the location (on the substrate) and the identity of each are known. The polynucleotide probes can be attached to one of a variety of solid substrates capable of withstanding the reagents and conditions necessary for use of the array. Examples include, but are not limited to, polymers, such as (poly)tetrafluoroethylene, (poly)vinylidenedifluoride, polystyrene, polycarbonate, polypropylene and polystyrene; ceramic; silicon; silicon dioxide; modified silicon; (fused) silica, quartz or glass; functionalized glass; paper, such as filter paper; diazotized cellulose; nitrocellulose filter; nylon membrane; and polyacrylamide gel pad. Substrates that are transparent to light are useful for arrays that may be used in an assay that involves optical detection.

Examples of array formats include membrane or filter arrays (for example, nitrocellulose, nylon arrays), plate arrays (for example, multiwell, such as a 24-, 96-, 256-, 384-, 864- or 1536-well, microtitre plate arrays), pin arrays, and bead arrays (for example, in a liquid "slurry"). Arrays on substrates such as glass or ceramic slides are often referred to as chip arrays or "chips." Such arrays are well known in the art.

Data Analysis

In some embodiments, one or more pattern recognition methods can be used in analyzing the expression level of target sequences. The pattern recognition method can comprise a linear combination of expression levels, or a nonlinear combination of expression levels. In some embodiments, expression measurements for RNA transcripts or combinations of RNA transcript levels are formulated into linear or non-linear models or algorithms (e.g., an 'expression signature') and converted into a likelihood score. This likelihood score indicates the probability that a biological sample is from a patient who may exhibit no evidence of disease, who may exhibit systemic cancer, or who may exhibit biochemical recurrence. The likelihood score can be used to distinguish these disease states. The models and/or algorithms can be provided in machine readable format, and may be used to correlate expression levels or an expression profile with a disease state, and/or to designate a treatment modality for a patient or class of patients.

Assaying the expression level for a plurality of targets may comprise the use of an algorithm or classifier. Array data can be managed, classified, and analyzed using techniques known in the art. Assaying the expression level for a plurality of targets may comprise probe set modeling and data pre-processing. Probe set modeling and data pre-processing can be derived using the Robust Multi-Array (RMA) algorithm or variants GC-RMA, RMA, Probe Logarithmic Intensity Error (PLIER) algorithm or variant iterPLIER. Variance or intensity filters can be applied to pre-process data using the RMA algorithm, for example by removing target sequences with a standard deviation of <10 or a mean intensity of <100 intensity units of a normalized data range, respectively.

Alternatively, assaying the expression level for a plurality of targets may comprise the use of a machine learning algorithm. The machine learning algorithm may comprise a supervised learning algorithm. Examples of supervised learning algorithms may include Average One-Dependence Estimators (AODE), Artificial neural network (e.g., Backpropagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

The machine learning algorithms may also comprise an unsupervised learning algorithm. Examples of unsupervised learning algorithms may include artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering.

In some instances, the machine learning algorithms comprise a reinforcement learning algorithm Examples of reinforcement learning algorithms include, but are not limited to, temporal difference learning, Q-learning and Learning Automata. Alternatively, the machine learning algorithm may comprise Data Pre-processing.

Preferably, the machine learning algorithms may include, but are not limited to, Average One-Dependence Estimators (AODE), Fisher's linear discriminant, Logistic regression, Perceptron, Multilayer Perceptron, Artificial Neural Networks, Support vector machines, Quadratic classifiers, Boosting, Decision trees, C4.5, Bayesian networks, Hidden Markov models, High-Dimensional Discriminant Analysis, and Gaussian Mixture Models. The machine learning algorithm may comprise support vector machines, Naive Bayes classifier, k-nearest neighbor, high-dimensional discriminant analysis, or Gaussian mixture models. In some instances, the machine learning algorithm comprises Random Forests.

Selection of Patients for Treatment

Factors known in the art for diagnosing and/or suggesting, selecting, designating, recommending or otherwise determining a course of treatment for a patient or class of patients suspected of having bladder cancer can be employed in combination with measurements of the target sequence expression. The methods disclosed herein may include additional techniques such as cytology, histology, ultrasound analysis, MRI results, CT scan results, and measurements of other biomarker levels.

Certified tests for classifying disease status and/or designating treatment modalities may also be used in diagnosing, predicting, and/or monitoring the status or outcome of a cancer in a subject. A certified test may comprise a means for characterizing the expression levels of one or more of the target sequences of interest, and a certification from a government regulatory agency endorsing use of the test for classifying the disease status of a biological sample.

In some embodiments, the certified test may comprise reagents for amplification reactions used to detect and/or quantitate expression of the target sequences to be characterized in the test. An array of probe nucleic acids can be used, with or without prior target amplification, for use in measuring target sequence expression.

The test is submitted to an agency having authority to certify the test for use in distinguishing disease status and/or outcome. Results of detection of expression levels of the target sequences used in the test and correlation with disease status and/or outcome are submitted to the agency. A certification authorizing the diagnostic and/or prognostic use of the test is obtained.

The classifiers and/or biomarkers disclosed herein may outperform current classifiers or clinical variables in providing clinically relevant analysis of a sample from a subject. In some instances, the classifiers or biomarkers may more accurately predict a clinical outcome or status as compared to current classifiers or clinical variables. For example, a classifier or biomarker may more accurately predict metastatic disease. Alternatively, a classifier or biomarker may more accurately predict no evidence of disease. In some instances, the classifier or biomarker may more accurately predict death from a disease. The performance of a classifier or biomarker disclosed herein may be based on the AUC value, odds ratio, 95% CI, difference in range of the 95% CI, p-value or any combination thereof.

The performance of the classifiers and/or biomarkers disclosed herein may be determined by the odds ratios and an improvement in performance may be determined by comparing the odds ratio of the classifier or biomarker disclosed herein and the odds ratio of current classifiers or clinical variables. Comparison of the performance of two or more classifiers, biomarkers, and/or clinical variables can be generally be based on the comparison of the absolute value of (1-odds ratio) of a first classifier, biomarker or clinical variable to the absolute value of (1-odds ratio) of a second classifier, biomarker or clinical variable. Generally, the classifier, biomarker or clinical variable with the greater absolute value of (1-odds ratio) can be considered to have better performance as compared to the classifier, biomarker or clinical variable with a smaller absolute value of (1-odds ratio).

In some embodiments, the methods disclosed herein may comprise the use of a genomic classifier (GC) model. A general method for developing a GC model may comprise (a) providing a sample from a subject suffering from a cancer; (b) assaying the expression level for a plurality of targets; (c) generating a model by using a machine learning algorithm. In some instances, the machine learning algorithm comprises Random Forests. In another example, a GC model may be developed by using a machine learning algorithm to analyze and rank genomic features. Analyzing the genomic features may comprise classifying one or more genomic features. The method may further comprise validating the classifier and/or refining the classifier by using a machine learning algorithm The methods disclosed herein may comprise generating one or more clinical classifiers (CC). The clinical classifier can be developed using one or more clinicopathologic variables. The clinicopathologic variables may be selected from the group comprising Lymph node invasion status (LNI); Surgical Margin Status (SMS); Seminal Vesicle Invasion (SVI); Extra Capsular Extension (ECE); Pathological Gleason Score; and the pre-operative PSA. The method may comprise using one or more of the clinicopathologic variables as binary variables. Alternatively, or additionally, the one or more clinicopathologic variables may be converted to a logarithmic value (e.g., log 10). The method may further comprise assembling the variables in a logistic regression. In some instances, the CC is combined with the GC to produce a genomic clinical classifier (GCC).

In some instances, the methods disclosed herein may comprise the use of a genomic-clinical classifier (GCC) model. A general method for developing a GCC model may comprise (a) providing a sample from a subject suffering from a cancer; (b) assaying the expression level for a plurality of targets; (c) generating a model by using a machine learning algorithm. In some instances, the machine learning algorithm comprises Random Forests.

Target sequences can be grouped so that information obtained about the set of target sequences in the group can be used to make or assist in making a clinically relevant judgment such as a diagnosis, prognosis, or treatment choice.

A patient report is also provided comprising a representation of measured expression levels of a plurality of target sequences in a biological sample from the patient, wherein the representation comprises expression levels of target sequences corresponding to any one, two, three, four, five, six, eight, ten, twenty, thirty, fifty or more of the target sequences corresponding to a target selected from any of Tables 2-5, or of the subsets described herein, or of a combination thereof. In some embodiments, the representation of the measured expression level(s) may take the form of a linear or nonlinear combination of expression levels of the target sequences of interest. The patient report may be provided in a machine (e.g., a computer) readable format and/or in a hard (paper) copy. The report can also include standard measurements of expression levels of said plurality of target sequences from one or more sets of patients with known disease status and/or outcome. The report can be used to inform the patient and/or treating physician of the expression levels of the expressed target sequences, the likely medical diagnosis and/or implications, and optionally may recommend a treatment modality for the patient.

Also provided are representations of the gene expression profiles useful for treating, diagnosing, prognosticating, and otherwise assessing disease. In some embodiments, these profile representations are reduced to a medium that can be automatically read by a machine such as computer readable media (magnetic, optical, and the like). The articles can also include instructions for assessing the gene expression profiles in such media. For example, the articles may comprise a readable storage form having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms can assist in the visualization of such data.

Kits

Kits for characterizing a marker of the invention are also provided, and comprise a container or housing for holding the components of the kit, one or more vessels containing one or more nucleic acid(s), and optionally one or more vessels containing one or more reagents. The reagents include those described in the composition of matter section above, and those reagents useful for performing the methods described, including amplification reagents, and may include one or more probes, primers or primer pairs, enzymes (including polymerases and ligases), intercalating dyes, labeled probes, and labels that can be incorporated into amplification products.

In some embodiments, the kit comprises primers or primer pairs specific for those subsets and combinations of target sequences described herein. At least two, three, four or five primers or pairs of primers suitable for selectively amplifying the same number of target sequence-specific polynucleotides can be provided in kit form. In some embodiments, the kit comprises from five to fifty primers or pairs of primers suitable for amplifying the same number of target sequence-representative polynucleotides of interest. In some embodiments, the primers or primer pairs of the kit, when used in an amplification reaction, specifically amplify a non-coding target, coding target, or non-exonic target described herein.

The reagents may independently be in liquid or solid form. The reagents may be provided in mixtures. Control samples and/or nucleic acids may optionally be provided in the kit. Control samples may include tissue and/or nucleic acids obtained from or representative of tumor samples from patients showing no evidence of disease, as well as tissue and/or nucleic acids obtained from or representative of tumor samples from patients that develop systemic cancer.

The nucleic acids may be provided in an array format, and thus an array or microarray may be included in the kit. The kit optionally may be certified by a government agency for use in prognosing the disease outcome of cancer patients and/or for designating a treatment modality.

Instructions for using the kit to perform one or more methods of the invention can be provided with the container, and can be provided in any fixed medium. The instructions may be located inside or outside the container or housing, and/or may be printed on the interior or exterior of any surface thereof. A kit may be in multiplex form for concurrently detecting and/or quantitating one or more different target polynucleotides representing the expressed target sequences.

The practice of the present invention employs, unless otherwise indicated, conventional techniques of molecular biology (including recombinant techniques), microbiology, cell biology, biochemistry, and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology"; "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction" (Mullis, 1994); and "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Demographic, Clinical, and Pathological Data 412 chemotherapy-naive, invasive, high-grade urothelial tumors (T1 [n=1], T2-T4a, N0-3, M0-1,) from 36 tissue source sites were re-reviewed by 4 expert genitourinary pathologists, who classified them as pure urothelial or mixed histology (FIG. 1A, FIG. 1B, FIG. 1C, FIG. 1D, FIG. 1E, FIG. 1F, FIG. 1G, FIG. 1H,), and assessed immune infiltrates. 52 (13%) had urothelial carcinoma with variant histology, including 42 squamous, 4 small cell/neuroendocrine, 2 micropapillary, and 4 plasmacytoid. 5 additional tumors that met screening criteria were included: 3 pure squamous cell bladder carcinomas, 1 squamous cell carcinoma of non-bladder origin, and 1 bladder adenocarcinoma. Complete clinical data were available for 406 tumors. 35 patients had received prior intravesical immunotherapy with Bacillus Calmette-Guérin (BCG), and 12 had received neoadjuvant chemotherapy (NAC) after tumor acquisition. 230 were alive, 163 had recurred, and 182 had died. The median follow-up was 20.9 months for those alive at last follow-up. At least 122 (67%) deaths were cancer-related. The samples were characterized by clinical data and by 6 molecular profiling platforms (See Table 1, below).

TABLE 1

Analysis Platforms

| Data type | Qualified cases with complete data (n) |
| --- | --- |
| Somatic mutation-whole exome | 412 |
| SNP arrays | 412 |
| DNA Methylation | 414 |
| mRNA | 408 |
| miRNA | 409 |
| Protein (RPPA) | 344 |
| Clinical | 406 |

Example 2: Somatic DNA Alterations

Affymetrix SNP6.0 arrays were used to assess somatic copy number alterations (SCNAs). Genomic Identification of Significant Targets in Cancer (GISTIC) analysis identified 34 amplified and 32 deleted genomic regions (q<0.1). Many of the focal SCNAs involved genes known to be amplified in bladder cancer, including AHR, BCL2L1, CCND1, CCNE1, E2F3, EGFR, ERBB2, FGFR3, GATA3, KRAS, MDM2, MYCL1, PPARG, PVRL4, SOX4, TERT, YWHAZ and ZNF703 (Cancer Genome Atlas Research Network, 2014a). The most common recurrent (22%) focal deletion (copy number <1) contained CDKN2A (9p21.3). Recurrent focal deletions in RAD51B (14q24.1) were not observed in the first 131 cases.

Figure 1:
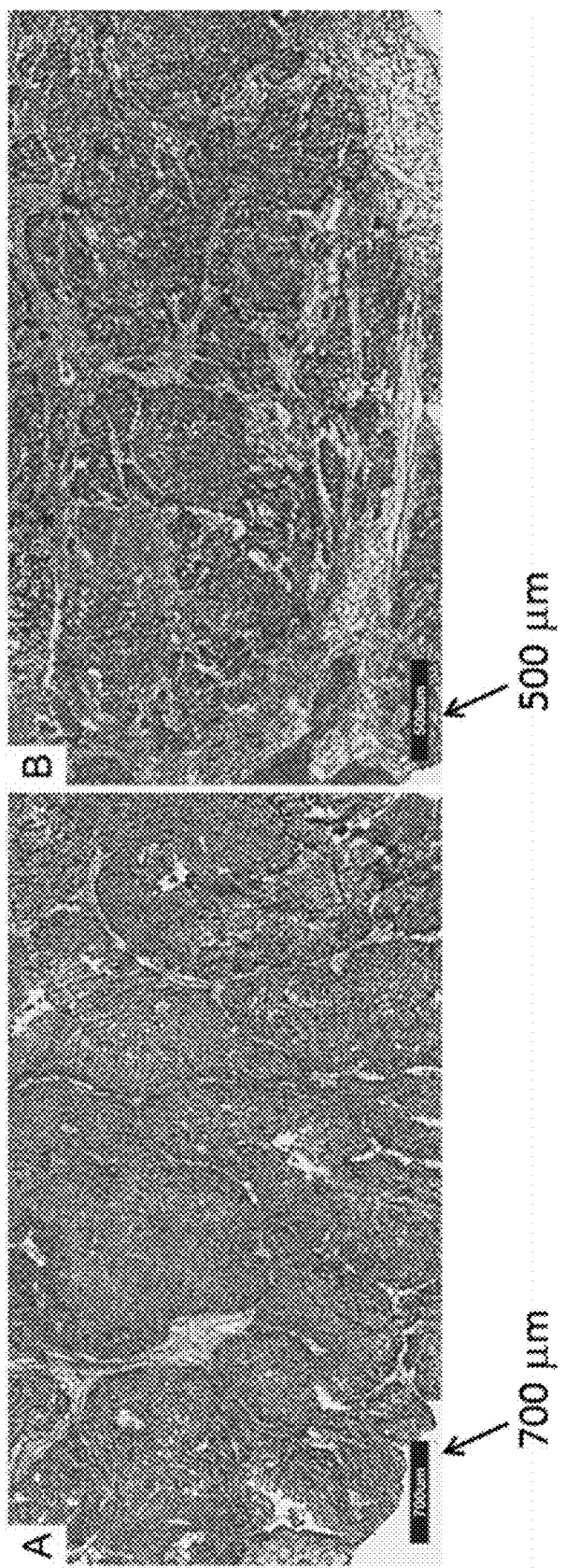
FIGS. 1A-1H show representative micrograph images of analyzed tumors related to "Example 1 Demographic, Clinical, and Pathological Data," below.
Figure 1:
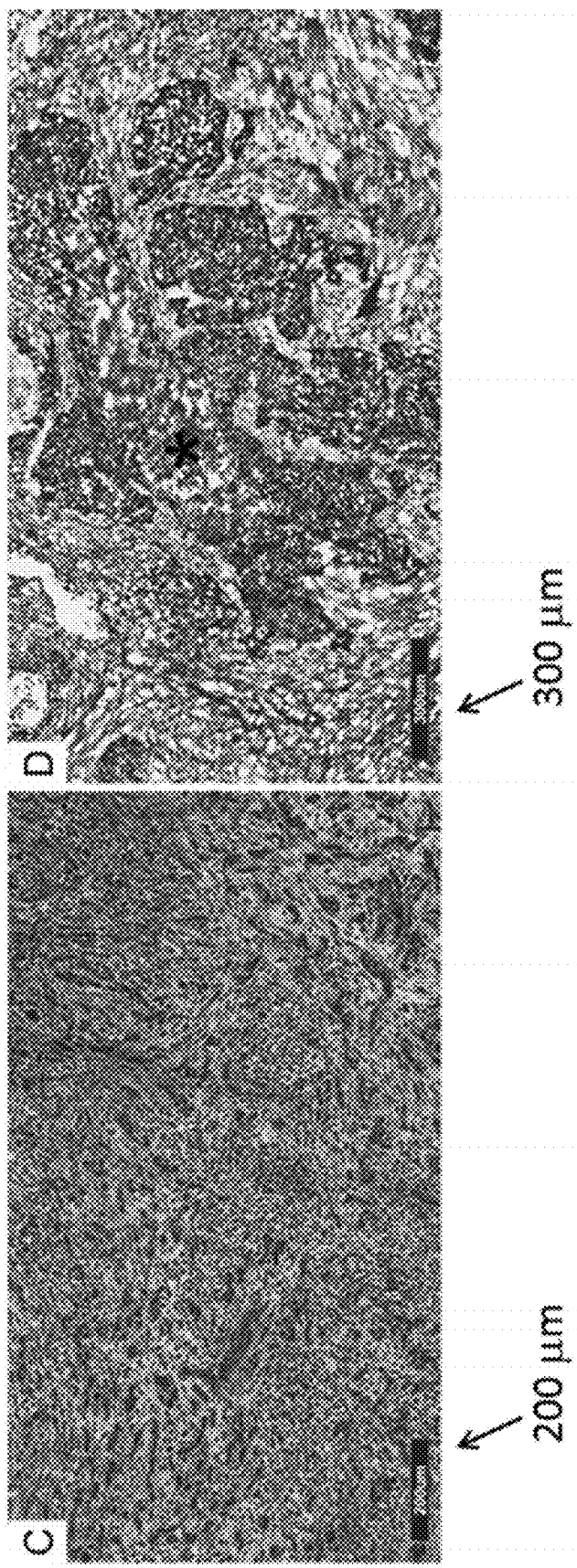
Figure 1:
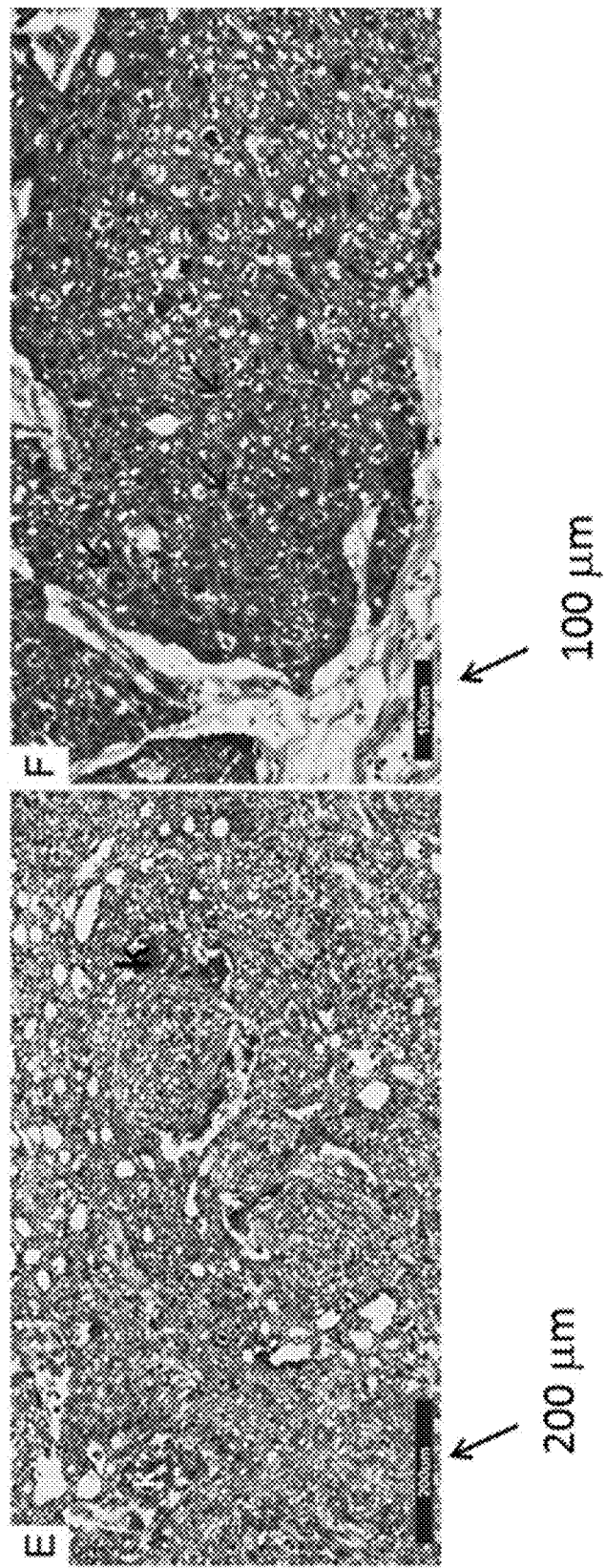
Figure 1:
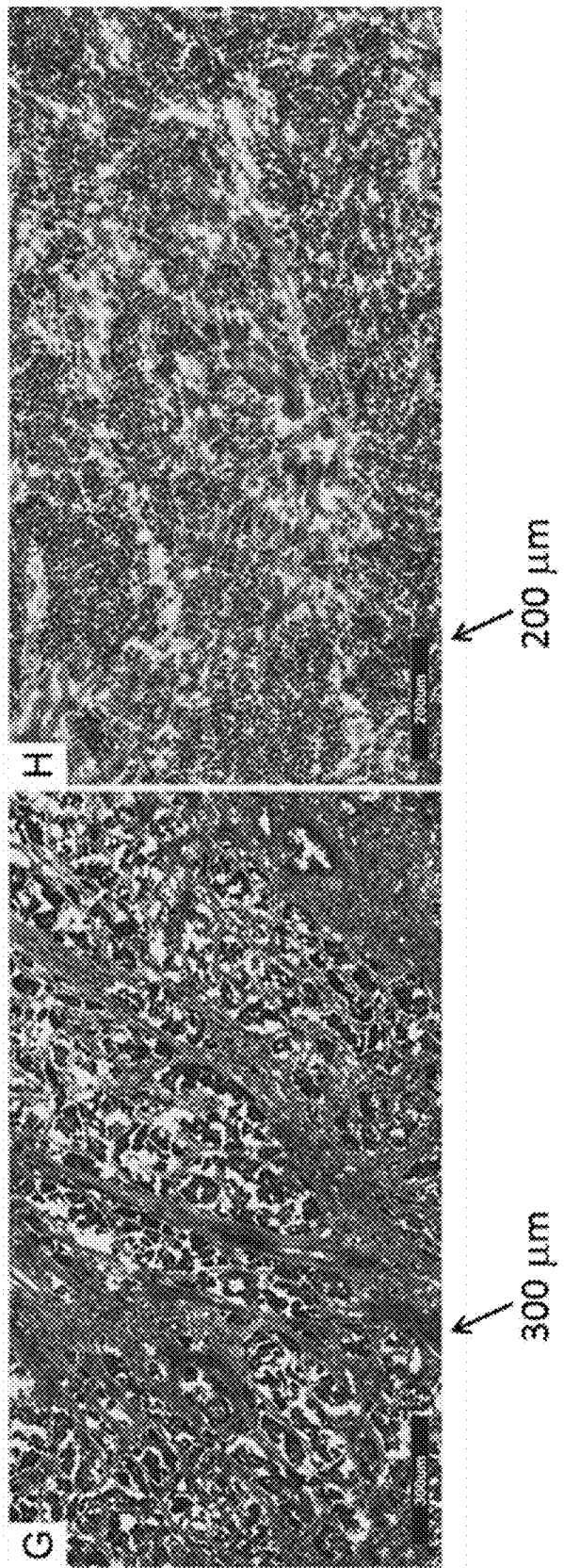
Figure 2:
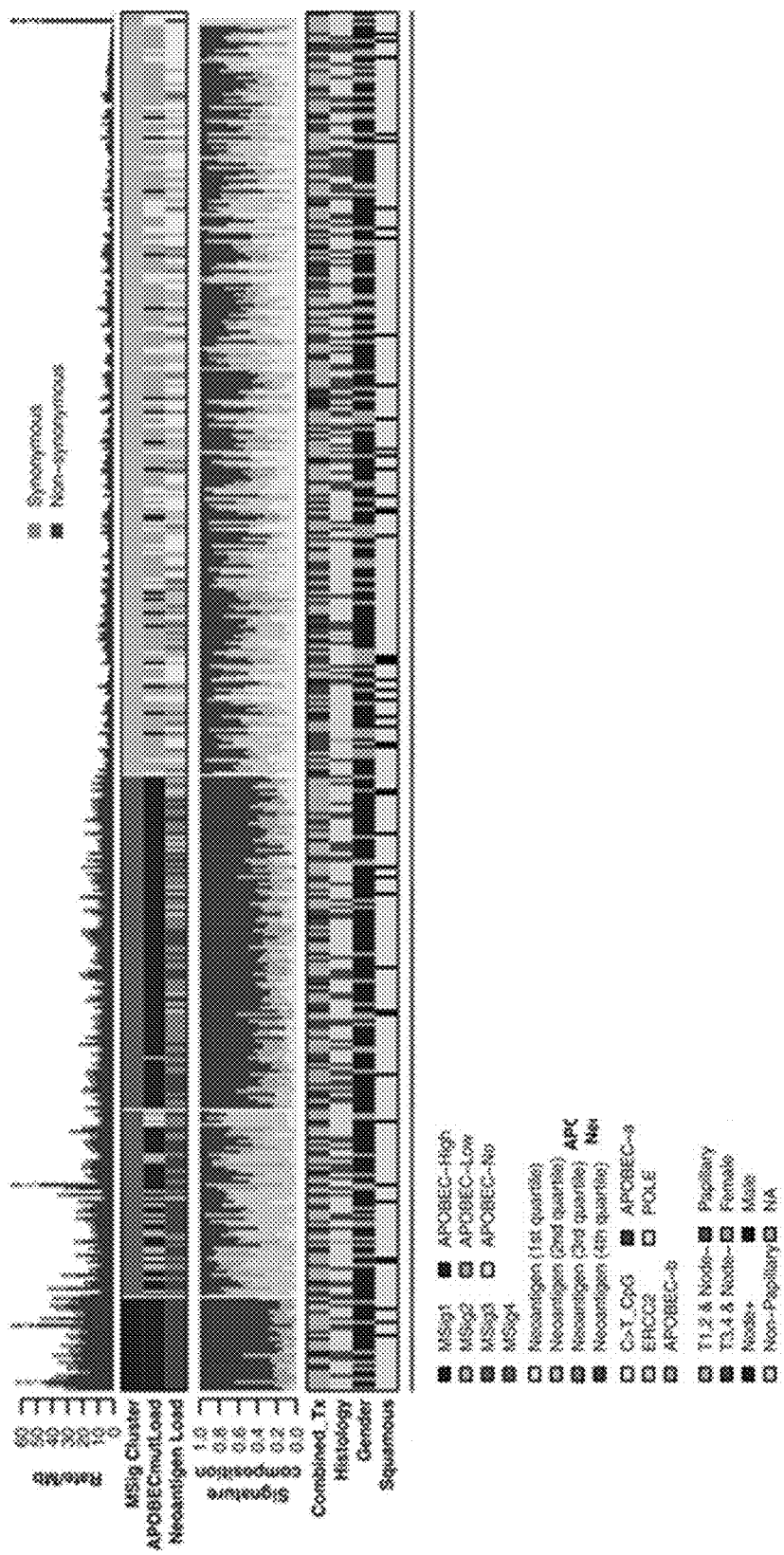
FIGS. 2A and 2B are images and graphs showing the landscape of mutational signatures, mutations and copy number alterations.
Figure 2:
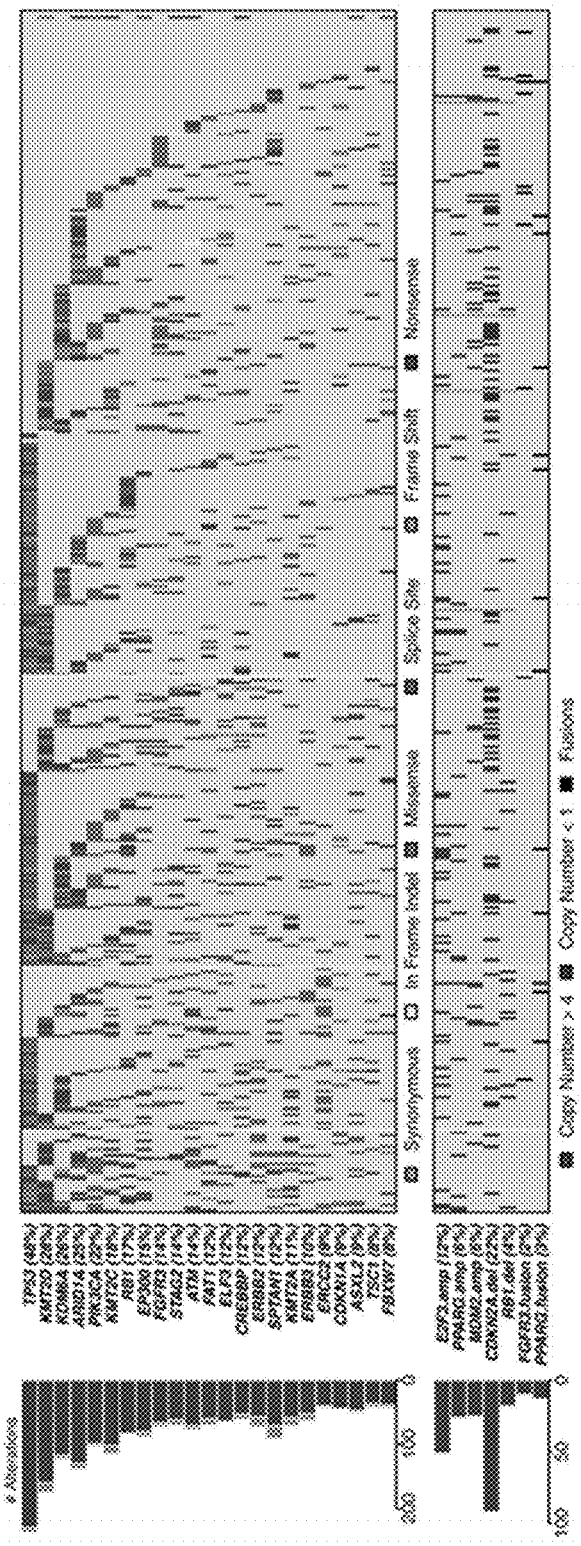
Figure 2:
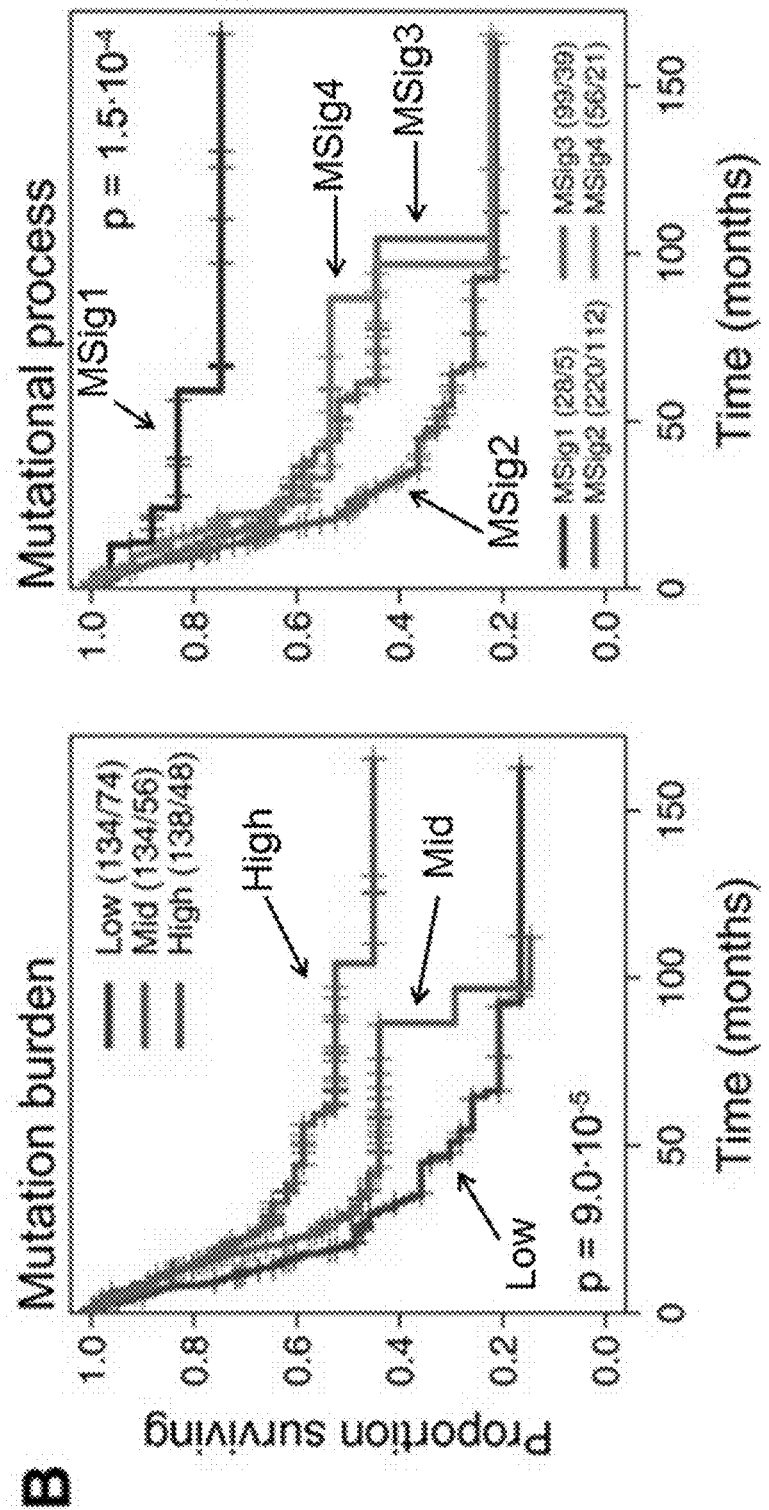
Figure 2:
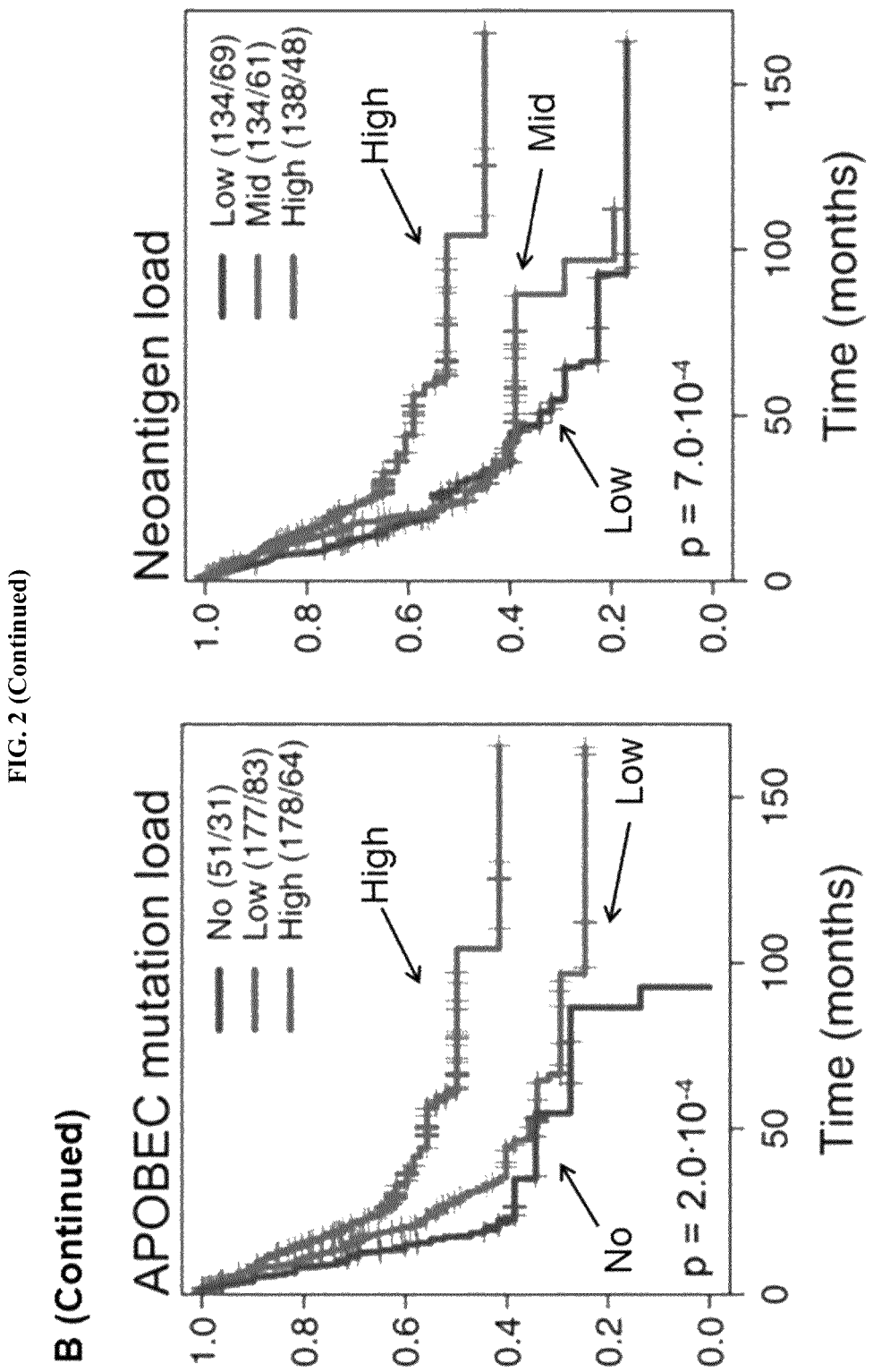

Whole-exome sequencing (WES) of 412 tumors and matched normal samples targeted 193,094 exons in 18,862 genes (mean coverage 85×, 79% of target bases >30×). MuTect analysis identified 131,660 somatic mutations (128,772 single-nucleotide variants (SNVs) and 2,888 indels), with high non-synonymous mutation rates (mean 8.2 and median 5.8 per megabase [Mb]) (FIG. 2A). Most mutations were C>G transversions (27%) or C>T transitions (51%). Whole genome—the events were found in 221 (54%) tumors. To identify processes contributing to the high mutation rate, Bayesian non-negative matrix factorization (NMF) was used to identify 5 mutation signatures (FIG. 3A). Apolipoprotein B mRNA editing enzyme, catalytic polypeptide-like (APOBEC)-a and APOBEC-b were variants of the hallmark APOBEC mutagenesis signature. A third signature, consisting of C>T transitions at CpG dinucleotides, was likely due to 5-methylcytosine deamination. A fourth, in the gene for DNA polymerase epsilon catalytic subunit (POLE), was present in a single ultra-mutated sample, with >4000 SNVs and a POLE mutation (P286R). The fifth, ERCC2, had a relatively uniform spectrum of base changes and has been associated with ERCC2 mutations (Kim et al., 2016b).

The APOBEC-a and -b signatures accounted for 67% of all SNVs. Results from an independent method for identifying APOBEC-signature mutations (Roberts et al., 2013) strongly correlated with mutation load assigned to APOBEC-a and -b groups (FIG. 3B). The total count of mutations with a stringent APOBEC signature correlated with the remaining mutation burden (r=0.48, FIG. 3C), suggesting that some mutations not assigned to APOBEC-signature mutagenesis were also APOBEC-mediated. As expected (Roberts et al., 2013), levels of APOBEC-signature mutagenesis correlated with expression of APOBEC3A and APOBEC3B (FIG. 3D). C>T at CpG and ERCC2 mutation signatures accounted for 20% and 8% of total SNVs, respectively. 64% of all mutations, as well as 62% of APOBEC-a—and 75% of APOBEC-b-signature mutations (likelihood of signature association ≥0.7; Methods) (Kasar et al., 2015) were clonal (cancer cell fraction ≥0.9), suggesting that more than half of the APOBEC-signature mutation load was likely generated early in bladder cancer development.

Unsupervised clustering of APOBEC-a and -b, ERCC2, and C>T-at-CpG signatures identified four mutational signature clusters, MSig1 to MSig4 (FIG. 2A, FIG. 2B, FIG. 3E), which were associated with overall survival (FIG. 2B, $p=1.4 \cdot 10^{-4}$). Patients with MSig1 cancers (high APOBEC-signature mutagenesis and high mutation burden) showed an exceptional 75% 5-year survival probability. Better survival was also seen in subsets defined by high mutation burden or high APOBEC-signature mutation load (FIG. 2B). MSig2 cancers had the lowest mutation rate and poorest 5-year survival (22%). MSig4 cluster samples were enriched in both ERCC2 signature mutations (average contribution 49% vs. 17% in all others, FIG. 2A) and ERCC2 mutations (24 out of 39, $p=10^{-13}$). ERCC2 signature mutations were highest in smokers with ERCC2 mutations ($p=6.9 \times 10^{-11}$); for cases with wild type ERCC2, ERCC2 signature mutations were at higher levels in smokers than in non-smokers (FIG. 3F).

Mutation analysis using MutSig 2CV identified 58-significantly mutated genes (SMGs) (q<0.1; Table 2 and Table 3). 34 of the 58 SMGs had not been identified as SMGs in an earlier analysis (Cancer Genome Atlas Research Network, 2014a); further, 16 of the 34 SMGs had not been implicated as cancer SMGs in a recent pan-cancer analysis (Lawrence et al., 2014). 7 of the 34 genes were mutated in >10% of samples: KMT2C (18%), ATM (14%), FAT1 (12%), CREBBP (12%), ERBB2 (12%), SPTAN1 (12%), and KMT2A (11%). Alterations were mutually exclusive between CDKN2A and TP53, CDKN2A and RB1, CDKN2A and E2F3, TP53 and MDM2, FGFR3 and E2F3, and FGFR3 and RB1. Similar analyses showed co-occurrence of alterations in TP53 and RB1, TP53 and E2F3, and FGFR3 and CDKN2A (q<0.2). FGFR3 mutations and CDKN2A focal SCNAs co-occurred in 27 (7%) tumors (Table 2), which may be muscle-invasive bladder cancers (MIBCs) that have progressed from non-invasive tumors (Rebouissou et al., 2012). 3 of 4 tumors with plasmacytoid histology had nonsense CDH1 mutations, consistent with a previous report (Al-Ahmadie et al., 2016).

TABLE 2

SMGs

| Column name<br>Case ID | TCGA label<br>CLIN_bcr_patient_barcode | Description/values*<br>Case ID, BCR barcode |
|---|---|---|
| mutation in TP53 | SMG_TP53 | yes/no |
| mutation in RB1 | SMG_RB1 | yes/no |
| mutation in RHOB | SMG_RHOB | yes/no |
| mutation in PIK3CA | SMG_PIK3CA | yes/no |
| mutation in KDM6A | SMG_KDM6A | yes/no |
| mutation in TSC1 | SMG_TSC1 | yes/no |
| mutation in ELF3 | SMG_ELF3 | yes/no |
| mutation in KMT2D | SMG_KMT2D | yes/no |
| mutation in CREBBP | SMG_CREBBP | yes/no |
| mutation in CDKN1A | SMG_CDKN1A | yes/no |
| mutation in EP300 | SMG_EP300 | yes/no |
| mutation in ZFP36L1 | SMG_ZFP36L1 | yes/no |
| mutation in ARID1A | SMG_ARID14 | yes/no |
| mutation in STAG2 | SMG_STAG2 | yes/no |
| mutation in CDKN2A | SMG_CDKN24 | yes/no |
| mutation in HRAS | SMG_HRAS | yes/no |
| mutation in KRAS | SMG_KRAS | yes/no |
| mutation in FBXW7 | SMG_FBXW7 | yes/no |
| mutation in ERCC2 | SMG_ERCC2 | yes/no |
| mutation in ASXL2 | SMG_ASXL2 | yes/no |
| mutation in RHOA | SMG_RHOA | yes/no |
| mutation in KMT2A | SMG_KMT2A | yes/no |

TABLE 2-continued

| | SMGs | |
|---|---|---|
| Column name | TCGA label | Description/values* |
| Case ID | CLIN_bcr_patient_barcode | Case ID, BCR barcode |
| mutation in FGFR3 | SMG_FGFR3 | yes/no |
| mutation in NFE2L2 | SMG_NFE2L2 | yes/no |
| mutation in KMT2C | SMG_KMT2C | yes/no |
| mutation in PSIP1 | SMG_PSIP1 | yes/no |
| mutation in KANSL1 | SMG_KANSL1 | yes/no |
| mutation in C3orf70 | SMG_C3orf70 | yes/no |
| mutation in FAT1 | SMG_FAT1 | yes/no |
| mutation in SPTAN1 | SMG_SPTAN1 | yes/no |
| mutation in RXRA | SMG_RXRA | yes/no |
| mutation in ZBTB7B | SMG_ZBTB7B | yes/no |
| mutation in PTEN | SMG_PTEN | yes/no |
| mutation in ATM | SMG_ATM | yes/no |
| mutation in KLF5 | SMG_KLF5 | yes/no |
| mutation in PARD3 | SMG_PARD3 | yes/no |
| mutation in CUL1 | SMG_CUL1 | yes/no |
| mutation in NRAS | SMG_NRAS | yes/no |
| mutation in SF3B1 | SMG_SF3B1 | yes/no |
| mutation in GNA13 | SMG_GNA13 | yes/no |
| mutation in RBM10 | SMG_RBM10 | yes/no |
| mutation in ACTB | SMG_ACTB | yes/no |
| mutation in MBD1 | SMG_MBD1 | yes/no |
| mutation in CASP8 | SMG_CASP8 | yes/no |
| mutation in HIST1H3B | SMG_HIST1H3B | yes/no |
| mutation in TAF11 | SMG_TAF11 | yes/no |
| mutation in ERBB2 | SMG_ERBB2 | yes/no |
| mutation in NUP93 | SMG_NURP93 | yes/no |
| mutation in SF1 | SMG_SF1 | yes/no |
| mutation in ERBB3 | SMG_ERBB3 | yes/no |
| mutation in METTL3 | SMG_METTL3 | yes/no |
| mutation in SPN | SMG_SPN | yes/no |
| mutation in MB21D2 | SMG_MB21D2 | yes/no |
| mutation in SSH3 | SMG_SSH3 | yes/no |
| mutation in USP28 | SMG_USP28 | yes/no |
| mutation in ASXL1 | SMG_ASXL1 | yes/no |
| mutation in TMCO4 | SMG_TMCO4 | yes/no |
| mutation in HES1 | SMG_HES1 | yes/no |
| mutation in ZNF773 | SMG_ZNF773 | yes/no |

TABLE 3

Mutation Exclusivity

| Event1 | Event2 | n1 | n2 | n.overlap | pval | qval |
|---|---|---|---|---|---|---|
| RB1.mut | CDKN2A.del | 72 | 91 | 0 | 2.34E-09 | 2.01E-06 |
| TP53.mut | MDM2.amp | 198 | 25 | 1 | 9.14E-07 | 0.00039302 |
| TP53.mut | FGFR3.mut | 198 | 58 | 13 | 1.49E-05 | 0.00427133 |
| TP53.mut | CDKN2A.del | 198 | 91 | 27 | 3.76E-05 | 0.008084 |
| RB1.mut | FGFR3.mut | 72 | 58 | 2 | 0.000679 | 0.116788 |
| E2F3.amp | CDKN2A.del | 50 | 91 | 3 | 0.00101 | 0.14476667 |
| ERCC2.mut | CDKN2A.del | 39 | 91 | 2 | 0.00316 | 0.36597778 |
| ARID1A.mut | FGFR3.mut | 101 | 58 | 6 | 0.00346 | 0.36597778 |
| KMT2A.mut | CDKN2A.del | 45 | 91 | 3 | 0.00383 | 0.36597778 |
| RB1.mut | NFE2L2.mut | 72 | 26 | 0 | 0.00569 | 0.48934 |
| FGFR3.mut | KMT2A.mut | 58 | 45 | 1 | 0.00666 | 0.52069091 |
| RB1.mut | CCND1.amp | 72 | 35 | 1 | 0.00845 | 0.60558333 |
| KMT2D.mut | KDM6A.mut | 117 | 107 | 21 | 0.012 | 0.79384615 |
| TP53.mut | CDKN1A.mut | 198 | 37 | 11 | 0.0143 | 0.87842857 |
| FGFR3.mut | E2F3.amp | 58 | 50 | 2 | 0.0157 | 0.897625 |
| FGFR3.mut | PPARG.amp | 58 | 26 | 0 | 0.0167 | 0.897625 |
| FGFR3.mut | PARD3.mut | 58 | 25 | 0 | 0.0199 | 0.93694737 |
| YWHAZ.amp | CDKN2A.del | 36 | 91 | 3 | 0.0201 | 0.93694737 |
| KDM6A.mut | FAT1.mut | 107 | 51 | 7 | 0.0207 | 0.93694737 |
| KMT2C.mut | YWHAZ.amp | 76 | 36 | 2 | 0.0231 | 0.97057143 |
| FGFR3.mut | ATM.mut | 58 | 57 | 3 | 0.0237 | 0.97057143 |
| ZFP36L1.mut | CDKN2A.del | 28 | 91 | 2 | 0.0282 | 1 |
| STAG2.mut | SF3B1.mut | 57 | 23 | 0 | 0.0294 | 1 |
| RB1.mut | YWHAZ.amp | 72 | 36 | 2 | 0.0324 | 1 |
| NFE2L2.mut | E2F3.amp | 26 | 50 | 0 | 0.033 | 1 |
| STAG2.mut | KMT2A.mut | 57 | 45 | 2 | 0.0338 | 1 |
| KMT2A.mut | ZFP36L1.mut | 45 | 28 | 0 | 0.0349 | 1 |

TABLE 3-continued

| | Mutation Exclusivity | | | | | |
|---|---|---|---|---|---|---|
| Event1 | Event2 | n1 | n2 | n.overlap | pval | qval |
| FAT1.mut | E2F3.amp | 51 | 50 | 2 | 0.039 | 1 |
| ERBB2.mut | E2F3.amp | 50 | 50 | 2 | 0.039 | 1 |
| FAT1.mut | SF3B1.mut | 51 | 23 | 0 | 0.0437 | 1 |
| TP53.mut | ATM.mut | 198 | 57 | 21 | 0.0456 | 1 |

Four DNA-based clusters were identified using unsupervised NMF clustering with SMG mutations (Mut) and focal SCNAs (CN) (FIG. 3G, FIG. 3H, FIG. 25). The four MutCN clusters were characterized by: TP53 and RB1 mutations, SOX4/E2F3 amplification, mutations in chromatin-modifying genes, and FGFR3, KDM6A, and STAG2 mutations.

Neoantigen load was strongly correlated with mutation burden, elevated in the MSig1 cluster ($p=2.9 \times 10^{-12}$), and associated with survival ($p=5.2 \times 10^{-4}$; FIG. 2B). It was an independent predictor of outcome in addition to age, AJCC tumor stage, and squamous differentiation ($p=8 \times 10^{-4}$). Polysolver-based HLA mutation detection identified 21 non-synonymous variants in 19 of 412 tumors (4.6%). HLA mutations were more common in MSig1 cluster ($p=0.039$), suggesting that they may have resulted from APOBEC-signature mutagenesis. HLA mutations were somewhat more common in patients with prior BCG treatment, 4 of 35 (11.4%) vs. 8 of 261 (3.1%) without prior BCG treatment ($p=0.04$, Chi-square test), perhaps positively selected in response to immunological pressure.

Using RNA-seq data, 784 gene fusions were identified. The most common was an intra-chromosomal FGFR3-TACC3 fusion (n=10). There were 9 cases of an intra-chromosomal translocation ITGB6-LOC100505984, whose functional significance was uncertain. PPARG was involved in 4 TSEN2-PPARG and 2 MKRN2-PPARG fusions, and PPARG expression levels were higher than in samples without such fusions ($p=6 \times 10^{-3}$). Four of the six PPARG fusions led to mRNA products for which the predicted proteins retained both PPARG's DNA-binding and ligand-binding domains, suggesting that they were functional (FIG. 3I). Similar fusions were searched for in RNA-seq data from 30 human bladder cancer cell lines. In lines 5637 and 1A6, CASC15-PPARG fusions were identified that retained PPARG's full DNA binding domain; in UC9 an NR2C2-PPARG fusion was identified that retained 75% of PPARG's ligand-binding domain. PPARG was overexpressed in all three of these cell lines ($p<0.05$).

Example 3: DNA Methylation

Unsupervised clustering using tumor-associated hypermethylated cytosine-phosphate-guanine (CpG) sites or, independently, tumor-associated hypomethylated sites, identified 5 major clusters that were significantly correlated with other data types (FIG. 4A and FIG. 4B). Of particular interest was a group of tumors with high purity that showed marked loss of DNA methylation (hypomethylation cluster 4, FIG. 4B, FIG. 4C). This group significantly overlapped with the DNA hypermethylation cluster 2, which showed a low frequency of DNA hypermethylation ($p=3.2 \times 10^{-8}$, odds ratio 9.5, FIG. 4D). Samples in cluster 4 showed frequent FGFR3 mutation ($p=6 \times 10^{-9}$) and CDKN2A deletion ($p=4 \times 10^{-13}$), and had no TP53 or RB1 mutations. Further, those tumors that belonged to the luminal-papillary mRNA subtype, exhibited papillary histology ($p=5 \times 10^{-12}$), were almost all node-negative ($p=5 \times 10^{-12}$), were from younger patients (median age 61 vs. 69; $p<4 \times 10^{-3}$), and showed better survival ($p<0.05$; log-rank test, FIG. 4E). DNA hypomethylation appeared more widespread in low-stage, noninvasive urothelial tumors (Wolff et al., 2010). Analysis of hypomethylated CpG sites in this group revealed 12 genes whose hypomethylation was significantly correlated with increased expression (FIG. 4F).

Integrated analysis of DNA methylation and gene expression identified 158 genes that were epigenetically silenced (Table 4, FIG. 4G; FIG. 27).

TABLE 4

Epigenetically Silenced Genes

| Gene | Official Symbol | Gene ID | Probe with the lowest Z-score | Z-score | Estimated % of tumors silenced | MAP | Official Full Name |
|---|---|---|---|---|---|---|---|
| ABCB6 | ABCB6 | 10058 | cg07100128 | −1.84 | 12 | 2q36 | ATP binding cassette subfamily B member 6 (Langereis blood group) |
| ACOT9 | ACOT9 | 23597 | cg24547622 | −2.35 | 6 | Xp22.11 | acyl-CoA thioesterase 9 |
| ADRBK2 | GRK3 | 157 | cg15154002 | −1.78 | 4 | 22q12.1 | adrenergic, beta, receptor kinase 2 |
| ALDH7A1 | ALDH7A1 | 501 | cg19551232 | −2.2 | 39 | 5q31 | aldehyde dehydrogenase 7 family member A1 |
| ANXA5 | ANXA5 | 308 | cg08831277 | −1.68 | 5 | 4q27 | annexin A5 |
| APOBEC3G | APOBEC3G | 60489 | cg22902400 | −1.7 | 5 | 22q13.1-q13.2 | apolipoprotein B mRNA editing enzyme catalytic subunit 3G |
| ARPM1 | ACTRT3 | 84517 | cg15981995 | −2.24 | 24 | 3q26.2 | actin-related protein T3 |
| BCL11A | BCL11A | 53335 | cg15091323 | −1.72 | 5 | 2p16.1 | B-cell CLL/lymphoma 11A |
| BST2 | BST2 | 684 | cg11558551 | −2 | 18 | 19p13.1 | bone marrow stromal cell antigen 2 |
| C14orf59 | C14orf59 | 80017 | cg26288577 | −1.93 | 10 | 14q32.11 | chromosome 14 open reading frame 159 |
| C15orf37 | ST20-AS1 | 283687 | cg02183105 | −1.7 | 13 | 15q25.1 | ST20 antisense RNA 1 |
| C15orf56 | C15orf56 | 644809 | cg01036164 | −1.68 | 6 | 15q15.1 | chromosome 15 open reading frame 56 |
| C18orf18 | LINC00526 | 147525 | cg05390530 | −1.66 | 15 | 18p11.31 | long intergenic non-protein coding RNA 526 |
| C19orf63 | EMC10 | 284361 | cg04541675 | −2.26 | 6 | 19q13.33 | ER membrane protein complex subunit 10 |
| C21orf56 | SPATC1L | 84221 | cg12016809 | −1.86 | 19 | 21q22.3 | spermatogenesis and centriole associated 1-like |

TABLE 4-continued

Epigenetically Silenced Genes

| Gene | Official Symbol | Gene ID | Probe with the lowest Z-score | Z-score | Estimated % of tumors silenced | MAP | Official Full Name |
|---|---|---|---|---|---|---|---|
| C2orf43 | LDAH | 60526 | cg14903097 | −2.14 | 5 | 2p24.1 | lipid droplet associated hydrolase |
| C2orf74 | C2orf74 | 339804 | cg16328106 | −1.98 | 53 | 2p15 | chromosome 2 open reading frame 74 |
| C3orf14 | C3orf14 | 57415 | cg15059608 | −1.71 | 19 | 3p14.2 | chromosome 3 open reading frame 14 |
| C6orf150 | MB21D1 | 115004 | cg16353624 | −1.65 | 6 | 6q13 | Mab-21 domain containing 1 |
| C7orf13 | C7orf13 | 129790 | cg26816688 | −1.66 | 36 | 7q36.3 | chromosome 7 open reading frame 13 |
| C9orf167 | TOR4A | 54863 | cg14409810 | −1.76 | 36 | 9q34.3 | torsin family 4 member A |
| CASP8 | CASP8 | 841 | cg00978584 | NA | 1 | 2q33-q34 | caspase 8 |
| CCDC106 | CCDC106 | 29903 | cg25230111 | −1.65 | 12 | 19q13.42 | coiled-coil domain containing 106 |
| CCNJ | CCNJ | 54619 | cg08461586 | −3.02 | 10 | 10q23.33 | cyclin J |
| CD320 | CD320 | 51293 | cg23963136 | −1.97 | 20 | 19p13.2 | CD320 molecule |
| CDK20 | CDK20 | 23552 | cg13685727 | −2.16 | 7 | 9q22.1 | cyclin-dependent kinase 20 |
| CDKN2A | CDKN2A | 1029 | cg13601799 | NA | 1 | 9p21 | cyclin-dependent kinase inhibitor 2A |
| CHCHD5 | CHCHD5 | 84269 | cg11528832 | −1.88 | 4 | 2q13 | coiled-coil-helix-coiled-coil-helix domain containing 5 |
| CLIP4 | CLIP4 | 79745 | cg26052635 | −1.76 | 6 | 2p23.2 | CAP-Gly domain containing linker protein family member 4 |
| CSTF2T | CSTF2T | 23283 | cg12402038 | −2.88 | 6 | 10q11 | cleavage stimulation factor, 3' pre-RNA, subunit 2, tau variant |
| DCP1B | DCP1B | 196513 | cg10179964 | −2.32 | 4 | 12p13.33 | decapping mRNA 1B |
| DYRK1B | DYRK1B | 9149 | cg15475080 | −1.65 | 9 | 19q13.2 | dual specificity tyrosine phosphorylation regulated kinase 1B |
| ENPP4 | ENPP4 | 22875 | cg06768203 | −1.69 | 6 | 6p21.1 | ectonucleotide pyrophosphatase/ phosphodiesterase 4 (putative) |
| ENPP5 | ENPP5 | 59084 | cg23889391 | −1.73 | 6 | 6p21.1-p11.2 | ectonucleotide pyrophosphatase/ phosphodiesterase 5 (putative) |
| EPHX2 | EPHX2 | 2053 | cg10348756 | −1.76 | 15 | 8p21 | epoxide hydrolase 2 |
| EPHX3 | EPHX3 | 79852 | cg17476026 | −1.85 | 39 | 19p13.12 | epoxide hydrolase 3 |
| FAM109B | FAM109B | 150368 | cg11915388 | −2.02 | 20 | 22q13.2 | family with sequence similarity 109 member B |
| FAM131A | FAM131A | 131408 | cg00205703 | −2.39 | 13 | 3q27.1 | family with sequence similarity 131 member A |
| FAM24B | FAM24B | 196792 | cg11729970 | −1.72 | 18 | 10q26.13 | family with sequence similarity 24 member B |
| FAT1 | FAT1 | 2195 | cg19428336 | NA | 1 | 4q35 | FAT atypical cadherin 1 |
| FUZ | FUZ | 80199 | cg21712019 | −1.94 | 9 | 19q13.33 | fuzzy planar cell polarity protein |
| GALC | GALC | 2581 | cg10122474 | −1.77 | 5 | 14q31 | galactosylceramidase |
| GLB1L2 | GLB1L2 | 89944 | cg07759394 | −1.67 | 5 | 11q25 | galactosidase beta 1 like 2 |
| HCG11 | HCG11 | 493812 | cg10414736 | −1.72 | 13 | 6p22.2 | HLA complex group 11 (non-protein coding) |
| HCG4 | HCG4 | 54435 | cg13688808 | −1.71 | 58 | 6p21.3 | HLA complex group 4 (non-protein coding) |
| HFE | HFE | 3077 | cg08320659 | −2.28 | 8 | 6p21.3 | hemochromatosis |
| HIST1H2AE | HIST1H2AE | 3012 | cg04808283 | −1.7 | 9 | 6p22.2 | histone cluster 1, H2ae |
| HIST1H2BH | HIST1H2BH | 8345 | cg02578368 | −1.68 | 22 | 6p22.2 | histone cluster 1, H2bh |
| HOXA7 | HOXA7 | 3204 | cg09017619 | −1.67 | 32 | 7p15.2 | homeobox A7 |
| HOXA9 | HOXA9 | 3205 | cg21001184 | −1.67 | 53 | 7p15.2 | homeobox A9 |
| HOXC13 | HOXC13 | 3229 | cg16856286 | −1.69 | 9 | 12q13.3 | homeobox C13 |
| HPDL | HPDL | 84842 | cg14913111 | −1.65 | 37 | 1p34.1 | 4-hydroxyphenylpyruvate dioxygenase-like |
| HSD17B8 | HSD17B8 | 7923 | cg05507546 | −1.68 | 10 | 6p21.3 | hydroxysteroid (17-beta) dehydrogenase 8 |
| IL1RL2 | IL1RL2 | 8808 | cg01376829 | −2.16 | 13 | 2q12 | interleukin 1 receptor like 2 |
| INA | INA | 9118 | cg24680586 | −1.75 | 10 | 10q24.33 | internexin neuronal intermediate filament protein alpha |
| IRX5 | IRX5 | 10265 | cg05362516 | −1.65 | 9 | 16q12.2 | iroquois homeobox 5 |
| KCNK1 | KCNK1 | 3775 | cg11382055 | −1.89 | 3 | 1q42.2 | potassium two pore domain channel subfamily K member 1 |
| KLHDC9 | KLHDC9 | 126823 | cg17132124 | −1.81 | 11 | 1q23.3 | kelch domain containing 9 |
| LOC339290 | NA | NA | cg20134241 | −1.68 | 16 | NA | NA |
| LOC387647 | NA | NA | cg16036409 | −1.81 | 6 | NA | NA |
| LPCAT2 | LPCAT2 | 54947 | cg01751134 | −1.79 | 10 | 16q12.2 | lysophosphatidylcholine acyltransferase 2 |
| LXN | LXN | 56925 | cg14019186 | −1.64 | 27 | 3q25.32 | latexin |
| LY75 | LY75 | 4065 | cg02280532 | −1.77 | 7 | 2q24 | lymphocyte antigen 75 |
| MAP9 | MAP9 | 79884 | cg03405515 | −1.73 | 19 | 4q32.1 | microtubule associated protein 9 |
| MBIP | MBIP | 51562 | cg21443584 | −1.74 | 7 | 14q13.3 | MAP3K12 binding inhibitory protein 1 |
| ME3 | ME3 | 10873 | cg13391116 | −2.19 | 7 | 11cen-q22.3 | malic enzyme 3, NADP(+)-dependent, mitochondrial |
| METT11D1 | METTL17 | 64745 | cg06609882 | −1.73 | 5 | 14q11.2 | methyltransferase like 17 |
| MRPS21 | MRPS21 | 54460 | cg09808343 | −1.67 | 17 | 1q21 | mitochondrial ribosomal protein S21 |
| MYH14 | MYH14 | 79784 | cg06553312 | −1.83 | 6 | 19q13.33 | myosin, heavy chain 14, non-muscle |
| NAPRT1 | NAPRT | 93100 | cg16316162 | −1.65 | 13 | 8q24.3 | nicotinate phosphoribosyltransferase |
| NHLRC1 | NHLRC1 | 378884 | cg06497198 | −2.03 | 5 | 6p22.3 | NHL repeat containing E3 ubiquitin protein ligase 1 |
| NME3 | NME3 | 4832 | cg00485296 | −2.04 | 8 | 16q13.3 | NME/NM23 nucleoside diphosphate kinase 3 |
| NMNAT3 | NMNAT3 | 349565 | cg18116154 | −1.66 | 20 | 3q23 | nicotinamide nucleotide adenylyltransferase 3 |
| NQO1 | NQO1 | 1728 | cg19194454 | −1.87 | 5 | 16q22.1 | NAD(P)H dehydrogenase, quinone 1 |
| NRSN2 | NRSN2 | 80023 | cg07611334 | −1.91 | 27 | 20p13 | neurensin 2 |
| NUDT12 | NUDT12 | 83594 | cg13665998 | −1.69 | 8 | 5q21.2 | nudix hydrolase 12 |

TABLE 4-continued

Epigenetically Silenced Genes

| Gene | Official Symbol | Gene ID | Probe with the lowest Z-score | Z-score | Estimated % of tumors silenced | MAP | Official Full Name |
|---|---|---|---|---|---|---|---|
| NUDT16P1 | NUDT16P1 | 152195 | cg19962116 | −2.15 | 9 | 3q22.1 | nudix hydrolase 16 pseudogene 1 |
| NUDT19 | NUDT19 | 390916 | cg24149930 | −2.15 | 9 | 19q13.11 | nudix hydrolase 19 |
| OAT | OAT | 4942 | cg03092918 | −1.64 | 31 | 10q26 | ornithine aminotransferase |
| OPLAH | OPLAH | 26873 | cg23830937 | −1.91 | 9 | 8q24.3 | 5-oxoprolinase (ATP-hydrolysing) |
| PARP6 | PARP6 | 56965 | cg08294267 | −2.61 | 26 | 15q23 | poly(ADP-ribose) polymerase family member 6 |
| PXMP4 | PXMP4 | 11264 | cg18669346 | −2.16 | 8 | 20q11.22 | peroxisomal membrane protein 4 |
| RAB34 | RAB34 | 83871 | cg19982230 | −1.73 | 28 | 17q11.2 | RAB34, member RAS oncogene family |
| RANBP17 | RANBP17 | 64901 | cg07848601 | −1.96 | 18 | 5q34 | RAN binding protein 17 |
| RANGRF | RANGRF | 29098 | cg26053771 | −2.25 | 6 | 17p13.1 | RAN guanine nucleotide release factor |
| RIPK3 | RIPK3 | 11035 | cg13066043 | −1.82 | 8 | 14q11.2 | receptor interacting serine/threonine kinase 3 |
| RNLS | RNLS | 55328 | cg06981182 | −1.67 | 13 | 10q23.31 | renalase, FAD-dependent amine oxidase |
| RTP4 | RTP4 | 64108 | cg19383430 | −1.92 | 11 | 3q27.3 | receptor (chemosensory) transporter protein 4 |
| SCAND3 | ZBED9 | 114821 | cg06535324 | −1.66 | 7 | 6p22.1 | zinc finger BED-type containing 9 |
| SDK1 | SDK1 | 221935 | cg20150591 | −1.73 | 5 | 7p22.2 | sidekick cell adhesion molecule 1 |
| SDR42E1 | SDR42E1 | 93517 | cg04821708 | −2.67 | 29 | 16q23.3 | short chain dehydrogenase/reductase family 42E, member 1 |
| SETD6 | SETD6 | 79918 | cg09132913 | −1.65 | 7 | 16q21 | SET domain containing 6 |
| SLC25A20 | SLC25A20 | 788 | cg23732368 | −1.86 | 6 | 3p21.31 | solute carrier family 25 member 20 |
| SNX19 | SNX19 | 399979 | cg22079354 | −2.63 | 4 | 11q25 | sorting nexin 19 |
| SOX15 | SOX15 | 6665 | cg14824495 | −1.72 | 44 | 17p13.1 | SRY-box 15 |
| SPAG16 | SPAG16 | 79582 | cg01372071 | −1.75 | 7 | 2q34 | sperm associated antigen 16 |
| SPG20 | SPG20 | 23111 | cg10558887 | −1.67 | 6 | 13q13.3 | spastic paraplegia 20 (Troyer syndrome) |
| ST20 | ST20 | 400410 | cg26829925 | −1.69 | 14 | 15q25.1 | suppressor of tumorigenicity 20 |
| TAF7 | TAF7 | 6879 | cg24717875 | −1.89 | 2 | 5q31 | TATA-box binding protein associated factor 7 |
| THEM4 | THEM4 | 117145 | cg03147210 | −1.65 | 8 | 1q21 | thioesterase superfamily member 4 |
| TMBIM1 | TMBIM1 | 64114 | cg18357696 | −1.74 | 8 | 2q35 | transmembrane BAX inhibitor motif containing 1 |
| TMEM101 | TMEM101 | 84336 | cg08372947 | −2.74 | 6 | 17q21.31 | transmembrane protein 101 |
| TMEM106A | TMEM106A | 113277 | cg21504064 | −1.68 | 72 | 17q21.31 | transmembrane protein 106A |
| TP53I13 | TP53I13 | 90313 | cg00265578 | −1.81 | 4 | 17q11.2 | tumor protein p53 inducible protein 13 |
| TRDMT1 | TRDMT1 | 1787 | cg04884102 | −1.69 | 4 | 10p15.1 | tRNA aspartic acid methyltransferase 1 |
| TRMT12 | TRMT12 | 55039 | cg00846483 | −1.73 | 5 | 8q24.13 | tRNA methyltransferase 12 homolog (*S. cerevisiae*) |
| TRPS1 | TRPS1 | 7227 | cg12396523 | −1.8 | 67 | 8q24.12 | transcriptional repressor GATA binding 1 |
| TSGA14 | CEP41 | 95681 | cg05751159 | −2.76 | 11 | 7q32 | centrosomal protein 41kDa |
| TSPYL5 | TSPYL5 | 85453 | cg22319311 | −1.69 | 37 | 8q22.1 | TSPY-like 5 |
| TSTD1 | TSTD1 | 100131187 | cg11731300 | −2.07 | 6 | 1q23.3 | thiosulfate sulfurtransferase (rhodanese)-like domain containing 1 |
| TXNRD2 | TXNRD2 | 10587 | cg07019740 | −1.81 | 22 | 22q11.21 | thioredoxin reductase 2 |
| UBB | UBB | 7314 | cg27351675 | −2.74 | 7 | 17p12-p11.2 | ubiquitin B |
| WBP5 | TCEAL9 | 51186 | cg14986136 | −1.79 | 5 | Xq22.2 | transcription elongation factor A like 9 |
| ZFP28 | ZFP28 | 140612 | cg05292954 | −1.64 | 32 | 19q13.43 | ZFP28 zinc finger protein |
| ZFP3 | ZFP3 | 124961 | cg10507028 | −1.91 | 23 | 17p13.2 | ZFP3 zinc finger protein |
| ZFP37 | ZFP37 | 7539 | cg14016089 | −1.65 | 24 | 9q32 | ZFP37 zinc finger protein |
| ZFP41 | ZFP41 | 286128 | cg12736937 | −1.76 | 4 | 8q24.3 | ZFP41 zinc finger protein |
| ZFP82 | ZFP82 | 284406 | cg13252583 | −1.8 | 12 | 19q13.12 | ZFP82 zinc finger protein |
| ZIK1 | ZIK1 | 284307 | cg26246807 | −1.75 | 27 | 19q13.43 | zinc finger protein interacting with K protein 1 |
| ZNF135 | ZNF135 | 7694 | cg18430128 | −1.73 | 55 | 19q13.4 | zinc finger protein 135 |
| ZNF214 | ZNF214 | 7761 | cg22235417 | −1.69 | 10 | 11p15.4 | zinc finger protein 214 |
| ZNF215 | ZNF215 | 7762 | cg26870460 | −1.76 | 22 | 11p15.4 | zinc finger protein 215 |
| ZNF229 | ZNF229 | 7772 | cg22720041 | −1.84 | 34 | 19q13.31 | zinc finger protein 229 |
| ZNF256 | ZNF256 | 10172 | cg13359948 | −1.8 | 6 | 19q13.43 | zinc finger protein 256 |
| ZNF285 | ZNF285 | 26974 | cg23513318 | −1.72 | 12 | NA | zinc finger protein 285 |
| ZNF300 | ZNF300 | 91975 | cg21521779 | −1.67 | 21 | 5q33.1 | zinc finger protein 300 |
| ZNF311 | ZNF311 | 282890 | cg00105025 | −1.7 | 20 | 6p22.1 | zinc finger protein 311 |
| ZNF415 | ZNF415 | 55786 | cg18301583 | −2.16 | 5 | 19q13.42 | zinc finger protein 415 |
| ZNF418 | ZNF418 | 147686 | cg11788523 | −1.68 | 51 | 19q13.43 | zinc finger protein 418 |
| ZNF43 | ZNF43 | 7594 | cg21537383 | −1.74 | 7 | 19p13.1-p12 | zinc finger protein 43 |
| ZNF439 | ZNF439 | 90594 | cg12169233 | −1.99 | 7 | 19p13.2 | zinc finger protein 439 |
| ZNF470 | ZNF470 | 388566 | cg15170743 | −1.83 | 19 | 19q13.43 | zinc finger protein 470 |
| ZNF471 | ZNF471 | 57573 | cg11539780 | −1.79 | 33 | 19q13.43 | zinc finger protein 471 |
| ZNF501 | ZNF501 | 115560 | cg10108389 | −1.69 | 12 | 3p21.31 | zinc finger protein 501 |
| ZNF502 | ZNF502 | 91392 | cg15604051 | −1.83 | 28 | 3p21.31 | zinc finger protein 502 |
| ZNF518B | ZNF518B | 85460 | cg25112312 | −1.71 | 21 | 4p16.1 | zinc finger protein 518B |
| ZNF542 | ZNF542P | 147947 | cg08697092 | −1.76 | 31 | 19q13.43 | zinc finger protein 542, pseudogene |
| ZNF544 | ZNF544 | 27300 | cg21155461 | −1.78 | 6 | 19q13.43 | zinc finger protein 544 |
| ZNF549 | ZNF549 | 256051 | cg07054095 | −2.22 | 7 | 19q13.43 | zinc finger protein 549 |
| ZNF568 | ZNF568 | 374900 | cg03060201 | −1.97 | 5 | 19q13.12 | zinc finger protein 568 |
| ZNF569 | ZNF569 | 148266 | cg17778441 | −1.65 | 6 | 19q13.12 | zinc finger protein 569 |
| ZNF570 | ZNF570 | 148268 | cg11237751 | −1.76 | 6 | 19q13.12 | zinc finger protein 570 |
| ZNF572 | ZNF572 | 137209 | cg11497957 | −2.11 | 14 | 8q24.13 | zinc finger protein 572 |

TABLE 4-continued

Epigenetically Silenced Genes

| Gene | Official Symbol | Gene ID | Probe with the lowest Z-score | Z-score | Estimated % of tumors silenced | MAP | Official Full Name |
|---|---|---|---|---|---|---|---|
| ZNF582 | ZNF582 | 147948 | cg09568464 | −1.71 | 16 | 19q13.43 | zinc finger protein 582 |
| ZNF583 | ZNF583 | 147949 | cg11718235 | −1.94 | 6 | 19q13.43 | zinc finger protein 583 |
| ZNF655 | ZNF655 | 79027 | cg08024409 | −1.97 | 7 | 7q22.1 | zinc finger protein 655 |
| ZNF665 | ZNF665 | 79788 | cg12360029 | −2.02 | 5 | 19q13.42 | zinc finger protein 665 |
| ZNF681 | ZNF681 | 148213 | cg01615818 | −1.69 | 8 | 19p12 | zinc finger protein 681 |
| ZNF71 | ZNF71 | 58491 | cg22995684 | −1.87 | 10 | 19q13.4 | zinc finger protein 71 |
| ZNF717 | ZNF717 | 100131827 | cg27409478 | −1.99 | 7 | 3p12.3 | zinc finger protein 717 |
| ZNF718 | ZNF718 | 255403 | cg12717203 | −1.77 | 9 | 4p16.3 | zinc finger protein 718 |
| ZNF737 | ZNF737 | 100129842 | cg11948055 | −1.88 | 7 | 19p12 | zinc finger protein 737 |
| ZNF772 | ZNF772 | 400720 | cg03526224 | −1.92 | 5 | 19q13.43 | zinc finger protein 772 |
| ZNF773 | ZNF773 | 374928 | cg22411784 | −1.83 | 9 | 19q13.43 | zinc finger protein 773 |
| ZNF844 | ZNF844 | 284391 | cg04476062 | −1.78 | 7 | 19p13.2 | zinc finger protein 844 |
| ZNF879 | ZNF879 | 345462 | cg00594128 | −1.74 | 19 | 5q35.3 | zinc finger protein 879 |
| ZNF883 | ZNF883 | 169834 | cg08476595 | −1.7 | 24 | 9q32 | zinc finger protein 883 |
| ZSCAN18 | ZSCAN18 | 65982 | cg06243556 | −1.77 | 35 | 19q13.43 | zinc finger and SCAN domain containing 18 |

Although some of the silencing events were probably background epigenetic noise, CDKN2A, FAT1, and CASP8 were mutated in some tumors and (mutually exclusively) epigenetically silenced in others (FIG. 4H). Silenced genes included latexin (LXN), the only known endogenous carboxypeptidase inhibitor (silenced in 27%), Poly(ADP-ribose) polymerase PARP6 (26%), nicotinate phosphoribosyltransferase (NAPRT) (13%), and spermatogenesis and centriole associated 1-like (SPATC1L) (19%). In contrast, no evidence was found for promoter DNA hypermethylation of other classical tumor suppressor genes, including TP53, PTEN, TSC1, TSC2, NF1, NF2, and RB1.

Example 4: mRNA Expression-Based Molecular Subtypes

Unbiased NMF consensus clustering of RNA-seq data (n=408) identified five expression subtypes (FIG. 5): luminal-papillary (n=142, 35%), luminal-infiltrated (n=78, 19%), luminal (n=26, 6%), basal-squamous (n=142, 35%), and neuronal (n=20, 5%). Five expression subtypes strongly correlated to a survival outcome; Luminal (L), Luminal-Infiltrated (LI), Basal-Squamous (BS), Neuronal (N), and Luminal-Papillary (LP) (FIG. 15, FIG. 22). The subtypes were associated with overall survival (p=4×10$^{-4}$) (FIG. 6A, FIG. 20, FIG. 21 Panel A, FIG. 21 Panel B, FIG. 21 Panel C). The analysis confirmed the two major luminal and basal transcriptional subtypes identified by TCGA and other groups (Choi et al., 2014b; Damrauer et al., 2014; Sjodahl et al., 2012), while discriminating within those subtypes and identifying luminal and neuronal subtypes (see below). The subtypes were concordant with the four subtypes that were reported for the 131-tumor subset of the current cohort (Cancer Genome Atlas Research Network, 2014a) (FIG. 5; Table 5; FIG. 28).

TABLE 5 mRNA subtype comparison

| TCGA_408 | TCGA_131 Cluster-I | Cluster-II | Cluster-III | Cluster-IV |
|---|---|---|---|---|
| Luminal | 3 | 8 | 0 | 0 |
| Luminal_papillary | 33 | 4 | 0 | 0 |
| Luminal_infiltrated | 1 | 23 | 0 | 0 |
| Basal_squamous | 4 | 4 | 27 | 13 |
| Neuronal | 0 | 2 | 2 | 2 |

| TCGA_408 | UNC Basal | Luminal |
|---|---|---|
| Luminal | 0 | 15 |
| Luminal_papillary | 2 | 79 |
| Luminal_infiltrated | 19 | 26 |
| Basal_squamous | 83 | 1 |
| Neuronal | 7 | 2 |

| TCGA_408 | MD Anderson Basal | Luminal | TP53-like |
|---|---|---|---|
| Luminal | 0 | 12 | 3 |
| Luminal_papillary | 2 | 74 | 5 |
| Luminal_infiltrated | 3 | 6 | 36 |
| Basal_squamous | 80 | 1 | 3 |
| Neuronal | 6 | 1 | 2 |

TABLE 5-continued mRNA subtype comparison

| TCGA_408 | Hoglund CC1-1 | CC1-2 | CC2-1 | CC2-2 | CC3-1 | CC3-2 |
|---|---|---|---|---|---|---|
| Luminal | 0 | 0 | 2 | 0 | 12 | 1 |
| Luminal_papillary | 0 | 0 | 39 | 30 | 5 | 7 |
| Luminal_infiltrated | 0 | 1 | 0 | 0 | 44 | 0 |
| Basal_squamous | 53 | 23 | 0 | 0 | 6 | 2 |
| Neuronal | 0 | 0 | 0 | 0 | 2 | 7 |

| TCGA_408 | SCC-like/ Urobasal B Lund MS1a | Infiltrated mesenchymal MS1b | Genomically unstable MS2a1 | Urobasal MS2a2 | Infiltrated epithelial MS2b1 | Variant MS2b2.1 | MS2b2.2 |
|---|---|---|---|---|---|---|---|
| Luminal | 0 | 8 | 7 | 0 | 0 | 0 | 0 |
| Luminal_papillary | 11 | 44 | 24 | 1 | 0 | 1 | 0 |
| Luminal_infiltrated | 2 | 2 | 0 | 14 | 24 | 1 | 2 |
| Basal_squamous | 0 | 2 | 1 | 1 | 18 | 11 | 51 |
| Neuronal | 0 | 0 | 1 | 4 | 0 | 0 | 4 |

Figure 5:
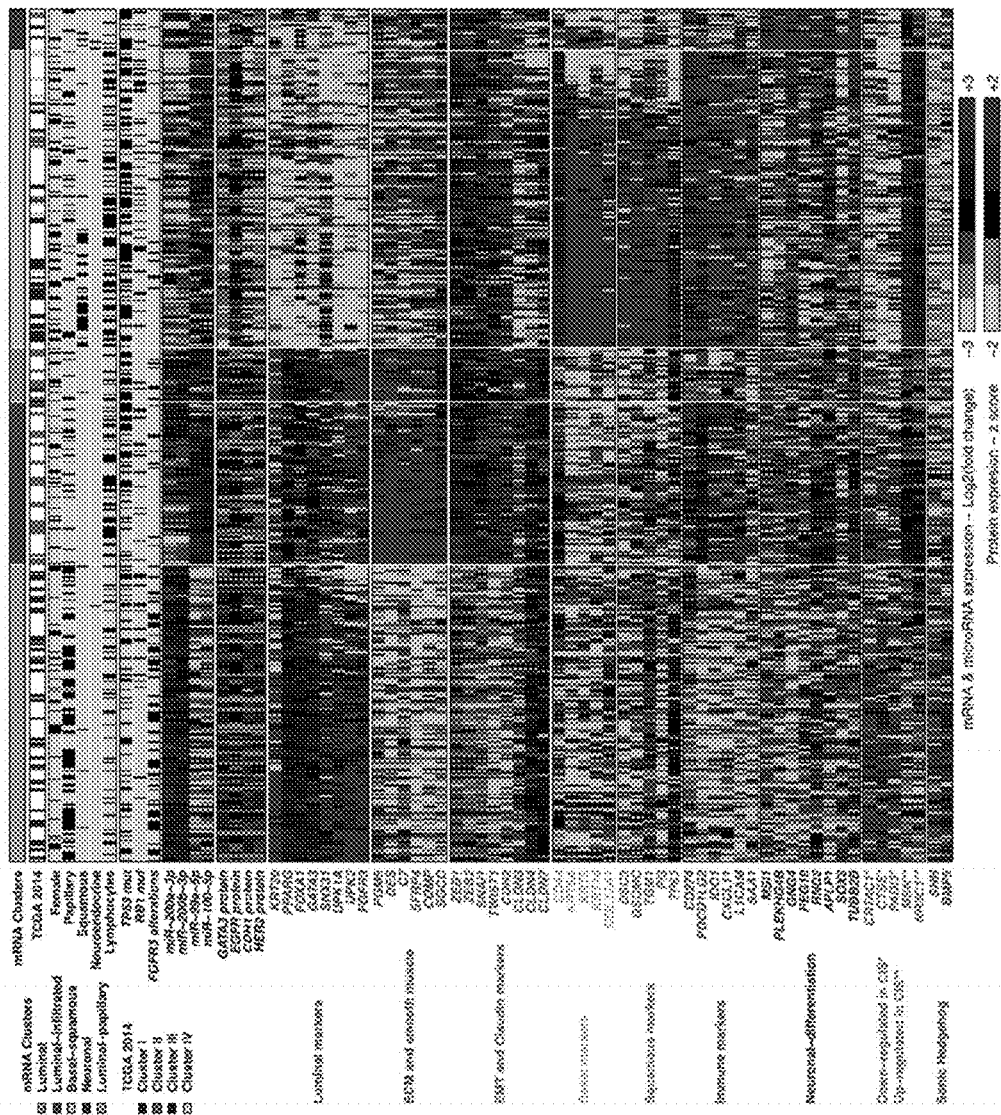
FIG. 5 is an image showing mRNA expression subtypes. Top, Left to Right: 5 mRNA expression subtypes: luminal-papillary, luminal-infiltrated, luminal, basal-squamous and neuronal. Covariates: 4 previously reported The Cancer Genome Atlas (TCGA) subtypes; selected clinical covariates and key genetic alterations; normalized expression for miRNAs and proteins; $\log_2$ (fold change against the median expression across samples) for selected genes, for labeled gene sets. Samples within the three luminal subtypes, the basal-squamous subtype, and the neuronal subtype are ordered by luminal, basal, and neuroendocrine signature scores, respectively. Genes that are down-regulated* vs. up-regulated** in carcinoma-in-situ (CIS).

Most samples in the luminal subtypes showed high expression of uroplakins (UPK2 and UPK1A) and urothelial differentiation markers (FOXA1, GATA3, PPARG) (FIG. 5). Although differences in purity appeared to contribute to their separation into different clusters (FIG. 6B), each of the three subtypes also showed distinctive expression features with respect to wild type p53, epithelial-mesenchymal transition (EMT), and stromal gene signatures (FIG. 6C, FIG. 17, FIG. 18, FIG. 19; FIG. 23 Panel A; FIG. 23 Panel B; FIG. 23 Panel C; FIG. 24 Panel A; FIG. 24 Panel B; FIG. 24 Panel C; Methods: mRNA Expression Profiling: Gene expression signature scores).

The luminal-papillary cluster was enriched in tumors with papillary morphology (58% vs. 20% in other subtypes; $p<10^{-13}$), lower stage (T2, 55% vs. 23%; $p<10^{-8}$), and higher purity (median 0.84 vs. 0.50 in other luminal subtypes). Several features suggested a dominant role of FGFR3 in 44% of the luminal-papillary tumors: enrichment with FGFR3 mutations (42/57; $p<10^{-9}$), amplification (5/5; $p=5\times10^{-3}$), overexpression (4-fold vs. median, 49/67; $p<10^{-11}$), and FGFR3-TACC3 fusions (8/10, $p=4\times10^{-3}$). These tumors also had low carcinoma-in-situ (CIS) expression signature scores (FIG. 6C) (Dyrskjot et al., 2004). They retained sonic-hedgehog signaling (SHH, FIG. 5). Together, these features suggested that many tumors in this cluster developed from a precursor non-muscle-invasive papillary bladder cancer.

The luminal-infiltrated subtype was distinguished from other luminal subtypes by lower purity (median 0.46 vs. 0.68; $p<10^{-11}$), consistent with the presence of lymphocytic infiltrates, and by strong expression of smooth muscle and myofibroblast gene signatures (FIG. 5 and FIG. 6C). 36 of 45 (80%) of the tumors in this subtype had features similar to an expression subtype that has been associated with chemoresistance and characterized by a wild type p53 signature (Choi et al., 2014b). The wild type p53 signature score was inversely correlated with tumor purity (Pearson $r=-0.4$; $p<0.001$), suggesting the presence of smooth muscle and fibroblast cells as a driver of the signature. This subtype contained 23 of 24 tumors that were previously classified as Cluster-II, which was reported to benefit most from anti-PDL1 treatment (Rosenberg et al., 2016), and had an intermediate 5-year survival, comparable to basal-squamous and luminal subtypes (FIG. 6A). These tumors had increased expression of several immune markers, including CD274 (PD-L1) and PDCD1 (PD-1) (FIG. 5).

The luminal subtype had the highest expression levels of several uroplakins (UPK1A, UPK2) and genes that are highly expressed in terminally differentiated urothelial umbrella cells (KRT20, SNX31) (FIG. 5). This suggested that these tumors were derived from intermediate cells that have a transcriptional program that leads to expression of markers characteristic of normal umbrella cells.

The basal-squamous subtype was characterized by high expression of basal and stem-like markers (CD44, KRT5, KRT6A, KRT14) and squamous differentiation markers (TGM1, DSC3, PI3). The subtype included 37 of 45 tumors squamous features ($p<10^{-11}$), was enriched in TP53 mutations ($p=5\times10^{-3}$), and was more common in females (33% vs. 21% in other subtypes; $p=0.024$). Many tumors in this subtype also showed strong expression of CIS signature genes (FIG. 5 and FIG. 6A) and loss of SHH signaling (FIG. 5), suggesting that they developed from basal cells and CIS lesions. This subtype also showed the strongest immune expression signature, including T-cell markers and inflammation genes (FIG. 6C), consistent with relatively low purity (median 0.49) (FIG. 6B) and the presence of lymphocytic infiltrates ($p<1\times10^{-4}$). Approximately 20 samples (right portion of this subtype in FIG. 5) lacked expression of both basal and squamous markers, but clustered with this subtype because they lacked luminal marker expression and had high immune gene expression.

The neuronal subtype included 3 of 4 with neuroendocrine (NE) histology ($p=5\times10^{-3}$) and an additional 17 tumors that had no histopathologic features suggestive of NE origin. All 20 tumors showed relatively high expression of neuronal differentiation and development genes, as well as typical NE markers (FIG. 5 and FIG. 6C; $p<10^{-4}$). Loss of TP53 and RB1 is a hallmark of small cell NE cancer, and 10 of 20 (50%) samples had mutations in both TP53 and RB1, or TP53 mutation and E2F3 amplification. 17 (85%) of the 20 tumors had alterations in genes in the p53/cell cycle pathway. Notably, this subtype had the poorest survival ($p=4\times10^{-4}$, log-rank test), consistent with the known aggressive phenotype of NE bladder cancers.

As previously shown (Cancer Genome Atlas Research Network, 2014a), several proteins (GATA3, EGFR, CDH1, HER2) and miRNAs (miR-200s, miR-99a, miR-100) were strongly differentially expressed among the mRNA subtypes (FIG. 5, FIG. 6D, FIG. 6E and FIG. 7A).

Example 5: Altered Pathways

Many canonical signaling pathways were altered (FIG. 8). The p53/Cell Cycle pathway was inactivated in 89% of tumors, with TP53 mutations in 48%, MDM2 amplification (copy number >4) in 6%, and MDM2 overexpression (>2-fold above the median) in 19%. TP53 mutations were enriched in tumors with genome-doubling events ($p<10^{-7}$), suggesting that loss of TP53 activity facilitates genome doubling (Zack et al., 2013).

RB1 mutations (17%) were mostly inactivating and associated with reduced mRNA levels. CDKN1A mutations (11%) were predominantly inactivating. CDKN2A mutations (7%) and homozygous deletions (22%) were common, as previously described (Williamson et al., 1995).

Alterations in DNA repair pathways included mutations in ATM (n=57; 14%) and ERCC2 (n=40; 9%) and deletions in RAD51B (n=10; 2%). All non-silent ERCC2 mutations were missense, and many mapped within, or within ±10 amino acids of, the conserved helicase domain, suggesting that they impair ERCC2 function and may have dominant negative effects (Van Allen et al., 2014).

The FGFR3, PIK3CA, and RAS oncogenes harbored recurrent hotspot mutations. Most FGFR3 mutations were the known S249C or Y373C, which were more frequent in lower-stage tumors (21% in T2 vs. 10% in T3, T4; p=0.003), and were associated with better survival (p=0.04). PIK3CA mutations (n=100; 22%) were more common in the helical domain (E542 and E545; n=54 total) than in the kinase domain (M1043, H1047; n=10 total), and were likely due to APOBEC mutagenic activity (Cancer Genome Atlas Research Network, 2017; Roberts et al., 2013). ERBB2 mutations were common at S310 (S280 in the LRG_724t1 transcript) in the extracellular domain (24 of 57, 42%), and were also likely due to APOBEC-signature mutagenesis.

Ten of the 39 SMGs with mutation frequency >5% were in chromatin-modifying or chromatin-regulatory genes: a histone demethylase (KDM6A), histone methyltransferases (KMT2A, KMT2C, KMT2D), histone acetylases (CREBBP, EP300, KANSL1), a member of the SWI/SNF chromatin remodeling complex (ARID1A), and Polycomb group genes (ASXL1, ASXL2). Mutations in these genes were predominantly inactivating (50% frame-shift or nonsense mutations vs. 26% in other SMGs; $p=10^{-30}$), strongly suggesting that they are functionally relevant. ARID1A, CREBBP, and KDM6A were also targets of genomic deletion (4.2%, 14.2%, 4.9%, respectively, Table 2).

Figure 9:
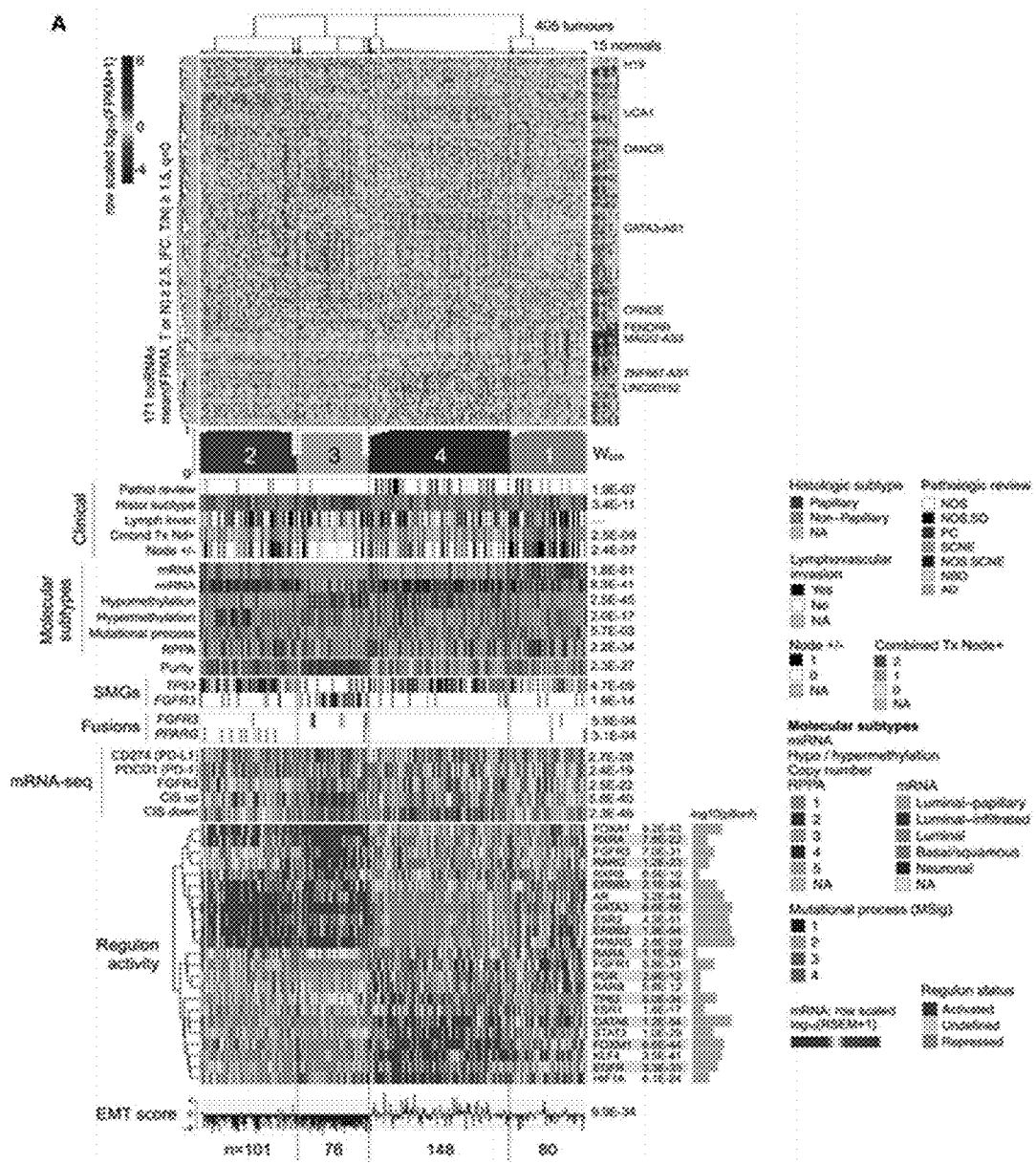
Figure 9:
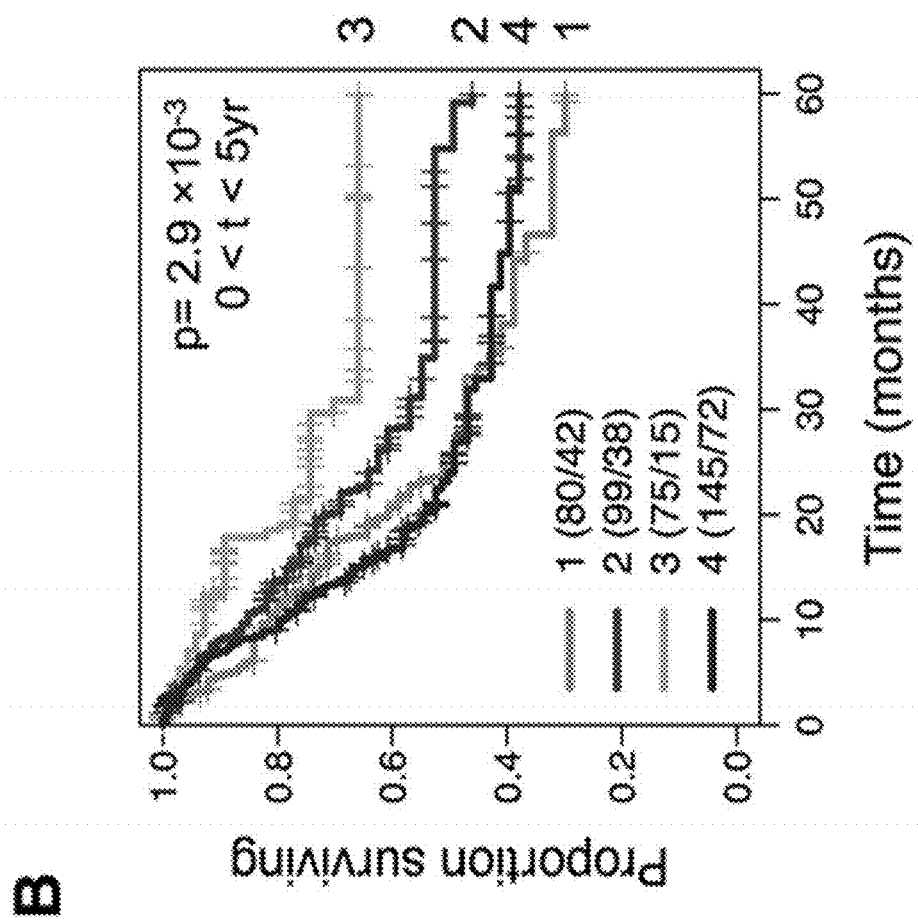

Example 6: Noncoding RNAs (lncRNAs and miRNAs) Subdivide mRNA Expression Subtypes Because long non-coding RNAs (lncRNAs) can be more specific to biological state than coding RNAs (Nguyen and Carninci, 2016), the transcript abundances were calculated for 8167 (Ensembl v82) lncRNAs and processed transcripts. Four unsupervised consensus clusters were associated with purity ($p=2.3\times10^{-27}$), epithelial-mesenchymal transition (EMT) score ($p=9.9\times10^{-34}$), expression of carcinoma in situ (CIS) gene sets ($p<1\times10^{-39}$) (Dyrskjot et al., 2004), and 5-year survival (p=0.015) (FIG. 9).

The lncRNA clusters were concordant with the messenger (mRNA) subtypes ($p=2\times10^{-81}$) and further discriminated within them. For example, lncRNA cluster 3 (n=76), a better-survival subset of the luminal-papillary subtype, was depleted in TP53 mutations but enriched in FGRF3 mutations and fusions. It consisted largely of high-purity, papillary histology, and organ-confined cancers. Levels of many cancer-associated lncRNAs, including DANCR, GAS5, MALAT1, NEAT1, NORAD (LINC00657), and UCA1, were high; others, including ZNF667-AS1 (MORT) and LINC00152 (associated with lower EMT scores), were low (FIG. 7B).

Figure 10:
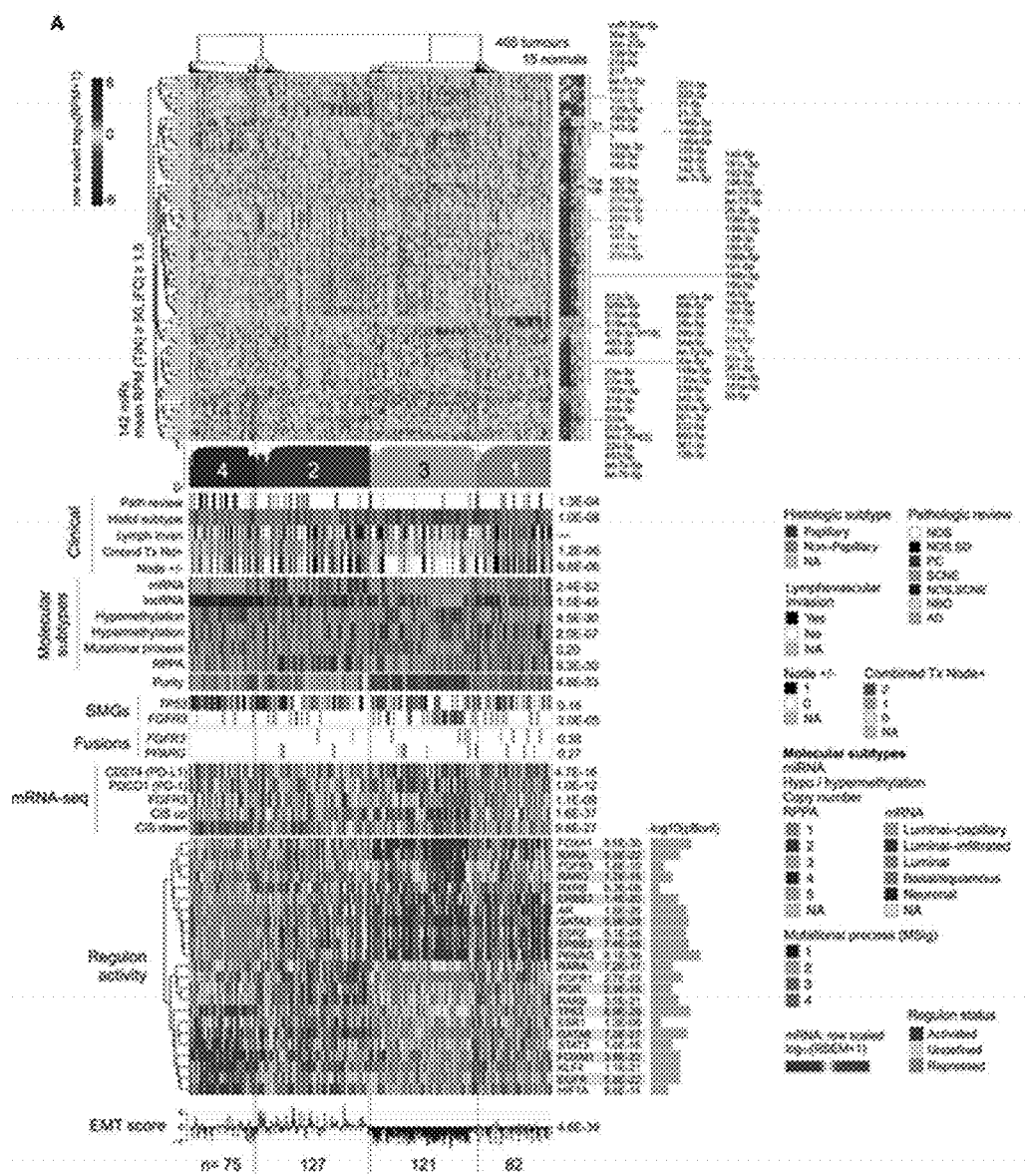
Figure 10:
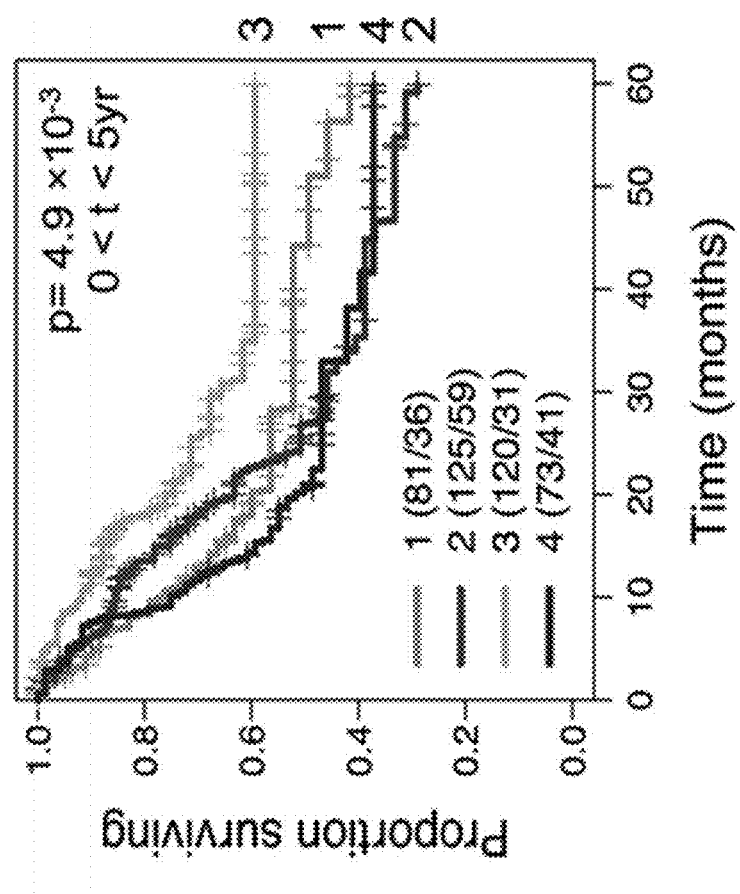

For microRNA (miRNA) mature strands, four unsupervised consensus clusters were associated with purity ($p=5\times10^{-33}$), EMT scores ($p=5\times10^{-39}$), and 5-year survival ($p=1.7\times10^{-3}$) (FIG. 10). They were concordant with subtypes for mRNA ($p=2\times10^{-52}$), lncRNA ($p=2\times10^{-45}$), hypomethylation ($p=5\times10^{-30}$), reverse phase protein array (RPPA) ($p=9\times10^{-30}$), and with histological subtype (papillary vs. non-papillary), combined T-stage/Node+, node positive/negative, and CIS gene sets (Dyrskjot et al., 2004). Many cancer-associated miRNAs were differentially abundant across the subtypes (FIG. 7C).

MiRNA subtype 3 was enriched in lncRNA 3 and showed the best survival among the 4 subtypes, consistent with low EMT scores and high miR-200 levels; CD274 (PD-L1) and PDCD1 (PD-1) levels were low. MiRNA subtypes defined subsets within the mRNA subtypes, with miR 4 (n=75) and miR 2 (n=127) containing most of the basal/squamous mRNA subtype samples, showed relatively poor survival, which was consistent with the relatively high EMT scores.

Example 7: Regulon Activity Differences Among RNA Subtypes

To further characterize the molecular differences between RNA-based subtypes, the activity profiles of 23 candidate 'regulator' genes were analyzed that have been associated with urothelial cancer (see Methods section below) By 'regulator' is meant mean a gene whose product induces and/or represses a target gene set, which has previously been referred to as a 'regulon' (Castro et al., 2016a). The analysis was performed for this cohort of 412 samples, and also for an independent, mixed non-muscle invasive/MIBC cohort (n=308) (Sjodahl et al., 2012). In both cohorts, the inferred regulon activity profiles sorted covariates that included histology, mRNA subtype, and EMT score (FIG. 7D, FIG. 7E). Segregating by activated vs. repressed profiles identified survival-associated regulators with Kaplan-Meier plots and hazard ratios that were consistent in the two cohorts (FIG. 7F, FIG. 7G). This analysis suggested that regulon analysis was robust and biologically relevant.

The regulon activity was then compared across RNA-based subtypes, which found that activities varied most strongly for mRNA and lncRNA subtypes, and somewhat less strongly for miRNA subtypes (FIG. 9A, FIG. 9B, FIG. 10A, FIG. 10B, and FIG. 7H). In luminal-papillary cases, 11 regulons were activated. lncRNA subtypes 2 and 3 (FIG. 9A) were both associated with the luminal-papillary mRNA subtype and showed similar activation profiles for 9 regulons. Their profiles were consistent with the hypothesis that transcription factors GATA3, FOXA1, and PPARγ drive luminal cell biology in bladder cancer (Warrick et al., 2016). The better-survival lncRNA 3 differed from lncRNA 2 by having, among other characteristics, an activated regulon for FGFR3 and undefined (i.e. neither activated nor repressed) regulon activity for TP63. Twelve regulons were activated in the basal/squamous cases, which were associated with miRNA clusters 2 and 4 (FIG. 10A). The TP63 regulon was generally activated in miR 4 but repressed in miR 2, and the EGFR regulon was largely activated in miR 4 but had variable activity in miR 2. Overall, the analysis implicated certain regulators as important drivers of the differences in expression phenotype among bladder cancer subtypes.

Example 8: Microbe Analysis

RNA-sequencing (n=408), WES (n=412), and whole-genome sequencing (n=136) data were used to identify evidence of infection by Human Papillomaviruses (HPV) (n=11), (Human Herpesviruses 4) HHV4 (n=6), (Human Herpesviruses 5) HEWS (n=6), and Polyomavirus (n=1). For HPV genomic integration was identified in 4 tumors, with breakpoints associated with BCL2L1, SLC2A1-AS1, DEC1, SEC16A, and CCDC68. BK polyoma integration breakpoints were associated with FIGN and LIMA1 genes. For HHV4 and HHV5 no evidence was found for genomic integration. Hence, viral infection may contribute to a small percentage of urothelial carcinomas.

Example 9: Proteomic Analysis by RPPA

Unsupervised consensus clustering of RPPA proteomic data for 208 antibodies and 343 of the 412 tumors resulted in five robust clusters that differed in protein expression profiles, pathway activities, and overall survival (p=0.019) (FIG. 11A, FIG. 11B; FIG. 26). RPPA cluster 1 (epithelial/papillary) showed the best outcomes, a low EMT pathway score (FIG. 11C, FIG. 11D), and enrichment with papillary samples. Cluster 2 (epithelial/intermediate) was intermediate in profile and outcomes. Elevated HER2 expression levels in clusters 1 and 2 suggest that these cases may respond to anti-HER2 directed therapies (e.g. Herceptin, T-DM1).

Cluster 3 (proliferative/low signaling) had a high cell cycle pathway score, principally due to high CYCLINB1 and PCNA expression, with low MAPK, PI3K, and mTOR pathway signaling (FIG. 11D). Although cluster 3 tumors showed low levels of signaling, they expressed high levels of EGFR, suggesting that these cases are possible candidates for EGFR inhibitors.

Clusters 4 and 5 had higher EMT pathway scores (FIG. 11D) and were enriched with non-papillary and pathologic stage III and IV tumors. Cluster 4 (EMT/hormone signaling) had the worst outcome and relatively high reactive and hormone receptor pathway scores. Cluster 5 (reactive) had high levels of MYH11, HSP70, FIBRONECTIN, COLLAGEN VI, CAVEOLIN1 and RICTOR, as well as remarkably low levels of the proapoptotic mediator BAK, perhaps contributing to the cluster's poor outcomes. Reactive cancer subtypes showed high levels of proteins that are likely produced in the tumor microenvironment as the result of interactions between cancer cells and cells in the microenvironment, including fibroblasts, as discussed previously for reactive breast cancer subtypes (Cancer Genome Atlas Network, 2012; Dennison et al., 2016).

Example 10: Integrative Clustering Analysis

The Cluster of Cluster Assignments method (COCA) (Hoadley et al., 2014) was used to integrate and compare the cluster assignments obtained by clustering mRNA, lncRNA, miRNA data independently. The analysis identified overlapping subtype classifications. Although COCA subtypes were largely determined by the mRNA subtypes, lncRNA and miRNA data created finer-grained subdivisions (FIG. 12A).

Example 11: Univariate and Multivariate Survival

This rich data set enabled a detailed analysis of clinical and molecular variables for association with overall survival. While follow-up times remain limited, the event rate was high enough that results were informative.

Of 101 covariates analyzed by univariate log-rank tests, 20 had a Benjamini-Hochberg-adjusted p<0.05. 7 were removed with many missing cases, leaving 13 for multivariate Cox regression analysis (FIG. 13A). Since the results of nine candidate penalized methods were approximately equivalent (FIG. 13B), the LASSO regression (Hutmacher and Kowalski, 2015; Walter and Tiemeier, 2009) was chosen to fit a multivariate model. For mRNA, lncRNA, miRNA and MSig subtypes, the best-survival subtype was set as the reference variable.

After filtering regression coefficients at $|\beta|>0.1$, 7 variables representing 4 covariates were retained (FIG. 12B). A coefficient's sign and magnitude associates a variable with poorer or better survival rates, relative to its reference variable, in the context of the set of regression variables retained in the model. The variables with largest coefficients were American Joint Committee on Cancer (AJCC) stages III and IV, mRNA neuronal and luminal subtypes, low mutation rate MSig 2, and miRNA subtype 4, which is a subset of basal-squamous cases, and KLF4 regulon activity, all of which were associated with worse survival. The mRNA luminal-infiltrated subtype, age, GATA3 regulon activity, and MSig4 were retained with smaller coefficients (FIG. 12B).

The fitted model assigned weights to variables and generated a score for each sample. Thresholding these scores segregated the cohort into predicted risk groups or strata. Tertile thresholds generated three groups that were associated with survival (p<0.001) (FIG. 12C).

Multivariate Cox regressions were assessed that included age and AJCC stage, and subtypes for mRNA, lncRNA, miRNA, or mutational process (MSig), setting the best-survival subtype as the reference. Each molecular covariate had at least one subtype associated with worse survival, independent of age and stage (FIG. 13C).

Example 12: Subtype-Stratified Potential Treatments

In FIG. 14, results from the multiple platform analyses have been integrated, as well as proposed therapeutic considerations stratified by expression subtyping. For each subtype the key drivers are summarized, and treatment strategies are proposed that may be appropriate in multiple clinical scenarios, including peri-operative therapy (neoadjuvant and adjuvant) combined with radical cystectomy, systemic therapy combined with locoregional radiation, or systemic therapy for measurable metastatic disease. This schema has been suggested as a framework for prospective hypothesis testing in clinical trials, as well as for validation in ongoing or completed clinical trials that test, or have tested, treatment strategies.

Example 13: Marker Selection for TCGA Subtype Classifier

The experiments of this example quantified the normalized association of an individual sample to the TCGA subtypes—H matrix (FIG. 16, FIG. 29). Given expression fold changes X (up and down separately), NMF determined the gene association matrix (W) to the TCGA subtypes as X~WH where $(X_{up}, X_{dn})$~$(W_{up}, W_{dn})$ H. Fold changes were taken to make a classifier applicable to other platform data, such as microarray data. 354 expression markers were analyzed: (i) the top 10% most strongly associated genes to the determined subtypes, in terms of the normalized association of $W_{up}$ and Log 2(fold changes)>1.75 between each subtype and others, resulted in 335 genes; and (ii) 19 genes were manually curated. The weight matrix for markers was determined as $W_{up}$ for markers. In the experiments of this example, only up-regulated genes were considered.

The experiments of this example allowed for overlapping of memberships to the subtypes i.e., a marker could be associated with multiple subtypes with different affinities. This allowed for more extensive neuronal markers. Each marker had a different weight to the determined subtypes. Classifier determined a subtype with minimizing $|x_{up}-W_{up} h|^2$, $x_{up}$ is a vector of fold changes and h is the inferred association to TCGA subtypes.

Applications

Bladder cancer, both non-muscle invasive (NMIBC) and muscle-invasive (MIBC), is a major source of morbidity and mortality worldwide. In the United States, there will be an estimated 79,000 new cases and 17,000 deaths in 2017 (Siegel et al., 2017). NMIBC occurs mainly as papillary disease with frequent FGFR3 mutations, whereas MIBC has a more diverse mutation spectrum as well as copy-number instability (Balbas-Martinez et al., 2013; Cappellen et al., 1999; Gui et al., 2011; Knowles and Hurst, 2015; van Rhijn et al., 2001).

In the following, essential findings are highlighted from the complete cohort of 412 TCGA cases and suggestions are provided as to how these findings may contribute to the understanding of therapeutic possibilities. 34 additional SMGs and 158 genes were identified that are subject to epigenetic silencing, both of which may offer additional potential therapeutic targets, fusion events that implicate PPARG as a key gene in bladder cancer development, and refined subtypes defined by considering both miRNA and lncRNA profiling.

MIBCs show high overall mutation rates similar to those of melanoma and non-small cell lung cancers, and the present invention confirms that these high rates are principally associated with mutation signatures for an endogenous mutagenic enzyme, APOBEC cytidine deaminase (Roberts et al., 2013). Most bladder cancer mutations are clonal, suggesting that APOBEC's mutagenic activity occurs early in bladder cancer development. A better understanding of the origin and regulation of APOBEC expression and activity in normal bladder could lead to preventive strategies that target APOBEC as a key mutagenic source in bladder cancer.

MSig1's high mutation burden consisted largely of APOBEC-signature mutations. The subset's unusually good survival contributes to and correlates with the improved survival of subjects with higher mutational burden and higher neo-antigen load (FIG. 2B). It is proposed that this is due to a natural host immune reaction to the high mutation burden, curbing further tumor growth and metastasis. This hypothesis should be tested in additional bladder cancer cohorts, and the MSig1 subset should be recognized in ongoing clinical trials, including trial of immune checkpoint therapy, as having a much better prognosis than average (see further below).

Chromatin modifier gene mutations are common in bladder cancer and also open potential therapeutic opportunities through rebalancing acetylation and deacetylation, and through other chromatin modifications. Recent studies have identified BRD4-EZH2 chromatin modification as an important growth pathway in bladder cancer, especially in tumors with loss of KDM6A, and shown in preclinical models that the BET inhibitor JQ1 and inhibition of EZH2 have therapeutic benefit (Ler et al., 2017; Wu et al., 2016). Recently, a Phase 2 study of Mocetinostat, a histone deacetylase inhibitor, in patients with locally advanced or metastatic urothelial carcinoma has completed accrual and results are awaited (NCT02236195).

The altered canonical signaling pathways provide multiple opportunities for therapeutic intervention. As one example the p53/Rb pathway is being targeted in a multicenter phase II trial evaluating palbociclib (PD-0332991) in patients with metastatic urothelial carcinoma who have cyclin-dependent kinase inhibitor 2A (CDKN2A) loss and retained retinoblastoma (Rb) expression (NCT02334527).

The mRNA expression clustering experiments in the examples identified the well-known luminal and basal subtypes of bladder cancer and further stratified them into 5 distinct subtypes. Included are two that were not identify previously, neuronal and luminal, which have recently been corroborated in an independent cohort (Sjodahl et al., 2017). The neuronal subtype (5%) showed, in most cases, no histopathological distinction from other types of MIBC. Nonetheless, it had high levels of TP53 and RB1 mutations, as do small cell carcinomas in other tissues. It had the worst survival of the mRNA expression subtypes, making it important to recognize clinically. The luminal subtype had the highest expression level of uroplakin genes and may have adopted an umbrella cell phenotype. The luminal infiltrated subtype is similar to the previous TCGA subtype II and also similar to a subtype identified by Choi et al (Choi et al., 2014b), is characterized by a mesenchymal expression signature. It appears to be resistant to cisplatin-based chemotherapy and particularly sensitive to immunotherapy with checkpoint inhibitors.

LncRNA and miRNA expression patterns identified survival-related subsets of cases within the mRNA luminal-papillary subtype and basal-squamous subtypes, respectively. Many cancer-associated lncRNAs and miRNAs were differentially abundant among the bladder cancer subtypes. Multivariate regression analyses identified lncRNA and miRNA subtypes as independent predictors of survival.

The regulon analysis identified the importance of transcriptional driver events in bladder cancer development. In this analysis, regulator activity was associated with survival, as described previously for breast cancer (Castro et al., 2016a). Certain regulon activity profiles varied greatly between the different coding and noncoding gene expression subtypes, suggesting that the regulators are key drivers of those expression subtypes. These findings provide potential targets for intervention, and could be used for subtype discrimination and therapy selection (Castro et al., 2016a).

Integrating RNA subtype classification, pathway information, EMT and CIS signatures, and immune infiltrate analyses leads us to propose a model of mRNA-based expression subtypes that may be associated with unique response to therapies and can be prospectively tested in clinical trials (FIG. 14). It is noted that subsequent therapy was not included in this integrated analysis. Neoadjuvant cisplatin-based chemotherapy is the current standard of care in cisplatin-eligible patients without risk stratification. However, as not all patients derive benefit from chemotherapy, subtype-specific personalized therapies could help to optimize global patient outcome, while preventing unnecessary toxicity to non-responders. The following observations are hypothesis-generating, and thus are not ready to be used for clinical decision making.

The luminal-papillary subtype (35%) is characterized by FGFR3 mutations, fusions with TACC3, and/or amplification; by papillary histology; by active sonic hedgehog signaling; and by low CIS scores. Such cancers have low risk for progression, and preliminary data suggests a low likelihood of response to cisplatin-based neoadjuvant chemotherapy (NAC) (Seiler et al., 2017). The frequency of FGFR3 alterations in luminal papillary tumors suggests that tyrosine kinase inhibitors of FGFR3 may be an effective treatment approach, especially since early phase clinical trials show benefit of pan-FGFR inhibitor agents in FGFR3-selected advanced solid tumors (Karkera et al., 2017; Nogova et al., 2017).

The luminal-infiltrated subtype (19%) is characterized by the lowest purity, with high expression of EMT and myofibroblast markers, and of the miR-200s. It shows medium expression of CD270 (PD-L1) and CTLA4 immune markers. This subtype, corresponding to TCGA subtype II (Cancer Genome Atlas Research Network, 2014a), has been reported to respond to immune checkpoint therapy with atezolizumab in patients with metastatic or unresectable bladder cancer (Rosenberg et al., 2016). Validation of this subtype as a predictive marker for response to immunotherapy is ongoing in multiple clinical trials. Tumors with a luminal-infiltrated subtype may be resistant to cisplatin-based chemotherapy. Clinical trials may therefore be directed to validating this subtype as a negative predictive biomarker for chemotherapy response and for exploring alternative treatment strategies including targeted therapies.

The luminal subtype (6%) shows high expression of luminal markers, as well as KRT20 and SNX31. Due to its novelty, optimal therapy is less not defined. Future trial designs may compare the relative efficacy of either NAC or a therapy targeted to each cancer's specific mutation profile.

The basal-squamous subtype (35%) is characterized by higher incidence in women, squamous differentiation, basal keratin expression, high expression of CD274 (PD-L1) and CTLA4 immune markers, and other signs of immune infiltration. Both cisplatin-based NAC and immune checkpoint therapy (Sharma et al., 2016) are appropriate therapeutic options, and trials comparing those treatments should be performed.

Finally, the neuronal subtype (5%) is characterized by expression of both neuroendocrine and neuronal genes, as well as a high cell-cycle signature reflective of a proliferative state. The neuronal subtype was recently recognized by others in an independent cohort (Sjodahl et al., 2017). Identifying this subtype currently depends on detecting expression of neuroendocrine/neuronal markers by either mRNA-seq or immunohistochemistry, as they do not exhibit the typical morphologic features associated with neuroendocrine tumors. Etoposide-cisplatin therapy is recommended in neoadjuvant and metastatic settings, as for neuroendocrine neoplasms arising in other sites, but this should also be tested in prospective clinical trials.

The results from the experiments of the examples suggest that mRNA subtype classification may be possible with a reduced gene set, enabling validation in independent cohorts and informing clinical trial designs that test new personalized therapies. However, additional integrative analyses that include assessment of lncRNAs, miRNAs, and regulon relationships can be expected to refine the subtyping of bladder cancers and aid in the search for optimal personalized targeted therapies.

Example 14: Tumors Expressing SOX2, TUBB2B, and PEG10 Respond to Atezolizumab

Analysis of the IMvigor 210 trials (NCT02951767 and NCT02108652) of patients with platinum refractory or cis-platin-ineligible urothelial carcinoma (UC) who were treated with the PD-L1 inhibitor, atezolizumab, identified a resistance signature as an immune biomarker. Based on transcriptome profiling of 368 tumor samples from this trial, the "genomically unstable" Lund subtype classification was associated with best response. A novel single-patient subtype classifier based on the TCGA2017 expression-based molecular subtypes was developed and applied. This identified 11 patients with a neuronal subtype with a 100% response rate in 8 confirmed cases (2 complete response, 6 partial response), and 72% overall, including 3 of 11 patients with unconfirmed response. The survival probability was extraordinarily high for the neuronal subtype, which are a high-risk cohort with advanced disease and may be secondary to low levels of TGF-B expression and high mutation/neoantigen burden.

Using unbiased non-negative matrix factorization (NMF) consensus clustering, 5 RNA-seq expression subtypes: luminal-papillary, luminal-infiltrated, luminal, basal-squamous, and neuronal. An association of these subtypes with overall survival (OS) was identified with luminal papillary having the best overall survival and neuronal the worst overall survival. In a LASSO-penalized multivariate Cox regression analysis, which included 15 covariates (that were significant in univariate overall survival calculations), neuronal, luminal infiltrated and luminal subtypes retained independent association with worse overall survival. These results suggested a hypothetical model for subtype-directed therapy for testing in prospective clinical trials. In a subsequent analysis, a bladder cancer RNA expression single patient classifier based on analysis of a reduced set of genes was developed (n=354; Table 2, below) that faithfully reproduced each of the subtypes derived from unsupervised clustering (that was based on the 3,347 most variable genes).

TABLE 6

| Gene | Weight_to_Lum | Weight_to_Lum-Inf | Weight_to_BS |
| --- | --- | --- | --- |
| PI4KAP2 | 3.676038643 | 0.515120045 | 0.154711809 |
| MYCL1 | 3.206825867 | 0.902922982 | 0 |
| SNX31 | 3.943840662 | 1.209005734 | 0 |
| IGFL1 | 6.007783301 | 2.131390192 | 0.914247541 |
| SCNN1G | 3.597962975 | 0.961464272 | 0 |
| HIC2 | 3.931161798 | 0.564708907 | 0.249643721 |
| C17orf55 | 4.337279598 | 0.92749519 | 0.48443043 |
| PI4KAP1 | 3.348395906 | 0.547096325 | 0.12071389 |
| SCNN1B | 3.274053149 | 1.199708162 | 0 |
| CCR7 | 5.119860502 | 2.384440192 | 0.35705206 |
| HS3ST6 | 3.771495584 | 1.934398104 | 0 |
| AGAP11 | 3.057739161 | 0.669215265 | 0.008986466 |
| BHMT | 6.871113581 | 1.652930665 | 0 |
| UPK2 | 3.990785812 | 1.789158074 | 0 |
| SLC1A6 | 5.461111946 | 2.198270637 | 0.891953866 |
| FMO9P | 3.818772232 | 1.86997372 | 0 |
| PSD2 | 4.148327694 | 1.266212559 | 0.198837107 |
| SLC6A4 | 3.607584306 | 1.664378877 | 0.103137128 |
| INA | 4.064201051 | 1.498001122 | 0.03967659 |
| C19orf45 | 3.293705782 | 0.821353469 | 0 |
| DHRS2 | 3.691203445 | 1.484386511 | 0 |
| GPLD1 | 3.100596902 | 1.321275632 | 0.144229756 |
| KIAA1984 | 3.649448751 | 1.009239331 | 0.11467039 |
| PVALB | 5.22962592 | 3.04974699 | 0.06791063 |
| PTN | 4.879841924 | 2.500893799 | 0.530702408 |
| KRT20 | 3.982795236 | 1.759031127 | 0 |
| EMX1 | 3.333593655 | 1.283170701 | 0.289605232 |
| SLC30A2 | 3.560894429 | 2.088295258 | 0.038796877 |
| UPK1A | 3.54631912 | 2.149316615 | 0 |
| SNAP91 | 3.936411761 | 1.25789073 | 0.153668916 |
| GABBR2 | 5.566241058 | 3.704295332 | 0.216057084 |
| PPARG | 1.342338024 | 0.32972463 | 0.047380332 |
| UPK3A | 3.498830602 | 2.739906066 | 0 |
| IGDCC3 | 5.28276054 | 2.128459171 | 0.309363129 |

TABLE 6-continued

| Gene | Weight_to_Lum | Weight_to_Lum-Inf | Weight_to_BS |
|---|---|---|---|
| IGF2 | 5.191903225 | 2.042515903 | 0.736403418 |
| MYCN | 4.408451801 | 2.017149171 | 0.160590801 |
| BAMBI | 3.463662267 | 1.608900542 | 0 |
| PM20D1 | 5.458163605 | 3.31816156 | 0 |
| KIAA1751 | 2.860143024 | 1.022029721 | 0.20153664 |
| SIGL3C5 | 3.310961296 | 2.921008742 | 0.913847962 |

This classifier appears to be robust in discriminating subtypes of bladder cancer with different prognoses in multiple previously published data sets. The classifier gene set analysis was applied to the RNA expression data used for the analysis of IMvigor 210 reported by Mariathasan et al. FIG. 30A-D shows the distribution of subtype calls for the 348 patients, including comparison to the Lund classification (FIG. 30A), the probability of assignment of patients to the five different TCGA 2017 subtypes (FIG. 30C), and strong correlation with multiple previous expression-based discriminants of bladder cancer subtypes (FIG. 30D). Comparison of the subtype calls with the TCGA 2014 and Lund classifications shows the highest correlation between the TCGA 2017 and the Lund classification with the adjusted rand index (ARI) of 0.38 (FIG. 30B; Table 7).

TABLE 7

| Sample | TCGA2017 |
|---|---|
| SAM85e41e7f33f9 | Basal-squamous |
| SAMdf3e42c8672a | Basal-squamous |
| SAM36d87392593b | Basal-squamous |
| SAM4edbe45817b3 | Basal-squamous |
| SAMe7bf6c015192 | Basal-squamous |
| SAM6dd7ad1d797d | Basal-squamous |
| SAM468a9e1dc821 | Basal-squamous |
| SAMb963dda93cfd | Basal-squamous |
| SAM9fb814c22bdb | Basal-squamous |
| SAM7fb6987514a4 | Basal-squamous |
| SAM63045b04ab2d | Basal-squamous |
| SAM7d2dfba6cd84 | Basal-squamous |
| SAMd1bd63734394 | Basal-squamous |
| SAMe5bc41772bc9 | Basal-squamous |
| SAM9cafb905b36a | Basal-squamous |
| SAM3f2033c90438 | Basal-squamous |
| SAM032c642382a7 | Basal-squamous |
| SAM8884fe446d20 | Basal-squamous |
| SAM0ce9c983b20f | Basal-squamous |
| SAM297c0301e861 | Basal-squamous |
| SAMcabb6d58ff55 | Basal-squamous |
| SAM2e9ac0b1b250 | Basal-squamous |
| SAM30b5c6c54cf7 | Basal-squamous |
| SAMd98bac0a070f | Basal-squamous |
| SAM8e8ef2368dfa | Basal-squamous |
| SAM943df5cf15df | Basal-squamous |
| SAMb3c02294aba7 | Basal-squamous |
| SAM39eb94fa504d | Basal-squamous |
| SAMc0da5d48686d | Basal-squamous |
| SAM2570ff4aae6e | Basal-squamous |
| SAM2dc3f04e45e9 | Basal-squamous |
| SAM4501e41e4751 | Basal-squamous |
| SAM714285adf612 | Basal-squamous |
| SAM025b45c27e05 | Basal-squamous |
| SAM2dc578e0165f | Basal-squamous |
| SAM560f23d6a3ad | Basal-squamous |
| SAM73b653ae20d1 | Basal-squamous |
| SAM28687037e4ff | Basal-squamous |
| SAM45c8e6412c66 | Basal-squamous |
| SAM0a7c2091dd56 | Basal-squamous |

Figure 31:
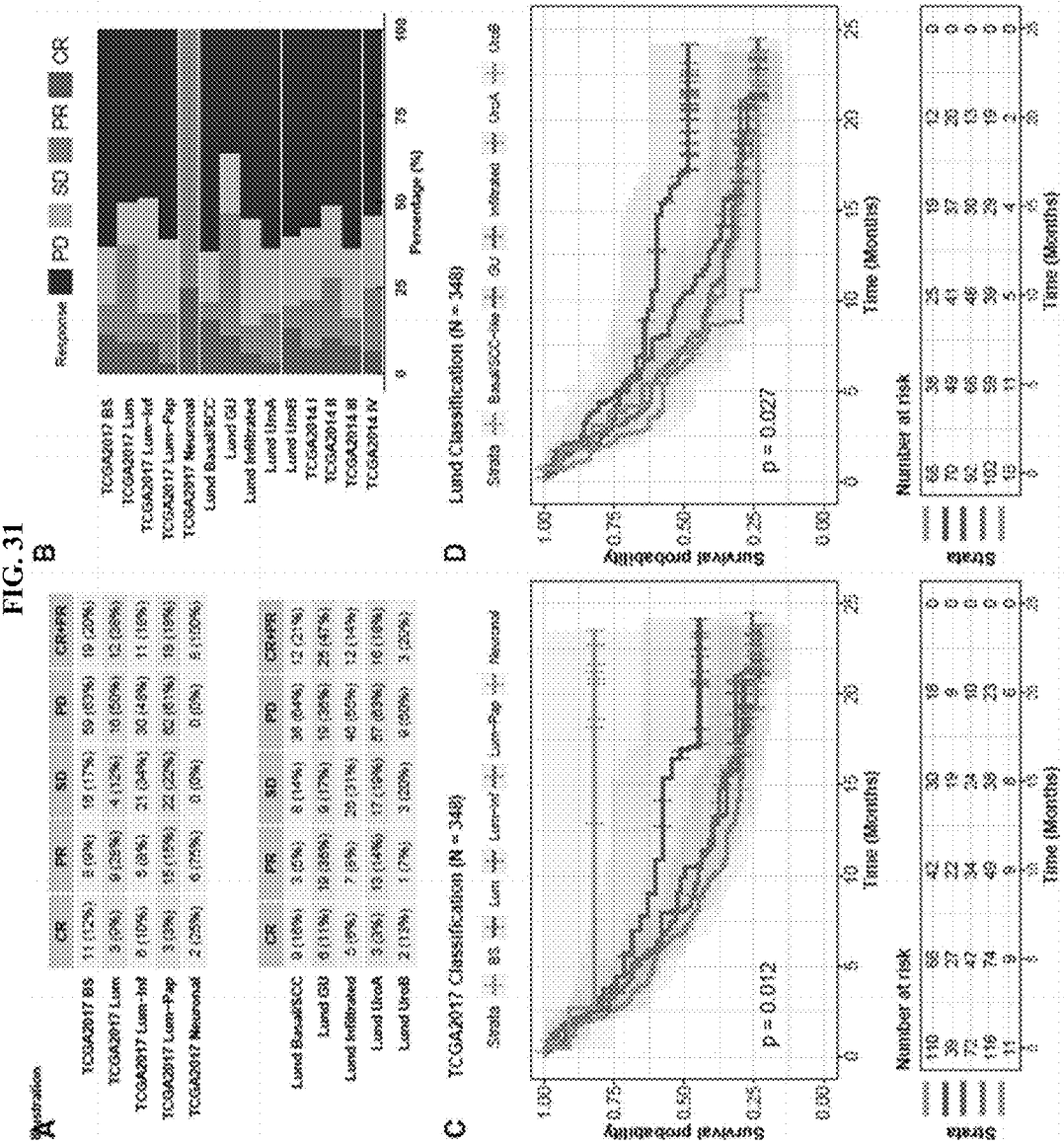

Interestingly, the TCGA 2017 classifier assigned the Lund GU samples to each of the five TCGA categories. Both mutation and transcriptome profiles of the TCGA2017 subtypes were highly consistent with the previous analysis (FIG. 30E); the luminal-papillary was characterized by frequent FGFR3 mutations (39% vs 8% in others) and the lowest carcinoma-in-situ (CIS) score, the luminal-infiltrated had the highest p53-like and EMT signature expression, and the basalsquamous was enriched in samples with a predominant expression of CD8+ Teff and immunecheck point genes, and the luminal had the highest level of uroplakins with more frequent TP53 mutations (64%). Notably all neuronal samples (n=11) harbored TP53 mutations, and 7 of those (64%) had concomitant RB1 loss by either mutation (n=5) or down-regulation (n=2; log 2(fold change)<−1.5), consistent with the hallmark loss of wild-type TP53 and RB1 in neuroendocrine tumors, and all showed high expression of both neuroendocrine and neuronal markers (FIG. 30E). The association between subtypes defined using the classifier, and response to atezolizumab therapy was examined. Remarkably, the neuronal subtype defined by the TCGA 2017 classifier (SOX2, TUBB2B, PEG10) showed a high objective response rate and had the best overall survival (p=0.012, FIG. 31 A,B, C). The luminal subtype was also associated with both a better response rate (38%) and overall survival than the other three subtypes, but to a much smaller degree (FIG. 31C).

Infiltrated and basal subtypes in both the TCGA 2017 and Lund classifications were associated with poor response and survival (FIG. 31C, D). The better survival association of neuronal and luminal subtypes persisted when the analysis was repeated for 298 patients with response data (FIG. 32). It is striking that the neuronal subtype had the worst survival in the TCGA 2017 cohort3, while it had the best survival in this atezolizumab-treated cohort. None of the 11 neuronal subtype tumors were immune-inflamed (as defined in the Mariathasan report), and 8 of 11 (77%) were immune excluded, suggesting no major role for CD8+ Teff activity in the response of this subtype (FIG. 30A-E). In addition, the neuronal subtype had an average tumor mutation burden (TMB) and tumor neoantigen burden (TNB), while luminal subtype tumors were highest by those measures (FIG. 33A). Remarkably, the neuronal subtype had the lowest level of TGFB1 and TGFBR1 expression in comparison to other subtypes (FIG. 33B), which was also associated with response in the Mariathasan report.

The current observations indicate that the TCGA 2017 classifier described herein has value in the identification of patients most likely to have the best response to immune checkpoint therapy for metastatic UC, namely the neuronal subtype. Without intending to be bound by theory, the mechanism of response may relate to the relative low expression of TGFB1 and TGFBR2 by neuronal subtype cancers, and their high expression of neuronal/neuroendocrine proteins that could serve as tissue-restricted antigens and enhance the immune response to atezolizumab.

The results described herein above, were obtained using the following methods and materials.

Methods for Examples 1-13

Experimental Model and Subject Details

Tumor and normal whole blood samples were obtained from patients at contributing centers with informed consent according to their local Institutional Review Boards (IRBs, see below). Biospecimens were centrally processed and DNA, RNA, and protein were distributed to TCGA analysis centers. In total, 412 evaluable primary tumors with associated clinicopathologic data were assayed on at least one molecular-profiling platform.

TCGA Project Management has collected necessary human subjects documentation to ensure the project complies with 45-CFR-46 (the "Common Rule"). The program has obtained documentation from every contributing clinical site to verify that IRB approval has been obtained to participate in TCGA. Such documented approval may include one or more of the following:

- An IRB-approved protocol with Informed Consent specific to TCGA or a substantially similar program. In the latter case, if the protocol was not TCGA-specific, the clinical site PI provided a further finding from the IRB that the already-approved protocol is sufficient to participate in TCGA.
- A TCGA-specific IRB waiver has been granted.
- A TCGA-specific letter that the IRB considers one of the exemptions in 45-CFR-46 applicable. The two most common exemptions cited were that the research falls under 46.102(f)(2) or 46.101(b)(4). Both exempt requirements for informed consent, because the received data and material do not contain directly identifiable private information.
- A TCGA-specific letter that the IRB does not consider the use of these data and materials to be human subjects research. This was most common for collections in which the donors were deceased.

Biospecimen Collection; Pathological and Clinical Data
Sample Inclusion Criteria Biospecimens were collected from patients diagnosed with muscle-invasive urothelial carcinoma undergoing surgical resection with either transurethral resection or radical cystectomy. No patient had received prior chemotherapy or radiotherapy for their disease. Prior intravesical Bacille Calmette Guerin (BCG) was allowed but not intravesical chemotherapy. Institutional review boards at each tissue source site reviewed protocols and consent documentation and approved submission of cases to TCGA. Cases were staged according to the American Joint Committee on Cancer (AJCC) staging system. Each frozen primary tumor specimen had a companion normal tissue specimen. This could be blood/blood components (including DNA extracted at the tissue source site), adjacent normal tissue taken from greater than 2 cm from the tumor, or both. Specimens were shipped overnight from 36 tissue source sites (TSS) using a cryoport that maintained an average temperature of less than −180° C. Each tumor and adjacent normal tissue specimen (if available) were embedded in optimal cutting temperature (OCT) medium and a histologic section was obtained for review. Each Haemotoxylin and Eosin (H&E)-stained case was reviewed by a board-certified pathologist to confirm that the tumor specimen was histologically consistent with urothelial carcinoma and that the adjacent normal specimen contained no tumor cells. Divergent histologies within the sample could not represent less than 50% of the cancer specimen. Tumor sections were required to contain an average of 60% tumor cell nuclei with equal to or less than 20% necrosis for inclusion in the study, per TCGA protocol requirements.

Sample Processing

RNA and DNA were extracted from tumor and adjacent normal tissue specimens using a modification of the DNA/RNA AllPrep kit (Qiagen). The flow-through from the Qiagen DNA column was processed using a mirVana miRNA Isolation Kit (Ambion). This latter step generated RNA preparations that included RNA <200 nt suitable for miRNA analysis. DNA was extracted from blood using the QiaAmp blood midi kit (Qiagen). Each specimen was quantified by measuring Abs260 with a UV spectrophotometer or by PicoGreen assay. DNA specimens were resolved by 1% agarose gel electrophoresis to confirm high molecular weight fragments. A custom Sequenom SNP panel or the AmpFISTR Identifier (Applied Biosystems) was utilized to verify tumor DNA and germline DNA were derived from the same patient. Five hundred nanograms of each tumor and normal DNA were sent to Qiagen for REPLI-g whole genome amplification using a 100 μg reaction scale. Only specimens yielding a minimum of 6.9 μg of tumor DNA, 5.15 μg RNA, and 4.9 μg of germline DNA were included in this study. RNA was analyzed via the RNA6000 nano assay (Agilent) for determination of an RNA Integrity Number (RIN), and only the cases with RIN >7.0 were included in this study. A total of 722 bladder urothelial carcinoma cases were received by the BCR and 412 (57%) passed final quality control. Reasons for rejection are described at https://cancergenome.nih.gov/cancersselected/biospeccriteria. Normal controls included peripheral blood (n=392), and/or tumor-adjacent, histologically normal-appearing bladder tissue (n=37).

Pathology Review

All samples were subjected to central review by four urological pathologists (HAA, DEH, BAC, VER), using digitally scanned whole slides of a representative section from a fresh frozen tumor sample submitted for molecular analysis. All samples were systematically evaluated to confirm the histopathologic diagnosis and any variant histology according to the most recent World Health Organization (WHO) classification (Moch et al., 2016). Additionally, all tumor samples were assessed for tumor content (% tumor nuclei), the presence and extent of tumor necrosis and the presence of invasion into muscularis propria. Tumor samples were also evaluated for the presence and extent of inflammatory infiltrate as well as the type of the infiltrating cells in the tumor microenvironment (lymphocytes, neutrophils, eosinophils, histiocytes, plasma cells). Any non-concordant diagnoses among the four pathologists were re-reviewed and resolution achieved after discussion.

Clinical Data

Clinical data were submitted for all cases passing quality control. Patient information was completed immediately following the notification of qualification, and a follow-up submission was required for all living patients one year after the case's qualification date; follow-up data beyond this were submitted voluntarily. For the work reported here, clinical data for all 412 cases were downloaded from the Genomics Data Commons Data Portal (https://portal.gdc.cancer.gov/) on May 5, 2017. The majority of the fields included in the dataset used for analysis were found in the patient section of the clinical XML files (e.g. nationwidechildrens.org_clinical.TCGA-HQ-A5ND.xml). This information had been collected during the initial submission from the participating Tissue Source Sites (TSSs). For survival analysis, the follow-up information was also considered, in order to capture each case's longest number of days to follow-up or death; this information changed survival information for a subset of cases reported in the previous TCGA publication (Cancer Genome Atlas Research Network, 2014a).

Copy Number Analysis

DNA from each tumor or germline sample was hybridized to Affymetrix SNP 6.0 arrays using protocols at the Genome Analysis Platform of the Broad Institute as previously described (McCarroll et al., 2008). Briefly, from raw .CEL files, Birdseed was used to infer a preliminary copy-number at each probe locus (Korn et al., 2008). For each tumor, genome-wide copy number estimates were refined using tangent normalization, in which tumor signal intensities are divided by signal intensities from the linear combination of all normal samples that are most similar to the tumor. This linear combination of normal samples tends to match the noise profile of the tumor better than any set of individual normal samples, thereby reducing the contribution of noise to the final copy-number profile. Individual copy-number estimates then underwent segmentation using Circular Binary Segmentation (Olshen et al., 2004). Segmented copy number profiles for tumor and matched control DNAs were analyzed using Ziggurat Deconstruction, an algorithm that parsimoniously assigns a length and amplitude to the set of inferred copy-number changes underlying each segmented copy number profile, and the analysis of broad copy-number alterations was then conducted as previously described (Mermel et al., 2011). Significant focal copy number alterations were identified from segmented data using GISTIC 2.0 (Mermel et al., 2011). Allelic copy number, regions of homozygous deletions, whole genome doubling and purity and ploidy estimates were calculated using the ABSOLUTE algorithm (Carter et al., 2012a).

DNA Sequencing

DNA Sequencing and Data Processing

Exome capture was performed using Agilent SureSelect Human All Exon 50 Mb according to the manufacturers' instructions. Briefly, 0.5-3 micrograms of DNA from each sample were used to prepare the sequencing library through shearing of the DNA followed by ligation of sequencing adaptors. All whole exome (WES) and whole genome (WGS) sequencing was performed on the Illumina HiSeq platform. Paired-end sequencing (2×101 bp for WGS and 2×76 bp for WE) was carried out using HiSeq sequencing instruments; the resulting data was analyzed with the current Illumina pipeline. Basic alignment and sequence QC was done on the Picard and Firehose pipelines at the Broad Institute. Sequencing data were processed using two consecutive pipelines:

Sequencing Data Processing Pipeline ('Picard Pipeline')

Picard (http://picard.sourceforge.net/) uses the reads and qualities produced by the Illumina software for all lanes and libraries generated for a single sample (either tumor or normal) and produces a single BAM file (http://samtools.sourceforge.net/SAM1.pdf) representing the sample. The final BAM file stores all reads and calibrated qualities along with their alignments to the genome.

Cancer Genome Analysis Pipeline ('Firehose Pipeline')

Firehose (http://www.broadinstitute.org/cancer/cga/Firehose) takes the BAM files for the tumor and patient matched normal samples and performs analyses including quality control, local realignment, mutation calling, small insertion and deletion identification, rearrangement detection, coverage calculations and others as described briefly below. The pipeline represents a set of tools for analyzing massively parallel sequencing data for both tumor DNA samples and their patient_matched normal DNA samples. Firehose uses GenePattern (Reich et al., 2006) as its execution engine for pipelines and modules based on input files specified by Firehose. The pipeline contains the following steps:

Quality control. This step confirms identity of individual tumor and normal to avoid mix-ups between tumor and normal data for the same individual.

Local realignment of reads. This step realigns reads at sites that potentially harbor small insertions or deletions in either the tumor or the matched normal, to decrease the number of false positive single nucleotide variations caused by misaligned reads.

Identification of somatic single nucleotide variations (SSNVs)—This step detects candidate SSNVs using a statistical analysis of the bases and qualities in the tumor and normal BAMs, using Mutect (Cibulskis et al., 2013).

Identification of somatic small insertions and deletions—In this step putative somatic events were first identified within the tumor BAM file and then filtered out using the corresponding normal data, using Indellocator (Ratan et al., 2015)

Mutation Significance Analysis

Genes with a significant excess of the number of non-synonymous mutations relative to the estimated density of background mutations were identified using MutSig algorithm. MutSig has been used to identify significantly mutated genes (SMGs) in several previous TCGA tumor sequencing projects and has undergone a development path starting from the most basic approach implemented in MutSig 1.0 (Getz et al., 2007) to the current version MutSig 2CV (Lawrence et al., 2014; Lawrence et al., 2013). This study made use of MutSig 2CV to produce a robust list of significantly mutated genes (Table 3).

Mutation Clonality Analysis

The ABSOLUTE algorithm (Carter et al., 2012b) was used with copy number and mutation data to infer purity and ploidy for 400 tumor samples, and the cancer cell fraction (CCF) was estimated for each mutation. Mutations were classified with CCF $\geq 0.9$ as clonal and all other mutations as sub-clonal.

Mutation Signature Analysis

Mutation signature discovery involves deconvolving cancer somatic mutations, stratified by mutation contexts or biologically meaningful subgroups, into a set of characteristic patterns (signatures), and inferring the contributions of signature activity across samples (Alexandrov et al., 2013). Single nucleotide variants (SNVs) in the 412 samples were classified into 96 base substitution types, i.e. the six base substitutions C>A, C>G, C>T, T>A, T>C, and T>G, within the tri-nucleotide sequence context that includes the bases immediately 5' and 3' to each mutated base. Thus the input data for the mutation signature analysis is given as the mutation counts matrix X (96 by N=412), where each element represents an observed mutation count at the context i in the sample j. A Bayesian variant of the non-negative matrix factorization (NMF) was applied with an exponential prior (BayesNMF) (et al., 2016a; Tan and Fevotte, 2013) to enable a de novo signature discovery with an optimal inference for the number of signatures (K*) best explaining the observed X. The mutation count matrix was taken as an input for the BayesNMF and factored into two matrices, W' (96 by K*) and H' (K* by N), approximating X by W'H'. All fifty independent BayesNMF runs with a different initial condition for 409 samples converged to the solution of K*=4, identifying four distinct mutational processes, C>T_CpG, ERCC2, APOBC-b, and APOBEC-a.

To enumerate the number of mutations associated with each mutation signature we performed a scaling transformation, X~W'H'=WH, W=W'U$^{-1}$ and H=UH', where U is a K* by K* diagonal matrix with the element corresponding to the 1-norm of column vectors of W', resulting in the final signature matrix W and the activity matrix H. Note that the kth column vector of W represents a normalized mutability along 96 tri-nucleotide mutation contexts in the kth signature, and the kth row vector of H dictates the number of mutations associated with the kth signature across samples.

The MSig clustering analysis for 409 samples was performed using a standard hierarchical clustering in R, with a 'euclidian' distance for the signature activity matrix H and a 'ward.D' linkage. The number of MSig clusters was chosen by manual inspection.

Using the W and H matrices determined by BayesNMF each mutation was annotated with the probability (likelihood of association) that it was generated by each of the discovered mutational signatures, $p_{ms}$, where 'm' denotes a mutation and 's' refers to the signature. Specifically, the likelihood of association to the kth signature for a set of mutations corresponding to the i-th mutation context and j-th sample was defined as $[w_k h_k / \Sigma_k w_k h_k]_{ij}$, where $w_k$ and $h_k$ correspond to the kth column vector and kth row vector of W and H, respectively (Kasar et al., 2015).

Unsupervised Clustering of Mutations in SMGs and Focal SCNAs

A binary event matrix, Q (n by m) was first created, comprised of mutations in 53 SMGs and focal SCNAs in the 25 genes that had more than ten SMG mutations and more than ten focal SCNAs across 408 samples. The resulting event matrix was used to compute a consensus matrix, $M_K$, in which the element $M_{ij}$ represents how often both event i and sample j clustered together, with K being the number of clusters, by iterating conventional NMF with Frobenius norm (K*25) times to approximate Q~WH. The cluster membership for event i and sample j was determined by the "maximum association criterion" as i*=max_k $[w_{ik}]$ and j*=max_k $[h_{kj}]$ (k=1 through K). Then the cumulative consensus matrix, M, was computed by summing up all $M_K$ with K increasing through 2 to 8, and normalized by the total number of iterations, resulting in the normalized M*. To determine the optimal number of consensus clusters, K*, i.e. that best explain the observed M*, we applied Bayesian non-negative matrix factorization (NMF) with a half-normal prior, finding the best approximation, M*~W*H*, where $w_{ik}$ in W* (m by K) and $h_{kj}$ in H* (K by m) represents a clustering affinity or an association of the event i and the sample j to the cluster k, respectively. Twelve out of 20 independent BayesNMF runs with different initial conditions converged to the solution of K*=4, while eight runs converged to the solution of K*=5. After manual inspection we chose the K*=4 solution, and reported four MutCN clusters.

Quantitation of Mutagenesis by APOBEC Cytidine Deaminases

The exome-wide prevalence of the APOBEC mutagenesis signature and the enrichment of this signature over its presence expected for random mutagenesis was evaluated with Pattern of Mutagenesis by APOBEC Cytidine Deaminases (P-MACD) analysis pipeline as outlined in (Roberts et al., 2013) and described in detail in Broad Institute TCGA Genome Data Analysis Center (2016): Analysis of mutagenesis by APOBEC cytidine deaminases (P-MACD). Broad Institute of MIT and Harvard (doi:10.7908/C1CC1013). Briefly, analysis is based on previous findings that APOBECs deaminate cytidines predominantly in a tCw motif and that the APOBEC mutagenesis signature is composed of approximately equal numbers of two kinds of changes in this motif—tCw→G and tCw→T mutations (flanking nucleotides shown in small letters; w=A or T). Calculations were performed on a per sample basis, the enrichment of the APOBEC mutation signature among all mutated cytosines in comparison to the fraction of cytosines that occur in the tCw motif among the +/−20 nucleotides surrounding each mutated cytosine ("APOBEC_enrich" column in data files). In addition, several other parameters that characterize the prevalence of the APOBEC mutagenesis pattern in a sample and/or that are useful for downstream analyses and comparisons. The main parameter used in this disclosure was the minimum estimate of the number of APOBEC induced mutations in a sample—"APOBEC_MutLoad_MinEstimate". It was calculated using the formula: ["tCw→G+tCw→T"]×[("APOBEC_enrich"−1)/ "APOBEC_enrich"], which allows estimating the number of APOBEC signature mutations in excess of what would be expected by random mutagenesis. For example, if statistically significant enrichment in a sample would be =2, the minimum estimate of APOBEC-induced mutations would be 50% of total number of APOBEC-signature mutations (["tCw→G+tCw→T"]). Calculated values are rounded to the nearest whole number. "APOBEC_MutLoad_MinEstimate" was calculated only for samples with passing 0.05 FDR threshold for APOBEC enrichment (["BH_Fisher_p-value_tCw"]=<0.05. Samples with "BH_Fisher_p-value_tCw" value greater than 0.05 received a value of 0. For some analyses and figures "APOBEC_MutLoad_MinEstimate" parameter was converted into categorical values as follows:

"no": "APOBEC_MutLoad_MinEstimate"=0

"low": 0<"APOBEC_MutLoad_MinEstimate"≤median of non-zero values in the set of 412 BLCA samples "high": "APOBEC_MutLoad_MinEstimate">median of non-zero values in the set of 412 BLCA samples (median of non-zero values in the set of 412 BLCA samples=61.5).

Class I HLA Mutation and Neoantigen Analysis

Class I HLA Typing and Mutation Detection

HLA typing and detection of mutations in class I HLA genes (HLA-A/B/C) was performed using Polysolver (Shukla et al., 2015). Briefly, the HLA typing algorithm employs a Bayesian model that first estimates the prior probabilities of different alleles based on the ethnicity of the individual. These probabilities are then updated with a model that takes into account the base qualities and alignments of putative HLA-derived reads against the reference HLA allele database. The alleles for each of the three HLA genes are inferred based on the computed scores in a two-stage process. These inferred HLA alleles served as the reference for the HLA mutation detection step. Putative HLA reads from the tumor and the germline sample are extracted and aligned to the inferred allele sequences, followed by mutation and insertion/deletion identification with the Mutect (Cibulskis et al., 2013) and Strelka (Saunders et al., 2012) tools respectively.

A Chi-square test was used to assess whether HLA mutations were more common in patients with prior BCG treatment.

Neoantigen Prediction

For each patient, a list of all possible 9 and 10-mer peptides bearing somatic mutations were first enumerated, or overlapping open reading frame derived from frameshifting indels or nonstop mutations. These peptides were then evaluated for binding against the patient's inferred HLA type using the NetMHCpan-3.0 algorithm (Nielsen and Andreatta, 2016). The neoantigen load was defined as the total number of predicted peptide:allele binders with rank percentile score less than or equal to the weak binder threshold (2%). Univariate survival analysis of neoantigen load was evaluated using the Kaplan-Meier method. The effect of neoantigen load in the context of other variables was assessed using the Cox proportional hazards model. The comparison of number of HLA mutations or number of predicted binders between groups (e.g. MSig1 vs MSig2-4 clusters) was performed with two-sided t-tests.

DNA Methylation and Epigenetic Silencing

Assay Platform

The Illumina Infinium HumanMethylation450 (HM450) DNA methylation platform (Bibikova et al., 2011; Bibikova et al., 2009) was used to obtain DNA methylation profiles of 412 tumor samples and 21 tumor-adjacent, histologically normal-appearing bladder tissue samples. The HM450 assay analyzes the DNA methylation status of up to 482,421 CpG and 3,091 non-CpG (CpH) sites throughout the genome. It covers 99% of RefSeq genes with multiple probes per gene and 96% of CpG islands from the UCSC database and their flanking regions. The assay probes sequences and information for each interrogated CpG site on the Infinium DNA methylation platform, which is available from Illumina (www.illumina.com).

The DNA methylation score for each assayed CpG or CpH site is represented as a beta ($\beta$) value ($\beta=M/(M+U)$) in which M and U indicate the mean methylated and unmethylated signal intensities for each assayed CpG or CpH, respectively. B values range from zero to one, with scores of "0" indicating no DNA methylation and scores of "1" indicating complete DNA methylation. An empirically derived detection p value accompanies each data point and compares the signal intensity with an empirical distribution of signal intensities derived from a set of negative control probes on the array. Any data point with a corresponding p value greater than 0.05 was deemed to not be statistically significantly different from background and is thus masked as "NA" in the Level 3 data packages as described below. Further details on the Illumina Infinium DNA methylation assay technology have been described previously (Bibikova et al., 2011; Bibikova et al., 2009).

Sample and Data Processing

Bisulfite conversion of 1 µg of genomic DNA from each sample was performed using the EZ-96 DNA Methylation Kit (Zymo Research, Irvine, Calif.) according to the manufacturer's instructions. The amount of bisulfite-converted DNA was assessed and completeness of bisulfite conversion using a panel of MethyLight-based quality control (QC) reactions as previously described (Campan et al., 2009). All the TCGA samples passed the QC tests and entered the Infinium DNA methylation assay pipeline. Bisulfite-converted DNAs were whole-genome-amplified (WGA) and enzymatically fragmented prior to hybridization to BeadChip arrays as per the Infinium protocol. BeadArrays were scanned using the Illumina iScan technology to produce IDAT files. Raw IDAT files for each sample were processed with the R/Bioconductor package methylumi. TCGA DNA methylation data packages were then generated using the EGC.tools R package which was developed internally and is publicly available on GitHub (https://github.com/uscepigenomecenter/EGC.tools).

TCGA Data Packages

The data levels and the files contained in each data level package are described below and are present on the NCI Genomic Data Commons (https://gdc.cancer.gov).

Level 1 data contain raw IDAT files (two per sample) as produced by the iScan system and as mapped by the Sample and Data Relationship Format (SDRF). These IDAT files were directly processed by the R/Bioconductor package methylumi. A disease-mapping file (BLCA.mappings.csv) was provided in the AUX directory to facilitate this process. Level 2 data contained background-corrected methylated (M) and unmethylated (U) summary intensities as extracted by the R/Bioconductor package methylumi. Detection p values were computed as the minimum of the two values (one per methylation state measurement) for the empirical cumulative density function of the negative control probes in the appropriate color channel. Background correction was performed via normal-exponential deconvolution (Triche et al., 2013). Multiple-batch archives had the intensities in each of the two channels multiplicatively scaled to match a reference sample. The reference sample is defined in each array as the sample having R/G ratio of the normalization control probes closest to 1.0. Level 3 data contain $\beta$ value calculations with annotations for HGNC gene symbol, chromosome, and genomic coordinates (UCSC hg19, February 2009) for each targeted CpG/CpH site on the array. Probes having a common SNP (dbSNP build 135, Minor Allele Frequency >1%) within 10 bp of the interrogated CpG site or having an overlap with a repetitive element (as detected by RepeatMasker and Tandem Repeat Finder based on UCSC hg19, February 2009) within 15 bp (from the interrogated CpG site) were masked as "NA" across all samples, and probes with a detection p value greater than 0.05 in a given sample were masked as "NA" on that array. Probes that were mapped to multiple sites in the human genome (UCSC hg19, February 2009) were annotated as "NA" for chromosome and 0 for the CpG/CpH coordinate.

Level 3 DNA methylation data was used for the analyses described in this invention.

Unsupervised Clustering Analysis of DNA Methylation Data

Probes were removed which had any "NA"-masked data points and probes that were designed for sequences on X or Y chromosomes or non-CpG sites.

To capture cancer-specific DNA hypermethylation events, CpG sites were first selected that were not methylated in normal tissues (mean $\beta$ value <0.2). To minimize the influence of variable tumor purity levels on a clustering result, the data was dichotomized using a $\beta$ value of ≥0.3 to define positive DNA methylation and <0.3 to specify lack of methylation. The dichotomization not only ameliorated the effect of tumor sample purity on the clustering, but also removed a great portion of residual batch/platform effects that are mostly reflected in small variations near the two ends of the range of $\beta$ values. CpG sites were also removed that were methylated in leukocytes, a major source of contamination present in a tumor sample (mean $\beta$-value >0.2). Consensus clustering was then performed with the dichotomized data on 31,249 CpG sites that were methylated in at least 5% of the tumor samples. The optimal number of clusters was assessed based on 80% probe and tumor resampling over 1,000 iterations of hierarchical clustering for K=2, 3, 4 . . . 20 using the binary distance metric for clustering and Ward's method for linkage as implemented in the R/Bioconductor ConsensusClusterPlus package.

Similarly, in order to investigate subgroups based on cancer-specific DNA hypomethylation, CpG sites were identified that were highly methylated in normal tissues (mean $\beta$ value >0.8). The data was dichotomized using a $\beta$ value of <0.7 as a threshold for loss of DNA methylation. Consensus clustering was then performed with the dichotomized data on 53,862 CpG sites that showed hypomethylation in at least 10% of the tumors.

Heatmaps were generated to assess clustering results based on the original $\beta$ values for a subset of the most variably methylated CpG sites across the tumors. The probes were displayed based on the order of unsupervised hierarchal clustering of the $\beta$ values using the Euclidean distance metric and Ward's linkage method. Covariate association p values were calculated with Chi-square tests.

Identification of Epigenetically Silenced Genes

DNA methylation probes overlapping with SNPs were first removed, repeats or designed for sequences on X or Y chromosomes or non-CpG sites. The remaining probes were mapped against UCSC Genes using the GenomicFeatures R/Bioconductor package. Probes unmethylated in normal tissues (mean β value <0.2) and located in a promoter region (defined as the 3 kb region spanning from 1,500 bp upstream to 1,500 bp downstream of the transcription start site) were identified. mRNA expression data were log 2 transformed [log 2(RSEM+1)] and used to assess the gene expression levels associated with DNA methylation changes. DNA methylation and gene expression data were merged by Entrez Gene IDs.

The DNA methylation data was dichotomized using a β value of >0.3 as a threshold for positive DNA methylation and eliminated CpG sites methylated in fewer than 3% of the tumor samples. For each probe/gene pair, the following algorithm was applied: 1) classify the tumors as either methylated (β≥0.3) or unmethylated (β<0.3); 2) compute the mean expression in the methylated and unmethylated groups; 3) compute the standard deviation of the expression in the unmethylated group. Probes were then selected for which the mean expression in the methylated group was less than 1.64 standard deviations from the mean expression of the unmethylated group. Each individual tumor sample was labeled as epigenetically silenced for a specific probe/gene pair if: a) it belonged to the methylated group and b) the expression of the corresponding gene was lower than the mean of the unmethylated group of samples. If there were multiple probes associated with the same gene, a sample that was identified as epigenetically silenced at more than half the probes for the corresponding gene was also labeled as epigenetically silenced at the gene level. For each gene, the resulting silencing call was evaluated based scatter plot of DNA methylation vs. expression and a heatmap.

The list of genes that were significantly mutated was then manually examined. Additional genes were identified having evidence for epigenetic silencing at low frequencies. CDKN2A DNA methylation status was assessed based on the probe (cg13601799) located in the p16INK4 promoter CpG island. p16INK4 expression was determined by the log 2(RPKM+1) level of its first exon (chr9:21974403-21975038).

The complete list of 158 genes identified as epigenetically silenced is provided in Table 4.

Genes Upregulated in Hypomethylated Subtype 4

Four types of data was used: 1) β values for 5386 probes for 412 primary tumor samples and 21 adjacent normal samples, 2) RSEM gene-level expression data for 408 primary tumors and 19 adjacent normals, and 3) clinical and molecular data for 412 tumor samples, and 4) pathology review of micrograph images for the adjacent normals, which indicated that BT-A20U-11, BT-A2LB-11, GD-A2C5-11, and GD-A3OP-11 should be removed.

Of the 408 tumor samples with RSEM data, 36 were in hypomethylation subtype 4 ('subtype 4'), and 372 in the other hypomethylation subtypes.

10368 genes were identified that had a mean RSEM abundance of at least 1.0 in each of the tumor groups (subtype 4 vs. other), and an absolute value fold change of at least 1.25 between the two groups. 1863 genes were differentially abundant between the two groups (Benjamini-Hochberg (BH)-corrected p<0.01, Wilcoxon test), and 436 of the 1863 genes were more abundant in subtype 4, with a fold change of at least 1.5.

2646 of the 5386 methylation probes that were identified had a fold change more negative than −1.5 between subtype 4 and other samples, i.e. had lower β values in subtype 4. These had BH-corrected Wilcoxon p values <0.003, and −1/FC ranging from −5.6 to −1.5.

Using the 'annotations' from the IlluminaHumanMethylation450kanno.ilmn12.hg19 v0.6.0 R package, 1784 of the 2646 probe IDs were associated with one or more gene symbols. Of these, 681 records had gene symbols that were semicolon-separated lists, e.g. SIRPG; SIRPG;SIRPG, or NCRNA00175;NCRNA00175; COL18A1. Such lists were collapsed into unique symbols, and arbitrarily took the last of these symbols, even when the list contained more than one symbol. This associated each probe ID with one RefSeq gene symbol. Because some symbols have more than one associated probe, the 1784 gene symbols contained 1240 unique symbols.

187 unique RefSeq gene symbols were present in both a) the differentially abundant RSEM genes and b) genes associated with differential probes. For each probe-associated gene we retained only the probe with the most significant BH-corrected p value, accepting all annotated relationships of a probe to a CpG island (i.e. Island, N_Shelf, N_Shore, S_Shelf, S_Shore, or OpenSea).

From the 187 RefSeq genes, 39 were identified for which, in hypomethylation subtype 4, the RSEM gene abundance was higher, and the beta value for the associated DNA methylation probe was lower. Scatterplots were then inspected of beta vs. RSEM abundance, which included the 14 adjacent normals that were present in both DNA methylation and RSEM datasets, and had passed pathology review. A subset of 12 genes were identified for which DNA hypomethylation in subtype 4 may have resulted in higher RSEM abundance in that subtype.

Statistics

Statistical analysis and data visualization were carried out using the R/Biocoductor software packages (www.bioconductor.org).

mRNA Expression Profiling mRNA Sequencing and Expression Quantification

RNA was extracted, prepared into mRNA libraries, and sequenced by Illumina HiSeq resulting in paired 50 nt reads, and subjected to quality control as previously described (Cancer Genome Atlas Research, 2012). RNA reads were aligned to the hg19 genome assembly using Mapsplice (Wang et al., 2010), and RNA fusion events were automatically detected by MapSplice as previously described. Gene expression was quantified for the transcript models corresponding to the TCGA GAF2.1 (https://gdc-api.nci.nih.gov/v0/data/a0bb9765-3f03-485b-839d-7dce4a9bcfeb), using RSEM (Pasqualucci et al., 2011) and normalized within-sample to a fixed upper quartile. For further details on this processing, refer to GDC Description file under the V2_MapSpliceRSEM workflow (https://gdc-api.nci.nih.gov/legacy/data/cf4559f9-6beb-4bb3-ac43-c99ba6cf7f0f). Data for genes were median-centered across samples for downstream analysis.

Unsupervised mRNA Expression Clustering

For unsupervised clustering analysis the $\log_2$(RSEM) gene expression data for N=408 samples was pre-processed to determine the most highly expressed and variable 3,347 genes across samples. Genes were removed with NA values more than 10% across samples and then selected top 25% most-varying genes by standard deviation of gene expression across samples. The resulting expression matrix R (3347 by 408) was further transformed to the matrix R* of fold changes centered at the median expression. The expression clustering analysis was done by combining BayesNMF (Tan and Fevotte, 2013) with a consensus hierarchical clustering approach, as follows. Using the distance matrix of 1-C, the element $C_{ij}$ representing the Spearman correlation between the sample i and j across 3347 genes in R*, a consensus matrix is first computed, $M_K$, the element $M_{ij}$ representing how often both samples i and j clustered together, and K being the number of clusters, by iterating a standard hierarchical clustering (K*500) times with the average linkage option and 80% resampling in sample space. Then the cumulative consensus matrix, M, was computed by summing up all $M_K$ with K increasing through 2 to 10, and normalized by the total number of iterations, resulting in the normalized M*. To determine the optimal number of clusters, K*, i.e. that best explain the observed M*, Bayesian non-negative matrix factorization (NMF) was applied with a half-normal prior, finding the best approximation, $M^* \sim H^T H$, where $h_{kj}$ in H (K* by N) represents a clustering affinity or an association of the sample j to the cluster k and $H^T$ is a transpose of H. Nine out of 20 independent BayesNMF runs with different initial conditions converged to the solution of K*=5, while 11 runs converged to the solution of K*=4. After manual inspection the K*=5 solution was chosen, giving rise to the five mRNA expression subtypes: luminal, luminal-infiltrated, basal-squamous, neuronal, and luminal-papillary. Both luminal and luminal-infiltrated clusters were noted as merged together to form a single cluster in the K*=4 solution, indicating that expression patterns in these two clusters were relatively more similar than any other subtypes. The cluster membership for sample j was determined by the "maximum association criterion" as k*=max_k $[h_{kj}]$ (k=1 through K*). The concordance of the derived expression subtypes was examined in the comparison to those in TCGA marker paper (Cancer Genome Atlas Research Network, 2014a) and other various subtype classifications for 234 TCGA samples (Aine et al., 2015).

Subtype-specific marker genes were selected in FIG. 5 by performing an additional non-negative matrix factorization to the $\log_2$(RSEM) gene expression data X with the fixed K* and H* (a column-wise normalization of H) to determine the optimal W (18197 by K*) as X~WH*. Note that the element $w_{ik}$ in W represents an inferred contribution of the cluster k to the expression of the gene i, i.e. measures an affinity or association of the gene i to the cluster k. The clustering membership of the gene i was determined by the maximum association criterion as k*=max_k $[w_{kj}]$ (k=1 through K*). The top 1% genes were considered in descending order of $w_{ik}$, with $d_{ik} \geq 2.75$, where $d_{ik}$ refers to the mean expression difference in $\log_2$(RSEM) between samples in the cluster k and other samples.

Gene Expression Signature Scores

The raw gene expression signature score in FIG. 6A, FIG. 6B FIG. 6C, FIG. 6D, and FIG. 6E was defined as a mean of $\log_2$(RSEM) for the basal markers (CD44, CDH3, KRT1, KRT14, KRT16, KRT5, KRT6A, KRT6B, KRT6C), luminal markers (CYP2J2, ERBB2, ERBB3, FGFR3, FOXA1, GATA3, GPX2, KRT18, KRT19, KRT20, KRT7, KRT8, PPARG, XBP1, UPK1A, UPK2), p53-like markers (ACTG2, CNN1, MYH11, MFAP4, PGM5, FLNC, ACTC1, DES, PCP4), squamous-differentiation markers (DSC1, DSC2, DSC3, DSG1, DSG2, DSG3, S100A7, S100A8), neuroendocrine markers (CHGA, CHGB, SCG2, ENO2, SYP, NCAM1), CIS (carcinoma-in-situ) markers (Dyrskjot et al., 2004), cell-cycle genes (Cuzick et al., 2011), cancer-stem cell markers (CD44, KRT5, RPSA, ALDH1A1I) (Chan et al., 2010), a set of markers known to be associated with EMT (epithelial-mesenchymal; ZEB1, ZEB2, VIM, SNAIL, TWIST1, FOXC2, CDH2), claudin-low markers (CLDN3, CLDN7, CLDN4, CDH1, VIM, SNAI2, TWIST1, ZEB1, ZEB2), and CIT (Cartes d'Identité des Tumeurs) gene sets (Biton et al., 2014). CIT sets included tumor cell component 9; stromal components 3, 8, and 12; and components 5 and 14, which could not be attributed to either tumor or stromal cells. The basal, luminal, p53-like, and claudin-low markers were adapted from (Dadhania et al., 2016), and the squamous, neuroendocrine, and EMT markers were manually chosen based on prior knowledge and literatures. To highlight a differential activity of each signature the raw gene expression signature scores were rank-normalized in FIG. 4C. The CIS signature score was defined as a mean difference of $\log_2$(RSEM) between up-regulated and down-regulated genes (Dyrskjot et al., 2004).

miRNAs and RPPAs that were Differentially Abundant Across mRNA Subtypes

The 1212 miRNA mature strands were reduced to 303 expressed strands by requiring a mean RPM of at least 10 across n=405 tumor samples. A SAM (samr v2.0) multiclass analysis was run using 1000 permutations, no array centering, a Wilcoxon test statistic, and an FDR output threshold of 0.05. The same settings were used for RPPA normalized abundance data for 195 antibodies and 344 primary tumors.

Detecting Somatic Gene Fusions

A modified version of VirusSeq (Chen et al., 2013) that implements a greedy algorithm with a robust statistical model was used in gene fusion discovery for RNA-Seq data. Specifically, MOSAIK aligner (Lee et al., 2014) was used to align paired-end reads to human genome reference (hg19). A given paired-end read alignment was then quantified in terms of the genomic location (L) of the aligned read pair, the distance (D) between the aligned read pair of the fragment (insert), and the orientation (O) of the read pair. The specific pattern in (L, D, O) space was used as a constraint to define the discordant read pair. For example, a discordant read pair may have an exceptionally long D spanning a region in the reference genome. All discordant reads were then annotated using the genes defined in UCSC refFlat file, and clustered into the ones that support the same fusion event (e.g., FGFR3-TACC3). Finally, each fusion candidate was defined and selected as the discordant read clusters in which a statistical model-based algorithm with greedy strategy was implemented to accurately detect the boundaries of discordant read clusters and in silico fusion junctions. Here, in silico fusion junction is the nucleotide-level genomic coordinate on either side of the gene fusion and is not necessary to be at the ends of known exons. Specifically, the boundary for each discordant read cluster of candidate fusion was estimated on the basis of discordant read mapping locations and orientations with fragment length distribution (e.g., within mean plus three SDs, $\mu+3*\sigma$) as a constraint of cluster size. The cluster size of discordant reads was measured by using reads' genomic location excluding introns if mapped reads are located across adjacent exons in a candidate fusion gene. Finally, to help PCR primer design, which facilitates rapid PCR validations, an in silico sequence was generated using the consensus of reads within discordant read clusters for each fusion candidate.

Bladder Cancer Cell Lines

Thirty human bladder cancer cell lines were obtained from the MD Anderson (MDA) Bladder SPORE Tissue Bank. Cell line identities were validated by the MDA Characterized Cell Line Core, using DNA fingerprinting with AmpFlSTR Identifier Amplification (Applied Biosystems, Foster City, Calif.). Cell lines were cultured in MEM supplemented with 10% fetal bovine serum, vitamins, sodium pyruvate, L-glutamine, penicillin, streptomycin, and nonessential amino acids at 37° C. in 5% CO2 incubator. Total RNA was isolated using a mirVana miRNA isolation kit (ThermoFisher Scientific, Waltham Mass.). RNA-Seq data was generated with a TruSeq Stranded Total RNA Library Prep Kit, and 76-bp PE reads on an Illumina HiSeq 2500.

Integrative Pathway Analysis

Somatic mutations and copy number changes were evaluated at the gene level, within the context of well-studied signaling pathways. Pathway alteration frequencies were based on the following genes:
- TP53/Cell Cycle pathway: ATM, TP53, MDM2, CDKN2A, RB1, CCND1, CDKN1A, PTEN, CCNE1, FBXW7, CDKN1B, CCND1/2/3, and CDK4/6
- RTK/RAS/PI3K pathway: PIK3CA, FGFR1/3, ERBB2/3, RAF1, PTEN, TSC1/2, EGFR, AKT1/2, NF1, RAC1, H/N/KRAS, JAK1/2, and BRAF
- Histone modification pathway: EP300, CREBBP, KMT2C/D, KDM6A, BAP1, ASXL1/2 and SETD2
- SWI/SNF pathway: ARID1A, ARID1B and ARID2
- DNA Damage pathway: ERCC2, BRIP1, ATM, BRCA1/2, RAD21/50 and CHEK1
- Cohesin complex pathway: STAG1/2, RAD21 and SMC1A/3 (Losada, 2014)
- Oxidative stress pathway: NFE2L2, KEAP1, CUL3 and TXNIP
- Alternative splicing pathway: RMB10, SF3B1, U2AF1 and CDK12.

Oncogenic relevance was assessed using OncoKB, a knowledgebase for the oncogenic effects of cancer genes that is manually curated by researchers and physicians at Memorial Sloan Kettering (Chakravarty et al., 2017). More precisely, a mutation is counted and included in the diagrams if (1) it has been reported 4 or more times in COSMIC (Forbes et al., 2011), or (2) it has been labeled as oncogenic, or likely oncogenic, in OncoKB.

Amplifications and deep deletions are based on GISTIC calls and indicate somatic alterations in more than half of the baseline gene copies. They were counted and included in the diagrams only if they are labeled as oncogenic, or likely oncogenic, in OncoKB. The actual list of oncogenic and likely oncogenic alterations is regularly updated based on the literature; the most recent version can be retrieved online from the OncoKB public website (www.oncokb.org) or visualized when viewing the data in the cBioPortal (www.cbioportal.org). For known oncogenes, only genetic alterations inferred to be activating were considered; for genes with tumor suppressive roles, only alterations inferred to be inactivating were considered.

Non-Coding RNA (lncRNA and miRNA) Sequencing and Analysis

Mapping RNA-Seq Reads for lncRNAs

RNA sequence reads were aligned to the human reference genome (hg38) and transcriptome (Ensembl v82, September 2015) using STAR 2.4.2a (Dobin et al., 2013). STAR was run with the following parameters: minimum/maximum intron sizes were set to 30 and 500,000, respectively; noncanonical, unannotated junctions were removed; maximum tolerated mismatches was set to 10; and the outSAMstrandField intron motif option was enabled. The Cuffquant command included with Cufflinks 2.2.1 (Trapnell et al., 2013) was used to quantify the read abundances per sample, with fragment bias correction and multiread correction enabled, and all other options set to default. To calculate normalized abundance as fragments per kilobase of exon per million fragments mapped (FPKM), the cuffnorm command was used with default parameters. From the FPKM matrix for the 80 tumor samples, 8167 genes were extracted with "lincRNA" and "processed_transcript" Ensembl biotypes.

miRNA Sequencing miRNA sequencing (miRNA-seq) data was generated from messenger RNA-depleted RNA (Chu et al., 2016). Briefly, reads were aligned to the GRCh37/hg19 reference human genome, assigned read count abundances to miRBase v16 stem-loops and 5p and 3p mature strands, and assigned miRBase v20 mature strand names to MIMAT accession IDs. Note that while only reads were used with exact-match alignments in calculating miRNA abundances, BAM files available from the Genomics Data Commons (https://gdc.cancer.gov/) include all sequence reads.

Unsupervised Clustering for lncRNAs, miRNAs lncRNAs were extracted that were robustly expressed (mean FPKM≥1) and highly variable across the n=80 tumor cohort (≥95th FPKM variance percentile) from the matrix of 8167 lncRNAs (above), and identified groups of samples with similar abundance profiles by unsupervised consensus clustering with ConsensusClusterPlus (CCP) 1.20.0 (Wilkerson and Hayes, 2010). Calculations were performed using Spearman correlations, partitioning around medoids (PAM) and 10,000 iterations. From solutions with 2, 3, 4 and 5 clusters we selected a four-cluster solution after assessing consensus membership heatmaps and dendrograms, CCP clustering metrics, Kaplan-Meier (KM) plots, and clustering results from other platforms. To visualize typical vs. atypical cluster members, a profile of silhouette widths ($W_{cm}$) was calculated from the consensus membership matrix. To generate an abundance heatmap lncRNAs were identified that had a mean FPKM≥5 and a SAM multiclass (samr 2.0) (Li and Tibshirani, 2013) q≤0.01 across the unsupervised clusters (see differential abundance, below), transformed each row of the matrix by $\log_{10}$(FPKM+1), then used the pheatmap R package (v1.0.2) to scale and cluster only the rows, using a Pearson distance metric and Ward clustering.

For miRNA mature strand data we used a similar approach. The input was a reads-per-million (RPM) data matrix for the 303 (25% of 1212) most-variant 5p or 3p mature strands, which we transformed by applying $\log_{10}$(RPM+1), then median-centering each miRNA's record. Using Pearson distances, PAM, and 5000 iterations with a 0.85 random fraction of miRNAs in each iteration, we assessed solutions with between two and eight clusters. After assessing information as for lncRNAs, we focused on a four-cluster solution. As for lncRNAs, to generate a clustering heatmap miRNAs were first identified that were differentially abundant between the unsupervised miRNA clusters using a SAM multiclass analysis (samr 2.0) (Li and Tibshirani, 2013) in R, with a read-count input matrix and a FDR threshold of 0.05. miRNAs were included that had the largest SAM scores and median abundances >25 RPM. The RPM filtering acknowledged that miRNAs that are more abundant are more likely to be influential (Mullokandov et al., 2012; Thomson and Dinger, 2016). Each row of the matrix was transformed by $\log_{10}$(RPM+1), then used the pheatmap R package (v0.7.7 or v1.0.2) to scale and cluster only the rows.

Carcinoma in situ (CIS) Signature Genes

RSEM gene-level data and the pheatmap R package was used with row scaling to generate heatmaps of normalized expression for 32 'up' and 36 'down' carcinoma in situ (CIS) signature gene sets (Dyrskjot et al., 2004). 'Up' genes were (genes are given as in the RSEM file: HGNC symbol|Entrez gene ID): AKR1B10|57016, CALD1|800, CDH11|1009, CLIC4|25932, COL15A1|1306, COL3A1|1281, CXCR4|7852, DCN|1634, DPYSL2|1808, EFEMP1|2202, FLNA|2316, HLA-DQA1|3117, HLA-DQB1|3119, HOXA9|3205, ITM2A|9452, KPNA2|3838, KYNU|8942, LHFP|10186, LUM|4060, LYZ|4069, MAN1C1|57134, MSN|4478, NR3C1|2908, PDGFC|56034, PRG1|23574, RARRES1|5918, S100A8|6279, SGCE|8910, SPARC|6678, TOP2A|7153, TUBB|203068, and UAP1|6675. 'Down' genes were: ACSBG1|23205, ANXA10|11199, BBC3|27113, BCAM|4059, BMP7|655, BST2|684, CA12|771, CLCA4|22802, CRTAC1|55118, CTSE|1510, CYP2J2|1573, EEF1A2|1917, ENTPD3|956, FABP4|2167, FGFR3|2261, GRB7|2886, HBG1|3047, HOXA1|3198, HOXB2|3212, INA|9118, ITGB4|3691, IVL|3713, KCNQ1|3784, LAD1|3898, LAMB3|3914, LTBP3|4054, MAPRE3|22924, MST1R|4486, PADI3|51702, PLA2G2A|5320, SOX15|6665, TMPRSS4|56649, TNNI2|7136, TRIM29|23650, UPK2|7379, UPK3B|80761.

To generate compact 'collapsed' covariate expression tracks for the 'up' and 'down' CIS signature gene sets, Bonferroni-corrected Kruskal-Wallis p values were calculated for RSEM gene expression across lncRNA, miRNA and regulon status clusters. For each of the three clustering solutions, for the two gene sets, these p values were used to select a subset of strongly differentially expressed genes. A profile of the median RSEM expression for each gene subset was calculated, across the cluster-ordered cases, and used pheatmap to generate a row-scaled normalized expression track for the median profile. P value-selected gene sets were as follows. For the lncRNA clusters, we used the 21 of 32 'up' genes and 18 of 36 'down' genes that passed a threshold of a Bonferroni-corrected Kruskal $p \leq 1E-15$. For the miRNA clusters, the 20 'up' genes were used that passed a Kruskal $p \leq 1E-15$ threshold, and the 11 'down' genes that passed Kruskal $p \leq 1E-10$.

Covariates Associated with Unsupervised Clusters

Unsupervised clusters were compared to clinical and molecular covariates by calculating contingency table association p values using R, with a Chi-square or Fisher exact test for categorical data, and a Kruskal-Wallis test for real-valued data.

Pathology Review of Adjacent Tissue Normal Samples

After pathology review, four of the 19 adjacent tissue cases were removed from the expression data for lncRNAs and miRNAs: BT-A20U, BT-A2LB, GD-A2C5, and GD-A3OP.

EMT Scores from RNA-seq Data

The samples were scored based on expression of EMT signature genes (Mak et al., 2016). Briefly, the EMT score for each sample is calculated as the mean expression of epithelial markers subtracted from the mean expression of mesenchymal markers. Higher EMT scores correlate with a more mesenchymal expression pattern.

Regulon Analysis

Candidate Regulators

The relative activity of 23 candidate 'regulator' genes were inferred that had previously been reported as associated with bladder cancer: the steroid hormone receptors ESR1/2, AR and PGR; the nuclear receptors PPARG, three RARs (A/B/G), and three RXRs (A/B/G); the receptor tyrosine kinases ERBB2/3 and FGFR1/3; and the transcription factors FOXA1, FOXM1, GATA3/6, HIF1A, KLF4 and STAT3 and TP63 (Breyer et al., 2016; Choi et al., 2014a; Dadhania et al., 2016; DeGraff et al., 2013; Eriksson et al., 2015; Godoy et al., 2016; Jones et al., 2016; Kardos et al., 2016; Lim et al., 2016). By 'regulator' is meant a gene whose product induces and/or represses a target gene set, which we call a 'regulon' (Castro et al., 2016a).

Reconstruction of RTN Regulons

The BLCA regulator-target associations are inferred using the R package RTN (Castro et al., 2016b), which is extensively described elsewhere for reconstructing regulatory units for transcriptions factors and upstream regulators (Campbell et al., 2016; Castro et al., 2016a; Fletcher et al., 2013). Briefly, gene expression matrices for a set of samples are used to estimate the associations between a regulator and all potential targets. Two metrics to identify potential regulator-target associations were used: Mutual Information (MI) and Spearman's correlation. MI-based inference indicates whether a given regulator is informative of the status of a given target gene, while Spearman's correlation indicates the direction of the inferred associations. Associations with less than a minimum MI threshold are eliminated by permutation analysis (BH-adjusted p value <1e-5), and unstable interactions are additionally removed by bootstrapping (n=1000 resamples, consensus bootstrap >95%), to create a regulatory network. RTN regulons are additionally evaluated by the Data Processing Inequality (DPI) algorithm with tolerance=0.01 (Margolin et al., 2006). Note that MI-based inference computes regulons irrespective of positive or negative associations, and Spearman's correlation is then used only to assign direction to the predicted regulons. As an optional step, the stability of the main observations were assessed by filtering regulons using the Bioconductor package genefilter v1.56.0 (Gentleman et al., 2016). Feature selection was performed using the coxfilter function on the Sjodahl 2012 cohort (see below) and used to filter genes in the TCGA cohort. Since overfiltering discards both false and true null hypotheses, the fraction of filtered genes and the total number of observations (i.e. overall results should be stable irrespective of the fractions removed) were also looked at.

Regulon Activity Estimated by Two-Tailed GSEA

The two-tailed gene set enrichment analysis (GSEA) is described elsewhere (Castro et al., 2016a). Briefly, this approach assesses the skewness of two distributions of a selected gene set in a list of genes that is ranked by a particular phenotype, as follows. The gene set represented for a given regulon is split into positive (A) and negative (B) targets using Spearman's correlation, and the phenotype corresponds to the gene-wise differential expression observed when comparing a given tumor with the average expression of all tumors in the cohort. The distribution of A and B is then tested by the GSEA statistics in the ranked phenotype, producing independent per-sample enrichment scores (ES), and then differential enrichment scores (dES), which are obtained by subtracting the enrichment score for positive targets (ESA) from that obtained for negative targets (ESB). A large positive dES indicates an induced regulon status while a large negative dES indicates the opposite case. Differential enrichment score values that are near zero (with ESA and ESB distributions skewed to the same side) are assigned as inconclusive. The two-tailed GSEA was performed in R (R-Core-Team, 2012) using the function tni.gsea2 in the RTN package (Castro et al., 2016a).

Regulon Activity as Readout of Clinical and Molecular Variables

For each case in a cohort an enrichment score (dES) was assigned using the two-tailed GSEA approach described above. Then, ordering the cohort's cases by dES, one can assess how a given regulon is associated with clinical and molecular variables. The cohort cases are also stratified by positive vs. negative dES values, and the stratified cases are used to plot Kaplan-Meier survival curves, with p values calculated using log-rank statistics (Castro et al., 2016a). The survival analysis is performed in R using the functions coxph, survfit and survdiff.

Independent BLCA Cohort and Transcriptome Data

Data used to assess survival statistics in BLCA from an independent cohort are obtained from a large-scale microarray study for n=308 BLCA cases (Sjodahl et al., 2012), which were downloaded from GEO (accession number GSE32894). The gene sets in the regulons were used that can be inferred from TCGA data to assess the Sjodahl cohort. For each regulon's gene set, the regulon activity is initially estimated for all tumors of the Sjodahl cohort with the two-tailed GSEA approach, and then the regulon activity is used as readout of clinical and molecular variables, as described above.

Microbial Analysis

Microbial Screening and Genomic Integration (British Columbia Cancer Agency)

Microbe analysis consists of two stages: read screening and genomic integration. In the first stage we classify read sequences using a pipeline based on BBT (Release 1.2.10), a fast Bloom filter-based method (Chu et al., 2014). For 48-bp PE RNAseq data, we processed data for 408 tumor samples and 19 tissue normal samples; for 76-bp PE WES data we processed 412 tumor samples and 429 blood or tissue normals; and for 51-bp PE WGS data (high and low pass) we processed 136 tumor samples and 145 blood or tissue normal samples. We ran BBT with a sliding window size (i.e. k-mer length) of 25 bp and a false discovery rate of 0.02. We generated 43 filters from 'complete' NCBI genome reference sequences for microbial species that included bacteria, viruses, fungi and protozoa. In a single-pass scan, BBT categorizes each read as matching a filter for human or a single specific microbe, as matching two or more species (multi-match), or as matching none of the filters (no-match). For each filter, we calculated a reads-per-million (RPM) abundance metric (below) and applied a threshold of 0.2 RPM (Cancer Genome Atlas Research Network, 2014b) to identify samples as being positive for specific microbes. For HPV-positive samples, we identified HPV strains with a second BBT run that uses strain-specific filters.

$$RPM = \left(\frac{\text{reads mapped to the microbe}}{\text{reads mapped to human}} * 10^6\right)$$

In the second stage of analysis we assessed whether viruses had integrated into the human genome, working only with data sets for which BBT results for HPV, HHV4 or HHV5 were above or close to the 0.2 RPM screening threshold, and with BK-Polyomavirus in DK-A3IT. We performed de novo assembly (Robertson et al., 2010) with ABySS v1.3.4 on each library, using every fourth k-mer value from k=24 to 48 for RNA-seq data, every fourth k-mer from k=52 to 96 for WES data, and k=24, 36 and 48 for WGS data. For HPV analysis we assembled only the reads that BBT had classified as human, HPV match, multi-match, and no-match. We used a similar approach for the HHV4 and HHV5 assemblies. For each library, we merged the contig sets for all k-mer assemblies with Trans-ABySS v1.4.8 to generate a working contig set. We reran BBT on each of these contig sets, applying only human and either HPV or herpes virus filters, identifying the contigs that matched to only a viral filter, or to both the human filter and a viral filter. For HPV-only contigs we confirmed the strain by using BLAT v34 to align each contig to 48 HPV reference sequences. For chimeric multi-match contigs we confirmed the HPV strain, and, for HPV, HHV4 and HHV5, identified integration breakpoints by using BLAT v34 (Kent, 2002) to align each contig to the human GRCh37/hg19 reference sequence, and to 110 HHV4, 22 HHV5, or 48 HPV reference sequences. We retained contig alignments in which the aligned human and viral sequences summed to at least 90% of the contig length, and the human and viral aligned overlapped by less than 50%. We annotated human breakpoint coordinates against RefSeq and UCSC gene annotations (downloaded from the UCSC genome browser on 30 Jun. 2013) (Kuhn et al., 2013). Breakpoints that had supporting evidence consisting of at least 3 spanning mate-pair reads or 5 flanking mate-pair reads were considered potential integration sites.

Microbial Detection from RNAseq Data by PathSeq (the Broad Institute)

PathSeq Microbial Detection

The PathSeq algorithm (Kostic et al., 2011) (https://github.com/ChandraPedamallu/PathSeq) was used to perform computational subtraction of human reads, followed by alignment of residual reads to a combined database of human reference genomes and microbial reference genomes (which includes but is not limited to Human Papillomaviruses (HPV's), BK Polyomaviruses (BK), Human Herpesviruses (HHV's)), resulting in the identification of reads mapping to HPV, BK, and HHV genomes in RNA sequencing data.

In brief, for PathSeq human reads were subtracted by first mapping reads to a database of human genomes using BWA (version 0.6.1) (Li and Durbin, 2009), Megablast (version 2.2.23), and Blastn (version 2.2.23) (Altschul et al., 1997). Only sequences with perfect or near perfect matches to the human genome were removed in the subtraction process. To identify HPV/HBK/HHV reads, the resultant non-human reads were aligned with Megablast to a database of microbial genomes that includes multiple HPV, BK and HHV reference genomes. HPV, BK and HHV reference genomes were obtained from the NCBI nucleotide database (downloaded in June 2012).

Subjects were classified as HPV by RNA sequencing if at least 1 HPV read in 1 million human reads were present; otherwise, subjects were classified as HPV-negative. In addition, subjects were classified as BK-positive by RNA sequencing if at least 1 BK reads in 1 million human reads were present; otherwise, subjects were classified as BK-negative. Similar thresholds are used for Human Herpesviruses.

Identification of Human Papillomavirus and BK Polyomavirus Integration Events

An HPV-positive sample was considered integration positive if there were at least 5 spanning read pairs or 10 flanking reads supporting an integration event. In case of HPV-positive, flanking read pairs were defined as having one end of the paired-end read mapped to the HPV genome and its mate pair mapped to the human genome. Spanning reads were defined as having one end of the paired end read spanning the integration junction and its mate pair mapped to either the human or HPV genome. Once HPV reads were obtained, we extracted all pair mates and used Tophat-2.0.84 (Trapnell et al., 2009) with the fusion option enabled to map these paired end reads to a combined database containing the human genome and an HPV genome. Next, spanning reads and flanking reads are identified from the aligned BAM file.

Human genes involved in the integration are identified using the breakpoint coordinates against RefSeq and UCSC gene annotations (last modified on 30 Jun. 2013) from the UCSC genome browser (Kuhn et al., 2013). A similar approach is followed for identification of BK Polyomavirus integration from RNAseq data.

RPPA Protein Expression Profiling
RPPA Experiments and Data Processing

RPPA lysis buffer was used to extract protein from human tumors and RPPA was performed as described previously (Hennessy et al., 2007; Hu et al., 2007; Liang et al., 2007; Tibes et al., 2006). Frozen tumors were lysed by Precellys homogenization, adjusted to 1 µg/µL concentration as assessed by bicinchoninic acid assay (BCA), boiled with 1% SDS, and manually serial diluted in two-fold of 5 dilutions with lysis buffer. Details on slide preparation, analysis and quantification of spot intensities to generate spot signal intensities (level 1 data), SuperCurve-based QC metric to filter slides with highest QC for each antibody (level 2 data) (Hu et al., 2007), loading control across antibodies for protein measurements (level 3 data) (Gonzalez-Angulo et al., 2011; Hu et al., 2007), and final selection of antibodies for specificity and sensitivity (Hennessy et al., 2010) are given in (Cancer Genome Atlas Research Network, 2014a). In total, 215 antibodies and 343 muscle invasive urothelial/bladder carcinoma (BLCA) samples were used in the analysis, including 109 papillary and 224 non-papillary samples. Forty-two of these 343 samples were squamous cell carcinomas that were mostly non-papillary (40 non-papillary and 2 papillary) samples. RPPA raw data (level 1), SuperCurve nonparametric model fitting on a single array (level 2), and loading corrected data (level 3) (Ju et al., 2015; Zhang et al., 2009) were deposited at the DCC.

Data Normalization

Median centering was performed across all the antibodies for each sample to correct for sample loading differences. These differences could arise because protein concentrations are not uniformly distributed per unit volume of lysate due to several factors such as differences in protein concentrations of large and small cells, differences in the amount of proteins per cell, or heterogeneity of the cells comprising the samples. The expression levels across many different proteins in a sample could be used to estimate differences in the total amount of protein in that sample vs. other samples. Further, subtracting the median protein expression level forces the median value to become zero, allowing for a comparison of protein expressions across samples. These median-centered data were used for the analysis of BLCA samples.

Surprisingly, processing similar sets of samples on different slides of the same antibody may result in datasets that have very different means and variances. Neely et al. (Neeley et al., 2009) processed clinically similar ALL samples in two batches and observed differences in their protein data distributions. There were additive and multiplicative effects in the data that could not be accounted by biological or sample loading differences. We observed similar effects when we compared the two batches of bladder tumor protein expression data. A new algorithm, replicates-based normalization (RBN), was therefore developed using replicate samples run across multiple batches to adjust the data for batch effects. The underlying hypothesis is that any observed variation between replicates in different batches is primarily due to linear batch effects plus a component due to random noise. Given a sufficiently large number of replicates, the random noise is expected to cancel out (mean=zero by definition). Remaining differences are treated as systematic batch effects. We can compute those effects for each antibody and subtract them out. Many samples were run in both batches. One batch was arbitrarily designated the "anchor" batch and was to remain unchanged. We then computed the means and standard deviations of the common samples in the anchor batch, as well as the other batch. The difference between the means of each antibody in the two batches and the ratio of the standard deviations provided an estimate of the systematic effects between the batches for that antibody (both location-wise and scale-wise). To cancel out those systematic differences, each data point in the non-anchor batch was adjusted by subtracting the difference in means, then multiplying by the inverse ratio of the standard deviations. The normalization procedure significantly reduced technical effects, thereby allowing us to merge the datasets from different batches.

RPPA Clusters and Pathway Scores

BLCA samples (n=343), including 109 papillary and 224 non-papillary samples, were clustered based on 208 antibodies by consensus clustering using the partitioning around medoids algorithm and a Euclidean dissimilarity measure (Wilkerson and Hayes, 2010). The role of cell signaling networks in urothelial carcinomas was illustrated by computing twelve pathway scores similar to those described previously (Akbani et al., 2014).

Kaplan-Meier Curves for Overall Survival

P values are based on the G-rho family of Harrington and Fleming (Xu and Harrington, 2001) tests to evaluate the difference between two or more survival curves.

Carcinoma-in-situ (CIS) Gene Sets

Carcinoma-in-situ (CIS) gene sets were from (Dyrskjot et al., 2004).

Univariate and Multivariate Survival Analysis
Data Preparation and Univariate Survival Analysis As described, we recoded values of certain covariates (columns E vs. F), then excluded from the analysis covariates that had many missing values (column C), including CLIN_ajcc_nodes_pathologic_pn and CLIN_ajcc_tumor_pathologic_pt, or that were highly unbalanced between two categories (i.e. one category contained <5% of the cases) (column H). We removed PATH.NOS and PATH_squamous covariates, retaining PATH_Short.Path, because the information in the first two was close to what the latter offered. After excluding all copy number covariates for technical reasons, we had retained 101 covariates. For univariate calculations we used the survdiff function from the R survival v2.40-1 package, and adjusted the log-rank p values with a Benjamini-Hochberg (BH) correction. The univariate analysis identified 18 covariates that were statistically associated with overall survival (BH-adjusted p value <0.05).

LASSO and Cox Regression Analysis

As input covariates we used 13 of the 18 that the univariate calculations returned as significant, rejecting five because they had relatively large numbers of missing values: CLIN_Node_positive_vs_negative (47 cases missing), CLIN_Combined_Tx_Node_positive (64), CLIN_ajcc_nodes_pathologic_pn (47), CLIN_T12_vs_T34 (39), CLIN_ajcc_tumor_pathologic_pt (43). We tested nine types of penalized estimation methods: lasso, adaptive lasso, fused lasso, elastic-net, adaptive elastic-net, SCAD, Snet, MCP, and Mnet assessing the performance of each approach with time-dependent ROC curves (tAUC) (Xiao et al., 2016). When no fitting strategy was significantly better, we choose to use LASSO to fit the final model.

We performed the multivariate Cox regression analysis in R (R Core Development Team, 2016), assuming additive effects. For MSig, mRNA, lncRNA and miRNA subtypes we set, as a reference, a subtype with the best survival (Table S2.29). All LASSO models were fit using the glmnet v2.0-5 and hdnom v4.6 packages (cv.glmnet and hdcox.lasso functions) (Friedman et al., 2010; Xiao et al., 2016). For comparison, we also used a stepwise selection algorithm for model selection (stepAIC function in the R MASS package); stepwise model selection, while widely used, has poor predictive performance compared to modern approaches like LASSO penalized regression (Hutmacher and Kowalski, 2015; Walter and Tiemeier, 2009). We selected the LASSO-penalized Cox model that resulted in minimal prediction error, using Leave-One-Out Cross-Validation (LOOCV), and assessed the stability of the results by bootstrap analysis (n=1000 times).

We determined risk groups from the LASSO model, as follows. The set of regression coefficients is equivalent to a predictive model that is a sum of terms, each of which is a covariate's coefficient multiplied by the value of that covariate for a case. The cohort is split into training and validation sets in the k-fold cross-validation. The final model is used to estimate a survival probability for each case, at a chosen end-point (e.g. 48 months). The risk groups are then determined from the predicted probabilities; FIG. 12C shows low-, medium- and high-risk tertiles. This process, called model calibration, is used to assess how far the model predictions are from actual survival outcomes. For the work reported here, the predictions were made on the samples that were used to build the model; when new cases that have data for the model's covariates are available, predictions can be made on them using the same approach.

Quantification and Statistical Analysis

Quantitative and statistical methods are noted above according to their respective technologies and analytic approaches.

Data and Software Availability

The data and analysis results are available and can be explored through the Genomic Data Commons (https://gdc.cancer.gov), the Broad Institute GDAC FireBrowse portal (http://gdac.broadinstitute.org), the Memorial Sloan Kettering Cancer Center cBioPortal (http://www.cbioportal.org), and the TCGA publication page (https://tcga-data.nci.nih.gov/docs/publications/). RNA-Seq data for 30 human bladder cancer cell lines are available at the Gene Expression Omnibus (GEO).

Methods for Example 14

TCGA Expression Subtype Classifier

We developed a classifier for the TCGA expression subtypes for use on both RNA-seq and microarray expression data, using non-negative matrix factorization (NMF). There were four steps in this procedure: (i) determine the sample relevance matrix H*TCGA quantifying an association or a "degree of participation" of individual samples to the TCGA subtypes; (ii) determine the gene relevance matrix W*TCGA strictly conditional on H*TCGA in term of expression fold changes, quantifying an association of individual genes to the TCGA subtypes; (iii) identify differentially over-expressed subtype markers (n=354) for the classifier using W*TCGA and mean differences of fold changes; and (iv) generate an NMF-based subtype classification scheme explicitly modeling the gene expression vector of a new sample xnew conditioned on W*TCGA to best approximate xnew~W*TCGA hnew for the selected 354 markers, determining an association of the new sample to the TCGA subtypes.

Data Acquisition

Both expression data and relevant clinical data, including the TCGA2014 and Lund classification, were downloaded from http://research-pub.gene.com/IMvigor210CoreBiologies/. The expression data were log 2-transformed and median-centered, and digested by the classifier.

REFERENCES

Aine, M., Eriksson, P., Liedberg, F., Sjodahl, G., and Hoglund, M. (2015). Biological determinants of bladder cancer gene expression subtypes. Sci Rep 5, 10957.

Akbani, R., Ng, P. K., Werner, H. M., Shahmoradgoli, M., Zhang, F., Ju, Z., Liu, W., Yang, J. Y., Yoshihara, K., Li, J., et al. (2014). A pan-cancer proteomic perspective on The Cancer Genome Atlas. Nat Commun 5, 3887.

Al-Ahmadie, H. A., Iyer, G., Lee, B. H., Scott, S. N., Mehra, R., Bagrodia, A., Jordan, E. J., Gao, S. P., Ramirez, R., Cha, E. K., et al. (2016). Frequent somatic CDH1 loss-of-function mutations in plasmacytoid variant bladder cancer. Nat Genet 48, 356-358.

Alexandrov, L. B., Nik-Zainal, S., Wedge, D. C., Aparicio, S. A., Behjati, S., Biankin, A. V., Bignell, G. R., Bolli, N., Borg, A., Borresen-Dale, A. L., et al. (2013). Signatures of mutational processes in human cancer. Nature 500, 415-421.

Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic Acids Res 25, 3389-3402.

Balbas-Martinez, C., Sagrera, A., Carrillo-de-Santa-Pau, E., Earl, J., Marquez, M., Vazquez, M., Lapi, E., Castro-Giner, F., Beltran, S., Bayes, M., et al. (2013). Recurrent inactivation of STAG2 in bladder cancer is not associated with aneuploidy. Nat Genet.

Bibikova, M., Barnes, B., Tsan, C., Ho, V., Klotzle, B., Le, J. M., Delano, D., Zhang, L., Schroth, G. P., Gunderson, K. L., et al. (2011). High density DNA methylation array with single CpG site resolution. Genomics 98, 288-295.

Bibikova, M., Le, J., Barnes, B., Saedinia-Melnyk, S., Zhou, L., Shen, R., and Gunderson, K. L. (2009). Genome-wide DNA methylation profiling using Infinium® assay. Epigenomics 1, 177-200.

Biton, A., Bernard-Pierrot, I., Lou, Y., Krucker, C., Chapeaublanc, E., Rubio-Perez, C., Lopez-Bigas, N., Kamoun, A., Neuzillet, Y., Gestraud, P., et al. (2014). Independent component analysis uncovers the landscape of the bladder tumor transcriptome and reveals insights into luminal and basal subtypes. Cell Rep 9, 1235-1245.

Breyer, J., Wirtz, R. M., Laible, M., Schlombs, K., Erben, P., Kriegmair, M. C., Stoehr, R., Eidt, S., Denzinger, S., Burger, M., et al. (2016). ESR1, ERBB2, and Ki67 mRNA expression predicts stage and grade of non-muscle-invasive bladder carcinoma (NMIBC). Virchows Arch 469, 547-552.

Campan, M., Weisenberger, D. J., Trinh, B., and Laird, P. W. (2009). MethyLight. Methods Mol Biol 507, 325-337.

Campbell, T. M., Castro, M. A., de Santiago, I., Fletcher, M. N., Halim, S., Prathalingam, R., Ponder, B. A., and Meyer, K. B. (2016). FGFR2 risk SNPs confer breast cancer risk by augmenting oestrogen responsiveness. Carcinogenesis 37, 741-750.

Cancer Genome Atlas Network (2012). Comprehensive molecular portraits of human breast tumours. Nature 490, 61-70.

Cancer Genome Atlas Research, N. (2012). Comprehensive genomic characterization of squamous cell lung cancers. Nature 489, 519-525.

Cancer Genome Atlas Research Network (2014a). Comprehensive molecular characterization of urothelial bladder carcinoma. Nature 507, 315-322.

Cancer Genome Atlas Research Network (2014b). Integrated genomic characterization of papillary thyroid carcinoma. Cell 159, 676-690.

Cancer Genome Atlas Research Network (2017). Integrated genomic and molecular characterization of cervical cancer. Nature.

Cappellen, D., De Oliveira, C., Ricol, D., de Medina, S., Bourdin, J., Sastre-Garau, X., Chopin, D., Thiery, J. P., and Radvanyi, F. (1999). Frequent activating mutations of FGFR3 in human bladder and cervix carcinomas. Nat Genet 23, 18-20.

Carter, S. L., Cibulskis, K., Helman, E., McKenna, A., Shen, H., Zack, T., Laird, P. W., Onofrio, R. C., Winckler, W., Weir, B. A., et al. (2012a). Absolute quantification of somatic DNA alterations in human cancer. Nat Biotechnol 30, 413-421.

Carter, S. L., Cibulskis, K., Helman, E., McKenna, A., Shen, H., Zack, T., Laird, P. W., Onofrio, R. C., Winckler, W., Weir, B. A., et al. (2012b). Absolute quantification of somatic DNA alterations in human cancer. Nat Biotechnol 30, 413-421.

Castro, M. A., de Santiago, I., Campbell, T. M., Vaughn, C., Hickey, T. E., Ross, E., Tilley, W. D., Markowetz, F., Ponder, B. A., and Meyer, K. B. (2016a). Regulators of genetic risk of breast cancer identified by integrative network analysis. Nat Genet 48, 12-21.

Castro, M. A., Wang, X., Fletcher, M. N., Meyer, K. B., and Markowetz, F. (2016b). RTN: Reconstruction of transcriptional networks and analysis of master regulators (R/Bioconductor package).

Chakravarty, D., Gao, J., Phillips, S., Kundra, R., Zhang, H., Wang, J., Rudolph, J. E., Yaeger, R., Soumerai, T., Nissan, M. H., et al. (2017). OncoKB: A Precision Oncology Knowledge Base. JCO Precision Oncology 1, 1-16.

Chan, K. S., Volkmer, J. P., and Weissman, I. (2010). Cancer stem cells in bladder cancer: a revisited and evolving concept. Curr Opin Urol 20, 393-397.

Chen, Y., Yao, H., Thompson, E. J., Tannir, N. M., Weinstein, J. N., and Su, X. (2013). VirusSeq: software to identify viruses and their integration sites using next-generation sequencing of human cancer tissue. Bioinformatics 29, 266-267.

Choi, W., Czerniak, B., Ochoa, A., Su, X., Siefker-Radtke, A., Dinney, C., and McConkey, D. J. (2014a). Intrinsic basal and luminal subtypes of muscle-invasive bladder cancer. Nat Rev Urol 11, 400-410.

Choi, W., Porten, S., Kim, S., Willis, D., Plimack, E. R., Hoffman-Censits, J., Roth, B., Cheng, T., Tran, M., Lee, I. L., et al. (2014b). Identification of distinct basal and luminal subtypes of muscle-invasive bladder cancer with different sensitivities to frontline chemotherapy. Cancer Cell 25, 152-165.

Chu, A., Robertson, G., Brooks, D., Mungall, A. J., Birol, I., Coope, R., Ma, Y., Jones, S., and Marra, M. A. (2016). Large-scale profiling of microRNAs for The Cancer Genome Atlas. Nucleic Acids Res 44, e3.

Chu, J., Sadeghi, S., Raymond, A., Jackman, S. D., Nip, K. M., Mar, R., Mohamadi, H., Butterfield, Y. S., Robertson, A. G., and Birol, I. (2014). BioBloom tools: fast, accurate and memory-efficient host species sequence screening using bloom filters. Bioinformatics 30, 3402-3404.

Cibulskis, K., Lawrence, M. S., Carter, S. L., Sivachenko, A., Jaffe, D., Sougnez, C., Gabriel, S., Meyerson, M., Lander, E. S., and Getz, G. (2013). Sensitive detection of somatic point mutations in impure and heterogeneous cancer samples. Nat Biotechnol 31, 213-219.

Cuzick, J., Swanson, G. P., Fisher, G., Brothman, A. R., Berney, D. M., Reid, J. E., Mesher, D., Speights, V. O., Stankiewicz, E., Foster, C. S., et al. (2011). Prognostic value of an RNA expression signature derived from cell cycle proliferation genes in patients with prostate cancer: a retrospective study. Lancet Oncol 12, 245-255.

Dadhania, V., Zhang, M., Zhang, L., Bondaruk, J., Majewski, T., Siefker-Radtke, A., Guo, C. C., Dinney, C., Cogdell, D. E., Zhang, S., et al. (2016). Meta-analysis of the luminal and basal subtypes of bladder cancer and the identification of signature immunohistochemical markers for clinical use. EBioMedicine 12, 105-117.

Damrauer, J. S., Hoadley, K. A., Chism, D. D., Fan, C., Tiganelli, C. J., Wobker, S. E., Yeh, J. J., Milowsky, M. I., Iyer, G., Parker, J. S., et al. (2014). Intrinsic subtypes of high-grade bladder cancer reflect the hallmarks of breast cancer biology. Proc Natl Acad Sci USA 111, 3110-3115.

DeGraff, D. J., Cates, J. M., Mauney, J. R., Clark, P. E., Matusik, R. J., and Adam, R. M. (2013). When urothelial differentiation pathways go wrong: implications for bladder cancer development and progression. Urol Oncol 31, 802-811.

Dennison, J. B., Shahmoradgoli, M., Liu, W., Ju, Z., Meric-Bernstam, F., Perou, C. M., Sahin, A. A., Welm, A., Oesterreich, S., Sikora, M. J., et al. (2016). High Intratumoral Stromal Content Defines Reactive Breast Cancer as a Low-risk Breast Cancer Subtype. Clin Cancer Res 22, 5068-5078.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Dyrskjot, L., Kruhoffer, M., Thykjaer, T., Marcussen, N., Jensen, J. L., Moller, K., and Orntoft, T. F. (2004). Gene expression in the urinary bladder: a common carcinoma in situ gene expression signature exists disregarding histopathological classification. Cancer Res 64, 4040-4048.

Eriksson, P., Aine, M., Veerla, S., Liedberg, F., Sjodahl, G., and Hoglund, M. (2015). Molecular subtypes of urothelial carcinoma are defined by specific gene regulatory systems. BMC Med Genomics 8, 25.

Fletcher, M. N., Castro, M. A., Wang, X., de Santiago, I., O'Reilly, M., Chin, S. F., Rueda, O. M., Caldas, C., Ponder, B. A., Markowetz, F., et al. (2013). Master regulators of FGFR2 signalling and breast cancer risk. Nat Commun 4, 2464.

Forbes, S. A., Bindal, N., Bamford, S., Cole, C., Kok, C. Y., Beare, D., Jia, M., Shepherd, R., Leung, K., Menzies, A., et al. (2011). COSMIC: mining complete cancer genomes in the Catalogue of Somatic Mutations in Cancer. Nucleic Acids Res 39, D945-950.

Friedman, J., Hastie, T., and Tibshirani, R. (2010). Regularization paths for generalized linear models via coordinate descent. J Stat Softw 33, 1-22.

Gentleman, R., Carey, V., Huber, W., and Hahne, F. (2016). genefilter: methods for filtering genes from high-throughput experiments (Bioconductor).

Getz, G., Hofling, H., Mesirov, J. P., Golub, T. R., Meyerson, M., Tibshirani, R., and Lander, E. S. (2007). Comment on "The consensus coding sequences of human breast and colorectal cancers". Science 317, 1500.

Godoy, G., Gakis, G., Smith, C. L., and Fahmy, O. (2016). Effects of androgen and estrogen receptor signaling pathways on bladder cancer initiation and progression. Bladder Cancer 2, 127-137.

Gonzalez-Angulo, A. M., Hennessy, B. T., Meric-Bernstam, F., Sahin, A., Liu, W., Ju, Z., Carey, M. S., Myhre, S., Speers, C., Deng, L., et al. (2011). Functional proteomics can define prognosis and predict pathologic complete response in patients with breast cancer. Clinical proteomics 8, 11.

Gui, Y., Guo, G., Huang, Y., Hu, X., Tang, A., Gao, S., Wu, R., Chen, C., Li, X., Zhou, L., et al. (2011). Frequent mutations of chromatin remodeling genes in transitional cell carcinoma of the bladder. Nat Genet 43, 875-878.

Hennessy, B. T., Lu, Y., Gonzalez-Angulo, A. M., Carey, M. S., Myhre, S., Ju, Z., Davies, M. A., Liu, W., Coombes, K., Meric-Bernstam, F., et al. (2010). A Technical Assessment of the Utility of Reverse Phase Protein Arrays for the Study of the Functional Proteome in Non-microdissected Human Breast Cancers. Clinical proteomics 6, 129-151.

Hennessy, B. T., Lu, Y. L., Poradosu, E., Yu, Q. H., Yu, S. X., Hall, H., Carey, M. S., Ravoori, M., Gonzalez-Angulo, A. M., Birch, R., et al. (2007). Pharmacodynamic markers of perifosine efficacy. Clin Cancer Res 13, 7421-7431.

Hoadley, K. A., Yau, C., Wolf, D. M., Cherniack, A. D., Tamborero, D., Ng, S., Leiserson, M. D., Niu, B., McLellan, M. D., Uzunangelov, V., et al. (2014). Multiplatform analysis of 12 cancer types reveals molecular classification within and across tissues of origin. Cell 158, 929-944.

Hu, J., He, X., Baggerly, K. A., Coombes, K. R., Hennessy, B. T. J., and Mills, G. B. (2007). Non-parametric quantification of protein lysate arrays. Bioinformatics 23, 1986-1994.

Hutmacher, M. M., and Kowalski, K. G. (2015). Covariate selection in pharmacometric analyses: a review of methods. Br J Clin Pharmacol 79, 132-147.

Jones, R. T., Felsenstein, K. M., and Theodorescu, D. (2016). Pharmacogenomics: biomarker-directed therapy for bladder cancer. Urol Clin North Am 43, 77-86.

Ju, Z., Liu, W., Roebuck, P. L., Siwak, D. R., Zhang, N., Lu, Y., Davies, M. A., Akbani, R., Weinstein, J. N., Mills, G. B., et al. (2015). Development of a robust classifier for quality control of reverse-phase protein arrays. Bioinformatics 31, 912-918.

Kardos, J., Chai, S., Mose, L. E., Selitsky, S. R., Krishnan, B., Saito, R., Iglesia, M. D., Milowsky, M. I., Parker, J. S., Kim, W. Y., et al. (2016). Claudin-low bladder tumors are immune infiltrated and actively immune suppressed. JCI Insight 1, e85902.

Karkera, J. D., Martinez Cardona, G., Bell, K., Gaffney, D., Portale, J. C., Santiago-Walker, A., Moy, C., King, P., Sharp, M., Bahleda, R., et al. (2017). Oncogenic Characterization and Pharmacologic Sensitivity of Activating Fibroblast Growth Factor Receptor (FGFR) Genetic Alterations to the Selective FGFR Inhibitor Erdafitinib. Mol Cancer Ther.

Kasar, S., Kim, J., Improgo, R., Tiao, G., Polak, P., Haradhvala, N., Lawrence, M. S., Kiezun, A., Fernandes, S. M., Bahl, S., et al. (2015). Whole-genome sequencing reveals activation-induced cytidine deaminase signatures during indolent chronic lymphocytic leukaemia evolution. Nat Commun 6, 8866.

Kent, W. J. (2002). BLAT—the BLAST-like alignment tool. Genome Res 12, 656-664.

Kim, J., Mouw, K. W., Polak, P., Braunstein, L. Z., Kamburov, A., Kwiatkowski, D. J., Rosenberg, J. E., Van Allen, E. M., D'Andrea, A., and Getz, G. (2016a). Somatic ERCC2 mutations are associated with a distinct genomic signature in urothelial tumors. Nat Genet 48, 600-606.

Kim, J., Mouw, K. W., Polak, P., Braunstein, L. Z., Kamburov, A., Tiao, G., Kwiatkowski, D. J., Rosenberg, J. E., Van Allen, E. M., D'Andrea, A. D., et al. (2016b). Somatic ERCC2 mutations are associated with a distinct genomic signature in urothelial tumors. Nat Genet 48, 600-606.

Knowles, M. A., and Hurst, C. D. (2015). Molecular biology of bladder cancer: new insights into pathogenesis and clinical diversity. Nat Rev Cancer 15, 25-41.

Korn, J. M., Kuruvilla, F. G., McCarroll, S. A., Wysoker, A., Nemesh, J., Cawley, S., Hubbell, E., Veitch, J., Collins, P. J., Darvishi, K., et al. (2008). Integrated genotype calling and association analysis of SNPs, common copy number polymorphisms and rare CNVs. Nat Genet 40, 1253-1260.

Kostic, A. D., Ojesina, A. I., Pedamallu, C. S., Jung, J., Verhaak, R. G., Getz, G., and Meyerson, M. (2011). PathSeq: software to identify or discover microbes by deep sequencing of human tissue. Nat Biotechnol 29, 393-396.

Kuhn, R. M., Haussler, D., and Kent, W. J. (2013). The UCSC genome browser and associated tools. Brief Bioinform 14, 144-161.

Lawrence, M. S., Stojanov, P., Mermel, C. H., Robinson, J. T., Garraway, L. A., Golub, T. R., Meyerson, M., Gabriel, S. B., Lander, E. S., and Getz, G. (2014). Discovery and saturation analysis of cancer genes across 21 tumour types. Nature 505, 495-501.

Lawrence, M. S., Stojanov, P., Polak, P., Kryukov, G. V., Cibulskis, K., Sivachenko, A., Carter, S. L., Stewart, C., Mermel, C. H., Roberts, S. A., et al. (2013). Mutational heterogeneity in cancer and the search for new cancer-associated genes. Nature 499, 214-218.

Lee, W. P., Stromberg, M. P., Ward, A., Stewart, C., Garrison, E. P., and Marth, G. T. (2014). MOSAIK: a hash-based algorithm for accurate next-generation sequencing short-read mapping. PLoS One 9, e90581.

Ler, L. D., Ghosh, S., Chai, X., Thike, A. A., Heng, H. L., Siew, E. Y., Dey, S., Koh, L. K., Lim, J. Q., Lim, W. K., et al. (2017). Loss of tumor suppressor KDM6A amplifies PRC2-regulated transcriptional repression in bladder cancer and can be targeted through inhibition of EZH2. Sci Transl Med 9.

Li, H., and Durbin, R. (2009). Fast and accurate short read alignment with Burrows-Wheeler transform. Bioinformatics 25, 1754-1760.

Li, J., and Tibshirani, R. (2013). Finding consistent patterns: a nonparametric approach for identifying differential expression in RNA-Seq data. Stat Methods Med Res 22, 519-536.

Liang, J. Y., Shao, S. H., Xu, Z. X., Hennessy, B., Ding, Z. Y., Larrea, M., Kondo, S., Dumont, D. J., Gutterman, J. U., Walker, C. L., et al. (2007). The energy sensing LKB1-AMPK pathway regulates p27(kip1) phosphorylation mediating the decision to enter autophagy or apoptosis. Nat Cell Biol 9, 218-U125.

Lim, S., Koh, M. J., Jeong, H. J., Cho, N. H., Choi, Y. D., Cho do, Y., Lee, H. Y., and Rha, S. Y. (2016). Fibroblast growth factor receptor 1 overexpression is associated with poor survival in patients with reselected muscle invasive urothelial carcinoma. Yonsei Med J 57, 831-839.

Losada, A. (2014). Cohesin in cancer: chromosome segregation and beyond. Nat Rev Cancer 14, 389-393.

Mak, M. P., Tong, P., Diao, L., Cardnell, R. J., Gibbons, D. L., William, W. N., Skoulidis, F., Parra, E. R., Rodriguez-Canales, J., Wistuba, I. I., et al. (2016). A patient-derived, pan-cancer EMT signature identifies global molecular alterations and immune target enrichment following epithelial-to-mesenchymal transition. Clin Cancer Res 22, 609-620.

Margolin, A. A., Wang, K., Lim, W. K., Kustagi, M., Nemenman, I., and Califano, A. (2006). Reverse engineering cellular networks. Nat Protoc 1, 662-671.

McCarroll, S. A., Kuruvilla, F. G., Korn, J. M., Cawley, S., Nemesh, J., Wysoker, A., Shapero, M. H., de Bakker, P. I., Maller, J. B., Kirby, A., et al. (2008). Integrated detection and population-genetic analysis of SNPs and copy number variation. Nat Genet 40, 1166-1174.

Mermel, C. H., Schumacher, S. E., Hill, B., Meyerson, M. L., Beroukhim, R., and Getz, G. (2011). GISTIC2.0 facilitates sensitive and confident localization of the targets of focal somatic copy-number alteration in human cancers. Genome Biol 12, R41.

Moch, H., Cubilla, A. L., Humphrey, P. A., Reuter, V. E., and Ulbright, T. M. (2016). The 2016 WHO classification of tumours of the urinary system and male genital organs-part A: renal, penile, and testicular tumours. Eur Urol 70, 93-105.

Mullokandov, G., Baccarini, A., Ruzo, A., Jayaprakash, A. D., Tung, N., Israelow, B., Evans, M. J., Sachidanandam, R., and Brown, B. D. (2012). High-throughput assessment of microRNA activity and function using microRNA sensor and decoy libraries. Nat Methods 9, 840-846.

Neeley, E. S., Kornblau, S. M., Coombes, K. R., and Baggerly, K. A. (2009). Variable slope normalization of reverse phase protein arrays. Bioinformatics 25, 1384-1389.

Nguyen, Q., and Carninci, P. (2016). Expression Specificity of Disease-Associated lncRNAs: Toward Personalized Medicine. Curr Top Microbiol Immunol 394, 237-258.

Nielsen, M., and Andreatta, M. (2016). NetMHCpan-3.0; improved prediction of binding to MEW class I molecules integrating information from multiple receptor and peptide length datasets. Genome Med 8, 33.

Nogova, L., Sequist, L. V., Perez Garcia, J. M., Andre, F., Delord, J. P., Hidalgo, M., Schellens, J. H., Cassier, P. A., Camidge, D. R., Schuler, M., et al. (2017). Evaluation of BGJ398, a Fibroblast Growth Factor Receptor 1-3 Kinase Inhibitor, in Patients With Advanced Solid Tumors Harboring Genetic Alterations in Fibroblast Growth Factor Receptors: Results of a Global Phase I, Dose-Escalation and Dose-Expansion Study. J Clin Oncol 35, 157-165.

Olshen, A. B., Venkatraman, E. S., Lucito, R., and Wigler, M. (2004). Circular binary segmentation for the analysis of array-based DNA copy number data. Biostatistics 5, 557-572.

Pasqualucci, L., Dominguez-Sola, D., Chiarenza, A., Fabbri, G., Grunn, A., Trifonov, V., Kasper, L. H., Lerach, S., Tang, H., Ma, J., et al. (2011). Inactivating mutations of acetyltransferase genes in B-cell lymphoma. Nature 471, 189-195.

R Core Development Team (2016). R: A language and environment for statistical computing (Vienna, Austria: R Foundation for Statistical Computing).

Ratan, A., Olson, T. L., Loughran, T. P., Jr., and Miller, W. (2015). Identification of indels in next-generation sequencing data. BMC Bioinformatics 16, 42.

Rebouissou, S., Herault, A., Letouze, E., Neuzillet, Y., Laplanche, A., Ofualuka, K., Maille, P., Leroy, K., Riou, A., Lepage, M. L., et al. (2012). CDKN2A homozygous deletion is associated with muscle invasion in FGFR3-mutated urothelial bladder carcinoma. J Pathol 227, 315-324.

Reich, M., Liefeld, T., Gould, J., Lerner, J., Tamayo, P., and Mesirov, J. P. (2006). GenePattern 2.0. Nat Genet 38, 500-501.

Roberts, S. A., Lawrence, M. S., Klimczak, L. J., Grimm, S. A., Fargo, D., Stojanov, P., Kiezun, A., Kryukov, G. V., Carter, S. L., Saksena, G., et al. (2013). An APOBEC cytidine deaminase mutagenesis pattern is widespread in human cancers. Nat Genet 45, 970-976.

Robertson, G., Schein, J., Chiu, R., Corbett, R., Field, M., Jackman, S. D., Mungall, K., Lee, S., Okada, H. M., Qian, J. Q., et al. (2010). De novo assembly and analysis of RNA-seq data. Nat Methods 7, 909-912.

Rosenberg, J. E., Hoffman-Censits, J., Powles, T., van der Heijden, M. S., Balar, A. V., Necchi, A., Dawson, N., O'Donnell, P. H., Balmanoukian, A., Loriot, Y., et al. (2016). Atezolizumab in patients with locally advanced and metastatic urothelial carcinoma who have progressed following treatment with platinum-based chemotherapy: a single-arm, multicentre, phase 2 trial. Lancet 387, 1909-1920.

Saunders, C. T., Wong, W. S., Swamy, S., Becq, J., Murray, L. J., and Cheetham, R. K. (2012). Strelka: accurate somatic small-variant calling from sequenced tumor-normal sample pairs. Bioinformatics (Oxford, England) 28, 1811-1817.

Seiler, R., Ashab, H. A., Erho, N., van Rhijn, B. W., Winters, B., Douglas, J., Van Kessel, K. E., Fransen van de Putte, E. E., Sommerlad, M., Wang, N. Q., et al. (2017). Impact of Molecular Subtypes in Muscle-invasive Bladder Cancer on Predicting Response and Survival after Neoadjuvant Chemotherapy. Eur Urol.

Sharma, P., Callahan, M. K., Bono, P., Kim, J., Spiliopoulou, P., Calvo, E., Pillai, R. N., Ott, P. A., de Braud, F., Morse, M., et al. (2016). Nivolumab monotherapy in recurrent metastatic urothelial carcinoma (CheckMate 032): a multicentre, open-label, two-stage, multi-arm, phase 1/2 trial. Lancet Oncol 17, 1590-1598.

Shukla, S. A., Rooney, M. S., Rajasagi, M., Tiao, G., Dixon, P. M., Lawrence, M. S., Stevens, J., Lane, W. J., Dellagatta, J. L., Steelman, S., et al. (2015). Comprehensive analysis of cancer-associated somatic mutations in class I HLA genes. Nature biotechnology 33, 1152-1158.

Siegel, R. L., Miller, K. D., and Jemal, A. (2017). Cancer Statistics, 2017. CA Cancer J Clin 67, 7-30.

Sjodahl, G., Eriksson, P., Liedberg, F., and Hoglund, M. (2017). Molecular classification of urothelial carcinoma: global mRNA classification versus tumour-cell phenotype classification. J Pathol 242, 113-125.

Sjodahl, G., Lauss, M., Lovgren, K., Chebil, G., Gudjonsson, S., Veerla, S., Patschan, O., Aine, M., Ferno, M., Ringner, M., et al. (2012). A molecular taxonomy for urothelial carcinoma. Clin Cancer Res 18, 3377-3386.

Tan, V. Y., and Fevotte, C. (2013). Automatic relevance determination in nonnegative matrix factorization with the beta-divergence. IEEE Trans Pattern Anal Mach Intell 35, 1592-1605.

Thomson, D. W., and Dinger, M. E. (2016). Endogenous microRNA sponges: evidence and controversy. Nat Rev Genet 17, 272-283.

Tibes, R., Qiu, Y. H., Hennessy, B., Andreeff, M., Miiis, G. B., and Kornblau, S. M. (2006). Reverse phase protein array: validation of a novel proteomic technology and utility for analysis of primary leukemia specimens and hematopoietic stem cells. Mol Cancer Ther 5, 2512-2521.

Trapnell, C., Hendrickson, D. G., Sauvageau, M., Goff, L., Rinn, J. L., and Pachter, L. (2013). Differential analysis of gene regulation at transcript resolution with RNA-seq. Nat Biotechnol 31, 46-53.

Trapnell, C., Pachter, L., and Salzberg, S. L. (2009). TopHat: discovering splice junctions with RNA-Seq. Bioinformatics 25, 1105-1111.

Triche, T. J., Jr., Weisenberger, D. J., Van Den Berg, D., Laird, P. W., and Siegmund, K. D. (2013). Low-level processing of Illumina Infinium DNA Methylation BeadArrays. Nucleic Acids Res 41, e90.

Van Allen, E. M., Mouw, K. W., Kim, P., Iyer, G., Wagle, N., Al-Ahmadie, H., Zhu, C., Ostrovnaya, I., Kryukov, G. V., O'Connor, K. W., et al. (2014). Somatic ERCC2 mutations correlate with cisplatin sensitivity in muscle-invasive urothelial carcinoma. Cancer Discov 4, 1140-1153.

van Rhijn, B. W., Lurkin, I., Radvanyi, F., Kirkels, W. J., van der Kwast, T. H., and Zwarthoff, E. C. (2001). The fibroblast growth factor receptor 3 (FGFR3) mutation is a strong indicator of superficial bladder cancer with low recurrence rate. Cancer Res 61, 1265-1268.

Walter, S., and Tiemeier, H. (2009). Variable selection: current practice in epidemiological studies. Eur J Epidemiol 24, 733-736.

Wang, K., Singh, D., Zeng, Z., Coleman, S. J., Huang, Y., Savich, G. L., He, X., Mieczkowski, P., Grimm, S. A., Perou, C. M., et al. (2010). MapSplice: accurate mapping of RNA-seq reads for splice junction discovery. Nucleic Acids Res 38, e178.

Warrick, J. I., Walter, V., Yamashita, H., Chung, E., Shuman, L., Amponsa, V. O., Zheng, Z., Chan, W., Whitcomb, T. L., Yue, F., et al. (2016). FOXA1, GATA3 and PPAR cooperate to drive luminal subtype in bladder cancer: a molecular analysis of established human cell lines. Sci Rep 6, 38531.

Wilkerson, M. D., and Hayes, D. N. (2010). ConsensusClusterPlus: a class discovery tool with confidence assessments and item tracking. Bioinformatics 26, 1572-1573.

Williamson, M. P., Elder, P. A., Shaw, M. E., Devlin, J., and Knowles, M. A. (1995). p16 (CDKN2) is a major deletion target at 9p21 in bladder cancer. Hum Mol Genet 4, 1569-1577.

Wolff, E. M., Chihara, Y., Pan, F., Weisenberger, D. J., Siegmund, K. D., Sugano, K., Kawashima, K., Laird, P. W., Jones, P. A., and Liang, G. (2010). Unique DNA methylation patterns distinguish noninvasive and invasive urothelial cancers and establish an epigenetic field defect in premalignant tissue. Cancer Res 70, 8169-8178.

Wu, X., Liu, D., Tao, D., Xiang, W., Xiao, X., Wang, M., Wang, L., Luo, G., Li, Y., Zeng, F., et al. (2016). BRD4 Regulates EZH2 Transcription through Upregulation of C-MYC and Represents a Novel Therapeutic Target in Bladder Cancer. Mol Cancer Ther 15, 1029-1042.

Xiao, N., Xu, Q. S., and Li, M. Z. (2016). hdnom: building nomograms for penalized Cox models with high-dimensional survival data. bioRxiv, 065524.

Xu, R., and Harrington, D. P. (2001). A semiparametric estimate of treatment effects with censored data. Biometrics 57, 875-885.

Zack, T. I., Schumacher, S. E., Carter, S. L., Cherniack, A. D., Saksena, G., Tabak, B., Lawrence, M. S., Zhsng, C. Z., Wala, J., Mermel, C. H., et al. (2013). Pan-cancer patterns of somatic copy number alteration. Nat Genet 45, 1134-1140.

Zhang, L., Wei, Q., Mao, L., Liu, W., Mills, G. B., and Coombes, K. (2009). Serial dilution curve: a new method for analysis of reverse phase protein array data. Bioinformatics 25, 650-654.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating bladder cancer in a selected subject, the method comprising administering atezolizumab to the subject, wherein the subject is selected by detecting an increase in the level of polynucleotide markers SOX2, TUBB2B, and PEG10 in a biological sample from the subject using a polynucleotide probe that hybridizes to the marker, using a primer that hybridizes to and amplifies the marker, or using a nucleic acid array for expression-based measurement of the marker relative to a reference, wherein detecting an increase in said markers relative to the reference selects the subject for treatment with atezolizumab.

2. The method of claim 1, further comprising detecting proteins selected from the group consisting of GATA3, EGFR, CDH1, and HER2;
   detecting miRNAs selected from the group consisting of miR-200s, miR-99a, and miR-100;
   detecting TP53 and RB1 mutations; and/or
   detecting an RB1, CDKN1A4, CDKN2A, ATM, ERCC, FGFR3, PIK3CA, and RAS, ERBB2, KDM6A, KMT2A, KMT2C, KMT2D, CREBBP, EP300, KANSL1, ARID1A, ASXL1, and ASXL2 mutation or a homozygous deletion.

3. The method of claim 1, wherein the biological sample is a urothelial tumor.

4. The method of claim 1, comprising: (a) wherein the level of polynucleotide marker is determined by detecting the expression level of one or more transcripts of SOX2, TUBB2B, and PEG10 genes in the biological sample to provide an expression pattern profile, and (b) comparing said expression pattern profile with a reference expression pattern profile.

5. The method of claim 1, wherein the level of the markers is determined by detecting an expression profile for said markers from a sample obtained from the individual, and (b) comparing the expression profile from the sample to an expression profile of a control or standard.

6. A method of treating a subject for bladder cancer, comprising:
   (a) measuring levels of PEG10, SOX2, and TUBB2B neuronal marker polypeptides or polynucleotides in a bladder cancer sample of the subject;

(b) obtaining an expression profile for PEG10, SOX2, and TUBB2B neuronal marker polypeptides or polynucleotides in the sample obtained from the subject; and (c) comparing the expression profile of (b) from the sample to an expression profile of a control or standard, where an increase in the levels of said markers relative to a reference selects the subject for treatment with atezolizumab; and (d) administering atezolizumab to the selected subject of (c), thereby treating the bladder cancer.

7. A method of treating bladder cancer in a selected subject, the method comprising:

(a) detecting in a bladder cancer biological sample of the subject an increase in the expression of neuronal polypeptide or polynucleotide markers comprising or consisting of SOX2, TUBB2B, and PEG10 relative to a reference;

(b) selecting the subject for treatment with atezolizumab based on the detection of the increase in the expression level of SOX2, TUBB2B, and PEG10 relative to a reference in (a); and (c) administering atezolizumab to the subject selected in (b).

* * * * *